(12) United States Patent
Messier

(10) Patent No.: US 7,252,966 B2
(45) Date of Patent: Aug. 7, 2007

(54) EG307 POLYNUCLEOTIDES AND USES THEREOF

(75) Inventor: Walter Messier, Longmont, CO (US)

(73) Assignee: Evolutionary Genomics LLC, Aurora, CO (US)

( * ) Notice: Subject to any disclaimer, the term of this patent is extended or adjusted under 35 U.S.C. 154(b) by 100 days.

(21) Appl. No.: 10/079,042

(22) Filed: Feb. 19, 2002

(65) Prior Publication Data

US 2003/0148292 A1 Aug. 7, 2003

Related U.S. Application Data

(63) Continuation-in-part of application No. 09/875,666, filed on Jun. 6, 2001, now Pat. No. 6,743,580, which is a continuation of application No. 09/368,810, filed on Aug. 5, 1999, now Pat. No. 6,274,319, which is a continuation-in-part of application No. 09/240,915, filed on Jan. 29, 1999, now Pat. No. 6,228,586.

(60) Provisional application No. 60/349,088, filed on Jan. 16, 2002, provisional application No. 60/315,595, filed on Aug. 29, 2001.

(51) Int. Cl.
C12Q 1/68 (2006.01)
C07H 21/04 (2006.01)

(52) U.S. Cl. .................. 435/69.1; 435/410; 536/23.6; 514/1; 800/278; 800/295

(58) Field of Classification Search ............... 435/69.1, 435/410; 536/23.6; 514/1; 800/278, 295
See application file for complete search history.

(56) References Cited

U.S. PATENT DOCUMENTS

| | | | |
|---|---|---|---|
| 5,451,513 A | 9/1995 | Maliga et al. | |
| 5,492,820 A * | 2/1996 | Sonnewald et al. | 800/284 |
| 5,545,531 A | 8/1996 | Rava et al. | |
| 5,545,817 A | 8/1996 | McBride et al. | |
| 5,545,818 A | 8/1996 | McBride et al. | |
| 5,614,395 A | 3/1997 | Ryals et al. | |
| 5,625,136 A | 4/1997 | Koziel et al. | |
| 5,965,352 A | 10/1999 | Stoughton et al. | |
| 6,228,586 B1 * | 5/2001 | Messier et al. | 435/6 |
| 6,245,969 B1 * | 6/2001 | Chory et al. | 800/290 |
| 2002/0157143 A1 * | 10/2002 | Concibido et al. | 800/312 |
| 2007/0016976 A1 | 1/2007 | Katagiri | |

FOREIGN PATENT DOCUMENTS

| | | |
|---|---|---|
| EP | 0 120 658 A | 3/1984 |
| EP | 0332104 | 9/1989 |
| EP | 0359472 | 3/1990 |
| EP | 0385962 | 9/1990 |
| EP | 0452269 | 10/1991 |
| WO | WO 93/07278 | 4/1993 |
| WO | WO 95/16783 | 6/1995 |

OTHER PUBLICATIONS

Lin et al. (2000) Plant Physiol 122:379-388.
Nakazono et al. (1996) Curr. Genet. 29:412-416.
Brachmann et al. (1998) Yeast 14:115-132.
Essl et al. (1999) FEBS Letters 453:169-173.
Firek et al. (1993) Plant Molecular Biology 22:129-142.
Framond et al. (1991) FEBS 290(1,2):103-106.
Goldschmidt-Clermont (1991) Nuc. Acids Res. 19(15):4083-4089.
Hauser et al. (2001) Mol. Mem. Biol. 18:105-112.
Hauser (2000) J. Biol Chem 275:3037-3041.
Horie et al. (2001) Plant J. 27(2):129-138.
Hudspeth et al. (1989) Plant Mol. Biol. 12:579-589.
Joshi (1987) Nuc. Acids Res. 15(16):6643-6653.
Logeman et al. (1989) Plant Cell 1:151-158.
Lubkowitz et al. (1997) Microbiology 143:387-396.
Matsukura et al. (2000) Plant Physiol 124:85-93.
McBride et al. (1994) Proc Natl Acad Sci USA 91:7301-7305.
Morgenstern (1999) Bioinformatics 15(3):211-218.
Murray et al. (1989) Nuc. Acids Res. 17(2):477-498.
Peng et al. (1999) Nature 400:256-261.
Roessner (2001) Plant Cell 13:11-29.
Rohrmeier et al. (1993) Plant Mol. Biol. 22:783-792.
Seki et al. (2001) Plant Cell 13:61-72.
Sengupta-Gopalan et al. (1985) Proc. Natl. Acad. Sci USA 82:3320-3324.
Song et al. (1997) Plant Physiol 114:927-9358.
Stanford et al. (1989) Mol Gen Genet 215:200-208.
Staub et al. (1993) EMBO Jour. 12(2):601-606.
Steiner et al. (1994) Plant Cell 6:1289-1299.
Steiner et al. (1995) Mol Micro 16(5):825-834.
Svab et al. (1990) Proc Natl Acad Sci USA 87:8526-8530.
Svab et al. (1993) Proc Natl Acad Sci USA 90:913-917.
Warner et al. (1993) Plant Journal 3(2):191-201.
West et al. (1998) Plant Journal 15(2):221-229.
Wu et al. (2002) Plant Cell 14:525-535.
Xu et al. (1993) Plant Mol Biol 22:573-588.
Yan et al. (1997) Plant Physiol 115:915-924.
Raz et al. (1992) Mol Gen Genet 233:252-259.
Alter et al., (1984) Science 226:549-552.
Burger et al. (1994) J. Mol. Evol. 39:255-267.
Doebley et al. (Sep. 1992) Trends in Genetics 8:(9)302-307.
Doebley et al. (1990) Proc. Natl. Acad. Sci. USA 87:9888-9892.
Dorwieler et al. (1993) Science 262:233-235.
Edwards et al. (1995) Molecular Ecology 4:719-729.
Endo et al. (1996) Mol. Biol. Evol. 13:685-690.
Fultz et al. (1986) Journal of Virology 38:116-124.
Gibbons (Sep. 4, 1998) Science 281:1432-1434.

(Continued)

Primary Examiner—Kenneth R. Horlick
(74) Attorney, Agent, or Firm—Swanson & Bratschun, L.L.C.

(57) ABSTRACT

The present invention provides methods for identifying polynucleotide and polypeptide sequences which may be associated with commercially or aesthetically relevant traits in domesticated plants or animals. The methods employ comparison of homologous genes from the domesticated organism and its ancestor to identify evolutionarily significant changes and evolutionarily neutral changes. Sequences thus identified may be useful in enhancing commercially or aesthetically desirable traits in domesticated organisms or their wild ancestors.

12 Claims, 7 Drawing Sheets

OTHER PUBLICATIONS

Goodman et al. (1990) J. Mol. Evol. 30:260-266.
Goodwin et al. (1996) Mol. Biol. Evol. 13:346-358.
Herbert and Easteal (1996) Mol. Biol. Evol. 13:1054-1057.
Hughes (1997) Mol. Biol. Evol. 14:1-5.
Hughes and Nei (1988) Nature 335:167-170.
Jaeger et al. (1994) Immunogenetics 40:184-191.
Jenkins et al. (1995) Proc. R. Soc. Lond. 261:203-207.
Kreitman and Akashi, (1995) Annu. Rev. Ecol. Syst. 26:403-422.
Lee and Vacquier (1992) Biol. Bull. 182:97-104.
Lee et al. (1998) AIDS Research and Human Retroviruses 14:1323-1328.
Li (1997) in Molecular Evolution, Sinauer Associates, Inc. pub., Sunderland, MA, Table of Contents.
Li, (1993) J. Mol. Evol. 36:96-99.
Li, (1985) Mol. Biol. Evol. 2:150-174.
Lienert and Parham (1996) Immunol. Cell Biol. 74:349-356.
Lyn et al. (1995) Gene 155:241-245.
Malcolm et al., Nature 345:86-89 (1990).
McDonald and Kreitman (1991) Nature 351:652-654.
Messier and Stewart, Current Biology 4:911-913.
Messier and Stewart, (1997) Nature 385:151-154.
Metz and Palumbi, Mol. Biol. Evol. 13:397-406.
Nakashima et al. (1995) Proc. Natl. Acad. Sci. USA 92:5605-5609.
Nei (1987) in Molecular Evolutionary Genetics, Columbia University Press, New York, NY, Table of Contents.
Nei and Hughes (1991) in Evolution at the Molecular Level, Selander, R., Clark, A. and Whittam, T. eds. Sinauer Associates, Inc., Pub., Sunderland, Massachusetts, pp. 222-247.
Niewiesk and Bangham, J. Mol. Evol. 42:452-458.
Novembre et al. (1997) Journal of Virology 71:4086-4091.
Parham and Ohta (1996) Science 272:67-74.
Paterson et al. (1995) Science 269:1714-1718.
Sharp, Nature 385:111-112 (1997).
Swanson and Vacquier, Proc. Natl. Acad. Sci. USA 92:4957-4961.
Swanson and Vacquier, Science 281:710-712.
Turcich et al. (1996) Sex Plant Reprod. 9:65-74.
Wang et al. (1999) Nature 398:236-239.
Wettstein et al. (1996) Mol. Biol. Evol. 13:56-66.
White, S.E. et al. (Nov. 1999) Genetics 153:1455-1462.
Whitfield et al. (1993) Nature 364:713-715.
Wilson et al. (Sep. 1999) Genetics 153(1):453-473.
Wolinsky et al. (1996) Science 272:537-542.
Wu et al. (1997) J. Mol. Evol. 44:477-491.
Xiao et al. (Oct. 1998) Genetics 150:899-909.
Yang (1998) Mol. Biol. Evol. 15:568-573.
Zhou and Li (1996) Mol. Biol. Evol. 13:780-793.

\* cited by examiner

```
Nip:    1   gggggtgagcttaggccggacgccggggcatcagccatgtcgaggtgcttcccctacccg   60
            |||  ||||||||||||||||,|||,|||||||||||| |||||
Rufi:   1                    acgccggggcatcagccatgtcgaggtgcttcccctacccg   60
                                              START Nip:   61   ccgccgggtacgtgcgaaacccagtggtggccgtggccgcggccgaagcgcaggcgacc  120
            ||:|||,||,|||||||||||||||||||||||||||| |||||||||||| |||| |||
Rufi:  61   ccgccggggtacgtgcgaaacccagtcgtggccgtggccgcggccgaagcgcaggcgacc  120

Nip:  121   actaagctccagaaagaaagggaaaagcctgaaaagaagaaagagaaaaggagtgacagg  180
            |:||||||:|||,|||,|||||||||,||| |||:|:|||||||,||| !||||||:||
Rufi: 121   actaagctccagaaagaaagggaaaaggccgaaaagaagaaagagaaaaagagtgacagg  180

Nip:  181   aaagctcttccacatggtgagatatccaagcattcaaagcgaacccaccacaagaagaga  240
            !|||||||,|| ||||||||||||||||'|||||,||| |||||||:|||||'  ||||||||
Rufi: 181   aaagctcttccacatggtgagatatccaagcattcaaagcgaaccccac---aagaagaga  237

Nip:  241   aaacatgaagacatcaataatgctgatcagaagtcccggaaggtttcctccatggaacct  300
            ||||||!||||||||:||| | |||||||||,||||||||||||||||||||||:||||||||!
Rufi: 238   aaacatgaagacatcaataatgctgatcagaagtcccggaaggtttcctccatggaacct  297

Nip:  301   ggtgagcaattgcagaacagtgcactctcagaagagcatggagctccttcctttactcag  360
            |!|||||||||||,||||,|||||||||||| |||||||||||,|||||,|||||||||||!|
Rufi: 298   ggtgagcaattggagaagagtggactctcagaagagcatggagctccttgctttactcag  357

Nip:  361   acagagcatggctctccagagagttcacaggacagcagcaagagaagaaaggttgtgtta  420
            ||||  |||||||||||||||||||||||||:|||||||:|||||||||||| ||||| ||||||
Rufi: 358   acagtgcatggctctccagagagttcacaggacagcagcaagagaagaaaggttgtgtta  417

Nip:  421   cccagtcctagccaagctaacaatggtaacatccttcgaataaagataagaagagatcaa  480
            :|||||||!||||||||||| |:| ||||||| |'|||||||| |||||||||||||||||||
Rufi: 418   cccagtcctaccaagctaagaatggtaacatccttcgaataaagataagaagagatcaa  477

Nip:  481   gattcttcagcttcccttcggagaaatctaatgttgtacaaacaccagttcatcaaatg  540
            ||||||||||||||||||||,|,|||||||||||||||||||||||||:|||  ||||||||||'|:|
Rufi: 478   gattcttcagcttcccttcggagaaatctaatgttgtacaaacaccagttcatcaaatg  537

Nip:  541   ggatcagtttcatctctgccaagtaagaaaaactcaatgcaaccacacaacaccgaaatg  600
            |||!'||||:|||||  |||| ||||  ||||,|||||||||,| ||||| ||:|||||||'|
Rufi: 538   ggatcagtttcatctctgccaagtaagaaaaactcaatgcaaccacacaacaccgaaatg  597

Nip:  601   atggtgagaacagcatcaacccagcagcaaagcatcaaggtgattttcaagcagtaccg  660
            |||||  ||||||||||||||||||||||||||||||||' |||||||||| |||| |||| |
Rufi: 598   atggtgagaacagcatcaacccagcagcaaagcatcaaggtgattttcaagcagtactg  657

Nip:  661   aaacaaggtatgccaaccccagcaaaagtcatgccaacagtcgatgttcctccatctatg  720
            |||||:|||||||||||||||:| ||||||||||||||||| ||||||||||||||||||||||||
Rufi: 658   aaacaaggtatgccaaccccagcaaaagtcatgccaagagtcgatgttcctccatctatg  717
```

Figure 1

```
Nip:   721  agggcatcaaaggaaaggattggccttcgtcctgcagagatgttggccaatgttggtcct  780
            |||||||||||||||||| |||||||||||||||||||||||||||||||||||||||||
Rufi:  718  agggcatcaaaggaaagggttggccttcgtcctgcagagatgttggccaatgttggtcct  777

Nip:   781  tcaccctccaaggcaaaacagattgtcaatcctgcagctgctaaggttacacaaagagtt  840
            ||||||||||||||||||||||||||||||||||||||||||||||||||||||||||||
Rufi:  778  tcaccctccaaggcaaaacagattgtcaatcctgcagctgctaaggttacacaaagagtt  837

Nip:   841  gatcctccacctgccaaggcatctcagagaattgatcctctgttgccatccaaggttcat  900
            ||||||||||||||||||||||||||||||||||||||||||||||||||||||||||||
Rufi:  838  gatcctccacctgccaaggcatctcagagaattgatcctctgttgccatccaaggttcat  897

Nip:   901  atagatgctactcgatcttttacgaaggtctcccagacagagatcaagccggaagtacag  960
            |||||||||||||||||||||||||||| |||||||||||||||||||||||||||||||
Rufi:  898  atagatgctactcgatcttttacgaagctctcccagacagagatcaagccggaagtacag  957

Nip:   961  cccccaattctgaaggtgcctgtggctatgcctaccatcaatcgtcagcagattgacacc  1020
            ||||||||| ||||||||||||||||||| ||||||||||||||||||||||||||||||
Rufi:  958  cccccaattccgaaggtgcctgtggctatgcctaccatcaatcgtcagcagattgacacc  1017

Nip:  1021  tcgcagcccaaagaagagccttgctcctctggcaggaatgctgaagctgcttcagtatca  1080
            |||||||||||||||||||||||||||||||||||||||||||||||||||||||||||
Rufi: 1018  tcgcagcccaaagaagagccttgctcctctggcaggaatgctgaagctgcttcagtatca  1077

Nip:  1081  gtagagaagcagtccaagtcagatcgcaaaaagagccgcaaggctgagaagaaagagaag  1140
            ||||||||||||||||||||||||||||||||||||||||||||||||||||||||||||
Rufi: 1078  gtagagaagcagtccaagtcagatcgcaaaaagagccgcaaggctgagaagaaagagaag  1137

Nip:  1141  aagttcaaagatttatttgttacctgggatcctccgtctatggaaatggatgatatggat  1200
            ||||||||| |||||||||||||||||||||||||||||||||||||||||||||||||
Rufi: 1138  aagttcaaagatttatttgttacctgggatcctccgtctatggaaatggatgatatggat  1197

Nip:  1201  ctcggggaccaggattggctgcttgatagtacgaggaaacctgatgctggcattggcaac  1260
            || |||||| ||||||||||||||||| ||||||||||||||||||||||||||||||||
Rufi: 1198  cttggggaccaggattggctgcttggtagtacgaggaaacctgatgctggcattggcaac  1257

Nip:  1261  tgcagagaaattgttgatccacttacttctcaatcagcagagcagttctcattgcagcct  1320
            ||||| ||| ||||||||||||||||||||||||||||  ||||||||||||||||||||
Rufi: 1258  tgcagagaaattgttgatccacttacttctcaatcagcggagcagttctcattgcagcct  1317

Nip:  1321  agggcgattcatttaccagaccttcatgtctatcagttgccatatgtggttccattctag  1380
            ||||||||||||||||||||||||||||||||||||||||||||||||||||||||||||
Rufi: 1318  agggcgattcatttaccagaccttcatgtctatcagttgccatatgtggttccattctag  1377
                                                                      STOP
Nip:  (nucleotides 1-36 of SEQ ID NO:4 and SEQ ID NO:5)
Rufi: (nucleotides 1-17 of SEQ ID NO:27 and SEQ ID NO:29)
```

Figure 1 (continued)

```
Nip:     1  MSRCFPYPPPGYVRNPVVAVAAAEAQATTKLQKEREKAEKKKEKRSDRKALPHGEISKHS   180
Rufi:    1  MSRCFPYPPPGYVRNPVVAVAAAEAQATTKLQKEREKAEKKKEKKSDRKALPHGEISKHS   180

Nip:   181  KRTHHKKRKHEDINNADQKSRKVSSMEPGEQLEKSGLSEEHGAPCFTQTEHGSPESSQDS   360
Rufi:  181  KRTH-KKRKHEDINNADQKSRKVSSMEPGEQLEKSGLSEEHGAPCFTQTVHGSPESSQDS   360

Nip:   361  SKRRKVVLPSPSQAKNGNILRIKIRRDQDSSASLSEKSNVVQTPVHQMGSVSSLPSKKNS   540
Rufi:  361  SKRRKVVLPSPSQAKNGNILRIKIRRDQDSSASLSEKSNVVQTPVHQMGSVSSLPSKKNS   540

Nip:   541  MQPHNTEMMVRTASTQQQSIKGDFQAVPKQGMPTPAKVMPRVDVPPSMRASKERIGLRPA   720
Rufi:  541  MQPHNTEMMVRTASTQQQSIKGDFQAVLKQGMPTPAKVMPRVDVPPSMRASKERVGLRPA   720

Nip:   721  EMLANVGPSPSKAKQIVNPAAAKVTQRVDPPPAKASQRIDPLLPSKVHIDATRSFTKVSQ   900
Rufi:  721  EMLANVGPSPSKAKQIVNPAAAKVTQRVDPPPAKASQRIDPLLPSKVHIDATRSFTKLSQ   900

Nip:   901  TEIKPEVQPPILKVPVAMPTINRQQIDTSQPKEEPCSSGRNAEAASVSVEKQSKSDRKKS  1080
Rufi:  901  TEIKPEVQPPIPKVPVAMPTINRQQIDTSQPKEEPCSSGRNAEAASVSVEKQSKSDRKKS  1080

Nip:  1081  RKAEKKEKKFKDLFVTWDPPSMEMDDMDLGDQDWLLDSTRKPDAGIGNCREIVDPLTSQS  1260
Rufi: 1081  RKAEKKEKKFKDLFVTWDPPSMEMDDMDLGDQDWLLGSTRKPDAGIGNCREIVDPLTSQS  1260

Nip:  1261  AEQFSLQPRAIHLPDLHVYQLPYVVPF  1344  (SEQ ID NO:6)
Rufi: 1261  AEQFSLQPRAIHLPDLHVYQLPYVVPF  1344  (SEQ ID NO:30)
```

Figure 2

```
Maize:   1    gcatgtcgaggtgcttcccctacccgccaccggggtacgtgcggaacccagtggccgtgg  60
              | ||||||||||||||||||||||||||||||||||||||||||||||||||||||||||
Teo:     1     atgtcgaggtgcttcccctacccgccaccggggtacgtgcggaacccagtggccgtgg  60
              START Maize:  61    ccgagccggagtcgaccgctaagctcctgaaagaaaaggaaaaggccgaaaagaagaaag 120
              ||||||||||||||||||||||||||||||||||||||||||||||||||||||||||||
Teo:    61    ccgagccggagtcgaccgctaagctcctgaaagaaaaggaaaaggccgaaaagaagaaag 120

Maize: 121    agaaaaggagtgacaggaaagctcccaagcagtgtgagacgtccaaacattcaaagcaca 180
              ||||||||||||||||||||||||||||||||||||||||||||||||||||||||||||
Teo:   121    agaaaaggagtgacaggaaagctcccaagcagtgtgagacgtccaaacattcaaagcaca 180

Maize: 181    gccataagaagagaaagcttgaagatgtcatcaaagctgagcagggtcccaaaagagtac 240
              ||||||||||||||||||||||||||||||||||||||||||||||||||||||||||||
Teo:   181    gccataagaagagaaagcttgaagatgtcatcaaagctgagcagggtcccaaaagagtac 240

Maize: 241    ccaaagaatcagttgagcagttggagaagagtggactctcagaagagcatggagctcctt 300
              ||||||||||||||||||||||||||||||||||||||||||||||||||||||||||||
Teo:   241    ccaaagaatcagttgagcagttggagaagagtggactctcagaagagcatggagctcctt 300

Maize: 301    cttttgtacatacgatacgtgactctcctgagagctcacaggacagcggcaagagacgaa 360
              ||||||||||||||||||||||||||||||||||||||||||||||||||||||||||||
Teo:   301    cttttgtacatacgatacgtgactctcctgagagctcacaggacagcggcaagagacgaa 360

Maize: 361    aggttgtcctgtccagtcctagccaacctaagaatggaaacattcttcgcttcaagatta 420
              ||||||||||||||||||||||||||||||||||||||||||||||||||||||||||||
Teo:   361    aggttgtcctgtccagtcctagccaacctaagaatggaaacattcttcgcttcaagatta 420

Maize: 421    aaagtagtcaagayccccaatcagctgttctggagaaaccaagggttcttgagcaaccat 480
              |||||||||||| |||||||||||||||| ||||||||||||||||||||||||||||||
Teo:   421    aaagtagtcaagatccccaatcagctgttctggagaaaccaagggttcttgagcaaccat 480

Maize: 481    tggtccaacaaatgggatcaggttcatccctgtcgggcaagcaaaattcaatccatcata 540
              ||||||||||||||||||||||||||||||||||||||||||||||||||||||||||||
Teo:   481    tggtccaacaaatgggatcaggttcatccctgtcgggcaagcaaaattcaatccatcata 540

Maize: 541    agatgaatgtgagatctacctctggtcagcggagggtcgatggtgactcccaagcagtac 600
              |||||| ||||||||||||||||||||||||||||| |||||||||||||||||||||||
Teo:   541    agatgaatgtgagatctacctctggtcagcggagggtcaatggtgactcccaagcagtac 600

Maize: 601    aaaaatgtttgattacagaatccccggcaaagaccatgcagagacttgtcccccagcctg 660
              |||||||| |||||||||||||||||||||||||||||||||||||||||||||||||||
Teo:   601    aaaaatgtttgattacagaatccccggcaaagaccatgcagagacttgtcccccagcctg 660

Maize: 661    cagctaaggtcacacatcctgttgatccccagtcagctgttaaggtgccagttggaagat 720
              ||||||||||||||||||||||||||||||||||||||||||||||||||||||||||||
Teo:   661    cagctaaggtcacacatcctgttgatccccagtcagctgttaaggtgccagttggaagat 720
```

Figure 3

```
Maize:  721  cgggcctacctctgaagtcttcgggaagtgtggaccccttcgcctgctagagttatgagaa 780
             ||||||||||||||||||||||||||||||||| ||||||||||||||||||||||||||
Teo:    721  cgggcctacctctgaagtcttcgggaagtgtggaccccttcgcctgctagagttatgagaa 780

Maize:  781  gatttgatcctccacctgttaagatgatgtcacagagagttcaccatccagcttccatgg 840
             ||||||||||||||||||||||||||||||||||||||||||||||||||||||||||||
Teo:    781  gatttgatcctccacctgttaagatgatgtcacagagagttcaccatccagcttccatgg 840

Maize:  841  tgtcgcagaaagttgatcctccgtttccgaaggtattacataaggaaaccggatctgttg 900
             ||| |||||||||| ||||||||| |||||||||||||||||||||||||||||||||||
Teo:    841  tgtcgcagaaagttgatcctccgtttccgaaggtattacataaggaaaccggatctgttg 900

Maize:  901  ttcgcctaccagaagctacccggcctactgttcttcaaaaacccaaggacttgcctgcta 960
             |||||  |||||||||||||||||||||||||||||||||| ||||||||||||||||||
Teo:    901  ttcgcctaccagaagctacccggcctactgttcttcaaaaacccaaggacttgcctgcta 960

Maize:  961  tcaagcagcaggatatcaggacctcttcctcaaaagaagagccctgcttctctggtagga 1020
             ||||||||  |||||||  |||||||| ||||||||||||||||||||| ||||||||||
Teo:    961  tcaagcagcaggatatcaggacctcttcctcaaaagaagagccctgcttctctggtagga 1020

Maize: 1021  atgcagaagcagttcaagtgcaagatactaagctctcccggtcagacatgaagaaaatcc 1080
             ||||||||||||||||||||||||||||||||||||||||||||||||||||||||||||
Teo:   1021  atgcagaagcagttcaagtgcaagatactaagctctcccggtcagacatgaagaaaatcc 1080

Maize: 1081  gcaaagctgagaaaaaagataagaagttcagagatctgtttgttacctggaatccggtat 1140
             | ||||||||| |||||||||||||||||||||||||| |||||||||||||||||||||
Teo:   1081  gcaaagctgagaaaaaagataagaagttcagagatctgttgtttacctggaatccggtat 1140

Maize: 1141  tgatagagaatgaaggttcagatcttggtgatgaagactggctgttcagcagtaaaagga 1200
             ||||||||||||  ||||||||||||||||||||||||||||  ||||||| ||||||||
Teo:   1141  tgatagagaatgaaggttcagatcttggtgatgaagactggctgttcagcagtaaaagga 1200

Maize: 1201  actccgatgctatcatggttcaaagcagagctactgatagttcagtgccgatccatccaa 1260
             ||||||||||  ||||||||||||||||||||||||||||||||  |||||||||| |||
Teo:   1201  actccgatgctatcatggttcaaagcagagctactgatagttcagtgccgatccatccaa 1260

Maize: 1261  tggtgcagcagaagccttctttacaacccaggcaacattttgccggaccttaatatgt 1320
             ||||||||||||||||||||||||||||||||||||||||||||| ||||| ||||||||
Teo:   1261  tggtgcagcagaagccttctttacaacccaggcaacattttgccggaccttaatatgt 1320

Maize: 1321  accagctgccatatgtcgtaccattttaaacatctggcgaggtagatgagaattagatga 1380
             ||||||| ||||||||||||||||||||  ||||||||||||| |||||||||  |||||
Teo:   1321  accagctgccatatgtcgtaccattttaaacatctggcgaggtagatgagaattagatga 1380
                                        STOP Maize: 1381  gatgttgggagagagctg
             ||||||||| | ||||||
Teo:   1381  gatgttgggagagagctgtgtgaacagtaggccgggtagctt 1422

Maize:  (nucleotides 1-2 of SEQ ID NO:33, SEQ ID NO:35,
         and nucleotides 1399-1447 of SEQ ID NO:34)
Teo:    (SEQ ID NO:66, and nucleotides 2581-2620 of SEQ ID NO:67)
```

Figure 3 (continued)

```
Maize:    1  MSRCFPYPPPGYVRNPVAVAEPESTAKLLKEKEKAEKKKEKRSDRKAPKQCETSKHSKHS  180

Teo:      1  MSRCFPYPPPGYVRNPVAVAEPESTAKLLKEKEKAEKKKEKRSDRKAPKQCETSKHSKHS  180

Maize:  181  HKKRKLEDVIKAEQGPKRVPKESVEQLEKSGLSEEHGAPSFVHTIRDSPESSQDSGKRRK  360

Teo:    181  HKKRKLEDVIKAEQGPKRVPKESVEQLEKSGLSEEHGAPSFVHTIRDSPESSQDSGKRRK  360

Maize:  361  VVLSSPSQPKNGNILRFKIKSSQDPQSAVLEKPRVLEQPLVQQMGSGSSXSGKQNSIHHK  540

Teo:    361  VVLSSPSQPKNGNILRFKIKSSQDPQSAVLEKPRVLEQPLVQQMGSGSSLSGKQNSIHHK  540

Maize:  541  MNVRSTSGQRRVDGDSQAVQKCLITESPAKTMQRLVPQPAAKVTHPVDPQSAVKVPVGRS  720

Teo:    541  MNVRSTSGQRRVNGDSQAVQKCLITESPAKTMQRLVPQPAAKVTHPVDPQSAVKVPVGRS  720

Maize:  721  GLPLKSSGSVDPSPARVMRRFDPPPVKMMSQRVHHPASMVSQKVDPPFPKVLHKETGSVV  900

Teo:    721  GLPLKSSGSVDPSPARVMRRFDPPPVKMMSQRVHHPASMVSQKVDPPFPKVLHKETGSVV  900

Maize:  901  RLPEATRPTVLQKPKDLPAIKQQDIRTSSSKEEPCFSGRNAEAVQVQDTKLSRSDMKKIR  1080

Teo:    901  RLPEATRPTVLQKPKDLPAIKQQDIRTSSSKEEPCFSGRNAEAVQVQDTKLSRSDMKKIR  1080

Maize: 1081  KAEKKDKKFRDLFVTWNPVLIENEGSDLGDEDWLFSSKRNSDAIMVQSRATDSSVPIHPM  1260

Teo:   1081  KAEKKDKKFRDLFVTWNPVLIENEGSDLGDEDWLFSSKRNSDAIMVQSRATDSSVPIHPM  1260

Maize: 1261  VQQKPSLQPRATFLPDLNMYQLPYVVPF  1347        (SEQ ID NO:36)

Teo:   1261  VQQKPSLQPRATFLPDLNMYQLPYVVPF  1347        (SEQ ID NO:68)
```

EG307 POLYNUCLEOTIDES AND USES THEREOF

CROSS-REFERENCE TO RELATED APPLICATIONS

This application claims priority under 35 U.S.C. § 119 from U.S. application Ser. No. 60/349,088, filed Jan. 16, 2002 and U.S. application Ser. No. 60/315,595, filed Aug. 29, 2001. This application is also a continuation-in-part of U.S. application Ser. No. 09/875,666, filed Jun. 6, 2001, now U.S. Pat. No. 6,743,580, which is a continuation of U.S. application Ser. No. 09/368,810, filed Aug. 5, 1999, now U.S. Pat. No. 6,274,319, which is a continuation-in-part of U.S. application Ser. No. 09/240,915, filed Jan. 29, 1999, now U.S. Pat. No. 6,228,586, each of which is incorporated herein in its entirety by reference.

TECHNICAL FIELD

This invention relates to using molecular and evolutionary techniques to identify polynucleotide and polypeptide sequences corresponding to commercially or aesthetically relevant traits in domesticated plants and animals.

BACKGROUND ART

Humans have bred plants and animals for thousands of years, selecting for certain commercially valuable and/or aesthetic traits. Domesticated plants differ from their wild ancestors in such traits as yield, short day length flowering, protein and/or oil content, ease of harvest, taste, disease resistance and drought resistance. Domesticated animals differ from their wild ancestors in such traits as fat and/or protein content, milk production, docility, fecundity and time to maturity. At the present time, most genes underlying the above differences are not known, nor, as importantly, are the specific changes that have evolved in these genes to provide these capabilities. Understanding the basis of these differences between domesticated plants and animals and their wild ancestors will provide useful information for maintaining and enhancing those traits. In the case of crop plants, identification of the specific genes that control desired traits will allow direct and rapid improvement in a manner not previously possible.

Although comparison of homologous genes or proteins between domesticated species and their wild ancestors may provide useful information with respect to conserved molecular sequences and functional features, this approach is of limited use in identifying genes whose sequences have changed due to human imposed selective pressures. With the advent of sophisticated algorithms and analytical methods, much more information can be teased out of DNA sequence changes with regard to which genes have been positively selected. The most powerful of these methods, "$K_A/K_S$," involves pairwise comparisons between aligned protein-coding nucleotide sequences of the ratios of nonsynonymous nucleotide substitutions per nonsynonymous site ($K_A$) synonymous substitutions per synonymous site ($K_S$)

(where nonsynonymous means substitutions that change the encoded amino acid and synonymous means substitutions that do no t change the encoded amino acid). "$K_A/K_S$-type methods" include this and similar methods.

These methods have been used to demonstrate the occurrence of Darwinian (i.e., natural) molecular-level positive selection, resulting in amino acid differences in homologous proteins. Several groups have used such methods to document that a particular protein has evolved more rapidly than the neutral substitution rate, and thus supports the existence of Darwinian molecular-level positive selection. For example, McDonald and Kreitman (1991) *Nature* 351:652-654, propose a statistical test of the neutral protein evolution hypothesis based on comparison of the number of amino acid replacement substitutions to synonymous substitutions in the coding region of a locus. When they apply this test to the Adh locus of three *Drosophila* species, they conclude that it shows instead that the locus has undergone adaptive fixation of selectively advantageous mutations and that selective fixation of adaptive mutations may be a viable alternative to the clocklike accumulation of neutral mutations as an explanation for most protein evolution. Jenkins et al. (1995) *Proc. R. Soc. Lond. B* 261:203-207 use the McDonald & Kreitman test to investigate whether adaptive evolution is occurring in sequences controlling transcription (non-coding sequences).

Nakashima et al. (1995) *Proc. Natl. Acad. Sci USA* 92:5606-5609, use the method of Miyata and Yasunaga to perform pairwise comparisons of the nucleotide sequences of ten PLA2 isozyme genes from two snake species; this method involves comparing the number of nucleotide substitutions per site for the noncoding regions including introns ($K_N$) and the $K_A$ and $K_S$. They conclude that the protein coding regions have been evolving at much higher rates than the noncoding regions including introns. The highly accelerated substitution rate is responsible for Darwinian molecular-level evolution of PLA2 isozyme genes to produce new physiological activities that must have provided strong selective advantage for catching prey or for defense against predators. Endo et al. (1996) *Mol. Biol. Evol.* 13(5):685-690 use the method of Nei and Gojobori, wherein $d_N$ is the number of nonsynonymous substitutions and $d_S$ is the number of synonymous substitutions, for the purpose of documenting natural selection on genes. Metz and Palumbi (1996) *Mol. Biol. Evol.* 13(2):397-406 use the McDonald & Kreitman (supra) test as well as a method attributed to Nei and Gojobori, Nei and Jin, and Kumar, Tamura, and Nei; examining the average proportions of $P_n$, the replacement substitutions per replacement site, and $P_s$, the silent substitutions per silent site, to look for evidence of positive selection on binding genes in sea urchins to investigate whether they have rapidly evolved as a prelude to species formation. Goodwin et al. (1996) *Mol. Biol. Evol.* 13(2): 346-358 uses similar methods to examine the evolution of a particular murine gene family and conclude that the methods provide important fundamental insights into how selection drives genetic divergence in an experimentally manipulatable system. Edwards et al. (1995) use degenerate primers to pull out MHC loci from various species of birds and an alligator species, which are then analyzed by the Nei and Gojobori methods ($d_N$:$d_S$ ratios) to extend MHC studies to nonmammalian vertebrates. Whitfield et al. (1993) *Nature* 364:713-715 use $K_A/K_S$ analysis to look for directional selection in the regions flanking a conserved region in the SRY gene (that determines male sex). They suggest that the rapid evolution of SRY could be a significant cause of reproductive isolation, leading to new species. Wettsetin et al. (1996) *Mol. Biol. Evol.* 13(1):56-66 apply the MEGA program of Kumar, Tamura and Nei and phylogenetic analysis to investigate the diversification of MHC class I genes in squirrels and related rodents. Parham and Ohta (1996) *Science* 272:67-74 state that a population biology approach, including tests for selection as well as for gene conversion and neutral drift are required to analyze the generation and maintenance of human MHC class I polymorphism. Hughes (1997) *Mol. Biol. Evol*. 14(1):1-5 compared over one hundred orthologous immunoglobulin C2 domains between human and rodent, using the method of Nei and Gojobori ($d_N$:$d_S$ ratios) to test the hypothesis that proteins expressed in cells of the vertebrate immune system evolve unusually rapidly. Swanson and Vacquier (1998) *Science* 281:710-712 use $d_N$:$d_S$ ratios to demonstrate concerted evolution between the lysin and the egg receptor for lysin and discuss the role of such concerted evolution in forming new species (speciation). Messier and Stewart (1997) *Nature* 385:151-154, used $K_A/K_S$ to demonstrate positive selection in primate lysozymes.

The genetic changes associated with domestication have been most extensively investigated in maize (the preferred agricultural term for corn) (Dorweiler (1993) *Science* 262: 232-235). For maize, (*Zea mays* ssp. *mays*), a small number of single-gene changes apparently accounts for all the differences between our present domesticated maize plant and its wild ancestor, teosinte (*Zea mays* ssp *paruiglumis*) (Dorweiler, 1993). QTL (quantitative trait locus) analysis has demonstrated (Doebley (1990) *PNAS USA* 87:9888-9892) that no more than fifteen genes control traits of interest in maize and explain the profound difference in morphology between maize and teosinte (Wang (1999) *Nature* 398:236-239).

Importantly, a similarly small number of genes may control traits of interest in other grass-derived crop plants, including rice, wheat, millet and sorghum (Paterson (1995) *Science* 269:1714-1718). In fact, for most of these relevant genes in maize, the homologous gene may control similar traits in other grass-derived crop plants (Paterson, 1995). Thus, identification of these genes in one grass-derived crop plant would facilitate identification of homologous genes in all of the others.

As can be seen from the papers cited above, analytical methods of molecular evolution to identify rapidly evolving genes ($K_A/K_S$-type methods) can be applied to achieve many different purposes, most commonly to confirm the existence of Darwinian molecular-level positive selection, but also to assess the frequency of Darwinian molecular-level positive selection, to elucidate mechanisms by which new species are formed, or to establish single or multiple origin for specific gene polymorphisms. What is clear is from the papers cited above and others in the literature is that none of the authors applied $K_A/K_S$-type methods to identify evolutionary changes in domesticated plants and animals brought about by artificial selective pressures. While Turcich et al. (1996) *Sexual Plant Reproduction* 9:65-74, describes the use of $K_S$ analysis on plant genes, it is believed that no one has used $K_A/K_S$ type analysis as a systematic tool for identifying in domesticated plants and animals those genes that contain evolutionarily significant sequence changes that can be exploited in the development, maintenance or enhancement of desirable commercial or aesthetic traits.

The identification in domesticated species of genes that have evolved to confer unique, enhanced or altered functions compared to homologous ancestral genes could be used to develop agents to modulate these functions. The identification of the underlying domesticated species genes and the specific nucleotide changes that have evolved, and the further characterization of the physical and biochemical changes in the proteins encoded by these evolved genes, could provide valuable information on the mechanisms underlying the desired trait. This valuable information could be applied to developing agents that further enhance the function of the target proteins. Alternatively, further engineering of the responsible genes could modify or augment the desired trait. Additionally, the identified genes may be found to play a role in controlling traits of interest in other domesticated plants. A similar process can identify genes for traits of interest in domestic animals.

All references cited herein are hereby incorporated by reference in their entirety.

DISCLOSURE OF THE INVENTION

The subject invention concerns methods of identifying polynucleotides that control commercially valuable traits in domesticated plants or animals. These polynucleotides that, in accordance with the methods of the subject invention, are found to control commercially valuable traits can be used to further enhance those traits. Polynucleotides identified to control commercially valuable traits such as drought-, disease-, or stress-resistance or yield, protein content, short day length flowering, oil content, ease of harvest, taste, and the like can be used to develop compositions and methods to further enhance the commercial value of domesticated plants. While it is desired to identify polynucleotides that control valuable traits, it is challenging to identify such polynucleotides among the tens of thousands of genes in plant and animal genomes. The invention comprises narrowing the search for such polynucleotides by comparing the corresponding polynucleotide sequences of domesticated and ancestor organisms to select those sequences containing nucleotide changes that are evolutionarily significant, which is typically indicated by a Ka/Ks ratio of 1.0 or greater. For example, the subset of ancestor-modern plant polynucleotide pairs with Ka/Ks ratios of 1.0 should contain polynucleotides affected by neutral evolution, that is those for which the trait has not been under pressure, imposed by man or nature, to either be conserved or to change. Such polynucleotides can then be tested for those encoding traits such as such as drought-, disease-, or stress-resistance, because these functions have been dramatically supplemented by domestication, alleviating natural selection pressures on these polynucleotides. The subset of ancestor-modern plant polynucleotide pairs with Ka/Ks ratios greater than 1.0 should contain polynucleotides affected by selection. Such polynucleotides can then be tested for those encoding traits such as yield, protein content, short day length flowering, oil content, ease of harvest, taste, and the like, because these traits have been under intense, unidirectional, unremitting selective pressure by humans in the course of domestication of plants such as food crops.

Thus, in one embodiment, the present invention provides methods for identifying polynucleotide and polypeptide sequences having evolutionarily significant changes, which are associated with commercial or aesthetic traits in domesticated organisms including plants and animals. The invention uses comparative genomics to identify specific gene changes which may be associated with, and thus responsible for, structural, biochemical or physiological conditions, such as commercially or aesthetically relevant traits, and using the information obtained from these polynucleotide or polypeptide sequences to develop domesticated organisms with enhanced traits of interest.

In one preferred embodiment, a polynucleotide or polypeptide of a domesticated plant or animal has undergone artificial selection that resulted in an evolutionarily significant change present in the domesticated species that is not present in the wild ancestor. One example of this embodiment is that the polynucleotide or polypeptide may be associated with enhanced crop yield as compared to the ancestor. Other examples include short day length flowering (i.e., flowering only if the daily period of light is shorter than some critical length), protein content, oil content, ease of harvest, and taste. The present invention can thus be useful in gaining insight into the genes and/or molecular mechanisms that underlie functions or traits in domesticated organisms. This information can be useful in designing the polynucleotide so as to further enhance the function or trait. For example, a polynucleotide determined to be responsible for improved crop yield could be subjected to random or directed mutagenesis, followed by testing of the mutant genes to identify those which further enhance the trait.

Accordingly, in one aspect, methods are provided for identifying a polynucleotide sequence encoding a polypeptide of a domesticated organism (e.g., a plant or animal), wherein the polypeptide may be associated with a commercially or aesthetically relevant trait that is unique, enhanced or altered in the domesticated organism as compared to the ancestor of the domesticated organism, comprising the steps of: a) comparing protein-coding nucleotide sequences of said domesticated organism to protein-coding nucleotide sequences of said wild ancestor; and b) selecting a polynucleotide sequence in the domesticated organism that contains a nucleotide change as compared to a corresponding sequence in the wild ancestor, wherein said change is evolutionarily significant.

In another aspect of the invention, methods are provided for identifying an evolutionarily significant change in a protein-coding nucleotide sequence of a domesticated organism (e.g., a plant or animal), comprising the steps of: a) comparing protein-coding nucleotide sequences of the domesticated organism to corresponding sequences of a wild ancestor of the domesticated organism; and b) selecting a polynucleotide sequence in said domesticated organism that contains a nucleotide change as compared to the corresponding sequence of the wild ancestor, wherein the change is evolutionarily significant.

In some embodiments, the nucleotide change identified by any of the methods described herein is a non-synonymous substitution. In some embodiments, the evolutionary significance of the nucleotide change is determined according to the non-synonymous substitution rate ($K_A$) of the nucleotide sequence. In some embodiments, the evolutionarily significant changes are assessed by determining the $K_A/K_S$ ratio between the domesticated organism polynucleotide and the corresponding ancestral polynucleotide. In some of these embodiments, preferably the ratio is at least about 0.75, or more preferably 1.0. With increasing preference, the ratio is at least about 1.0, 1.25, 1.50, 2.00, or greater.

In another aspect, the invention provides a method of identifying an agent which may modulate the relevant trait in the domesticated organism, said method comprising contacting at least one candidate agent with a cell, model system or transgenic plant or animal that expresses the polynucleotide sequence having the evolutionarily significant change, or a composition comprising the evolutionarily significant polypeptide wherein the agent is identified by its ability to modulate function or synthesis of the polypeptide.

Also provided is a method for large scale sequence comparison between protein-coding nucleotide sequences of a domesticated organism and protein-coding sequences from a wild ancestor, said method comprising: a) aligning the domesticated organism sequences with corresponding sequences from the wild ancestor according to sequence homology; and b) identifying any nucleotide changes within the domesticated organism's sequences as compared to the homologous sequences from the wild ancestor organism.

In another aspect, the subject invention provides a method for correlating an evolutionarily significant nucleotide change to a commercially or aesthetically relevant trait that is unique, enhanced or altered in a domesticated organism, comprising: a) identifying a nucleotide sequence having an evolutionarily significant change according to the methods described herein; and b) analyzing the functional effect of the presence or absence of the identified sequence in the domesticated organism or in a model system.

The domesticated plants used in the subject methods can be maize, rice, tomatoes, potatoes or any domesticated plant for which the wild ancestor is extant and known. For example, the ancestor of maize is teosinte (*Zea mays parviglumis*); ancestors of wheat are *Triticum monococcum*, *T. speltoides* and *Aegilops tauschii*; and an ancestor of rice is *O. rufipogon*. The relevant trait can be any commercially or aesthetically relevant trait such as yield, short day length flowering, protein content, oil content, drought resistance, taste, ease of harvest or disease resistance. In a preferred embodiment, the domesticated plant is rice, and the relevant trait is yield.

In another embodiment of the invention, methods for the identification of polynucleotides associated with stress-resistance in an ancestor organism are provided. In this embodiment, a polynucleotide in the domesticated organism has undergone neutral evolution relative to a polynucleotide in the ancestor which is or is suspected of being associated with stress-resistance, whereby mutations have accumulated in the domesticated organism's polynucleotide. The stress-resistance trait in the ancestor may be unique, enhanced or altered relative to the domesticated organism.

The method for identifying the polynucleotide sequence comprises a) comparing polypeptide-coding nucleotide sequences of the domesticated organism to polypeptide coding nucleotide sequences of the wild ancestor; and b) selecting a polynucleotide sequence in the ancestor organism that contains at least one nucleotide change as compared to a corresponding sequence in the domesticated organism, wherein the change is evolutionarily neutral. The stress-resistance trait may be drought resistance, disease resistance, pest resistance, high salt level resistance or other stress-resistance traits of commercial interest.

Also provided is a method for identifying an evolutionarily neutral change in a polypeptide-coding polynucleotide sequence of a wild ancestor of a domesticated organism comprising: a) comparing polypeptide-coding polynucleotide sequences of said wild ancestor to corresponding sequences of said domesticated organism; and b) selecting a polynucleotide sequence in the domesticated organism that contains a nucleotide change as compared to the corresponding sequence of the wild ancestor, wherein the change is evolutionarily neutral and the polynucleotide is associated with a stress-resistance trait in the wild ancestor.

Neutral evolution is typically indicated by a $K_A/K_S$ ratio of between about 0.75 and 1.25, more preferably between about 0.9 and 1.1, and most preferably about 1.0. The $K_A/K_S$ comparison may be calculated as ancestor to domestic organism, or domestic to ancestor organism.

In another aspect, the invention provides for a method of identifying an agent that may modulate a stress-resistance trait in an organism (ancestor or domesticated organism), wherein at least one candidate agent is contacted with the ancestor, domesticated organism or with a cell or transgenic organism that expresses the polynucleotide sequence associated with stress-resistance, wherein the agent is identified by its ability to modulate the function of the polypeptide encoded by the polynucleotide.

Also provided is a method for large scale sequence comparison between polypeptide-coding nucleotide sequences of a wild ancestor and those of a domesticated organism, wherein the ancestor polypeptide confers or is suspected of conferring a stress-related trait that is unique, enhanced or altered in the wild ancestor as compared to the domesticated organism, comprising: a) aligning the ancestor and domesticated sequences according to sequence homology, and b) identifying any nucleotide changes in the domesticated organism sequence as compared to the ancestor homologous sequence, wherein said changes are evolutionarily neutral.

In another aspect, the subject invention provides a method for correlating an evolutionarily neutral nucleotide change to a commercially or aesthetically relevant trait that is unique, enhanced or altered in a domesticated organism, comprising: a) identifying a nucleotide sequence having an evolutionarily neutral change according to the methods described herein; and b) analyzing the functional effect of the presence or absence of the identified sequence in the domesticated organism or in a model system.

BRIEF DESCRIPTION OF THE FIGURES

FIG. 1 shows a nucleotide alignment of O. sativa cv. Nipponbare and O. rufipogon (NSGC5953) for EG307. This alignment includes untranslated regions (UTR) on the 5' end and notes the start and stop codons for this gene.

FIG. 2 shows a protein alignment of O. sativa cv. Nipponbare and O. rufipogon (NSGC5953) for EG307. This alignment includes the complete coding (CDS) region.

FIG. 3 shows a nucleotide sequence of EG307 in Zea mays mays and Zea mays parviglumis (teosinte, strain Benz967) for coding region of the gene. Start and stop codons are identified.

FIG. 4 shows a protein alignment of Zea mays mays and Zea mays parviglumis EG307. This alignment includes the full-length deduced protein sequence.

DETAILED DESCRIPTION OF THE INVENTION

Figure 5:
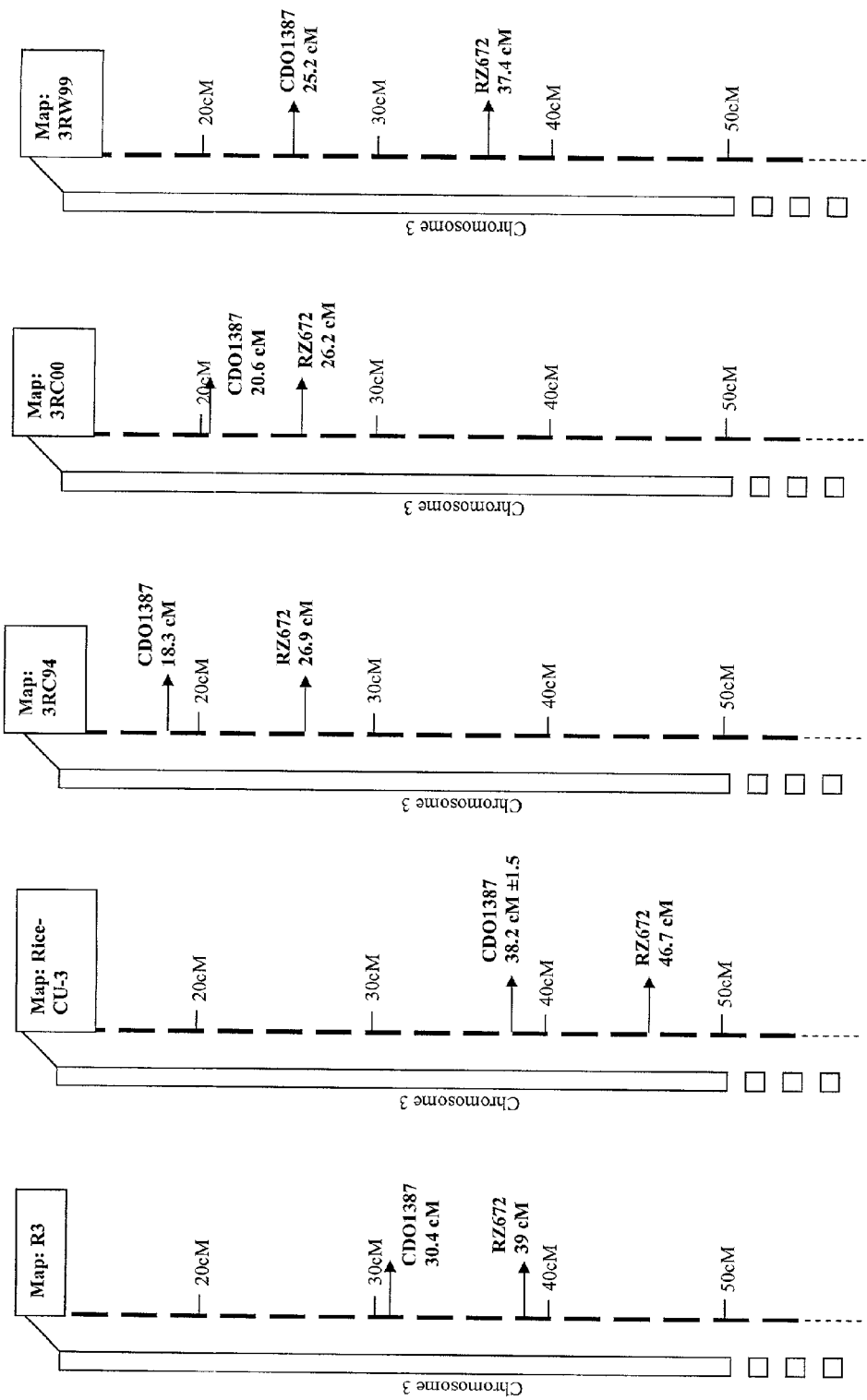
FIG. 5 shows markers CDO1387 and RZ672 mapped to five different genetic rice maps, indicating that the range of these markers is consistent among the five maps. EG307 is upstream of CDO1387 (about 200 kb) and a QTL for 1000 Grain Weight is associated with marker RZ672.

In one embodiment, the present invention utilizes comparative genomics to identify positively selected genes and specific gene changes which are associated with, and thus may contribute to or be responsible for, commercially or aesthetically relevant traits in domesticated organisms (e.g., plants and animals).

In another embodiment, the invention identifies evolutionarily neutral genes and gene changes that are associated with stress-resistance in ancestors of domesticated organisms.

The practice of the present invention employs, unless otherwise indicated, conventional techniques of molecular biology, genetics and molecular evolution, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Current Protocols in Molecular Biology" (F. M. Ausubel et al., eds., 1987); "PCR: The Polymerase Chain Reaction", (Mullis et al., eds., 1994); "Molecular Evolution", (Li, 1997).

I. Definitions

As used herein, a "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides, polynucleotides containing modified bases, backbone modifications, and the like. The terms "polynucleotide" and "nucleotide sequence" are used interchangeably.

As used herein, a "gene" refers to a polynucleotide or portion of a polynucleotide comprising a sequence that encodes a protein. It is well understood in the art that a gene also comprises non-coding sequences, such as 5' and 3' flanking sequences (such as promoters, enhancers, repressors, and other regulatory sequences) as well as introns.

The terms "polypeptide," "peptide," and "protein" are used interchangeably herein to refer to polymers of amino acids of any length. These terms also include proteins that are post-translationally modified through reactions that include glycosylation, acetylation and phosphorylation.

The term "domesticated organism" refers to an individual living organism or population of same, a species, subspecies, variety, cultivar or strain, that has been subjected to artificial selection pressure and developed a commercially or aesthetically relevant trait. In some preferred embodiments, the domesticated organism is a plant selected from the group consisting of maize, wheat, rice, sorghum, tomato or potato, or any other domesticated plant of commercial interest, where an ancestor is known. A "plant" is any plant at any stage of development, particularly a seed plant.

In other preferred embodiments, the domesticated organism is an animal selected from the group consisting of cattle, horses, pigs, cats and dogs. A domesticated organism and its ancestor may be related as different species, subspecies, varieties, cultivars or strains or any combination thereof.

The term "wild ancestor" or "ancestor" means a forerunner or predecessor organism, species, subspecies, variety, cultivar or strain from which a domesticated organism, species, subspecies, variety, cultivar or strain has evolved. A domesticated organism can have one or more than one ancestor. Typically, domesticated plants can have one or a plurality of ancestors, while domesticated animals usually have only a single ancestor.

The term "commercially or aesthetically relevant trait" is used herein to refer to traits that exist in domesticated organisms such as plants or animals whose analysis could provide information (e.g., physical or biochemical data) relevant to the development of improved organisms or of agents that can modulate the polypeptide responsible for the trait, or the respective polynucleotide. The commercially or aesthetically relevant trait can be unique, enhanced or altered relative to the ancestor. By "altered," it is meant that the relevant trait differs qualitatively or quantitatively from traits observed in the ancestor.

The term "$K_A/K_S$-type methods" means methods that evaluate differences, frequently (but not always) shown as a ratio, between the number of nonsynonymous substitutions and synonymous substitutions in homologous genes (including the more rigorous methods that determine non-synonymous and synonymous sites). These methods are designated using several systems of nomenclature, including but not limited to $K_A/K_S$, $d_N/d_S$, $D_N/D_S$.

The terms "evolutionarily significant change" and "adaptive evolutionary change" refer to one or more nucleotide or peptide sequence change(s) between two organisms, species, subspecies, varieties, cultivars and/or strains that may be attributed to either relaxation of selective pressure or positive selective pressure. One method for determining the presence of an evolutionarily significant change is to apply a $K_A/K_S$-type analytical method, such as to measure a $K_A/K_S$ ratio. Typically, a $K_A/K_S$ ratio of 1.0 or greater is considered to be an evolutionarily significant change.

Strictly speaking, $K_A/K_S$ ratios of exactly 1.0 are indicative of relaxation of selective pressure (neutral evolution), and $K_A/K_S$ ratios greater than 1.0 are indicative of positive selection. However, it is commonly accepted that the ESTs in GenBank and other public databases often suffer from some degree of sequencing error, and even a few incorrect nucleotides can influence $K_A/K_S$ ratios. For this reason, polynucleotides with $K_A/K_S$ ratios as low as 0.75 can be selected and carefully resequenced and re-evaluated for either relaxation of selective pressure of positive selective pressure.

The term "positive evolutionarily significant change" means an evolutionarily significant change in a particular organism, species, subspecies, variety, cultivar or strain that results in an adaptive change that is positive as compared to other related organisms. An example of a positive evolutionarily significant change is a change that has resulted in enhanced yield in crop plants. As stated above, positive selection is indicated by a $K_A/K_S$ ratio greater than 1.0. With increasing preference, the $K_A/K_S$ value is greater than 1.25, 1.5 and 2.0.

The term "neutral evolutionarily significant change" refers to a polynucleotide or polypeptide change that appears in a domesticated organism relative to its ancestral organism, and which has developed under neutral conditions. A neutral evolutionary change is evidenced by a $K_A/K_S$ value of between about 0.75-1.25, preferably between about 0.9 and 1.1, and most preferably equal to about 1.0. Also, in the case of neutral evolution, there is no "directionality" to be inferred. The gene is free to accumulate changes without constraint, so both the ancestral and domesticated versions are changing with respect to one another.

The term "resistant" means that an organism exhibits an ability to avoid, or diminish the extent of, a disease condition and/or development of the disease, preferably when compared to non-resistant organisms.

The term "susceptibility" means that an organism fails to avoid, or diminish the extent of, a disease condition and/or development of the disease condition, preferably when compared to an organism that is known to be resistant.

It is understood that resistance and susceptibility vary from individual to individual, and that, for purposes of this invention, these terms also apply to a group of individuals within a species, and comparisons of resistance and susceptibility generally refer overall to intra-specific differences, although comparisons between species may be used. Taxonomic classification of wild relatives is fairly changeable. Thus, a species difference based on a taxonomic classification may change to an intra-specific difference if taxonomic classifications are changed.

The term "stress-resistance" refers to the ability to withstand drought, disease, pests (including, but not limited to, insects, animal herbivores, and microbes), high salt levels, and other adverse stimuli, internal or external, that tend to disturb the plant's homeostasis, and may lead to disorder, disease, or death if uncorrected.

The term "homologous" or "homologue" or "ortholog" is known and well understood in the art and refers to related sequences that share a common ancestor and is determined based on degree of sequence identity. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to, (a) degree of sequence identity; (b) same or similar biological function. Preferably, both (a) and (b) are indicated. The degree of sequence identity may vary, but is preferably at least 50% (when using standard sequence alignment programs known in the art), more preferably at least 60%, more preferably at least about 75%, more preferably at least about 85%. Homology can be determined using software programs readily available in the art, such as those discussed in *Current Protocols in Molecular Biology* (F. M. Ausubel et al., eds., 1987) Supplement 30, section 7.718, Table 7.71. Preferred alignment programs are MacVector (Oxford Molecular Ltd, Oxford, U.K.) and ALIGN Plus (Scientific and Educational Software, Pennsylvania). Another preferred alignment program is Sequencher (Gene Codes, Ann Arbor, Mich.), using default parameters.

The term "nucleotide change" refers to nucleotide substitution, deletion, and/or insertion, as is well understood in the art.

"Housekeeping genes" is a term well understood in the art and means those genes associated with general cell function, including but not limited to growth, division, stasis, metabolism, and/or death. "Housekeeping" genes generally perform functions found in more than one cell type. In contrast, cell-specific genes generally perform functions in a particular cell type and/or class.

The term "agent", as used herein, means a biological or chemical compound such as a simple or complex organic or inorganic molecule, a peptide, a protein or an oligonucleotide that modulates the function of a polynucleotide or polypeptide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

The term "to modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly.

A "function of a polynucleotide" includes, but is not limited to, replication; translation; expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function.

A "function of a polypeptide" includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

The term "target site" means a location in a polypeptide which can be a single amino acid and/or is a part of, a structural and/or functional motif, e.g., a binding site, a dimerization domain, or a catalytic active site. Target sites may be useful for direct or indirect interaction with an agent, such as a therapeutic agent.

The term "molecular difference" includes any structural and/or functional difference. Methods to detect such differences, as well as examples of such differences, are described herein.

A "functional effect" is a term well known in the art, and means any effect which is exhibited on any level of activity, whether direct or indirect.

The term "ease of harvest" refers to plant characteristics or features that facilitate manual or automated collection of structures or portions (e.g., fruit, leaves, roots) for consumption or other commercial processing.

The term "yield" refers to the amount of plant or animal tissue or material that is available for use by humans for food, therapeutic, veterinary or other markets.

The term "enhanced economic productivity" refers to the ability to modulate a commercially or aesthetically relevant trait so as to improve desired features. Increased yield and enhanced stress resistance are two examples of enhanced economic productivity II. General Procedures Known in the Art For the purposes of this invention, the source of the polynucleotide from the domesticated plant or animal or its ancestor can be any suitable source, e.g., genomic sequences or cDNA sequences. Preferably, cDNA sequences are compared. Protein-coding sequences can be obtained from available private, public and/or commercial databases such as those described herein. These databases serve as repositories of the molecular sequence data generated by ongoing research efforts. Alternatively, protein-coding sequences may be obtained from, for example, sequencing of cDNA reverse transcribed from mRNA expressed in cells, or after PCR amplification, according to methods well known in the art. Alternatively, genomic sequences may be used for sequence comparison. Genomic sequences can be obtained from available public, private and/or commercial databases or from a sequencing of commercially available genomic DNA libraries or from genomic DNA, after PCR.

In some embodiments, the cDNA is prepared from mRNA obtained from a tissue at a determined developmental stage, or a tissue obtained after the organism has been subjected to certain environmental conditions. cDNA libraries used for the sequence comparison of the present invention can be constructed using conventional cDNA library construction techniques that are explained fully in the literature of the art. Total mRNAs are used as templates to reverse-transcribe cDNAs. Transcribed cDNAs are subcloned into appropriate vectors to establish a cDNA library. The established cDNA library can be maximized for full-length cDNA contents, although less than full-length cDNAs may be used. Furthermore, the sequence frequency can be normalized according to, for example, Bonaldo et al. (1996) *Genome Research* 6:791-806. cDNA clones randomly selected from the constructed cDNA library can be sequenced using standard automated sequencing techniques. Preferably, full-length cDNA clones are used for sequencing. Either the entire or a large portion of cDNA clones from a cDNA library may be sequenced, although it is also possible to practice some embodiments of the invention by sequencing as little as a single cDNA, or several cDNA clones.

In one preferred embodiment of the present invention, cDNA clones to be sequenced can be pre-selected according to their expression specificity. In order to select cDNAs corresponding to active genes that are specifically expressed, the cDNAs can be subject to subtraction hybridization using mRNAs obtained from other organs, tissues or cells of the same animal. Under certain hybridization conditions with appropriate stringency and concentration, those cDNAs that hybridize with non-tissue specific mRNAs and thus likely represent "housekeeping" genes will be excluded from the cDNA pool. Accordingly, remaining cDNAs to be sequenced are more likely to be associated with tissue-specific functions. For the purpose of subtraction hybridization, non-tissue-specific mRNAs can be obtained from one organ, or preferably from a combination of different organs and cells. The amount of non-tissue-specific mRNAs are maximized to saturate the tissue-specific cDNAs.

Alternatively, information from online databases can be used to select or give priority to cDNAs that are more likely to be associated with specific functions. For example, the ancestral cDNA candidates for sequencing can be selected by PCR using primers designed from candidate domesticated organism cDNA sequences. Candidate domesticated organism cDNA sequences are, for example, those that are only found in a specific tissue, such as skeletal muscle, or that correspond to genes likely to be important in the specific function. Such tissue-specific cDNA sequences may be obtained by searching online sequence databases in which information with respect to the expression profile and/or biological activity for cDNA sequences may be specified.

Sequences of ancestral homologue(s) to a known domesticated organism's gene may be obtained using methods standard in the art, such as PCR methods (using, for example, GeneAmp PCR System 9700 thermocyclers (Applied Biosystems, Inc.)). For example, ancestral cDNA candidates for sequencing can be selected by PCR using primers designed from candidate domesticated organism cDNA sequences. For PCR, primers may be made from the domesticated organism's sequences using standard methods in the art, including publicly available primer design programs such as PRIMER® (Whitehead Institute). The ancestral sequence amplified may then be sequenced using standard methods and equipment in the art, such as automated sequencers (Applied Biosystems, Inc.). Likewise, ancestors gene mimics can be used to obtain corresponding genes in domesticated organisms.

III. Identification of Positively Selected Polynucleotides in Domesticated Organisms In a preferred embodiment, the methods described herein can be applied to identify the genes that control traits of interest in agriculturally important domesticated plants. Humans have bred domesticated plants for several thousand years without knowledge of the genes that control these traits. Knowledge of the specific genetic mechanisms involved would allow much more rapid and direct intervention at the molecular level to create plants with desirable or enhanced traits.

Humans, through artificial selection, have provided intense selection pressures on crop plants. This pressure is reflected in evolutionarily significant changes between homologous genes of domesticated organisms and their wild ancestors. It has been found that only a few genes, e.g., 10-15 per species, control traits of commercial interest in domesticated crop plants. These few genes have been exceedingly difficult to identify through standard methods of plant molecular biology. The $K_A/K_S$ and related analyses described herein can identify the genes controlling traits of interest.

For any crop plant of interest, cDNA libraries can be constructed from the domesticated species or subspecies and its wild ancestor. As is described in U.S. Ser. No. 09/240,915, filed Jan. 29, 1999, the cDNA libraries of each are "BLASTed" against each other to identify homologous polynucleotides. Alternatively, the skilled artisan can access commercially and/or publicly available genomic or cDNA databases rather than constructing cDNA libraries.

Next, a $K_A/K_S$ or related analysis is conducted to identify selected genes that have rapidly evolved under selective pressure. These genes are then evaluated using standard molecular and transgenic plant methods to determine if they play a role in the traits of commercial or aesthetic interest. The genes of interest are then manipulated by, e.g., random or site-directed mutagenesis, to develop new, improved varieties, subspecies, strains or cultivars.

The general method of the invention is as follows. Briefly, nucleotide sequences are obtained from a domesticated organism and a wild ancestor. The domesticated organism's and ancestor's nucleotide sequences are compared to one another to identify sequences that are homologous. The homologous sequences are analyzed to identify those that have nucleic acid sequence differences between the domesticated organism and ancestor. Then molecular evolution analysis is conducted to evaluate quantitatively and qualitatively the evolutionary significance of the differences. For genes that have been positively selected, outgroup analysis can be done to identify those genes that have been positively selected in the domesticated organism (or by the ancestor). Next, the sequence is characterized in terms of molecular/genetic identity and biological function. Finally, the information can be used to identify agents that can modulate the biological function of the polypeptide encoded by the gene.

The general methods of the invention entail comparing protein-coding nucleotide sequences of ancestral and domesticated organisms. Bioinformatics is applied to the comparison and sequences are selected that contain a nucleotide change or changes that is/are evolutionarily significant change(s). The invention enables the identification of genes that have evolved to confer some evolutionary advantage and the identification of the specific evolved changes. In a preferred embodiment, the domesticated organism is *Oryza sativa* and the wild ancestor is *Oryza rufipogon*. In the case of the present invention, protein-coding nucleotide sequences were obtained from *O. rufipogon* clones by standard sequencing techniques.

Protein-coding sequences of a domesticated organism and its ancestor are compared to identify homologous sequences. Any appropriate mechanism for completing this comparison is contemplated by this invention. Alignment may be performed manually or by software (examples of suitable alignment programs are known in the art). Preferably, protein-coding sequences from an ancestor are compared to the domesticated species sequences via database searches, e.g., BLAST searches. The high scoring "hits," i.e., sequences that show a significant similarity after BLAST analysis, will be retrieved and analyzed. Sequences showing a significant similarity can be those having at least about 60%, at least about 75%, at least about 80%, at least about 85%, or at least about 90% sequence identity. Preferably, sequences showing greater than about 80% identity are further analyzed. The homologous sequences identified via database searching can be aligned in their entirety using sequence alignment methods and programs that are known and available in the art, such as the commonly used simple alignment program CLUSTAL V by Higgins et al. (1992) *CABIOS* 8:189-191.

The present invention provides a method for identifying a polynucleotide sequence encoding a polypeptide of a domesticated organism, wherein said polypeptide is or is suspected of being associated with improved yield in said domesticated organism as compared to a wild ancestor of said domesticated organism, comprising the steps of a) comparing polypeptide-coding nucleotide sequences of said domesticated organism to polypeptide-coding nucleotide sequences of said wild ancestor; and b) selecting a polynucleotide sequence in the domesticated organism that contains a nucleotide change as compared to a corresponding sequence in the wild ancestor, wherein said change is evolutionarily significant, whereby the domesticated organism's polynucleotide sequence is identified. In a preferred embodiment, the polypeptide that is associated with improved yield is an EG307 polypeptide.

In the present case, for example, nucleotide sequences obtained from *O. rufipogon* were used as query sequences in a search of *O. sativa* ESTs in GenBank to identify homologous sequences. It should be noted that a complete protein-coding nucleotide sequence is not required. Indeed, partial cDNA sequences may be compared. Once sequences of interest are identified by the methods described below, further cloning and/or bioinformatics methods can be used to obtain the entire coding sequence for the gene or protein of interest.

Alternatively, the sequencing and homology comparison of protein-coding sequences between the domesticated organism and its ancestor may be performed simultaneously by using the newly developed sequencing chip technology. See, for example, Rava et al. U.S. Pat. No. 5,545,531.

The aligned protein-coding sequences of domesticated organism and ancestor are analyzed to identify nucleotide sequence differences at particular sites. Again, any suitable method for achieving this analysis is contemplated by this invention. If there are no nucleotide sequence differences, the ancestor protein coding sequence is not usually further analyzed. The detected sequence changes are generally, and preferably, initially checked for accuracy. Preferably, the initial checking comprises performing one or more of the following steps, any and all of which are known in the art: (a) finding the points where there are changes between the ancestral and domesticated organism sequences; (b) checking the sequence fluorogram (chromatogram) to determine if the bases that appear unique to the ancestor or domesticated organism correspond to strong, clear signals specific for the called base; (c) checking the domesticated organism hits to see if there is more than one domesticated organism sequence that corresponds to a sequence change. Multiple domesticated organism sequence entries for the same gene that have the same nucleotide at a position where there is a different nucleotide in an ancestor sequence provides independent support that the domesticated sequence is accurate, and that the change is significant. Such changes are examined using database information and the genetic code to determine whether these nucleotide sequence changes result in a change in the amino acid sequence of the encoded protein. As the definition of "nucleotide change" makes clear, the present invention encompasses at least one nucleotide change, either a substitution, a deletion or an insertion, in a protein-coding polynucleotide sequence of a domesticated organism as compared to a corresponding sequence from the ancestor. Preferably, the change is a nucleotide substitution. More preferably, more than one substitution is present in the identified sequence and is subjected to molecular evolution analysis.

Any of several different molecular evolution analyses or $K_A/K_S$-type methods can be employed to evaluate quantitatively and qualitatively the evolutionary significance of the identified nucleotide changes between domesticated species gene sequences and those of corresponding ancestors. Kreitman and Akashi (1995) *Annu. Rev. Ecol. Syst.* 26:403-422; Li, *Molecular Evolution*, Sinauer Associates, Sunderland, Mass., 1997. For example, positive selection on proteins (i.e., molecular-level adaptive evolution) can be detected in protein-coding genes by pairwise comparisons of the ratios of nonsynonymous nucleotide substitutions per nonsynonymous site ($K_A$) to synonymous substitutions per synonymous site ($K_S$) (Li et al., 1985; Li, 1993). Any comparison of $K_A$ and $K_S$ may be used, although it is particularly convenient and most effective to compare these two variables as a ratio. Sequences are identified by exhibiting a statistically significant difference between $K_A$ and $K_S$ using standard statistical methods.

In the case of the present invention, homologous sequences from *O. rufipogon* and *O. sativa* were identified. Comparison of the sequences of one *O. rufipogon* clone, PBI0307H9, SEQ ID NO:31, and *O. sativa* in GenBank revealed a high $K_A/K_S$ ratio. Further cloning and PCR of several different strains of *O. sativa* were completed in order to obtain the entire gene, named EG307, so that the entire gene sequence could be subjected to $K_A/K_S$ analysis. These procedures are detailed in Example 10. The complete sequence of EG307 in *O. rufipogon*, SEQ ID NO:28, and *O. sativa* cv. Nipponbare 1, SEQ ID NO:25, are shown in FIG. 1. The corresponding protein sequences, SEQ ID NO:30, and SEQ ID NO:27, are shown in FIG. 2. A summary of the $K_A/K_S$ ratios is shown in Table 1 of Example 11. Some strains were more similar to *O. rufipogon* due to crossbreeding between *O. rufipogon* and the domestic strain. High $K_A/K_S$ ratios for some strains indicates an evolutionarily significant change.

Preferably, the $K_A/K_S$ analysis computer program by Li et al. is used to carry out the present invention, although other analysis programs that can detect positively selected genes between species can also be used. Li et al. (1985) *Mol. Biol. Evol.* 2:150-174; Li (1993); see also *J. Mol. Evol.* 36:96-99; Messier and Stewart (1997) *Nature* 385:151-154; Nei (1987) *Molecular Evolutionary Genetics* (New York, Columbia University Press). The $K_A/K_S$ method, which comprises a comparison of the rate of non-synonymous substitutions per non-synonymous site with the rate of synonymous substitutions per synonymous site between homologous protein-coding region of genes in terms of a ratio, is used to identify sequence substitutions that may be driven by adaptive selections or by neutral selections during evolution. A synonymous ("silent") substitution is one that, owing to the degeneracy of the genetic code, makes no change to the amino acid sequence encoded; a non-synonymous substitution results in an amino acid replacement. The extent of each type of change can be estimated as $K_A$ and $K_S$, respectively, the numbers of synonymous substitutions per synonymous site and non-synonymous substitutions per non-synonymous site. Calculations of $K_A/K_S$ may be performed manually or by using software. An example of a suitable program is MEGA (Molecular Genetics Institute, Pennsylvania State University).

For the purpose of estimating $K_A$ and $K_S$, either complete or partial protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared, in order to determine any and all significant changes. Publicly available computer programs, such as Li93 (Li (1993) *J. Mol. Evol.* 36:96-99) or INA, can be used to calculate the $K_A$ and $K_S$ values for all pairwise comparisons. This analysis can be further adapted to examine sequences in a "sliding window" fashion such that small numbers of important changes are not masked by the whole sequence. "Sliding window" refers to examination of consecutive, overlapping subsections of the gene (the subsections can be of any length).

Sliding window $K_A/K_S$ analysis of, for example, identified gene EG307 showed that there are a number of nonsynonymous changes on the 5'-end of EG307 in many of the *O. sativa* strains when compared to *O. rufipogon*. The 3'-end of the gene had a low ratio in all of the strains. These procedures and results are detailed in Example 11 and Tables 2-7.

The comparison of non-synonymous and synonymous substitution rates is represented by the $K_A/K_S$ ratio. $K_A/K_S$ has been shown to be a reflection of the degree to which adaptive evolution has been at work in the sequence under study. Full length or partial segments of a coding sequence can be used for the $K_A/K_S$ analysis. The higher the $K_A/K_S$ ratio, the more likely that a sequence has undergone adaptive evolution and the non-synonymous substitutions are evolutionarily significant. See, for example, Messier and Stewart (1997). Preferably, the $K_A/K_S$ ratio is at least about 0.75, more preferably at least about 1.0, more preferably at least about 1.25, more preferably at least about 1.50, or more preferably at least about 2.00. Preferably, statistical analysis is performed on all elevated $K_A/K_S$ ratios, including, but not limited to, standard methods such as Student's t-test and likelihood ratio tests described by Yang (1998) *Mol. Biol Evol.* 37:441-456.

For a pairwise comparison of homologous sequences, $K_A/K_S$ ratios significantly greater than unity strongly suggest that positive selection has fixed greater numbers of amino acid replacements than can be expected as a result of chance alone, and is in contrast to the commonly observed pattern in which the ratio is less than one. Nei (1987); Hughes and Hei (1988) *Nature* 335:167-170; Messier and Stewart (1994) *Current Biol.* 4:911-913; Kreitman and Akashi (1995) *Ann. Rev. Ecol. Syst.* 26:403-422; Messier and Stewart (1997). Ratios less than one generally signify the role of negative, or purifying selection: there is strong pressure on the primary structure of functional, effective proteins to remain unchanged. Ratios of about 1 indicate evolution under neutral conditions.

All methods for calculating $K_A/K_S$ ratios are based on a pairwise comparison of the number of nonsynonymous substitutions per nonsynonymous site to the number of synonymous substitutions per synonymous site for the protein-coding regions of homologous genes from the ancestral and domesticated organisms. Each method implements different corrections for estimating "multiple hits" (i.e., more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

Preferably, $K_A/K_S$ ratios should be calculated for orthologous gene pairs, as opposed to paralogous gene pairs (i.e., a gene which results from speciation, as opposed to a gene that is the result of gene duplication) Messier and Stewart (1997). This distinction may be made by performing additional comparisons with other ancestors, which allows for phylogenetic tree-building. Orthologous genes when used in tree-building will yield the known "species tree", i.e., will produce a tree that recovers the known biological tree. In contrast, paralogous genes will yield trees which will violate the known biological tree.

It is understood that the methods described herein could lead to the identification of ancestral or domesticated organism polynucleotide sequences that are functionally related to the protein-coding sequences. Such sequences may include, but are not limited to, non-coding sequences or coding sequences that do not encode proteins. These related sequences can be, for example, physically adjacent to the protein-coding sequences in the genome, such as introns or 5'- and 3'- flanking sequences (including control elements such as promoters and enhancers). These related sequences may be obtained via searching available public, private and/or commercial genome databases or, alternatively, by screening and sequencing the organism's genomic library with a protein-coding sequence as probe. Methods and techniques for obtaining non-coding sequences using related coding sequence are well known to one skilled in the art.

The evolutionarily significant nucleotide changes, which are detected by molecular evolution analysis such as the $K_A/K_S$ analysis, can be further assessed for their unique occurrence in the domesticated organism or the extent to which these changes are unique in the domesticated organism. For example, the identified changes in the domesticated gene can be tested for presence/absence in other sequences of related species, subspecies or other organisms having a common ancestor with the domesticated organism. This comparison ("outgroup analysis") permits the determination of whether the positively selected gene is positively selected for in the domesticated organism at issue (as opposed to the ancestor).

For example, the identified changes in the EG307 gene were identified to various degrees in a number of *O. sativa* strains. See Tables 2-7. Additionally, a counterpart to EG307 was identified in maize, *Zea mays mays*, its wild ancestor, teosinte, *Zea mays parviglumis*, and also wild relatives of maize, *Z. diploperennis* and *Z. luxurians*. See Example 13 and Table 9. While EG307 in rice and maize was somewhat different at the nucleotide level, the protein sequences were more similar. Observing that rice and corn were independently domesticated from their wild ancestors, a consistent pattern emerges: the majority of the amino acid replacements in the modern crop (whether maize or rice), as compared to the ancestral plant (teosinte or ancestral rice) result in increased charge/polarity, increased solubility, and decreased hydrophobicity. This pattern is most unlikely to have occurred by chance in these two independent domestication events. This suggests that these replacements were a similar response to human imposed domestication. This is powerful evidence that EG307 has been selected as a result of human domestication of these two cereals.

The sequences with at least one evolutionarily significant change between a domesticated organism and its ancestor can be used as primers for PCR analysis of other ancestor protein-coding sequences, and resulting polynucleotides are sequenced to see whether the same change is present in other ancestors. These comparisons allow further discrimination as to whether the adaptive evolutionary changes are unique to the domesticated lineage as compared to other ancestors or whether the adaptive change is unique to the ancestor as compared to the domesticated species and other ancestors. A nucleotide change that is detected in the domesticated organism but not other ancestors more likely represents an adaptive evolutionary change in the domesticated organism. Alternatively, a nucleotide change that is detected in an ancestor that is not detected in the domesticated organism or other ancestors likely represents an ancestor adaptive evolutionary change. Other ancestors used for comparison can be selected based on their phylogenetic relationships with the domesticated organism. Statistical significance of such comparisons may be determined using established available programs, e.g., t-test as used by Messier and Stewart (1997) *Nature* 385:151-154. Those genes showing statistically high $K_A/K_S$ ratios are very likely to have undergone adaptive evolution.

Sequences with significant changes can be used as probes in genomes from different domesticated populations to see whether the sequence changes are shared by more than one domesticated population. Gene sequences from different domesticated populations can be obtained from databases or, alternatively, from direct sequencing of PCR-amplified DNA from a number of unrelated, diverse domesticated populations. The presence of the identified changes in different domesticated populations would further indicate the evolutionary significance of the changes.

Sequences with significant changes between species can be further characterized in terms of their molecular/genetic identities and biological functions, using methods and techniques known to those of ordinary skill in the art. For example, the sequences can be located genetically and physically within the organism's genome using publicly available bio-informatics programs. The newly identified significant changes within the nucleotide sequence may suggest a potential role of the gene in the organism's evolution and a potential association with unique, enhanced or altered functional capabilities.

Using the techniques of the present invention, a heretofore unknown evolutionarily significant gene in rice, termed EG307, has been discovered as detailed in EXAMPLE 10. $K_A/K_S$ analysis, performed as described in EXAMPLE 11 between *O. rufipogon* and certain *O. sativa* strains indicated an evolutionarily significant change as shown in Table 1. The gene has been positively selected. Using several different rice maps, as described in EXAMPLE 12, it was found that EG307 was within about 10 cM of marker RZ672, a marker associated with a QTL for 1000 grain weight residing on chromosome 3. 1000-grain weight is the weight (mass) of three different samples of 1000 randomly chosen fully filled grains of rice. This is a sensitive measure of yield, which takes into account the individual variation in weight that occurs among rice grains. Thus, there only is about a 10% chance that the RZ672 marker will be separated from EG307 to crossing over in a single generation, strongly suggesting that EG307 plays an important role in controlling increased yield.

From the combination of the evolutionarily significant $K_A/K_S$ value and mapping data, one of skill in the art can reasonably conclude that that EG307 is a yield-related gene.

EG307's yield-increasing function could be easily confirmed by making and growing a mutant or transgenic plant. Using the EG307 sequence derived from rice, EG307 genes from rice or maize and its wild ancestor were obtained as detailed in EXAMPLE 13.

The putative gene with the identified sequences may be further characterized by, for example, homologue searching. Shared homology of the putative gene with a known gene may indicate a similar biological role or function. Another exemplary method of characterizing a putative gene sequence is on the basis of known sequence motifs. Certain sequence patterns are known to code for regions of proteins having specific biological characteristics such as signal sequences, DNA binding domains, or transmembrane domains.

The identified sequences with significant changes can also be further evaluated by looking at where the gene is expressed in terms of tissue- or cell type-specificity. For example, the identified coding sequences can be used as probes to perform in situ mRNA hybridization that will reveal the expression patterns of the sequences. Genes that are expressed in certain tissues may be better candidates as being associated with important functions associated with that tissue, for example developing endosperm tissue. The timing of the gene expression during each stage of development of a species member can also be determined.

As another exemplary method of sequence characterization, the functional roles of the identified nucleotide sequences with significant changes can be assessed by conducting functional assays for different alleles of an identified gene in the transfected domesticated organism, e.g., in the transgenic plant or animal. Current examples of plant functional assays include the use of microarrays, see Seki, et al., Monitoring the Exapression Pattern of 1300 *Arabidopsis* Genes Under Drought and Cold Stresses Using a Full-Length cDNA Microarray. *Plant Cell* 13:61-72 (2001), and metabolite profiling, see Roessner, et al, Metabolic Profiling Allows Comprhensive Phenotyping of Geneticaly or Environmentally Modified Plant Systems. *Plant Cell* 13:11-29 (2001).

As another exemplary method of sequence characterization, the use of computer programs may allow modeling and visualizing the three-dimensional structure of the homologous proteins from domesticated organism and ancestor. Specific, exact knowledge of which amino acids have been replaced in the ancestor protein(s) allows detection of structural changes that may be associated with functional differences. Thus, use of modeling techniques is closely associated with identification of functional roles discussed in the previous paragraph. The use of individual or combinations of these techniques constitutes part of the present invention.

A domesticated organism's gene identified by the subject method can be used to identify homologous genes in other species that share a common ancestor. For example, maize, rice, wheat, millet, sorghum and other cereals share a common ancestor, and genes identified in rice can lead directly to homologous genes in these other grasses. Likewise, tomatoes and potatoes share a common ancestor, and genes identified in tomatoes by the subject method are expected to have homologues in potatoes, and vice versa.

The present invention also provides a method of detecting a yield-increasing gene in a plant cell comprising: a) contacting the EG307 gene or a portion thereof greater than 12 nucleotides, preferably greater than 30 nucleotides in length with a preparation of genomic DNA from the plant cell under hybridization conditions providing detection of nucleic acid molecule sequences having about 50% or greater sequence identity to the a nucleic acid molecule selected from the group consisting of SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, SEQ ID NO:31, SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, SEQ ID NO:64, SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, SEQ ID NO:78, SEQ ID NO:80, SEQ ID NO:81, SEQ ID NO:82, SEQ ID NO:84 and SEQ ID NO:85; and b) detecting hybridization, whereby a yield-increasing gene may be identified.

The present invention also provides a method of isolating a yield-related gene from a recombinant plant cell library, comprising a) providing a preparation of plant cell DNA or a recombinant plant cell library; b) contacting the preparation or plant cell library with a detectably-labelled EG307 conserved oligonucleotide under hybridization conditions providing detection of genes having 50% or greater sequence identity; and c) isolating a yield-related gene by its association with the detectable label.

The present invention also provides a method of isolating a yield-related gene from plant cell DNA comprising a) providing a sample of plant cell DNA; b) providing a pair of oligonucleotides having sequence homology to a conserved region of an EG307 gene; c) combining the pair of oligonucleotides with the plant cell DNA sample under conditions suitable for polymerase chain reaction-mediated DNA amplification; and d) isolating the amplified yield-related gene or fragment thereof.

The sequences identified by the methods described herein can be used to identify agents that are useful in modulating domesticated organism-unique, enhanced or altered functional capabilities and/or correcting defects in these capabilities using these sequences. These methods employ, for example, screening techniques known in the art, such as in vitro systems, cell-based expression systems and transgenic animals and plants. The approach provided by the present invention not only identifies rapidly evolved genes, but indicates modulations that can be made to the protein that may not be too toxic because they exist in another species.

The present invention also provides a method of producing an EG307 polypeptide comprising: a) providing a cell transfected with a polynucleotide encoding an EG307 polypeptide positioned for expression in the cell; b) culturing the transfected cell under conditions for expressing the polynucleotide; and c) isolating the EG307 polypeptide.

A. EG307 Polypeptides

One embodiment of the present invention is an isolated plant EG307 polypeptide. As used herein, an EG307 polypeptide, in one embodiment, is a polypeptide that is related to (i.e., bears structural similarity to) the *O. sativa* polypeptide of about 447 amino acids and having the sequence depicted in FIG. 2 (SEQ ID NO:6). The original identification of such a polypeptide is detailed in the Examples. A preferred EG307 polypeptide is encoded by a polynucleotide that hybridizes under stringent hybridization conditions to at least one of the following genes: (a) a gene encoding an *O. sativa* EG307 polypeptide (i.e., an *O. sativa* gene); (b) a gene encoding an *O. rufipogon* EG307 polypeptide (i.e., an *O. rufipogon* gene); (c) a gene encoding a *Zea mays mays* EG307 gene; (d) a gene encoding a *Zea mays parviglumis* EG307 polypeptide (i.e., a. *Z. mays parviglumis* gene); (e) a gene encoding a *Zea diploperesnnis* EG307 polypeptide (i.e., a. *Z. diploperesnnis* gene); and (f) a gene encoding a *Zea luxurians* EG307 polypeptide (i.e., a. *Z. luxurians* gene). It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising," "including," and "having" can be used interchangeably.

As used herein, stringent hybridization conditions refer to standard hybridization conditions under which polynucleotides, including oligonucleotides, are used to identify molecules having similar nucleic acid sequences. Such standard conditions are disclosed, for example, in Sambrook et al., MOLECULAR CLONING: A LABORATORY MANUAL, Cold Spring Harbor Labs Press, 1989. Examples of such conditions are provided in the Examples section of the present application.

As used herein, an *O. sativa* EG307 gene includes all nucleic acid sequences related to a natural *O. sativa* EG307 gene such as regulatory regions that control production of the *O. sativa* EG307 polypeptide encoded by that gene (such as, but not limited to, transcription, translation or post-translation control regions) as well as the coding region itself. In one embodiment, an *O. sativa* EG307 gene includes the nucleic acid sequence SEQ ID NO:4. Nucleic acid sequence SEQ ID NO:4 represents the deduced sequence of a cDNA (complementary DNA) polynucleotide, the production of which is disclosed in the Examples. It should be noted that since nucleic acid sequencing technology is not entirely error-free, SEQ ID NO:4 (as well as other sequences presented herein), at best, represents an apparent nucleic acid sequence of the polynucleotide encoding an *O. sativa* EG307 polypeptide of the present invention.

In another embodiment, an *O. sativa* EG307 gene can be an allelic variant that includes a similar but not identical sequence to SEQ ID NO:4. An allelic variant of an *O. sativa* EG307 gene including SEQ ID NO:1 is a locus (or loci) in the genome whose activity is concerned with the same biochemical or developmental processes, and/or a gene that that occurs at essentially the same locus as the gene including SEQ ID NO:4, but which, due to natural variations caused by, for example, mutation or recombination, has a similar but not identical sequence. Because genomes can undergo rearrangement, the physical arrangement of alleles is not always the same. Allelic variants typically encode polypeptides having similar activity to that of the polypeptide encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given rice cultivar or strain since the genome is diploid and/or among a population comprising two or more rice cultivars or strains. For example, it is believed that the *O. sativa* polynucleotide having nucleic acid sequences reprepsented by SEQ ID NO:18, to be described in more detail below, represents allelic variants of the Kasalath strain of *O. sativa*.

Similarly, a *Zea mays mays* EG307 gene includes all nucleic acid sequences related to a natural *Z. mays mays* EG307 gene such as regulatory regions that control production of the *Z. mays mays* EG307 polypeptide encoded by that gene as well as the coding region itself. In one embodiment, a *Zea mays mays* EG307 gene includes the nucleic acid sequence SEQ ID NO:66. Nucleic acid sequence SEQ ID NO:66 represents the deduced sequence of a cDNA polynucleotide, the production of which is disclosed in the Examples. In another embodiment, a *Zea mays mays* EG307 gene can be an allelic variant that includes a similar but not identical sequence to SEQ ID NO:66.

According to the present invention, an isolated, or biologically pure, polypeptide, is a polypeptide that has been removed from its natural milieu. As such, "isolated" and "biologically pure" do not necessarily reflect the extent to which the polypeptide has been purified. An isolated EG307 polypeptide of the present invention can be obtained from its natural source, can be produced using recombinant DNA technology or can be produced by chemical synthesis. An EG307 polypeptide of the present invention may be identified by its ability to perform the function of natural EG307 in a functional assay. By "natural EG307 polypeptide," it is meant the full length EG307 polypeptide of *O. sativa, O. rufipogon, Z. mays mays*, and/or *Z. mays parviglumis*. The phrase "capable of performing the function of a natural EG307 in a functional assay" means that the polypeptide has at least about 10% of the activity of the natural polypeptide in the functional assay. In other preferred embodiments, the EG307 polypeptide has at least about 20% of the activity of the natural polypeptide in the functional assay. In other preferred embodiments, the EG307 polypeptide has at least about 30% of the activity of the natural polypeptide in the functional assay. In other preferred embodiments, the EG307 polypeptide has at least about 40% of the activity of the natural polypeptide in the functional assay. In other preferred embodiments, the EG307 polypeptide has at least about 50% of the activity of the natural polypeptide in the functional assay. In other preferred embodiments, the polypeptide has at least about 60% of the activity of the natural polypeptide in the functional assay. In more preferred embodiments, the polypeptide has at least about 70% of the activity of the natural polypeptide in the functional assay. In more preferred embodiments, the polypeptide has at least about 80% of the activity of the natural polypeptide in the functional assay. In more preferred embodiments, the polypeptide has at least about 90% of the activity of the natural polypeptide in the functional assay. Examples of functional assays include antibody-binding assays, or yield-increasing assays, as detailed elsewhere in this specification.

As used herein, an isolated plant EG307 polypeptide can be a full-length polypeptide or any homologue of such a polypeptide. Examples of EG307 homologues include EG307 polypeptides in which amino acids have been deleted (e.g., a truncated version of the polypeptide, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homolog has natural EG307 activity.

In one embodiment, when the homologue is administered to an animal as an immunogen, using techniques known to those skilled in the art, the animal will produce a humoral and/or cellular immune response against at least one epitope of a natural EG307 polypeptide. EG307 homologues can also be selected by their ability to perform the function of EG307 in a functional assay.

Plant EG307 polypeptide homologues can be the result of natural allelic variation or natural mutation. EG307 polypeptide homologues of the present invention can also be produced using techniques known in the art including, but not limited to, direct modifications to the polypeptide or modifications to the gene encoding the polypeptide using, for example, classic or recombinant DNA techniques to effect random or targeted mutagenesis.

In accordance with the present invention, a mimetope refers to any compound that is able to mimic the ability of an isolated plant EG307 polypeptide of the present invention to perform the function of an EG307 polypeptide of the present invention in a functional assay. Examples of mimetopes include, but are not limited to, anti-idiotypic antibodies or fragments thereof, that include at least one binding site that mimics one or more epitopes of an isolated polypeptide of the present invention; non-polypeptideaceous immunogenic portions of an isolated polypeptide (e.g., carbohydrate structures); and synthetic or natural organic molecules, including nucleic acids, that have a structure similar to at least one epitope of an isolated polypeptide of the present invention. Such mimetopes can be designed using computer-generated structures of polypeptides of the present invention. Mimetopes can also be obtained by generating random samples of molecules, such as oligonucleotides, peptides or other organic molecules, and screening such samples by affinity chromatography techniques using the corresponding binding partner.

The minimal size of an EG307 polypeptide homologue of the present invention is a size sufficient to be encoded by a polynucleotide capable of forming a stable hybrid with the complementary sequence of a polynucleotide encoding the corresponding natural polypeptide. As such, the size of the polynucleotide encoding such a polypeptide homologue is dependent on nucleic acid composition and percent homology between the polynucleotide and complementary sequence as well as upon hybridization conditions per se (e.g., temperature, salt concentration, and formamide concentration). It should also be noted that the extent of homology required to form a stable hybrid can vary depending on whether the homologous sequences are interspersed throughout the polynucleotides or are clustered (i.e., localized) in distinct regions on the polynucleotides. The minimal size of such polynucleotides is typically at least about 12 to about 15 nucleotides in length if the polynucleotides are GC-rich and at least about 15 to about 17 bases in length if they are AT-rich. Preferably, the polynucleotide is at least 12 bases in length.

As such, the minimal size of a polynucleotide used to encode an EG307 polypeptide homologue of the present invention is from about 12 to about 18 nucleotides in length. There is no limit, other than a practical limit, on the maximal size of such a polynucleotide in that the polynucleotide can include a portion of a gene, an entire gene, or multiple genes, or portions thereof. Similarly, the minimal size of an EG307 polypeptide homologue of the present invention is from about 4 to about 6 amino acids in length, with preferred sizes depending on whether a full-length, fusion, multivalent, or functional portions of such polypeptides are desired. Preferably, the polypeptide is at least 30 bases in length.

Any plant EG307 polypeptide is a suitable polypeptide of the present invention. Suitable plants from which to isolate EG307 polypeptides (including isolation of the natural polypeptide or production of the polypeptide by recombinant or synthetic techniques) include maize, wheat, barley, rye, millet, chickpea, lentil, flax, olive, fig almond, pistachio, walnut, beet, parsnip, citrus fruits, including, but not limited to, orange, lemon, lime, grapefruit, tangerine, minneola, and tangelo, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis*, and woody plants such as coniferous and deciduous trees, with rice and maize being preferred. Preferred rice plants from which to isolate EG307 polypeptides include Nipponbare 1 and 2, Lemont, IR64, Teqing, Azucena, and Kasalath 1, 2, 3, and 4 strains of *O. sativa*.

A preferred plant EG307 polypeptide of the present invention is a compound that when expressed or modulated in a plant, is capable of increasing the yield of the plant.

One embodiment of the present invention is a fusion polypeptide that includes an EG307 polypeptide-containing domain attached to a fusion segment. Inclusion of a fusion segment as part of a EG307 polypeptide of the present invention can enhance the polypeptide's stability during production, storage and/or use. Depending on the segment's characteristics, a fusion segment can also act as an immunopotentiator to enhance the immune response mounted by an animal immunized with an EG307 polypeptide containing such a fusion segment. Furthermore, a fusion segment can function as a tool to simplify purification of an EG307 polypeptide, such as to enable purification of the resultant fusion polypeptide using affinity chromatography. A suitable fusion segment can be a domain of any size that has the desired function (e.g., imparts increased stability, imparts increased immunogenicity to a polypeptide, and/or simplifies purification of a polypeptide). It is within the scope of the present invention to use one or more fusion segments. Fusion segments can be joined to amino and/or carboxyl termini of the EG307-containing domain of the polypeptide. Linkages between fusion segments and EG307-containing domains of fusion polypeptides can be susceptible to cleavage in order to enable straightforward recovery of the EG307-containing domains of such polypeptides. Fusion polypeptides are preferably produced by culturing a recombinant cell transformed with a fusion polynucleotide that encodes a polypeptide including the fusion segment attached to either the carboxyl and/or amino terminal end of a EG307-containing domain.

Preferred fusion segments for use in the present invention include a glutathione binding domain; a metal binding domain, such as a poly-histidine segment capable of binding to a divalent metal ion; an immunoglobulin binding domain, such as Polypeptide A, Polypeptide G, T cell, B cell, Fc receptor or complement polypeptide antibody-binding domains; a sugar binding domain such as a maltose binding domain from a maltose binding polypeptide; and/or a "tag" domain (e.g., at least a portion of â-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide.

Preferred plant EG307 polypeptides of the present invention are rice EG307 polypeptides and maize EG307 polypeptides. More preferred EG307 polypeptides are *O. sativa, O. rufipogon, Z. mays mays, Zea mays parviglumis, Z. diploperennis* and *Z. luzurians* EG307 polypeptides. *O. sativa* strains include Nipponbare, Azucena, Kasalath 1, 2, 3, and 4, Teqing, Lemont, and IR64. *Z. mays parviglumis* strains include Benz, BK4, IA19, and Wilkes. *Z. mays mays* strains include BS7, HuoBai, Makki, Min13, Pira, Sari, Smena, and W22.

One preferred *O. sativa* EG307 polypeptide of the present invention is a polypeptide encoded by an *O. sativa* polynucleotide that hybridizes under stringent hybridization conditions with complements of polynucleotides represented by SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, and/or SEQ ID NO:18. Such an EG307 polypeptide is encoded by a polynucleotide that hybridizes under stringent hybridization conditions with a polynucleotide having nucleic acid sequence SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, and/or SEQ ID NO:18.

Inspection of EG307 genomic nucleic acid sequences indicates that the genes comprise several regions, including a first exon region, a first intron region, a second exon region, a second intron region, and a third exon region.

Polynucleotides SEQ ID NO:4 and SEQ ID NO:91 represent the 5' and 3' ends of the EG307 gene in *O. sativa* (cv. Nipponbare). SEQ ID NO:4 and SEQ ID NO:91 are joined by a number of nucleotides, the exact number of which is unknown due to potential insertions/deletions in the non-coding portions of the gene, but is believed to be about 6. Translation of SEQ ID NO:4 and SEQ ID NO:91 suggests that the *O. sativa* EG307 polynucleotide includes an open reading frame. The reading frame encodes an *O. sativa* EG307 polypeptide of about 447 amino acids, the deduced amino acid sequence of which is represented herein as SEQ ID NO:6, assuming an open reading frame having an initiation (start) codon spanning from about nucleotide 37 through about nucleotide 39 of SEQ ID NO:4 and a termination (stop) codon spanning from about nucleotide 2278 through about nucleotide 2280 of SEQ ID NO:4, with the first exon spanning nucleotides 1-126 of SEQ ID NO:4, the first intron spanning nucleotides 9-822 of SEQ ID NO:91, the second exon spanning nucleotides 823-1141 of SEQ ID NO:91, the second intron spanning nucleotides 1142-1222 of SEQ ID NO:91, and the third exon spanning nucleotides 1223-2157 of SEQ ID NO:91. The open reading frame from nucleotide 37 through about nucleotide 2280 of SEQ ID NO:4 is represented herein as SEQ ID NO:5.

Similarly, translation of *O. sativa* (strain Azucena) polynucleotide SEQ ID NO:1 suggests an open reading frame from about nucleotide 3 to about nucleotide 2410 of SEQ ID NO:1, with the first exon spanning nucleotides 1-92 of SEQ ID NO:1, the first intron spanning nucleotides 93-1075 of SEQ ID NO:1, the second exon spanning nucleotides 1076-1394 of SEQ ID NO:1, the second intron spanning nucleotides 1395-1475 of SEQ ID NO:1, and the third exon spanning nucleotides 1476-2441 of SEQ ID NO:1. The open reading frame is represented herein as SEQ ID NO:2, and encodes a polypeptide represented herein as SEQ ID NO:3.

Similarly, translation of *O. sativa* (strain Teqing) polynucleotide SEQ ID NO:7 suggests an open reading frame from about nucleotide 21 to about nucleotide 2421, with the first exon spanning nucleotides 1-110 of SEQ ID NO:7, the first intron spanning nucleotides 111-1089 of SEQ ID NO:7, the second exon spanning nucleotides 1090-1405 of SEQ ID NO:7, the second intron spanning nucleotides 1406-1486 of SEQ ID NO:7, and the third exon spanning nucleotides 1487-2461 of SEQ ID NO:7. The open reading frame is represented herein as SEQ ID NO:8, and encodes a polypeptide represented herein as SEQ ID NO:9.

Similarly, polynucleotides SEQ ID NO:10 and SEQ ID NO:11 represent the 5' and 3' ends of the EG307 gene in *O. sativa* (strain Lemont). SEQ ID NO:10 and SEQ ID NO:11 are joined by an unknown number of nucleotides. In the genomic sequence, there may be insertions/deletions in the non-coding portions of the gene, thus the actual number of nucleotides is unknown, but is believed to be about 10. Translation of *O. sativa* (strain Lemont) polynucleotides SEQ ID NO:10 and SEQ ID NO:11 suggests an open reading frame from about nucleotide 166 of SEQ ID NO:10 to about nucleotide 1547 of SEQ ID NO:11, with the first exon spanning nucleotides 1-255 of SEQ ID NO:10, the first intron spanning nucleotides 255-451 of SEQ ID NO:10 and nucleotides 1-212 of SEQ ID NO:11, the second exon spanning nucleotides 213-531 of SEQ ID NO:11, the second intron spanning nucleotides 532-612 of SEQ ID NO:11, and the third exon spanning nucleotides 613-1616 of SEQ ID NO:11. The open reading frame is represented herein as SEQ ID NO:12, and encodes a polypeptide represented herein as SEQ ID NO:13.

Similarly, translation of *O. sativa* (strain IR64) polynucleotide SEQ ID NO:14 suggests an open reading frame from about nucleotide 1 to about nucleotide 2400, with the first exon spanning nucleotides 1-90 of SEQ ID NO:14, the first intron spanning nucleotides 91-1068 of SEQ ID NO:14, the second exon spanning nucleotides 1069-1384 of SEQ ID NO:14, the second intron spanning nucleotides 1385-1465 of SEQ ID NO:14, and the third exon spanning nucleotides 1466-2459 of SEQ ID NO:11. The open reading frame is represented herein as SEQ ID NO:14, and encodes a polypeptide represented herein as SEQ ID NO:15.

Similarly, translation of *O. sativa* (strain Kasalath) polynucleotide SEQ ID NO:17 suggests an open reading frame from about nucleotide 2 to about nucleotide 2402, with the first exon spanning nucleotides 1-91 of SEQ ID NO:17, the first intron spanning nucleotides 92-1070 of SEQ ID NO:17, the second exon spanning nucleotides 1071-1386 of SEQ ID NO:17, the second intron spanning nucleotides 1387-1467 of SEQ ID NO:17, and the third exon spanning nucleotides 1468-2432 of SEQ ID NO:17.

The open reading frame is represented as SEQ ID NO:18, and encodes a polypeptide represented herein as SEQ ID NO:19. In SEQ ID NO:18, "N" at position 889 is "G", and "N" at position 971 is "A" for strain Kasalath 1, making amino acid residue 297 in SEQ ID NO:19 a valine, and amino acid residue 324 a glutamine. In SEQ ID NO:18, "N" at position 889 is "G", and "N" at position 971 is "T" for strain Kasalath 2, making amino acid residue 297 in SEQ ID NO:19 a valine, and amino acid residue 324 a leucine. In SEQ ID NO:18, "N" at postion 889 is "C", and "N" at position 971 is "A" for strain Kasalath 3, making amino acid residue 297 in SEQ ID NO:19 a leucine, and amino acid residue 324 a glutamine. In SEQ ID NO:18, "N" at postion 889 is "C", and "N" at position 971 is "T" for strain Kasalath 4, making amino acid residue 297 in SEQ ID NO:19 a leucine, and amino acid residue 324 a leucine.

A preferred *O. sativa* EG307 polypeptide of the present invention is a polypeptide encoded by a polynucleotide that hybridizes under stringent hybridization conditions with polynucleotides represented by SEQ ID NO:1, SEQ ID NO:91, SEQ ID NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, and/or SEQ ID NO:18.

Preferred *O. rufipogon* EG307 polypeptides of the present invention are polypeptide encoded by an *O. rufipogon* polynucleotide that hybridizes under stringent hybridization conditions with complements of polynucleotides represented by SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, and/or SEQ ID NO:31. Such an EG307 polypeptide is encoded by a polynucleotide that hybridizes under stringent hybridization conditions with a polynucleotide having nucleic acid sequence SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, and/or SEQ ID NO:31.

Polynucleotides SEQ ID NO:27 and SEQ ID NO:28 represent the 5' and 3' ends of the EG307 gene in *O. rufpogon* (strain 5953). SEQ ID NO:27 and SEQ ID NO:28 are joined by a number of nucleotides, the exact number of which is unknown due to potential insertions/deletions in the non-coding portions of the gene, but is believed to be about 23. Translation of SEQ ID NO:27 and SEQ ID NO:28 suggests that the *O. rufipogon* EG307 polynucleotide includes an open reading frame. The reading frame encodes an *O. rufipogon* EG307 polypeptide of about 446 amino acids, the deduced amino acid sequence of which is represented herein as SEQ ID NO:30, assuming an open reading frame having an initiation (start) codon spanning from about nucleotide 18 through about nucleotide 20 of SEQ ID NO:27 and a termination (stop) codon spanning from about nucleotide 1330 through about nucleotide 1332 of SEQ ID NO:28, with the first exon spanning nucleotides 1-107 of SEQ ID NO:27, no first intron, the second exon spanning nucleotides 1-316 of SEQ ID NO:28, the second intron spanning nucleotides 317-397 of SEQ ID NO:28, and the third exon spanning nucleotides 398-1332 of SEQ ID NO:28. The open reading frame from nucleotide 18 of SEQ ID NO:27 through about nucleotide 1332 of SEQ ID NO:28 is represented herein as SEQ ID NO:29.

Similarly, translation of *O. rufipogon* (strain 5948) polynucleotide SEQ ID NO:20 suggests an open reading frame from about 15 nucelotides 5' of nucleotide 1 to about nucleotide 2385, first exon not represented, the first intron spanning nucleotides 1-1053 of SEQ ID NO:20, the second exon spanning nucleotides 1054-1369 of SEQ ID NO:20, the second intron spanning nucleotides 1370-1450 of SEQ ID NO:20, and the third exon spanning nucleotides 1451-2447 of SEQ ID NO:20. The open reading frame is represented herein as SEQ ID NO:21, and encodes a polypeptide represented herein as SEQ ID NO:22.

Similarly, polynucleotides SEQ ID NO:23 and SEQ ID NO:24 represent the 5' and 3' ends of the EG307 gene in *O. rufpogon* (strain 5949). SEQ ID NO:23 and SEQ ID NO:24 are joined by a number of nucleotides, the exact number of which is unknown due to potential insertions/deletions in the non-coding portions of the gene, but is believed to be about 13. Translation of SEQ ID NO:23 and SEQ ID NO:24 suggests an open reading frame from about nucleotide 57 of SEQ ID NO:23 to about nucleotide 1562 of SEQ ID NO:24, with the first exon spanning nucleotides 1-146 of SEQ ID NO:23, the first intron spanning nucleotides 1-230 of SEQ ID NO:24, the second exon spanning nucleotides 231-546 of SEQ ID NO:24, the second intron spanning nucleotides 547-627 of SEQ ID NO:24, and the third exon spanning nucleotides 628-1615 of SEQ ID NO:24. The open reading frame is represented as SEQ ID NO:25, and encodes a polypeptide represented herein as SEQ ID NO:26.

Similarly, translation of *O. rufpogon* (strain IRCG 105491) polynucleotide SEQ ID NO:90 suggests an open reading frame from about nucleotide 1 to about nucleotide 1341. The open reading frame is represented herein as SEQ ID NO:31 encoding a polypeptide represented herein as SEQ ID NO:32.

A preferred *O. rufipogon* EG307 polypeptide of the present invention is a polypeptide encoded by a polynucleotide that hybridizes under stringent hybridization conditions with a polynucleotide represented by SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, and/or SEQ ID NO:31.

One preferred *Zea mays parviglumis* EG307 polypeptide of the present invention is a polypeptide encoded by a *Zea mays parviglumis* polynucleotide that hybridizes under stringent hybridization conditions with complements of polynucleotides represented by SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, and/or SEQ ID NO:78. Such an EG307 polypeptide is encoded by a polynucleotide that hybridizes under stringent hybridization conditions with a polynucleotide having nucleic acid sequence SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, and/or SEQ ID NO:78.

Translation of SEQ ID NO:66 suggests that the *Zea mays parviglumis* EG307 polynucleotide (strain Benz) includes an open reading frame. The reading frame encodes an *Zea mays parviglumis* EG307 polypeptide of about 448 amino acids, the deduced amino acid sequence of which is represented herein as SEQ ID NO:68, assuming an open reading frame having an initiation (start) codon spanning from about nucleotide 1 through about nucleotide 3 of SEQ ID NO:66 and a termination (stop) codon spanning from about nucleotide 2569 through about nucleotide 2571 of SEQ ID NO:66, with the first exon spanning nucleotides 1-81 of SEQ ID NO:66, the first intron spanning nucleotides 82-1204 of SEQ ID NO:66, the second exon spanning nucleotides 1205-1517 of SEQ ID NO:66, the second intron spanning nucleotides 1518-1618 of SEQ ID NO:66, and the third exon spanning nucleotides 1619-2644 of SEQ ID NO:66. The open reading frame from nucleotide 3 through about nucleotide 2571 of SEQ ID NO:66 is represented herein as SEQ ID NO:67.

Similarly, polynucleotides SEQ ID NO:69 and SEQ ID NO:70 represent the 5' and 3' ends of the EG307 gene in *Z. mays parviglumis* (strain BK4). SEQ ID NO:69 and SEQ ID NO:70 are joined by a number of nucleotides, the exact number of which is unknown due to potential insertions/deletions in the non-coding portions of the gene, but is believed to be about 10. Translation of *Z. mays parviglumis* (strain BK4) polynucleotide SEQ ID NO:69 and SEQ ID NO:70 suggests an open reading frame from about nucleotide 10 of SEQ ID NO:69 to about nucleotide 1728 of SEQ ID NO:70, with the first exon spanning nucleotides 1-90 of SEQ ID NO:69, the first intron spanning nucleotides 91-586 of SEQ ID NO:69 and nucleotides 1-361 of SEQ ID NO:70, the second exon spanning nucleotides 362-674 of SEQ ID NO:70, the second intron spanning nucleotides 675-775 of SEQ ID NO:70, and the third exon spanning nucleotides 776-1775 of SEQ ID NO:11. The open reading frame is represented as SEQ ID NO:71, and encodes a polypeptide represented herein as SEQ ID NO:72.

Similarly, polynucleotides SEQ ID NO:73 and SEQ ID NO:74 represent the 5' and 3' ends of the EG307 gene in *Z. mays parviglumis* (strain IA19). SEQ ID NO:73 and SEQ ID NO:74 are joined by a number of nucleotides, the exact number of which is unknown due to potential insertions/deletions in the non-coding portions of the gene, but is believed to be about 12. Translation of *Z. mays parviglumis* (strain IA19) polynucleotides SEQ ID NO:73 and SEQ ID NO:74 suggests an open reading frame from about nucleotide 69 of SEQ ID NO:73 to about nucleotide 1280 of SEQ ID NO:74, with the first exon spanning nucleotides 1-149 of SEQ ID NO:73, the first intron spanning nucleotides 150-305 of SEQ ID NO:73, the second exon spanning nucleotides 1-226 of SEQ ID NO:74, the second intron spanning nucleotides 227-327 of SEQ ID NO:74, and the third exon spanning nucleotides 328-1309 of SEQ ID NO:74. The open reading frame is represented herein as SEQ ID NO:75, and encoding a polypeptide represented herein as SEQ ID NO:76.

Similarly, polynucleotides SEQ ID NO:77 and SEQ ID NO:59 represent the 5' and 3' ends of the EG307 gene in *Z. mays parviglumis* (strain Wilkes). SEQ ID NO:77 and SEQ ID NO:59 are joined by a number of nucleotides, the exact number of which is unknown due to potential insertions/deletions in the non-coding portions of the gene, but is believed to be about 14. Translation of *Z. mays parviglumis* (strain Wilkes) polynucleotide SEQ ID NO:77 and SEQ ID NO:59 suggests an open reading frame from about nucleotide 36 of SEQ ID NO:77 to about nucleotide 1598 of SEQ ID NO:59, with the first exon spanning nucleotides 1-86 of SEQ ID NO:77, the first intron spanning nucleotides 1-231 of SEQ ID NO:59, the second exon spanning nucleotides 232-544 of SEQ ID NO:59, the second intron spanning nucleotides 545-645 of SEQ ID NO:59, and the third exon spanning nucleotides 656-1640 of SEQ ID NO:59. The open reading frame is represented herein as SEQ ID NO:78, and encoding a polypeptide represented herein as SEQ ID NO:79. A preferred EG307 polypeptide of the present invention is a polypeptide encoded by a polynucleotide that hybridizes under stringent hybridization conditions with a polynucleotide represented by SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, and/or SEQ ID NO:64.

One preferred *Zea mays mays* EG307 polypeptide of the present invention is a polypeptide encoded by an *Zea mays mays* polynucleotide that hybridizes under stringent hybridization conditions with complements of polynucleotides represented by SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, and/or SEQ ID NO:64. Such an EG307 polypeptide is encoded by a polynucleotide that hybridizes under stringent hybridization conditions with a polynucleotide having nucleic acid sequence SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:59, SEQ ID NO:60, SEQ ID NO:62, SEQ ID NO:63, and/or SEQ ID NO:64.

Polynucleotides SEQ ID NO:33 and SEQ ID NO:34 represent the 5' and 3' ends of the EG307 gene in *Z. mays mays* (strain BS 7). SEQ ID NO:33 and SEQ ID NO:34 are joined by a number of nucleotides, the exact number of which is unknown due to potential insertions/deletions in the non-coding portions of the gene, but is believed to be about 21. Translation of SEQ ID NO:33 and SEQ ID NO:34 suggests that the *Zea mays mays* EG307 polynucleotide includes an open reading frame. The reading frame encodes an *Zea mays mays* EG307 polypeptide of about 448 amino acids, the deduced amino acid sequence of which is represented herein as SEQ ID NO:36, assuming an open reading frame having an initiation (start) codon spanning from about nucleotide 3 through about nucleotide 5 of SEQ ID NO:33 and a termination (stop) codon spanning from about nucleotide 1396 through about nucleotide 1398 of SEQ ID NO:34, with the first exon spanning nucleotides 1-83 of SEQ ID NO:33, the first intron spanning nucleotides 84-180 of SEQ ID NO:33 and nucleotides 1-31 of SEQ ID NO:34, the second exon spanning nucleotides 32-344 of SEQ ID NO:34, the second intron spanning nucleotides 345-445 of SEQ ID NO:34, and the third exon spanning nucleotides 446-1447 of SEQ ID NO:34. The open reading frame from nucleotide 3 of SEQ ID NO:33 through about nucleotide 1398 of SEQ ID NO:34 is represented herein as SEQ ID NO:35.

Similarly, translation of *Z. mays mays* (strain HuoBai) polynucleotide SEQ ID NO:37 suggests an open reading frame from about nucleotide 28 to about nucleotide 2599, with the first exon spanning nucleotides 1-108 of SEQ ID NO:37, the first intron spanning nucleotides 109-1232 of SEQ ID NO:37, the second exon spanning nucleotides 1233-1545 of SEQ ID NO:37, the second intron spanning nucleotides 1546-1646 of SEQ ID NO:37, and the third exon spanning nucleotides 1647-2646 of SEQ ID NO:37. The open reading frame is represented herein as SEQ ID NO:38, and encodes a polypeptide represented herein as SEQ ID NO:39.

Similarly, polynucleotides SEQ ID NO:40 and SEQ ID NO:41 represent 5' end to the 3' end of the EG307 gene in *Z. mays mays* (strain Makki). SEQ ID NO:40 and SEQ ID NO:41 are joined by a number of nucleotides, the exact number of which is unknown due to potential insertions/deletions in the non-coding portions of the gene, but is believed to be about 20. Translation of *Z. mays mays* (strain Makki) polynucleotides SEQ ID NO:40 and SEQ ID NO:41 suggests an open reading frame from about nucleotide 61 of SEQ ID NO:40 to about nucleotide 2263 of SEQ ID NO:41, with the first exon spanning nucleotides 1-141 of SEQ ID NO:40, the first intron spanning nucleotides 142-262 of SEQ ID NO:40 and nucleotides 1-896 of SEQ ID NO:41, the second exon spanning nucleotides 897-1209 of SEQ ID NO:41, the second intron spanning nucleotides 1210-1310 of SEQ ID NO:41, and the third exon spanning nucleotides 1311-2311 of SEQ ID NO:41. The open reading frame is represented as SEQ ID NO:42 encoding a polypeptide represented herein as SEQ ID NO:43.

Similarly, polynucleotides SEQ ID NO:44, SEQ ID NO:45 and SEQ ID NO:46 represent the three parts of the EG307 gene in *Z. mays mays* (strain Min13), from the 5' end to the 3' end. SEQ ID NO:44, SEQ ID NO:45 and SEQ ID NO:46 are joined by a number of nucleotides, the exact number of which is unknown due to potential insertions/deletions in the non-coding portions of the gene, but is belived to be 19 between SEQ ID NO:44 and SEQ ID NO:45, and 17 between SEQ ID NO:45 and SEQ ID NO:46.

Translation of *Z. mays mays* (strain Min13) polynucleotides SEQ ID NO:44, SEQ ID NO:45 and SEQ ID NO:46 suggests an open reading frame from about nucleotide 45 of SEQ ID NO:44 to about nucleotide 1741 of SEQ ID NO:46, with the first exon spanning nucleotides 1-125 of SEQ ID NO:44, the first intron spanning nucleotides 1-198 of SEQ ID NO:45 and nucleotides 1-374 of SEQ ID NO:46, the second exon spanning nucleotides 375-687 of SEQ ID NO:46, the second intron spanning nucleotides 688-788 of SEQ ID NO:46, and the third exon spanning nucleotides 789-1787 of SEQ ID NO:46. The open reading frame is represented herein as SEQ ID NO:47, and encodes a polypeptide represented herein as SEQ ID NO:48.

Similarly, polynucleotides SEQ ID NO:49 and SEQ ID NO:50 represent the 5' and 3' ends of the EG307 gene in *Z. mays mays* (strain Pira). SEQ ID NO:49 and SEQ ID NO:50 are joined by a number of nucleotides, the exact number of which is unknown due to potential insertions/deletions in the non-coding portions of the gene. Translation of *Z. mays mays* (strain Pira) polynucleotides SEQ ID NO:49 and SEQ ID NO:50 suggests an open reading frame from about nucleotide 31 of SEQ ID NO:49 to about nucleotide 1722 of SEQ ID NO:50, with the first exon spanning nucleotides 1-111 of SEQ ID NO:49, the first intron spanning nucleotides 112-495 of SEQ ID NO:49 and nucleotides 1-355 of SEQ ID NO:50, the second exon spanning nucleotides 356-668 of SEQ ID NO:50, the second intron spanning nucleotides 669-769 of SEQ ID NO:50, and the third exon spanning nucleotides 770-1768 of SEQ ID NO:50. The open reading frame is represented herein as SEQ ID NO:51, and encodes a polypeptide represented herein as SEQ ID NO:52.

Similarly, polynucleotides SEQ ID NO:53 and SEQ ID NO:54 represent the 5' and 3' ends of the EG307 gene in *Z. mays mays* (strain Sari). SEQ ID NO:53 and SEQ ID NO:54 are joined by a number of nucleotides, the exact number of which is unknown due to potential insertions/deletions in the non-coding portions of the gene, but is believed to be about 22. Translation of *Z. mays mays* (strain Pira) polynucleotides SEQ ID NO:53 and SEQ ID NO:54 suggests an open reading frame from about nucleotide 19 of SEQ ID NO:53 to about nucleotide 1756 of SEQ ID NO:54, with the first exon spanning nucleotides 1-99 of SEQ ID NO:53, the first intron spanning nucleotides 100-212 of SEQ ID NO:53 and nucleotides 1-389 of SEQ ID NO:54, the second exon spanning nucleotides 390-702 of SEQ ID NO:54, the second intron spanning nucleotides 703-803 of SEQ ID NO:54, and the third exon spanning nucleotides 804-1803 of SEQ ID NO:54. The open reading frame is represented herein as SEQ ID NO:55, and encodes a polypeptide represented herein as SEQ ID NO:56.

Similarly, polynucleotides SEQ ID NO:57 and SEQ ID NO:58 represent the 5' and 3' ends of the EG307 gene in *Z. mays mays* (strain Smena). SEQ ID NO:57 and SEQ ID NO:58 are joined by a number of nucleotides, the exact number of which is unknown due to potential insertions/deletions in the non-coding portions of the gene, but is believed to be 14. Translation of *Z. mays mays* (strain Smena) polynucleotides SEQ ID NO:57 and SEQ ID NO:58 suggests an open reading frame from about nucleotide 68 of SEQ ID NO:57 to about nucleotide 2199 of SEQ ID NO:58, with the first exon spanning nucleotides 1-148 of SEQ ID NO:57, the first intron spanning nucleotides 149-305 of SEQ ID NO:57 and nucleotides 1-834 of SEQ ID NO:58, the second exon spanning nucleotides 835-1147 of SEQ ID NO:58, the second intron spanning nucleotides 1148-1248 of SEQ ID NO:58, and the third exon spanning nucleotides 1249-2208 of SEQ ID NO:58. Additionally, sequence SEQ ID NO:59 contains a deletion at starting after nucleotide 738 of SEQ ID NO:59. The open reading frame is represented herein as SEQ ID NO:60, and encodes a polypeptide represented herein as SEQ ID NO:61.

Similarly, polynucleotides SEQ ID NO:62 and SEQ ID NO:63 represent the 5' and 3' ends of the EG307 gene in *Z. mays mays* (strain W22). SEQ ID NO:62 and SEQ ID NO:63 are joined by a number of nucleotides, the exact number of which is unknown due to potential insertions/deletions in the non-coding portions of the gene, but is believed to be about 22. Translation of *Z. mays mays* (strain W22) polynucleotides SEQ ID NO:62 and SEQ ID NO:63 suggests an open reading frame from about nucleotide 1 of SEQ ID NO:62 to about nucleotide 1367 of SEQ ID NO:63, with the first exon spanning nucleotides 1-81 of SEQ ID NO:62, the first intron spanning nucleotides 82-893 of SEQ ID NO:62, the second exon spanning nucleotides 1-313 of SEQ ID NO:63, the second intron spanning nucleotides 314-414 of SEQ ID NO:63, and the third exon spanning nucleotides 415-1411 of SEQ ID NO:63. The open reading frame is represented herein as SEQ ID NO:64, and encodes a polypeptide represented herein as SEQ ID NO:65.

A preferred *Z. mays mays* EG307 polypeptide of the present invention is a polypeptide encoded by a polynucleotide that hybridizes under stringent hybridization conditions with a polynucleotide represented by SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, and/or SEQ ID NO:64.

A preferred *O. rufipogon* EG307 polypeptide of the present invention is a polypeptide encoded by a polynucleotide that hybridizes under stringent hybridization conditions with a polynucleotide represented by SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, and/or SEQ ID NO:31.

One preferred *Zea diploperennis* EG307 polypeptide of the present invention is a polypeptide encoded by an *Zea mays parviglumis* polynucleotide that hybridizes under stringent hybridization conditions with complements of polynucleotides represented by SEQ ID NO:80, SEQ ID NO:81, and/or SEQ ID NO:82. Such an EG307 polypeptide is encoded by a polynucleotide that hybridizes under stringent hybridization conditions with a polynucleotide having nucleic acid sequence SEQ ID NO:80, SEQ ID NO:81, and/or SEQ ID NO:82.

Polynucleotides SEQ ID NO:80 and SEQ ID NO:81 represent the 5' and 3' ends of the EG307 gene in *Z. diploperennis* SEQ ID NO:80 and SEQ ID NO:81 are joined by a number of nucleotides, the exact number of which is unknown due to potential insertions/deletions in the non-coding portions of the gene, but is believed to be about 24. One preferred *Zea diploperennis* EG307 polypeptide of the present invention is a polypeptide encoded by an *Zea diploperennis* polynucleotide that hybridizes under stringent hybridization conditions with complements of polynucleotides represented by SEQ ID NO:80 and SEQ ID NO:81. Such an EG307 polypeptide is encoded by a polynucleotide that hybridizes under stringent hybridization conditions with a polynucleotide having nucleic acid sequence SEQ ID NO:80 and SEQ ID NO:81.

Translation of SEQ ID NO:80 and SEQ ID NO:81 suggests that the *Zea mays diploperennis* EG307 polynucleotides includes an open reading frame. The reading frame encodes an *Zea diploperennis* EG307 polypeptide of about 448 amino acids, the deduced amino acid sequence of which is represented herein as SEQ ID NO:83, assuming an open reading frame having an initiation (start) codon spanning from about nucleotide 21 through about nucleotide 23 of SEQ ID NO:80 and a termination (stop) codon spanning from about nucleotide 1656 through about nucleotide 1658 of SEQ ID NO:81, with the first exon spanning nucleotides 1-101 of SEQ ID NO:80, the first intron spanning nucleotides 102-225 of SEQ ID NO:80 and nucleotides 1-291 of SEQ ID NO:81, the second exon spanning nucleotides 292-313 of SEQ ID NO:81, the second intron spanning nucleotides 314-705 of SEQ ID NO:81, and the third exon spanning nucleotides 706-1672 of SEQ ID NO:81. The open reading frame from nucleotide 21 of SEQ ID NO:80 through about nucleotide 1658 of SEQ ID NO:81 is represented herein as SEQ ID NO:82.

A preferred *Z. diploperennis* EG307 polypeptide of the present invention is a polypeptide encoded by a polynucleotide that hybridizes under stringent hybridization conditions with polynucleotides represented by SEQ ID NO:80, SEQ ID NO:81, and/or SEQ ID NO:82.

One preferred *Zea luxurians* EG307 polypeptide of the present invention is a polypeptide encoded by an *Zea luxurians* polynucleotide that hybridizes under stringent hybridization conditions with complements of polynucleotides represented by SEQ ID NO:84 and/or SEQ ID NO:85. Such an EG307 polypeptide is encoded by a polynucleotide that hybridizes under stringent hybridization conditions with a polynucleotide having nucleic acid sequence SEQ ID NO:84 and/or SEQ ID NO:85.

Translation of SEQ ID NO:84 suggests that the *Zea luxurians* EG307 polynucleotide includes an open reading frame. The reading frame encodes an *Zea luxurians* EG307 polypeptide of about 448 amino acids, the deduced amino acid sequence of which is represented herein as SEQ ID NO:86, assuming an open reading frame having an initiation (start) codon spanning from about nucleotide 5 through about nucleotide 7 of SEQ ID NO:84 and a termination (stop) codon spanning from about nucleotide 2365 through about nucleotide 2367 of SEQ ID NO:84, with the first exon spanning nucleotides 1-85 of SEQ ID NO:84, the first intron spanning nucleotides 86-998 of SEQ ID NO:84, the second exon spanning nucleotides 999-1311 of SEQ ID NO:84, the second intron spanning nucleotides 1312-1414 of SEQ ID NO:84, and the third exon spanning nucleotides 1415-2423 of SEQ ID NO:84. The open reading frame from nucleotide 5 through about nucleotide 2367 of SEQ ID NO:84 is represented herein as SEQ ID NO:85.

A preferred *Z. luxurians* EG307 polypeptide of the present invention is a polypeptide encoded by a polynucleotide that hybridizes under stringent hybridization conditions with polynucleotides represented by SEQ ID NO:84, and/or SEQ ID NO:85.

Comparison of the various *O. sativa, O. rufipogon, Z. mays mays, Z. mays parviglumis, Z. diploperennis*, and *Z. luxurians* EG307 nucleic acid sequences and amino acid sequences indicates that these species of plants possess similar EG307 genes and polypeptides. The nucleotide sequences of the coding region of EG307 from the various strains of *O. sativa* and *O. rufipogon* have 99.0% sequence identity, when compared to each other, which makes clear that they are homologous. All rice sequences, both ancestral and modern, share the same stop codon (TAG), and (for the 5' UTR sequence that we have collected to date), the 5' UTR sequences have 98.4% sequence identity. The protein sequences of the various strains of *O. sativa* and *O. rufipogon* have 98.2% sequence identity, again demonstrating that these are homologous sequences. The protein sequence of EG307 from rice is about 94% identical to the protein sequence of EG307 from maize, again demonstrating their homology. The protein sequences of maize EG307 and teosinte EG307 have 99.8% sequence identity.

Finding this degree of identity between *O. sativa, O. rufipogon, Z. mays mays, Z. mays parviglumis, Z. diploperennis*, and *Z. luxurians* EG307 nucleic acid sequences and amino acid sequences supports the ability to obtain any plant EG307 polypeptide and polynucleotide given the polypeptide and nucleic acid sequences disclosed herein. These plant EG307 polypeptides, and the polynucleotides that encode them, represent novel compounds with utility in increasing yield in a plant.

Preferred plant EG307 polypeptides of the present invention include polypeptides comprising amino acid sequences that are at least about 30%, preferably at least about 50%, more preferably at least about 75% and even more preferably at least about 90% identical to one or more of the amino acid sequences disclosed herein for *O. sativa, O. rufipogon, Z. mays mays, Z. mays parviglumis, Z. diploperennis*, and *Z. luxurians* EG307 polypeptides of the present invention. More preferred plant EG307 polypeptides of the present invention include: polypeptides encoded by at least a portion of SEQ ID NO. 1 and/or SEQ ID NO:2 and, as such, have amino acid sequences that include at least a portion of SEQ ID NO:3; polypeptides encoded by at least a portion of SEQ ID NO:4, SEQ ID NO:81 and/or SEQ ID NO:5 and, as such, have amino acid sequences that include at least a portion of SEQ ID NO:6; polypeptides encoded by at least a portion of SEQ ID NO:7 and/or SEQ ID NO:8 and, as such, have amino acid sequences that include at least a portion of SEQ ID NO:9; polypeptides encoded by at least a portion of SEQ ID NO:10, SEQ ID NO:11, and/or SEQ ID NO:12 and, as such, have amino acid sequences that include at least a portion of SEQ ID NO:13; polypeptides encoded by at least a portion of SEQ ID NO:14 and/or SEQ ID NO:15 and, as such, have amino acid sequences that include at least a portion of SEQ ID NO:16; polypeptides encoded by at least a portion of SEQ ID NO:17 and/or SEQ ID NO:18 and, as such, have amino acid sequences that include at least a portion of SEQ ID NO:19; polypeptides encoded by at least a portion of SEQ ID NO:20 and/or SEQ ID NO:21 and, as such, have amino acid sequences that include at least a portion of SEQ ID NO:22; polypeptides encoded by at least a portion of SEQ ID NO:23, SEQ ID NO:24, and/or SEQ ID NO:25 and, as such, have amino acid sequences that include at least a portion of SEQ ID NO:26; polypeptides encoded by at least a portion of SEQ ID NO:27, SEQ ID NO:28 and/or SEQ ID NO:29 and, as such, have amino acid sequences that include at least a portion of SEQ ID NO:30; polypeptides encoded by at least a portion of SEQ ID NO:90 and/or SEQ ID NO:31 and, as such, have amino acid sequences that include at least a portion of SEQ ID NO:32; polypeptides encoded by at least a portion of SEQ ID NO:33, SEQ ID NO:34 and/or SEQ ID NO:35 and, as such, have amino acid sequences that include at least a portion of SEQ ID NO:36; polypeptides encoded by at least a portion of SEQ ID NO:37 and/or SEQ ID NO:38 and, as such, have amino acid sequences that include at least a portion of SEQ ID NO:39; polypeptides encoded by at least a portion of SEQ ID NO:40, SEQ ID NO:41, and/or SEQ ID NO:42 and, as such, have amino acid sequences that include at least a portion of SEQ ID NO:43; polypeptides encoded by at least a portion of SEQ ID NO:44, SEQ ID NO:45, SEQ ID NO:46, and/or SEQ ID NO:47 and, as such, have amino acid sequences that include at least a portion of SEQ ID NO:48; polypeptides encoded by at least a portion of SEQ ID NO:49, SEQ ID NO:50, and/or SEQ ID NO:51 and, as such, have amino acid sequences that include at least a portion of SEQ ID NO:52; polypeptides encoded by at least a portion of SEQ ID NO:53, SEQ ID NO:54, and/or SEQ ID NO:55 and, as such, have amino acid sequences that include at least a portion of SEQ ID NO:56; polypeptides encoded by at least a portion of SEQ ID NO:57, SEQ ID NO:58, and/or SEQ ID NO:60 and, as such, have amino acid sequences that include at least a portion of SEQ ID NO:61; polypeptides encoded by at least a portion of SEQ ID NO:62, SEQ ID NO:63, and/or SEQ ID NO:64 and, as such, have amino acid sequences that include at least a portion of SEQ ID NO:65; polypeptides encoded by at least a portion of SEQ ID NO:66, and/or SEQ ID NO:67 and, as such, have amino acid sequences that include at least a portion of SEQ ID NO:68; polypeptides encoded by at least a portion of SEQ ID NO:69, SEQ ID NO:70, and/or SEQ ID NO:71 and, as such, have amino acid sequences that include at least a portion of SEQ ID NO:72; polypeptides encoded by at least a portion of SEQ ID NO:73, SEQ ID NO:74, and/or SEQ ID NO:75 and, as such, have amino acid sequences that include at least a portion of SEQ ID NO:76; polypeptides encoded by at least a portion of SEQ ID NO:77, SEQ ID NO:59, and/or SEQ ID NO:78 and, as such, have amino acid sequences that include at least a portion of SEQ ID NO:79; polypeptides encoded by at least a portion of SEQ ID NO:80, SEQ ID NO:81, and/or SEQ ID NO:82 and, as such, have amino acid sequences that include at least a portion of SEQ ID NO:83; and polypeptides encoded by at least a portion of SEQ ID NO:84, and/or SEQ ID NO:85 and, as such, have amino acid sequences that include at least a portion of SEQ ID NO:86. As used herein, "at least a portion" of a polynucleotide or polypeptide means a portion having the minimal size characteristics of such sequences, as described above, or any larger fragment of the full length molecule, up to and including the full length molecule. For example, a portion of a polynucleotide may be 12 nucleotides, 13 nucleotides, 14 nucleotides, 15 nucleotides, and so on, going up to the full length polynucleotide. Similarly, a portion of a polypeptide may be 4 amino acids, 5 amino acids, 6 amino acids, 7 amino acids, and so on, going up to the full length polypeptide. The length of the portion to be used will depend on the particular application. As discussed above, a portion of a polynucleotide useful as hybridization probe may be as short as 12 nucleotides. A portion of a polypeptide useful as an epitope may be as short as 4 amino acids. A portion of a polypeptide that performs the function of the full-length polypeptide would generally be longer than 4 amino acids.

Particularly preferred plant EG307 polypeptides of the present invention are polypeptides that include SEQ ID NO:3, SEQ ID NO:6, SEQ ID NO:9, SEQ ID NO:13, SEQ ID NO:16, SEQ ID NO:19, SEQ ID NO:22, SEQ ID NO:26, SEQ ID NO:30, SEQ ID NO:32, SEQ ID NO:36, SEQ ID NO:39, SEQ ID NO:43, SEQ ID NO:48, SEQ ID NO:52, SEQ ID NO:56, SEQ ID NO:61, SEQ ID NO:65, SEQ ID NO:68. SEQ ID NO:72, SEQ ID NO:76, SEQ ID NO:79, SEQ ID NO:83and/or SEQ ID NO:86 (including, but not limited to the encoded polypeptides, full-length polypeptides, processed polypeptides, fusion polypeptides and multivalent polypeptides thereof) as well as polypeptides that are truncated homologues of polypeptides that include at least portions of the aforementioned SEQ ID NOs. Examples of methods to produce such polypeptides are disclosed herein, including in the Examples section.

B. EG307 Polynucleotides

One embodiment of the present invention is an isolated plant polynucleotide that hybridizes under stringent hybridization conditions with at least one of the following genes: an *O. sativa* EG307 gene, an *O. rufipogon* EG307 gene, a *Z. mays mays* EG307 gene, a *Z. mays parviglumis* EG307 gene, a *Z. diploperennis* EG307 gene, and a *Z. luxurians* gene. The identifying characteristics of such genes are heretofore described. A polynucleotide of the present invention can include an isolated natural plant EG307 gene or a homologue thereof, the latter of which is described in more detail below. A polynucleotide of the present invention can include one or more regulatory regions, full-length or partial coding regions, or combinations thereof. The minimal size of a polynucleotide of the present invention is the minimal size that can form a stable hybrid with one of the aforementioned genes under stringent hybridization conditions. Suitable and preferred plants are disclosed above.

In accordance with the present invention, an isolated polynucleotide is a polynucleotide that has been removed from its natural milieu (i.e., that has been subject to human manipulation). As such, "isolated" does not reflect the extent to which the polynucleotide has been purified. An isolated polynucleotide can include DNA, RNA, or derivatives of either DNA or RNA.

An isolated plant EG307 polynucleotide of the present invention can be obtained from its natural source either as an entire (i.e., complete) gene or a portion thereof capable of forming a stable hybrid with that gene. An isolated plant EG307 polynucleotide can also be produced using recombinant DNA technology (e.g., polymerase chain reaction (PCR) amplification, cloning) or chemical synthesis. Isolated plant EG307 polynucleotides include natural polynucleotides and homologues thereof, including, but not limited to, natural allelic variants and modified polynucleotides in which nucleotides have been inserted, deleted, substituted, and/or inverted in such a manner that such modifications do not substantially interfere with the polynucleotide's ability to encode an EG307 polypeptide of the present invention or to form stable hybrids under stringent conditions with natural gene isolates.

A plant EG307 polynucleotide homologue can be produced using a number of methods known to those skilled in the art (see, for example, Sambrook et al., ibid.). For example, polynucleotides can be modified using a variety of techniques including, but not limited to, classic mutagenesis techniques and recombinant DNA techniques, such as site-directed mutagenesis, chemical treatment of a polynucleotide to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of polynucleotides and combinations thereof. Polynucleotide homologues can be selected from a mixture of modified nucleic acids by screening for the function of the polypeptide encoded by the nucleic acid (e.g., ability to elicit an immune response against at least one epitope of an EG307 polypeptide, ability to increase yield in a transgenic plant containing an EG307 gene) and/or by hybridization with an *O. sativa* EG307 gene, with an *O. rufipogon* EG307 gene, with a *Z. mays mays* EG307 gene, with a *Z. mays parviglumis* EG307 gene, a *Z. diploperennis* EG307 gene and/or a *Z. luxurians* EG307 gene.

An isolated polynucleotide of the present invention can include a nucleic acid sequence that encodes at least one plant EG307 polypeptide of the present invention, examples of such polypeptides being disclosed herein. Although the phrase "polynucleotide" primarily refers to the physical polynucleotide and the phrase "nucleic acid sequence" primarily refers to the sequence of nucleotides on the polynucleotide, the two phrases can be used interchangeably, especially with respect to a polynucleotide, or a nucleic acid sequence, being capable of encoding an EG307 polypeptide. As heretofore disclosed, plant EG307 polypeptides of the present invention include, but are not limited to, polypeptides having full-length plant EG307 coding regions, polypeptides having partial plant EG307 coding regions, fusion polypeptides, multivalent protective polypeptides and combinations thereof.

At least certain polynucleotides of the present invention encode polypeptides that selectively bind to immune serum derived from an animal that has been immunized with an EG307 polypeptide from which the polynucleotide was isolated.

A preferred polynucleotide of the present invention, when expressed in a suitable plant, is capable of increasing the yield of the plant. As will be disclosed in more detail below, such a polynucleotide can be, or encode, an antisense RNA, a molecule capable of triple helix formation, a ribozyme, or other nucleic acid-based compound.

One embodiment of the present invention is a plant EG307 polynucleotide that hybridizes under stringent hybridization conditions to an EG307 polynucleotide of the present invention, or to a homologue of such an EG307 polynucleotide, or to the complement of such a polynucleotide. A polynucleotide complement of any nucleic acid sequence of the present invention refers to the nucleic acid sequence of the polynucleotide that is complementary to (i.e., can form a complete double helix with) the strand for which the sequence is cited. It is to be noted that a double-stranded nucleic acid molecule of the present invention for which a nucleic acid sequence has been determined for one strand, that is represented by a SEQ ID NO, also comprises a complementary strand having a sequence that is a complement of that SEQ ID NO. As such, polynucleotides of the present invention, which can be either double-stranded or single-stranded, include those polynucleotides that form stable hybrids under stringent hybridization conditions with either a given SEQ ID NO denoted herein and/or with the complement of that SEQ ID NO, which may or may not be denoted herein. Methods to deduce a complementary sequences are known to those skilled in the art. Preferred is an EG307 polynucleotide that includes a nucleic acid sequence having at least about 65 percent, preferably at least about 70 percent, more preferably at least about 75 percent, more preferably at least about 80 percent, more preferably at least about 85 percent, more preferably at least about 90 percent and even more preferably at least about 95 percent homology with the corresponding region(s) of the nucleic acid sequence encoding at least a portion of an EG307 polypeptide. Particularly preferred is an EG307 polynucleotide capable of encoding at least a portion of an EG307 polypeptide that naturally is present in plants.

Particularly preferred EG307 polynucleotides of the present invention hybridize under stringent hybridization conditions with at least one of the following polynucleotides: SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:90, SEQ ID NO:31, SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, SEQ ID NO:64, SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, SEQ ID NO:78, SEQ ID NO:80, SEQ ID NO:81, SEQ ID NO:82, SEQ ID NO:84, and/or SEQ ID NO:85, or to a homologue or complement of such polynucleotide.

A preferred polynucleotide of the present invention includes at least a portion of nucleic acid sequence SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, SEQ ID NO:31, SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, SEQ ID NO:64, SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, and/or SEQ ID NO:78 that is capable of hybridizing (i.e., that hybridizes under stringent hybridization conditions) to an *O. sativa* EG307 gene, to a *O. rufipogon* EG307 gene, to a *Z. mays mays* EG307 gene, to a *Z. mays parviglumis* EG307 gene, to a *Z. diploperennis* EG307 gene and/or to a *Z. luxurians* EG307 gene of the present invention, as well as a polynucleotide that is an allelic variant of any of those polynucleotides. Such preferred polynucleotides can include nucleotides in addition to those included in the SEQ ID NOs, such as, but not limited to, a full-length gene, a full-length coding region, a polynucleotide encoding a fusion polypeptide, and/or a polynucleotide encoding a multivalent protective compound.

The present invention also includes polynucleotides encoding a polypeptide including at least a portion of SEQ ID NO:3, polynucleotides encoding a polypeptide having at least a portion of SEQ ID NO:6, polynucleotides encoding a polypeptide having at least a portion of SEQ ID NO:9, polynucleotides encoding a polypeptide having at least a portion of SEQ ID NO:13, polynucleotides encoding a polypeptide having at least a portion of SEQ ID NO:16, polynucleotides encoding a polypeptide having at least a portion of SEQ ID NO:19, polynucleotides encoding a polypeptide having at least a portion of SEQ ID NO:22, polynucleotides encoding a polypeptide having at least a portion of SEQ ID NO:26, polynucleotides encoding a polypeptide having at least a portion of SEQ ID NO:30, polynucleotides encoding a polypeptide having at least a portion of SEQ ID NO:36, polynucleotides encoding a polypeptide having at least a portion of SEQ ID NO:39, polynucleotides encoding a polypeptide having at least a portion of SEQ ID NO:43, polynucleotides encoding a polypeptide having at least a portion of SEQ ID NO:48, polynucleotides encoding a polypeptide having at least a portion of SEQ ID NO:52, polynucleotides encoding a polypeptide having at least a portion of SEQ ID NO:56, polynucleotides encoding a polypeptide having at least a portion of SEQ ID NO:61, polynucleotides encoding a polypeptide having at least a portion of SEQ ID NO:65, polynucleotides encoding a polypeptide having at least a portion of SEQ ID NO:68, polynucleotides encoding a polypeptide having at least a portion of SEQ ID NO:72, polynucleotides encoding a polypeptide having at least a portion of SEQ ID NO:76, polynucleotides encoding a polypeptide having at least a portion of SEQ ID NO:79, polynucleotides encoding a polypeptide having at least a portion of SEQ ID NO:83, and/or polynucleotides encoding a polypeptide having at least a portion of SEQ ID NO:86, including polynucleotides that have been modified to accommodate codon usage properties of the cells in which such polynucleotides are to be expressed.

Knowing the nucleic acid sequences of certain plant EG307 polynucleotides of the present invention allows one skilled in the art to, for example, (a) make copies of those polynucleotides, (b) obtain polynucleotides including at least a portion of such polynucleotides (e.g., polynucleotides including full-length genes, full-length coding regions, regulatory control sequences, truncated coding regions), and (c) obtain EG307 polynucleotides for other plants, particularly since, as described in detail in the Examples section, knowledge of *O. sativa* EG307 polynucleotides of the present invention enabled the isolation of *O. rufipogon, Zea mays mays, Zea mays parviglumis, Z. diploperennis*, and *Z. luxurians* EG307 polynucleotides of the present invention. Such polynucleotides can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify polynucleotides include libraries such as genomic DNA libraries, BAC libraries, YAC libraries, cDNA libraries prepared from isolated plant tissues, including, but not limited to, stems, reproductive structures/tissues, leaves, roots, and tillers; and libraries constructed from pooled cDNAs from any or all of the tissues listed above. In the case of rice, BAC libraries, available from Clemson University, are preferred. Similarly, preferred DNA sources to screen or from which to amplify polynucleotides include plant genomic DNA. Techniques to clone and amplify genes are disclosed, for example, in Sambrook et al., ibid. and in Galun & Breiman, TRANSGENIC PLANTS, Imperial College Press, 1997.

The present invention also includes polynucleotides that are oligonucleotides capable of hybridizing, under stringent hybridization conditions, with complementary regions of other, preferably longer, polynucleotides of the present invention such as those comprising plant EG307 genes or other plant EG307 polynucleotides. Oligonucleotides of the present invention can be RNA, DNA, or derivatives of either. The minimal size of such oligonucleotides is the size required to form a stable hybrid between a given oligonucleotide and the complementary sequence on another polynucleotide of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional polynucleotides, as primers to amplify or extend polynucleotides, as targets for expression analysis, as candidates for targeted mutagenesis and/or recovery, or in agricultural applications to alter EG307 polypeptide production or activity. Such agricultural applications include the use of such oligonucleotides in, for example, antisense-, triplex formation-, ribozyme- and/or RNA drug-based technologies. The present invention, therefore, includes such oligonucleotides and methods to enhance economic productivity in a plant by use of one or more of such technologies.

C. Recombinant Molecules

The present invention also includes a recombinant vector, which includes at least one plant EG307 polynucleotide of the present invention, inserted into any vector capable of delivering the polynucleotide into a host cell. Such a vector contains heterologous nucleic acid sequences, that is nucleic acid sequences that are not naturally found adjacent to polynucleotides of the present invention and that preferably are derived from a species other than the species from which the polynucleotide(s) are derived. As used herein, a derived polynucleotide is one that is identical or similar in sequence to a polynucleotide or portion of a polynucleotide, but can contain modifications, such as modified bases, backbone modifications, nucleotide changes, and the like. The vector can be either RNA or DNA, either prokaryotic or eukaryotic, and typically is a virus or a plasmid. Recombinant vectors can be used in the cloning, sequencing, and/or otherwise manipulating of plant EG307 polynucleotides of the present invention. One type of recombinant vector, referred to herein as a recombinant molecule and described in more detail below, can be used in the expression of polynucleotides of the present invention. Preferred recombinant vectors are capable of replicating in the transformed cell.

Suitable and preferred polynucleotides to include in recombinant vectors of the present invention are as disclosed herein for suitable and preferred plant EG307 polynucleotides per se. Particularly preferred polynucleotides to include in recombinant vectors, and particularly in recombinant molecules, of the present invention include SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, SEQ ID NO:31, SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, SEQ ID NO:64, SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, and/or SEQ ID NO:78.

Isolated plant EG307 polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell that is capable of expressing the polypeptide, the recombinant cell being produced by transforming a host cell with one or more polynucleotides of the present invention. Transformation of a polynucleotide into a cell can be accomplished by any method by which a polynucleotide can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotides of the present invention can remain extrachromosomal or can integrate into one or more sites within a chromosome of the transformed (i.e., recombinant) cell in such a manner that their ability to be expressed is retained. Suitable and preferred polynucleotides with which to transform a cell are as disclosed herein for suitable and preferred plant EG307 polynucleotides per se. Particularly preferred polynucleotides to include in recombinant cells of the present invention include SEQ ID NO:1, SEQ ID NO:91, SEQ ID. NO:2, SEQ ID NO:4, SEQ ID NO:5, SEQ ID NO:7, SEQ ID NO:10, SEQ ID NO:11, SEQ ID NO:12, SEQ ID NO:14, SEQ ID NO:15, SEQ ID NO:17, SEQ ID NO:18, SEQ ID NO:20, SEQ ID NO:21, SEQ ID. NO:23, SEQ ID NO:24, SEQ ID NO:25, SEQ ID NO:27, SEQ ID NO:28, SEQ ID NO:29, SEQ ID NO:30, SEQ ID NO:31, SEQ ID NO:33, SEQ ID NO:34, SEQ ID. NO:35, SEQ ID NO:37, SEQ ID NO:38, SEQ ID NO:40, SEQ ID NO:41, SEQ ID NO:42, SEQ ID NO:44, SEQ ID NO:45, SEQ ID NO:46, SEQ ID NO:47, SEQ ID NO:49, SEQ ID. NO:50, SEQ ID NO:51, SEQ ID NO:53, SEQ ID NO:54, SEQ ID NO:55, SEQ ID NO:57, SEQ ID NO:58, SEQ ID NO:60, SEQ ID NO:62, SEQ ID NO:63, SEQ ID NO:64, SEQ ID NO:66, SEQ ID NO:67, SEQ ID NO:69, SEQ ID. NO:70, SEQ ID NO:71, SEQ ID NO:73, SEQ ID NO:74, SEQ ID NO:75, SEQ ID NO:77, SEQ ID NO:59, and/or SEQ ID NO:78.

Suitable host cells to transform include any cell that can be transformed with a polynucleotide of the present invention. Host cells can be either untransformed cells or cells that are already transformed with at least one polynucleotide. Host cells of the present invention either can be endogenously (i.e., naturally) capable of producing plant EG307 polypeptides of the present invention or can be capable of producing such polypeptides after being transformed with at least one polynucleotide of the present invention. Host cells of the present invention can be any cell capable of producing at least one polypeptide of the present invention, and include bacterial, fungal (including yeast and rice blast, *Magnaporthe grisea*), parasite (including nematodes, especially of the genera *Xiphinema, Helicotylenchus*, and *Tylenchlohynchus*), insect, other animal and plant cells.

Suitable host viruses to transform include any virus that can be transformed with a polynucleotide of the present invention, including, but not limited to, rice stripe virus, and echinochloa hoja blanca virus.

In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

A recombinant cell is preferably produced by transforming a host cell with one or more recombinant molecules, each comprising one or more polynucleotides of the present invention operatively linked to an expression vector containing one or more transcription control sequences. The phrase "operatively linked" refers to insertion of a polynucleotide into an expression vector in a manner such that the molecule is able to be expressed in the correct reading frame when transformed into a host cell. As used herein, an expression vector is a DNA or RNA vector that is capable of transforming a host cell and of effecting expression of a specified polynucleotide. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, fungal, insect and mammalian cells and more preferably in the cell types heretofore disclosed.

Recombinant molecules of the present invention may also (a) contain secretory signals (i.e., signal segment nucleic acid sequences) to enable an expressed EG307 polypeptide of the present invention to be secreted from the cell that produces the polypeptide and/or (b) contain fusion sequences which lead to the expression of polynucleotides of the present invention as fusion polypeptides. Examples of suitable signal segments and fusion segments encoded by fusion segment nucleic acids are disclosed herein. Eukaryotic recombinant molecules may include intervening and/or untranslated sequences surrounding and/or within the nucleic acid sequences of polynucleotides of the present invention. Suitable signal segments include natural signal segments or any heterologous signal segment capable of directing the secretion of a polypeptide of the present invention. Preferred signal and fusion sequences employed to enhance organ and organelle specific expression include, but are not limited to, arcelin-5, see Goossens, A. et. al. The arcelin-5 Gene of Phaseolus vulgaris directs high seed-specific expression in transgenic *Phaseolus acutifolius* and *Arabidopsis* plants. Plant Physiology (1999) 120:1095-1104, phaseolin, see Sengupta-Gopalan, C. et. al. Developmentally regulated expression of the bean beta-phaseolin gene in tobacco seeds. PNAS (1985) 82:3320-3324, hydroxyproline-rich glycoprotein, serpin, see Yan, X. et. al. Gene fusions of signal sequences with a modified beta-glucuronidase gene results in retention of the beta-glucuronidase protein in the secretory pathway/plasma membrane. Plant Physiology (1997) 115:915-924, N-acetyl glucosaminyl transferase 1, see Essl, D. et. al. The N-terminal 77 amino acids from tobacco N-acetylglucosaminyltransferase I are sufficient to retain reporter protein in the Golgi apparatus of Nicotiana benthamiana cells. Febs Letters (1999) 453(1-2): 169-73, albumin, see Vandekerckhove, J. et. al. Enkephalins produced in transgenic plants using modified 2S seed storage proteins. BioTechnology 7:929-932 (1989) and PR1, see Pen, J. et. al. Efficient production of active industrial enzymes in plants. Industrial Crops and Prod. (1993) 1:241-250.

Polynucleotides of the present invention can be operatively linked to expression vectors containing regulatory sequences such as transcription control sequences, translation control sequences, origins of replication, and other regulatory sequences that are compatible with the recombinant cell and that control the expression of polynucleotides of the present invention. In particular, recombinant molecules of the present invention include transcription control sequences. Transcription control sequences are sequences which control the initiation, elongation, and termination of transcription. Included are those transcription control sequences which are sufficient to render promoter-dependent gene expression controllable for cell-type specific, tissue-specific or inducible by external signals or agents; such elements may be located in the 5' or 3' regions of the native gene. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, fungal, insect and mammalian cells, such as, but not limited to, tac, lac, trp, trc, oxy-pro, omp/lpp, rrnb, bacteriophage lambda (ë) (such as ëp$_L$ and ëp$_R$ and fusions that include such promoters), bacteriophage T7, T7lac, bacteriophage T3, bacteriophage SP6, bacteriophage SP01, metallothionein, á-mating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Particularly preferred transcription control sequences are plant transcription control sequences. The choice of transcription control sequence will vary depending on the temporal and spatial requirements for expression, and also depending on the target species. Thus, expression of the nucleotide sequences of this invention in any plant organ (leaves, roots, seedlings, immature or mature reproductive structures, etc.) or at any stage of plant development is preferred. Although many transcription control sequences from dicotyledons have been shown to be operational in monocotyledons and vice versa, ideally dicotyledonous transcription control sequences are selected for expression in dicotyledons, and monocotyledonous promoters for expression in monocotyledons. However, there is no restriction to the provenance of selected transcription control sequences; it is sufficient that they are operational in driving the expression of the nucleotide sequences in the desired cell.

Preferred transcription control sequences that are expressed constitutively include but are not limited to promoters from genes encoding actin or ubiquitin and the CaMV 35S and 19S promoters. The nucleotide sequences of this invention can also be expressed under the regulation of promoters that are chemically regulated. This enables the EG307 polypeptide to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is induced by the physiological state of the plant (i.e. wound inducible, water-stress inducible, salt-stress inducible, disease inducible, and the like). Numerous promoters have been described which are expressed at wound sites and also at the sites of phytopathogen infection. Ideally, such a promoter should only be active locally at the sites of infection, and in this way the EG307 polypeptides only accumulate in cells in which the accumulation is desired. Preferred promoters of this kind include those described by Stanford et al. Mol. Gen. Genet. 215: 200-208 (1989), Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), and Warner et al. Plant J. 3: 191-201 (1993).

Preferred tissue-specific expression patterns include but are not limited to green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579-589 (1989)). A preferred promoter for root specific expression is that described by de Framond (FEBS 290: 103-106 (1991); EP 0 452 269 to Ciba-Geigy). A preferred stem specific promoter is that described in U.S. Pat. No. 5,625,136 (to Ciba-Geigy) and which drives expression of the maize trpA gene.

A recombinant molecule of the present invention is a molecule that can include at least one of any polynucleotide heretofore described operatively linked to at least one of any transcription control sequence capable of effectively regulating expression of the polynucleotide(s) in the cell to be transformed, examples of which are disclosed herein.

A recombinant cell of the present invention includes any cell transformed with at least one of any polynucleotide of the present invention. Suitable and preferred polynucleotides as well as suitable and preferred recombinant molecules with which to transfer cells are disclosed herein.

Recombinant cells of the present invention can also be co-transformed with one or more recombinant molecules including plant EG307 polynucleotides encoding one or more polypeptides of the present invention and one or more other polypeptides useful when expressed in plants.

It may be appreciated by one skilled in the art that use of recombinant DNA technologies can improve expression of transformed polynucleotides by manipulating, for example, the number of copies of the polynucleotides within a host cell, the efficiency with which those polynucleotides are transcribed, the efficiency with which the resultant transcripts are translated, and the efficiency of post-translational modifications. Recombinant techniques useful for increasing the expression of polynucleotides of the present invention include, but are not limited to, operatively linking polynucleotides to high-copy number plasmids, integration of the polynucleotides into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotides of the present invention to correspond to the codon usage of the host cell, deletion of sequences that destabilize transcripts, and use of control signals that temporally separate recombinant cell growth from recombinant enzyme production during fermentation. The activity of an expressed recombinant polypeptide of the present invention may be improved by fragmenting, modifying, or derivatizing polynucleotides encoding such a polypeptide.

Recombinant cells of the present invention can be used to produce one or more polypeptides of the present invention by culturing such cells under conditions effective to produce such a polypeptide, and recovering the polypeptide. Effective conditions to produce a polypeptide include, but are not limited to, appropriate media, bioreactor, temperature, pH and oxygen conditions that permit polypeptide production. An appropriate, or effective, medium refers to any medium in which a cell of the present invention, when cultured, is capable of producing an EG307 polypeptide of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant polypeptides of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the polypeptide" refers simply to collecting the whole fermentation medium containing the polypeptide and need not imply additional steps of separation or purification. Polypeptides of the present invention can be purified using a variety of standard polypeptide purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Polypeptides of the present invention are preferably retrieved in "substantially pure" form. As used herein, "substantially pure" refers to a purity that allows for the effective use of the polypeptide as a diagnostic or test compound, and means, with increasing preference, at least 50%, 60%, 70%, 80%, 90%, 95%, or 98% homogeneous.

D. Transfected Plant Cells and Transgenic Plants

With regard to EG307, particularly preferred recombinant cells are plant cells. By "eplant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

In a particularly preferred embodiment, at least one of the EG307 polypeptides or an allele thereof, of the invention is expressed in a higher organism, e.g., a plant. In this case, transgenic plants expressing effective amounts of the polypeptides exhibit improved economic productivity. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, millet, chickpea, lentil, flax, olive, fig almond, pistachio, walnut, beet, parsnip, citrus fruits, including, but not limited to, orange, lemon, lime, grapefruit, tangerine, minneola, and tangelo, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis*, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

Accordingly, the present invention provides a method for producing a transfected plant cell or transgenic plant comprising the steps of a) transfecting a plant cell to contain a heterologous DNA segment encoding a protein and derived from an EG307 polynucleotide not native to said cell (the polynucleotide indeed could be native but the expression pattern could be developmentally altered, still leading to the preferred effect); wherein said polynucleotide is operably linked to a promoter that can be used effectively for expression of transgenic proteins; b) optionally growing and maintaining said cell under conditions whereby a transgenic plant is regenerated therefrom; c) optionally growing said transgenic plant under conditions whereby said DNA is expressed, whereby the total amount of EG307 polypeptide in said plant is altered. In a preferred embodiment, the method further comprises the step of obtaining and growing additional generations of descendants of said transgenic plant which comprise said heterologous DNA segment wherein said heterologous DNA segment is expressed. As used herein, "heterologous DNA", or in some cases, "transgene" refers to foreign genes or polynucleotides, or additional, or modified versions of native or endogenous genes or polynucleotides (perhaps driven by different promoters) in order to alter the traits of a plant in a specific manner.

The invention also provides plant cells which comprise heterologous DNA encoding an EG307 polypeptide. In a preferred embodiment, the transgenic plant cell is a propagation material of a transgenic plant. The present invention also provides a transfected host cell comprising a host cell transfected with a construct comprising a promoter, enhancer or intron polynucleotide from an evolutionarily significant EG307 polynucleotide, and a polynucleotide encoding a reporter protein.

The present invention also provides a method of providing improved economic productivity in a plant comprising: a) producing a transfected plant cell having a transgene encoding an EG307 polypeptide whereby EG307 expression in said plant cell is altered; and b) growing a transgenic plant from the transfected plant cell wherein the EG307 transgene is expressed in the transgenic plant. The expression of the transgene includes an increase in EG307 expression. In some embodiments, the expression of the transgene produces an RNA that may interfere with a native EG307 gene such that the expression of the native gene is either eliminated or reduced, resulting in a useful outcome.

The invention also provides a transgenic plant containing heterologous DNA which encodes an EG307 polypeptide that is expressed in plant tissue, including expression in a vector introduced into the plant.

The present invention also provides an isolated polynucleotide which includes a transcription control element operably linked to a polynucleotide that encodes the EG307 gene in plant tissue. In preferred embodiment, the transcription control element is the promoter native to an EG307 gene.

The present invention also provides a method of making a transfected cell comprising a) identifying an evolutionarily significant EG307 polynucleotide in a domesticated plant; b) using said EG307 polynucleotide to identify a non-polypeptide coding sequence that may be a transcription or translation regulatory element, enhancer, intron or other 5' or 3' flanking sequence; c) assembling a construct comprising said non-polypeptide coding sequence and a polynucleotide encoding a reporter protein; and d) transfecting said construct into a host cell. The present invention also provides a transfected cell produced according to this method. In one embodiment, the host cell is a plant cell, and the method further comprises the step of growing and maintaining the cell under conditions suitable for regenerating a transgenic plant. Also provided is a transgenic plant produced by the method.

A nucleotide sequence of this invention is preferably expressed in transgenic plants, thus causing the biosynthesis of the corresponding EG307 polypeptide in the transgenic plants. In this way, transgenic plants with characteristics related to improved economic productivity are generated. For their expression in transgenic plants, the nucleotide sequences of the invention may require modification and optimization. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17. 477-498 (1989)). All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol), and WO 93/07278 (to Ciba-Geigy).

For efficient initiation of translation, sequences adjacent to the initiating methionine may require modification. For example, they can be modified by the inclusion of sequences known to be effective in plants. Joshi has suggested an appropriate consensus for plants (NAR 15: 6643-6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

Expression of the nucleotide sequences in transgenic plants is driven by transcription control elements shown to be functional in plants. Transformation of plants with a polynucleotide under the control of these regulatory elements provides for controlled expression in the transformed plant. Such transcription control elements have been described above. In addition to the selection of a suitable initiator of transcription, constructions for expression of EG307 polypeptide in plants require an appropriate transcription terminator to be attached downstream of the heterologous nucleotide sequence. Several such terminators are available and known in the art (e.g. tm1 from CaMV, E9 from rbcS). Any available terminator known to function in plants can be used in the context of this invention.

Numerous other sequences can be incorporated into expression cassettes described in this invention. These include sequences which have been shown to enhance expression such as intron sequences (e.g. from Adh1 and bronze1) and viral leader sequences (e.g. from TMV, MCMV and AMV).

The present invention also provides a method of increasing yield in a plant comprising a) producing a transgenic plant cell having a transgene encoding an EG307 polypeptide and the transgene is under the control of regulatory sequences suitable for controlled expression of the gene(s); and b) growing a transgenic plant from the transgenic plant cell wherein the EG307 transgene is expressed in the transgenic plant.

The present invention also provides a method of increasing yield in a plant comprising a) producing a transfected plant cell having a transgene containing the EG307 gene under the control of a promoter providing constitutive expression of the EG307 gene; and b) growing a transgenic plant from the transgenic plant cell wherein the EG307 transgene is expressed constitutively in the transgenic plant.

The present invention also provides a method of providing controllable yield in a transgenic plant comprising: a) producing a transfected plant cell having a transgene containing the EG307 gene under the control of a promoter providing controllable expression of the EG307 gene; and b) growing a transgenic plant from the transgenic plant cell wherein the EG307 transgene is controllably expressed in the transgenic plant. In one embodiment, the EG307 gene is expressed using a tissue-specific or cell type-specific promoter, or by a promoter that is activated by the introduction of an external signal or agent, such as a chemical signal or agent.

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of heterologous DNA encoded polypeptides is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093-1096 (1986)). For both direct gene transfer and *Agrobacterium*-mediated transfer, transformation is usually (but not necessarily) undertaken with a selectable marker which may provide resistance to an antibiotic (kanamycin, hygromycin or methotrexate) or a herbicide (basta). The choice of selectable marker is not, however, critical to the invention.

In another preferred embodiment, a nucleotide sequence of the present invention is directly transformed into the plastid genome. A major advantage of plastid transformation is that plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-polypeptide antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19: 4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant polypeptide. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

The present invention also provides a method of identifying a plant yield-related gene comprising: a) providing a plant tissue sample; b) introducing into the plant tissue sample a candidate plant yield-related gene; c) expressing the candidate plant yield-related gene within the plant tissue sample; and d) determining whether the plant tissue sample exhibits change in yield response, whereby a change in response identifies a plant yield-related gene. The present invention also provides plant yield-related genes isolated according to the method.

Yield response, as used herein, is measured by techniques well known to those skilled in the art. In the cereals yield response is determined, for example, by one or more of the following metrics, grain weight, grain length, grain weight/ 1000 grain, size of panicle, number of panicles, and number of grains/panicle.

E. EG307 Antibodies

The present invention also includes isolated antibodies capable of selectively binding to an EG307 polypeptide of the present invention or to a mimetope thereof. Such antibodies are also referred to herein as anti-EG307 antibodies. Particularly preferred antibodies of this embodiment include anti-*O. sativa* EG307 antibodies, anti-*O. rufipogon* EG307 antibodies, and anti-*Z. mays* EG307 antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified polypeptides and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid., and Harlow & Lane, 1990, ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the polypeptide or mimetope used to obtain the antibodies. Antibodies of the present invention also include chimeric antibodies that can bind to more than one epitope. Preferred antibodies are raised in response to polypeptides, or mimetopes thereof, that are encoded, at least in part, by a polynucleotide of the present invention.

A preferred method to produce antibodies of the present invention includes (a) administering to an animal an effective amount of a polypeptide or mimetope thereof of the present invention to produce the antibodies and (b) recovering the antibodies. In another method, antibodies of the present invention are produced recombinantly using techniques as heretofore disclosed to produce EG307 polypeptides of the present invention. Antibodies raised against defined polypeptides or mimetopes can be advantageous because such antibodies are not substantially contaminated with antibodies against other substances that might otherwise cause interference in a diagnostic assay.

Antibodies of the present invention have a variety of potential uses that are within the scope of the present invention. For example, such antibodies can be used (a) as reagents in assays to detect expression of EG307 by plant and/or (b) as tools to screen expression libraries and/or to recover desired polypeptides of the present invention from a mixture of polypeptides and other contaminants. Furthermore, antibodies of the present invention can be used to target cytotoxic agents to plants in order to directly kill such plants. Targeting can be accomplished by conjugating (i.e., stably joining) such antibodies to the cytotoxic agents using techniques known to those skilled in the art. Suitable cytotoxic agents are known to those skilled in the art. Suitable cytotoxic agents include, but are not limited to: double-chain polypeptides (i.e., toxins having A and B chains), such as diphtheria toxin, ricin toxin, Pseudomonas exotoxin, modeccin toxin, abrin toxin, and shiga toxin; single-chain toxins, such as pokeweed antiviral polypeptide, á-amanitin, and ribosome inhibiting polypeptides; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

F. Formulation of Growth-Enhancing Compositions

The invention also includes compositions comprising at least one of the EG307 polypeptides of the present invention. In order to effectively control growth such compositions preferably contain sufficient amounts of polypeptide. Such amounts vary depending on the target crop, and on the environmental conditions, such as humidity, temperature or type of soil. In a preferred embodiment, compositions comprising the EG307 polypeptide comprise host cells expressing the polypeptides without additional purification. In another preferred embodiment, the cells expressing the EG307 polypeptides are lyophilized prior to their use as a growth-enhancing agent. In another embodiment, the EG307 polypeptides are engineered to be secreted from the host cells. In cases where purification of the polypeptides from the host cells in which they are expressed is desired, various degrees of purification of the EG307 polypeptides are reached.

The present invention further embraces the preparation of compositions comprising at least one EG307 polypeptide of the present invention, which is homogeneously mixed with one or more compounds or groups of compounds described herein. The present invention also relates to methods of treating plants, which comprise application of the EG307 polypeptides or compositions containing the EG307 polypeptides, to plants. The EG307 polypeptides can be applied to the crop area in the form of compositions or plant to be treated, simultaneously or in succession, with further compounds. These compounds can be both fertilizers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying EG307 polypeptides of the present invention is by spraying the soil, water, or foliage of plants. The number of applications and the rate of application depend on the type of plant and the desired increase in yield. The EG307 polypeptides can also penetrate the plant through the roots via the soil (systemic action) by impregnating the locus of the plant with a liquid composition, or by applying the compounds in solid form to the soil, e.g. in granular form (soil application). The EG307 polypeptides may also be applied to seeds (coating) by impregnating the seeds either with a liquid formulation containing EG307 polypeptides, or coating them with a solid formulation. In special cases, further types of application are also possible, for example, selective treatment of the plant stems or buds.

The EG307 polypeptides are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances.

The formulations, compositions or preparations containing the EG307 polypeptides and, where appropriate, a solid or liquid adjuvant, are prepared in a known manner, for example by homogeneously mixing and/or grinding the EG307 polypeptides with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one C8-C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide. The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

IV. Identification of Genes Evolved Under Neutral Conditions

As described in detail herein, $K_A/K_S$ analysis allows the identification of positively selected protein-coding genes; however, this type of analysis can also be used to identify genes evolving under neutral conditions, and this can allow the identification of another set of commercially valuable genes.

A $K_A/K_S$ ratio>1 signifies the role of positive selection, while conversely, a $K_A/K_S$ ratio<1 suggests that a protein-coding gene has been negatively selected (i.e., has been conserved). As noted elsewhere herein, most genes (in fact, the vast majority) are conserved. Only rare genes exhibit a $K_A/K_S$ ratio>1, since very few genes are positively selected. As described herein, genes that were positively selected during domestication of the cereals (as well as other crops) have significant commercial value; however, another set of genes contained in the genomes of domesticated plants has been neither positively (to produce a desired, enhanced trait in the domesticated descendant) nor negatively selected (conserved). This subset of plant genes, as noted above, also has a significant commercial value, and this set of genes can be identified by using $K_A/K_S$ analysis, to be described here.

These genes comprise those that render the plant resistant to drought, disease, pests (including, but not limited to, insects, animal herbivores, and microbes), high salt levels, and other stresses. Attacks by pests, and damage by drought or high salt levels, etc, are responsible for annual losses of billions of dollars to farmers, seed companies, and the large agricultural companies. The identification of genes that render wild plants resistant to these stresses is thus of great value, both socially (to a hungry world), and economically.

The method to detect these genes is as follows. When plants are first domesticated (and subsequently, as the descendents are further domesticated), they are "pampered", in the sense, for example, that humans supply water in sufficient quantities to meet the plant's needs. Thus the plant is not required to deal with drought stress "on its own". Similarly, humans remove insect pests (either physically, or through the use of pesticides), and segregate domesticated plants away from animal herbivores, such that the domesticated plant is not constantly confronted with the need to deal with these pests. In fact, it has been well documented that domesticated cereals, for example, are usually much more vulnerable to drought, high salt levels, pests, and other stresses than are their wild relatives/ancestors. This is because organisms generally do not maintain abilities that are not required to survive. As humans take over these roles, domesticated plants can save the high metabolic costs ("metabolic extravagance") of maintaining genes that code for stress-related traits.

This loss of resistance must of course stem from genetic differences (i.e., changes) between the ancestor and its pampered domesticated descendent. These genetic changes that result in loss of function can occur through three different mechanisms. The genes that code for these traits may actually be lost from the genome of the descendent crop. Gene loss has been documented and is a well-known phenomenon. Similarly, the genes that code for "unneeded" traits in a descendent crop may still persist in the genome, but are no longer expressed, as a result of promoter changes, for example. Alternatively, the genes coding for these unneeded traits may still be part of the genome, and may still be expressed, but the genes may have accumulated nucleotide substitutions that render the protein product either nonfunctional or less fully functional than the ancestral homolog. These genes are thus evolving neutrally.

Neutral amino acid replacements accumulate in the protein product of a gene that is free of selective pressures (either positive or negative). For a domesticated plant that has been freed of the need to maintain a functional protein product for the gene of interest, a condition of molecular neutrality exits. This includes genes that code for traits like pest, disease, drought, salt, etc., resistance. Such fully unconstrained, neutrally evolving genes are perfect candidates for detection by $K_A/K_S$ analysis, as a neutrally evolving gene will ideally exhibit a $K_A/K_S$ ratio=1, when the homolog from the ancestral and descendant plants are compared.

Thus the method invented and described here involves high-throughput sequencing of a cDNA library for an ancestral plant, BLASTING the resulting ESTs against a database of ESTs from the modern descendent, and performing $K_A/K_S$ analysis for homologous pairs. The details of this process are explained elsewhere in this patent, for the case of a positively selected gene. The real innovation here is the realization that the genes with a $K_A/K_S$ ratio=1 will be the set of genes that control important stress resistant traits, and that these genes can be effectively and swiftly identified by use of this ratio. To reiterate, those $K_A/K_S$ comparisons that yield ratios of about 1 will include the set of neutrally evolving stress genes. This commercially valuable set of genes includes those coding for desirable traits such resistance to pests, disease, drought, high salt levels, etc. To best identify these genes, the EST sequencing from both the modern domesticated and the ancestral species should be performed very carefully, with a high standard of accuracy. While one can make use of cereal EST databases available in GenBank, one may also resequence ESTs from cDNA libraries prepared specifically for this purpose. The accuracy of sequencing is important, because this will give rise to a very narrow distribution of gene pair comparisons between ancestral and modern homologs that have a $K_A/K_S$ ratio equal to one. This will reduce the number of false positives to a minimum, thus expediting the process.

When the accuracy of the screening process is not stringently controlled, or is unknown, it is possible that sequencing errors will obscure a $K_A/K_S$ ratio of 1.0, and for this reason, $K_A/K_S$ values of between about 0.75-1.25 are checked carefully for evidence of neutral evolution. One way to determine whether a $K_A/K_S$ value in this range is due to neutral evolution or negative selection is to employ a statistical analysis. A $K_A/K_S$ of less than one, if supported by a high t value (of at least 1.645), will almost always indicate a negatively selected gene; however, because of the nature of the calculations, it is virtually impossible to ever find a $K_A/K_S$ value equal to one that would display a high t value.

Polynucleotides that have evolved under neutral conditions can then be mapped onto one of the known quantitative trait loci, or QTL, whereby the specific stress-resistance trait controlled by that polynucleotide may be rapidly and conclusively identified.

V. Screening Methods for Identification of Agents

The present invention also provides screening methods using the polynucleotides and polypeptides identified and characterized using the above-described methods. These screening methods are useful for identifying agents which may modulate the function(s) of the polynucleotides or polypeptides in a manner that would be useful for enhancing or diminishing a characteristic in a domesticated or ancestor organism. Generally, the methods entail contacting at least one agent to be tested with a domesticated organism, ancestor organism, or transgenic organism or cell that has been transfected with a polynucleotide sequence identified by the methods described above, or a preparation of the polypeptide encoded by such polynucleotide sequence, wherein an agent is identified by its ability to modulate function of either the polynucleotide sequence or the polypeptide. For example, an agent can be a compound that is applied or contacted with a domesticated plant or animal to induce expression of the identified gene at a desired time. Specifically in regard to plants, an agent could be used, for example, to induce flowering at an appropriate time.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

To "modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly. A "function" of a polynucleotide includes, but is not limited to, replication, translation, and expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function. The ways that an effective agent can act to modulate the expression of a polynucleotide include, but are not limited to 1) modifying binding of a transcription factor to a transcription factor responsive element in the polynucleotide; 2) modifying the interaction between two transcription factors necessary for expression of the polynucleotide; 3) altering the ability of a transcription factor necessary for expression of the polynucleotide to enter the nucleus; 4) inhibiting the activation of a transcription factor involved in transcription of the polynucleotide; 5) modifying a cell-surface receptor which normally interacts with a ligand and whose binding of the ligand results in expression of the polynucleotide; 6) inhibiting the inactivation of a component of the signal transduction cascade that leads to expression of the polynucleotide; and 7) enhancing the activation of a transcription factor involved in transcription of the polynucleotide.

A "function" of a polypeptide includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

Generally, the choice of agents to be screened is governed by several parameters, such as the particular polynucleotide or polypeptide target, its perceived function, its three-dimensional structure (if known or surmised), and other aspects of rational compound design. Techniques of combinatorial chemistry can also be used to generate numerous permutations of candidates. Those of skill in the art can devise and/or obtain suitable agents for testing.

The in vivo screening assays described herein may have several advantages over conventional drug screening assays: 1) if an agent must enter a cell to achieve a desired therapeutic effect, an in vivo assay can give an indication as to whether the agent can enter a cell; 2) an in vivo screening assay can identify agents that, in the state in which they are added to the assay system are ineffective to elicit at least one characteristic which is associated with modulation of polynucleotide or polypeptide function, but that are modified by cellular components once inside a cell in such a way that they become effective agents; 3) most importantly, an in vivo assay system allows identification of agents affecting any component of a pathway that ultimately results in characteristics that are associated with polynucleotide or potypeptide function.

In general, screening can be performed by adding an agent to a sample of appropriate cells which have been transfected with a polynucleotide identified using the methods of the present invention, and monitoring the effect, i.e., modulation of a function of the polynucleotide or the polypeptide encoded within the polynucleotide. The experiment preferably includes a control sample which does not receive the candidate agent. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, the interactions of the cells when exposed to infectious agents, and the ability of the cells to interact with other cells or compounds. Differences between treated and untreated cells indicate effects attributable to the candidate agent. Optimally, the agent has a greater effect on experimental cells than on control cells. Appropriate host cells include, but are not limited to, eukaryotic cells, preferably plant or animal cells. The choice of cell will at least partially depend on the nature of the assay contemplated.

To test for agents that upregulate the expression of a polynucleotide, a suitable host cell transfected with a polynucleotide of interest, such that the polynucleotide is expressed (as used herein, expression includes transcription and/or translation) is contacted with an agent to be tested. An agent would be tested for its ability to result in increased expression of mRNA and/or polypeptide. Methods of making vectors and transfection are well known in the art. "Transfection" encompasses any method of introducing the exogenous sequence, including, for example, lipofection, transduction, infection or electroporation. The exogenous polynucleotide may be maintained as a non-integrated vector (such as a plasmid) or may be integrated into the host genome.

To identify agents that specifically activate transcription, transcription regulatory regions could be linked to a reporter gene and the construct added to an appropriate host cell. As used herein, the term "reporter gene" means a gene that encodes a gene product that can be identified (i.e., a reporter protein). Reporter genes include, but are not limited to, alkaline phosphatase, chloramphenicol acetyltransferase, β-galactosidase, luciferase and green fluorescence protein (GFP). Identification methods for the products of reporter genes include, but are not limited to, enzymatic assays and fluorimetric assays. Reporter genes and assays to detect their products are well known in the art and are described, for example in Ausubel et al. (1987) and periodic updates. Reporter genes, reporter gene assays, and reagent kits are also readily available from commercial sources. Examples of appropriate cells include, but are not limited to, plant, fungal, yeast, mammalian, and other eukaryotic cells. A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element. The effect of an agent on transcription from the regulatory region in these constructs would be assessed through the activity of the reporter gene product.

Besides the increase in expression under conditions in which it is normally repressed mentioned above, expression could be decreased when it would normally be expressed. An agent could accomplish this through a decrease in transcription rate and the reporter gene system described above would be a means to assay for this. The host cells to assess such agents would need to be permissive for expression.

Cells transcribing mRNA (from the polynucleotide of interest) could be used to identify agents that specifically modulate the half-life of mRNA and/or the translation of mRNA. Such cells would also be used to assess the effect of an agent on the processing and/or post-translational modification of the polypeptide. An agent could modulate the amount of polypeptide in a cell by modifying the turn-over (i.e., increase or decrease the half-life) of the polypeptide. The specificity of the agent with regard to the mRNA and polypeptide would be determined by examining the products in the absence of the agent and by examining the products of unrelated mRNAs and polypeptides. Methods to examine mRNA half-life, protein processing, and protein turn-over are well known to those skilled in the art.

In vivo screening methods could also be useful in the identification of agents that modulate polypeptide function through the interaction with the polypeptide directly. Such agents could block normal polypeptide-ligand interactions, if any, or could enhance or stabilize such interactions. Such agents could also alter a conformation of the polypeptide. The effect of the agent could be determined using immunoprecipitation reactions. Appropriate antibodies would be used to precipitate the polypeptide and any protein tightly associated with it. By comparing the polypeptides immunoprecipitated from treated cells and from untreated cells, an agent could be identified that would augment or inhibit polypeptide-ligand interactions, if any. Polypeptide-ligand interactions could also be assessed using cross-linking reagents that convert a close, but noncovalent interaction between polypeptides into a covalent interaction. Techniques to examine protein-protein interactions are well known to those skilled in the art. Techniques to assess protein conformation are also well known to those skilled in the art.

It is also understood that screening methods can involve in vitro methods, such as cell-free transcription or translation systems. In those systems, transcription or translation is allowed to occur, and an agent is tested for its ability to modulate function. For an assay that determines whether an agent modulates the translation of mRNA or a polynucleotide, an in vitro transcription/translation system may be used. These systems are available commercially and provide an in vitro means to produce mRNA corresponding to a polynucleotide sequence of interest. After mRNA is made, it can be translated in vitro and the translation products compared. Comparison of translation products between an in vitro expression system that does not contain any agent (negative control) with an in vitro expression system that does contain an agent indicates whether the agent is affecting translation. Comparison of translation products between control and test polynucleotides indicates whether the agent, if acting on this level, is selectively affecting translation (as opposed to affecting translation in a general, non-selective or non-specific fashion). The modulation of polypeptide function can be accomplished in many ways including, but not limited to, the in vivo and in vitro assays listed above as well as in in vitro assays using protein preparations. Polypeptides can be extracted and/or purified from natural or recombinant sources to create protein preparations. An agent can be added to a sample of a protein preparation and the effect monitored; that is whether and how the agent acts on a polypeptide and affects its conformation, folding (or other physical characteristics), binding to other moieties (such as ligands), activity (or other functional characteristics), and/or other aspects of protein structure or functions is considered to have modulated polypeptide function.

In an example for an assay for an agent that binds to a polypeptide encoded by a polynucleotide identified by the methods described herein, a polypeptide is first recombinantly expressed in a prokaryotic or eukaryotic expression system as a native or as a fusion protein in which a polypeptide (encoded by a polynucleotide identified as described above) is conjugated with a well-characterized epitope or protein. Recombinant polypeptide is then purified by, for instance, immunoprecipitation using appropriate antibodies or anti-epitope antibodies or by binding to immobilized ligand of the conjugate. An affinity column made of polypeptide or fusion protein is then used to screen a mixture of compounds which have been appropriately labeled. Suitable labels include, but are not limited to fluorochromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. Similar methods can be used for screening for an agent(s) that competes for binding to polypeptides. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) *Cell* 80: 661-670) that is covalently coupled to polypeptide may be performed to determine the binding activity of different agents.

It is also understood that the in vitro screening methods of this invention include structural, or rational, drug design, in which the amino acid sequence, three-dimensional atomic structure or other property (or properties) of a polypeptide provides a basis for designing an agent which is expected to bind to a polypeptide. Generally, the design and/or choice of agents in this context is governed by several parameters, such as side-by-side comparison of the structures of a domesticated organism's and homologous ancestral polypeptides, the perceived function of the polypeptide target, its three-dimensional structure (if known or surmised), and other aspects of rational drug design. Techniques of combinatorial chemistry can also be used to generate numerous permutations of candidate agents.

Also contemplated in screening methods of the invention are transgenic animal and plant systems, which are known in the art.

The screening methods described above represent primary screens, designed to detect any agent that may exhibit activity that modulates the function of a polynucleotide or polypeptide. The skilled artisan will recognize that secondary tests will likely be necessary in order to evaluate an agent further. For example, a secondary screen may comprise testing the agent(s) in an assay using mice and other animal models (such as rat), which are known in the art or in the domesticated or ancestral plant or animal itself. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

The screening methods detailed earlier in this specification may be applied specifically to EG307. Accordingly, the invention provides a method of identifying an agent that modulates the function of the non-polypeptide coding regions of an EG307 polynucleotide, comprising contacting a host cell that has been transfected with a construct comprising the non-polypeptide coding region operabley linked to a reporter gene coding region, with at least one candidate agent, wherein the agent is identified by its ability to modulate the transcription or translation of said reporter polynucleotide. The present invention also provides agents identified by the method.

The present invention also provides a method of identifying an agent that modulates the function of the non-polypeptide coding regions of an evolutionarily significant EG307 polynucleotide, comprising contacting a plant or transgenic plant containing an EG307 polynucleotide with at least one candidate agent, wherein the agent is identified by its ability to modulate the transcription or translation of said reporter polynucleotide. The present invention also provides agents identified by the method.

The present invention also provides a method of identifying an agent which may modulate yield, said method comprising contacting at least one candidate agent with a plant or cell comprising an EG307 gene, wherein the agent is identified by its ability to modulate yield. In one embodiment the plant or cell is transfected with a polynucleotide encoding and EG307 gene. The present invention also provides agents identified by the method. In one embodiment, the identified agent modulates yield by modulating a function of the polynucleotide encoding the polypeptide. In another embodiment, the identified agent modulates yield by modulating a function of the polypeptide.

The invention also includes agents identified by the screening methods described herein.

The following examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

EXAMPLES

Example 1 cDNA Library Construction

A domesticated plant or animal cDNA library is constructed using an appropriate tissue from the plant or animal. A person of ordinary skill in the art would know the appropriate tissue or tissues to analyze according to the trait of interest. Alternately, the whole organism may be used. For example, 1 day old plant seedlings are known to express most of the plant's genes.

Total RNA is extracted from the tissue (RNeasy kit, Quiagen; RNAse-free Rapid Total RNA kit, 5 Prime-3 Prime, Inc., or any similar and suitable product) and the integrity and purity of the RNA are determined according to conventional molecular cloning methods. Poly A+ RNA is isolated (Mini-Oligo(dT) Cellulose Spin Columns, 5 Prime-3 Prime, Inc., or any similar and suitable product) and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. The library can be normalized and the numbers of independent recombinants in the library is determined.

Example 2

Sequence Comparison

Randomly selected ancestor cDNA clones from the cDNA library are sequenced using an automated sequencer, such as an ABI 377 or MegaBACE 1000 or any similar and suitable product. Commonly used primers on the cloning vector such as the M13 Universal and Reverse primers are used to carry out the sequencing. For inserts that are not completely sequenced by end sequencing, dye-labeled terminators or custom primers can be used to fill in remaining gaps.

The detected sequence differences are initially checked for accuracy, for example by finding the points where there are differences between the domesticated and ancestor sequences; checking the sequence fluorogram (chromatogram) to determine if the bases that appear unique to the domesticated organism correspond to strong, clear signals specific for the called base; checking the domesticated organism's hits to see if there is more than one sequence that corresponds to a sequence change; and other methods known in the art, as needed. Multiple domesticated organism sequence entries for the same gene that have the same nucleotide at a position where there is a different ancestor nucleotide provides independent support that the domesticated sequence is accurate, and that the domesticated/ancestor difference is real. Such changes are examined using public or commercial database information and the genetic code to determine whether these DNA sequence changes result in a change in the amino acid sequence of the encoded protein. The sequences can also be examined by direct sequencing of the encoded protein.

Example 3

Molecular Evolution Analysis

The domesticated plant or animal and wild ancestor sequences under comparison are subjected to $K_A/K_S$ analysis. In this analysis, publicly or commercially available computer programs, such as Li 93 and INA, are used to determine the number of non-synonymous changes per site ($K_A$) divided by the number of synonymous changes per site ($K_S$) for each sequence under study as described above. Full-length coding regions or partial segments of a coding region can be used. The higher the $K_A/K_S$ ratio, the more likely that a sequence has undergone adaptive evolution. Statistical significance of $K_A/K_S$ values is determined using established statistic methods and available programs such as the t-test.

To further lend support to the significance of a high $K_A/K_S$ ratio, the domesticated sequence under study can be compared to other evolutionarily proximate species. These comparisons allow further discrimination as to whether the adaptive evolutionary changes are unique to the domesticated plant or animal lineage compared to other closely related species. The sequences can also be examined by direct sequencing of the gene of interest from representatives of several diverse domesticated populations to assess to what degree the sequence is conserved in the domesticated plant or animal.

Example 4 cDNA Library Construction

A teosinte cDNA library is constructed using whole teosinte 1 day old seedlings, or other appropriate plant tissues. Total RNA is extracted from the seedling tissue and the integrity and purity of the RNA are determined according to conventional molecular cloning methods. Poly A+ RNA is selected and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. Recombinant DNA is used to transfect E. coli host cells, using established methods. The library can be normalized and the numbers of independent recombinants in the library is determined.

Example 5

Sequence Comparison

Randomly selected teosinte seedling cDNA clones from the cDNA library are sequenced using an automated sequencer, such as the ABI 377. Commonly used primers on the cloning vector such as the M13 Universal and Reverse primers are used to carry out the sequencing. For inserts that are not completely sequenced by end sequencing, dye-labeled terminators are used to fill in remaining gaps.

The resulting teosinte sequences are compared to domesticated maize sequences via database searches. Genome databases are publicly or commercially available for a number of species, including maize. One example of a maize database can be found at the MaizeDB website at the University of Missouri. MaizeDB is a public Internet gateway to current knowledge about the maize genome and its expression. Other appropriate maize EST (expressed sequence tag) databases are privately owned and maintained. The high scoring "hits," i.e., sequences that show a significant (e.g., >80%) similarity after homology analysis, are retrieved and analyzed. The two homologous sequences are then aligned using the alignment program CLUSTAL V developed by Higgins et al. Any sequence divergence, including nucleotide substitution, insertion and deletion, can be detected and recorded by the alignment.

The detected sequence differences are initially checked for accuracy by finding the points where there are differences between the teosinte and maize sequences; checking the sequence fluorogram (chromatogram) to determine if the bases that appear unique to maize correspond to strong, clear signals specific for the called base; checking the maize hits to see if there is more than one maize sequence that corresponds to a sequence change; and other methods known in the art as needed. Multiple maize sequence entries for the same gene that have the same nucleotide at a position where there is a different teosinte nucleotide provides independent support that the maize sequence is accurate, and that the teosinte/maize difference is real. Such changes are examined using public/commercial database information and the genetic code to determine whether these DNA sequence changes result in a change in the amino acid sequence of the encoded protein. The sequences can also be examined by direct sequencing of the encoded protein.

Example 6

Molecular Evolution Analysis

The teosinte and maize sequences under comparison are subjected to $K_A/K_S$ analysis. In this analysis, publicly or commercially available computer programs, such as Li 93 and INA, are used to determine the number of non-synonymous changes per site ($K_A$) divided by the number of synonymous changes per site ($K_S$) for each sequence under study as described above. This ratio, $K_A/K_S$, has been shown to be a reflection of the degree to which adaptive evolution, i.e., positive selection, has been at work in the sequence under study. Typically, full-length coding regions have been used in these comparative analyses. However, partial segments of a coding region can also be used effectively. The higher the $K_A/K_S$ ratio, the more likely that a sequence has undergone adaptive evolution. Statistical significance of $K_A/K_S$ values is determined using established statistic methods and available programs such as the t-test. Those genes showing statistically high $K_A/K_S$ ratios between teosinte and maize genes are very likely to have undergone adaptive evolution.

To further lend support to the significance of a high $K_A/K_S$ ratio, the sequence under study can be compared in other ancestral maize species. These comparisons allow further discrimination as to whether the adaptive evolutionary changes are unique to the domesticated maize lineage compared to other ancestors. The sequences can also be examined by direct sequencing of the gene of interest from representatives of several diverse maize populations to assess to what degree the sequence is conserved in the maize species.

Example 7

Application of $K_A/K_S$ Method to Maize and Teosinte Homologous Sequences Obtained from a Database Comparison of domesticated maize and teosinte sequences available on Genbank (accessable through the Entrez Nucleotides database at the National Center for Biotechnology Information web site) revealed at least four homologous genes: waxy, A1*, A1 and *globulin* for which sequence was available from both maize and teosinte. All available sequences for these genes for both maize and teosinte were compared. The $K_A/K_S$ ratios were determined using Li93 and/or INA:

| Gene | Avr. No. Syn. Substitutions | Avr. No. Non-Syn. Substitutions | $K_A/K_S$ |
|---|---|---|---|
| Waxy | 4 | 1 | 0.068 |
| A1* | 10 | 3 | 0.011 |
| A1 | 3 | 2 | 0.44–0.89 |
| Globulin | 10 | 7 | 0.42 |

Although it was anticipated that the polymorphism (multiple allelic copies) and/or the polyploidy (more than 2 sets of chromosomes per cell) observed in maize might make a $K_A/K_S$ analysis complex or difficult, it was found that this was not the case.

While the above $K_A/K_S$ values indicate that these genes are not positively selected, this example illustrates that the $K_A/K_S$ method can be applied to maize and its teosinte sequences obtained from a database.

Example 8

Study of Protein Function Using a Transgenic Plant

The functional roles of a positively selected maize gene obtained according to the methods of Examples 4-7 can be assessed by conducting assessments of each allele of the gene in a transgenic maize plant. A transgenic plant can be created using an adaptation of the method described in Peng et al. (1999) Nature 400:256-261. Physiological, morphological and/or biochemical examination of the transgenic plant or protein extracts thereof will permit association of each allele with a particular phenotype.

Example 9

Mapping of Positively Selected Genes to QTLs

QTL (quantitative trait locus) analysis has defined chromosomal regions that contain the genes that control several phenotypic traits of interest in maize, including plant height and oil content. By physically mapping each positively-selected gene identified by this method onto one of the known QTLs, the specific trait controlled by each positively-selected gene can be rapidly and conclusively identified.

Example 10

Discovery of New Gene EG307

A normalized cDNA library was constructed from pooled tissues (including leaves, panicles, and stems) of *Oryza rufipogon*, the species known to be ancestral to modern rice. A clone designated PBI0307H9 was first sequenced as part of a high-throughput sequencing project on a MegaBACE 1000 sequencer (AP Biotech). (SEQ ID NO:89) The sequence of this clone was used as a query sequence in a BLAST search of the GenBank database. Four anonymous rice ESTs (accession nos. AU093345, C29145, ISAJ0161, AU056792) were retrieved as hits. Further sequencing revealed that PBI307H9 was a partial cDNA clone. PBI307H9 had a high $K_A/K_S$ ratio when compared to the domesticated rice (*Oryza sativa*) ESTs in GenBank. cDNA amplification and sequencing were accomplished as follows: Total RNA was isolated from *O. rufipogon* (strain NSGC5953) and *O. sativa* cv. Nipponbare (Qiagen RNeasy Plant Mini Kit: cat #74903). First strand cDNA was synthesized using a dT primer (AP Biotech Ready-to-Go T-Primed First-Strand Kit: cat #27-9263-01) and then used for PCR analysis (Qiagen HotStarTaq Master Mix Kit: cat #203445).

For ease in nomenclature, the gene contained in clone PBI0307H9 is named EG307, both here and throughout. Initially, before final sequence confirmation, the Ka/Ks ratio for EG307 derived from modern rice (*O. sativa*) and ancestral rice (*O. rufipogon*) EG307 was 1.7.

Once these partial sequences were confirmed in both *O. rufipogon* and *O. sativa*, 5' RACE (Clontech SMART RACE cDNA Amplification Kit: cat #K1811-1) was performed with a gene specific primer to obtain the 5' end of this gene. The complete gene, termed EG307, has a coding region 1344 bp long. Final confirmation of the complete EG307 CDS (1344 bp) in *O. sativa* and *O. rufipogon* allowed pairwise comparisons of a number of strains of *O. rufipogon* and *O. sativa*. Many of these comparisons yield Ks/Ks ratios greater than one, some with statistical significance. This is compelling evidence for the role of positive selection on the EG307 gene. As the selection pressure imposed upon ancestral rice was human imposed, this is compelling evidence that EG307 is a gene that was selected for during human domestication of rice. No homologs to EG307 were identified by BLAST search to the non-redundant section of GenBank, and, as noted above, only four rice genes were identified by BLAST in the EST section of GenBank (AU093345, AU056792, C29145, and ISA0161). All four ESTs were essentially uncharacterized.

Example 11

$K_A/K_S$ Analysis of EG307

In order to ascertain the extent of genetic diversity present in *O. sativa* for the EG307 gene, genomic DNA was isolated from several different strains of *O. sativa* (acquired from the National Small Grains Collection, U.S.D.A., Aberdeen, Id.), using Qiagen's protocol (DNeasy Plant Mini Kit: cat #69103). EG307 was then sequenced in genomic DNA from six different *O. sativa* strains: Nipponbare, Lemont, IR64, Teqing, Azucena, and Kasalath. The $K_A/K_S$ ratios for each of these strains varied when compared to *O. rufipogon*. Table 1 shows results for the entire 1344 bases of coding region.

TABLE 1

Full CDS Ka/Ks ratios for *O. rufipogon* (strain IRGC105491) vs. all *O. sativa* strains examined.

| | Ka | Ks | Ka/Ks | size bp | Position (bp) in CDS | t |
|---|---|---|---|---|---|---|
| Azucena | 0.00668 | 0.00922 | 0.724 | 1341 | 1–1341 | 0.398 |
| Lemont | 0.00668 | 0.00922 | 0.724 | 1341 | 1–1341 | 0.398 |
| Nipponbare | 0.00668 | 0.00922 | 0.724 | 1341 | 1–1341 | 0.398 |
| Kasalath-1 | 0.00204 | 0.00483 | 0.422 | 1341 | 1–1341 | 0.552 |
| Kasalath-2 | 0.00293 | 0.00482 | 0.608 | 1341 | 1–1341 | 0.369 |
| Kasalath-3 | 0.00115 | 0.00483 | 0.238 | 1341 | 1–1341 | 0.740 |
| Kasalath-4 | 0.00204 | 0.00482 | 0.423 | 1341 | 1–1341 | 0.551 |
| IR64 | 0.00204 | 0.00700 | 0.291 | 1341 | 1–1341 | 0.902 |
| Teqing | 0.000 | 0.000 | DIV/0 | 1341 | 1–1341 | DIV/0 |

There were differences in the untranslated (UTR) regions between *O. rufipogon* and all these *O. sativa* strains. The wide range of $K_A/K_S$ ratios was expected due to the differing degrees of cross breeding among the *O. sativa* strains. Some were more similar to *O. rufipogon* than others due to cross breeding between *O. rufipogon* with the domesticated strains. Sliding window analysis was performed for all pairwise comparisons between the protein coding region of *O. rufipogon* EG307 to the protein coding region of each of the *O. sativa* strains we sequenced. This allowed identification of the specific areas of the protein that have been selected during domestication. Such pinpointing will allow a targeted approach to characterization of the changes that are important between the ancestral protein and the protein of the domesticated descendent crop plant. This may permit development of agents that target these vital domains of the protein, with the goal of increasing yield.

The length of the "window" was in most cases 150 bp, with a 50 bp overlap with adjacent windows. (Thus, as an example, if reading from the 5' end of a CDS, the first window was 150 bp in length, as was the adjacent second window to its 3' side. The second window, also 150 in length, overlapped the first window by 50 bp at the 5' end of the second window, and the third window, also 150 bp, overlapped the second window by 50 bp at the 5' end of the third window. Thus, the second window overlapped both its adjacent neighbors, each by 50 bp.) In addition a second window analysis was completed in which the CDS was divided approximately into halves. This allows a greater sample size of nucleotides, so that an accurate statistical sampling can be undertaken. It should also be noted that Ka/Ks, although conventionally expressed as a ratio, is really a way of asking "Does the Ka value exceed the Ks value by a statistically significant amount?" Thus, when Ks=0, as often happens in ancestral rice-to-modern rice comparisons (because there are only some 7,000-8,000 years of domestication), a ratio cannot be computed, since the denominator of the fraction would equal zero. However, such comparisons may still detect the action of positive selection, if the (Ka–Ks) difference is statistically significant. Thus for several comparisons shown in the following tables, positive selection can be detected, as long as the comparison is statistically significant. Like those comparisons for which the Ka/Ks ratio is significant, these are shown in bold.

It should also be noted that as a result of the stochastic nature of the nucleotide substitution process, not all comparisons to modern rice strains are expected to reveal evidence of positive selection, particularly since some cross breeding between *O. rufipogon* and modern *O. sativa* is known to have occurred.

TABLE 2

Sliding Window Ka/Ks Ratios for *O. rufipogon* (strain NSGC 5948) vs. *O. sativa*, strain "Nipponbare". Note that all statistically significant comparisons are shown in bold.

| | Ka | Ks | Ka/Ks | size bp | Position (bp) in CDS | t |
|---|---|---|---|---|---|---|
| Window #1 | 0.000 | 0.0178 | 0.000 | 165 | 91–255 | 0.965 |
| Window #2 | 0.00790 | 0.000 | DIV/0 | 150 | 256–405 | 0.999 |
| Window #3 | 0.000 | 0.000 | DIV/0 | 150 | 355–504 | DIV/0 |
| Window #4 | 0.000 | 0.000 | DIV/0 | 150 | 454–603 | DIV/0 |
| Window #5 | 0.0203 | 0.000 | DIV/0 | 150 | 556–705 | 1.40 |
| Window #6 | 0.0106 | 0.000 | DIV/0 | 150 | 655–804 | 0.994 |
| Window #7 | 0.0083 | 0.000 | DIV/0 | 150 | 754–903 | 0.999 |
| Window #8 | 0.0183 | 0.000 | DIV/0 | 150 | 856–1005 | 1.40 |
| Window #9 | 0.000 | 0.000 | DIV/0 | 150 | 955–1104 | DIV/0 |
| Window #10 | 0.00990 | 0.02231 | 0.444 | 150 | 1054–1203 | 0.493 |
| Window #11 | 0.00847 | 0.03236 | 0.262 | 186 | 1156–1341 | 0.942 |
| 1st large Window | 0.00791 | 0.000 | DIV/0 | 543 | 256–798 | 1.72 |
| 2nd large Window | 0.00788 | 0.0108 | 0.728 | 543 | 799–1341 | 0.326 |
| 80% CDS | 0.00789 | 0.00540 | 1.46 | 1086 | 256–1341 | 0.495 |
| Nearly full CDS | 0.00684 | 0.00701 | 0.976 | 1251 | 91–1341 | 0.0343 |

It is important to note here that there is statistical support for positive selection displayed in the comparison between *O. rufipogon* and Nipponbare, when the first large window is used. This is good evidence that positive selection has occurred (as a result of human domestication) between the ancestral *O. rufipogon*, and the domesticated *O. sativa* (strain Nipponbare) EG307 homologs. As noted above, as a result of the stochastic nature of the nucleotide substitution process, not all comparisons to modern rice strains are expected to reveal evidence of positive selection. In addition, as noted above, cross breeding has occurred between *O. rufipogon* and some domesticated strains, further obscuring the signal of selection. What this analysis makes clear, however, is that positive selection has occurred on the EG307 gene.

TABLE 3

Sliding Window Ka/Ks Ratios for *O. rufipogon*, strain NSGC 5948, vs. *O. sativa* (strain "Lemont"). Note that all statistically significant comparisons are shown in bold.

|  | Ka | Ks | Ka/Ks | size bp | Position (bp) in CDS | t |
|---|---|---|---|---|---|---|
| Window #1 | 0.000 | 0.0178 | 0.000 | 165 | 91–255 | 0.965 |
| Window #2 | 0.00790 | 0.000 | DIV/0 | 150 | 256–405 | 0.999 |
| Window #3 | 0.000 | 0.000 | DIV/0 | 150 | 355–504 | DIV/0 |
| Window #4 | 0.000 | 0.000 | DIV/0 | 150 | 454–603 | DIV/0 |
| Window #5 | 0.0203 | 0.000 | DIV/0 | 150 | 556–705 | 1.40 |
| Window #6 | 0.0106 | 0.000 | DIV/0 | 150 | 655–804 | 0.994 |
| Window #7 | 0.0083 | 0.000 | DIV/0 | 150 | 754–903 | 0.999 |
| Window #8 | 0.0183 | 0.000 | DIV/0 | 150 | 856–1005 | 1.40 |
| Window #9 | 0.000 | 0.000 | DIV/0 | 150 | 955–1104 | DIV/0 |
| Window #10 | 0.00990 | 0.02231 | 0.444 | 150 | 1054–1203 | 0.493 |
| Window #11 | 0.00847 | 0.03236 | 0.262 | 186 | 1156–1341 | 0.942 |
| 1st large Window | 0.00791 | 0.000 | DIV/0 | 543 | 256–798 | 1.72 |
| 2nd large Window | 0.00788 | 0.0108 | 0.728 | 543 | 799–1341 | 0.326 |
| 80% CDS | 0.00789 | 0.00540 | 1.46 | 1086 | 256–1341 | 0.495 |
| Nearly full CDS | 0.00684 | 0.00701 | 0.976 | 1251 | 91–1341 | 0.0343 |

It is important to note here that there is statistical support for positive selection displayed in the comparison between *O. rufipogon* and Lemont, when the first large window is used. This is good evidence that positive selection has occurred (as a result of human domestication) between the ancestral *O. rufipogon*, and the domesticated *O. sativa* (strain Lemont) EG307 homologs. As noted above, as a result of the stochastic nature of the nucleotide substitution process, not all comparisons to modern rice strains are expected to reveal evidence of positive selection. In addition, as noted above, cross breeding has occurred between *O. rufipogon* and some domesticated strains, further obscuring the signal of selection. What this analysis makes clear, however, is that positive selection has occurred on the EG307 gene.

TABLE 4

Sliding Window Ka/Ks Ratios for *O. rufipogon*, strain NSGC 5948, vs. *O. sativa* (strain "IR64"). Note that all statistically significant comparisons are shown in bold.

|  | Ka | Ks | Ka/Ks | size bp | Position (bp) in CDS | t |
|---|---|---|---|---|---|---|
| Window #1 | 0.000 | 0.000 | DIV/0 | 165 | 91–255 | DIV/0 |
| Window #2 | 0.000 | 0.000 | DIV/0 | 150 | 256–405 | DIV/0 |
| Window #3 | 0.000 | 0.000 | DIV/0 | 150 | 355–504 | DIV/0 |
| Window #4 | 0.000 | 0.000 | DIV/0 | 150 | 454–603 | DIV/0 |
| Window #5 | 0.000 | 0.000 | DIV/0 | 150 | 556–705 | DIV/0 |
| Window #6 | 0.000 | 0.000 | DIV/0 | 150 | 655–804 | DIV/0 |
| Window #7 | 0.000 | 0.000 | DIV/0 | 150 | 754–903 | DIV/0 |
| Window #8 | 0.000 | 0.000 | DIV/0 | 150 | 856–1005 | DIV/0 |
| Window #9 | 0.000 | 0.000 | DIV/0 | 150 | 955–1104 | DIV/0 |
| Window #10 | 0.000 | 0.000 | DIV/0 | 150 | 1054–1203 | DIV/0 |
| Window #11 | 0.000 | 0.000 | DIV/0 | 186 | 1156–1341 | DIV/0 |
| 1st large Window | 0.000 | 0.000 | DIV/0 | 543 | 256–798 | DIV/0 |
| 2nd large Window | 0.000 | 0.000 | DIV/0 | 543 | 799–1341 | DIV/0 |
| 80% CDS | 0.000 | 0.000 | DIV/0 | 1086 | 256–1341 | DIV/0 |
| Nearly full CDS | 0.000 | 0.000 | DIV/0 | 1251 | 91–1341 | DIV/0 |

Note that the protein coding region sequences of EG307 from *O. rufipogon* and from the *O. sativa* strain IR64 are identical, thus, the Ka/Ks values are equal to zero. IR64 is a low yielding modern strain (personal communication, Shannon Pinson, Research Geneticist, USDA-ARS Rice Research Unit, Beaumont, TX), suspected of massive amounts of interbreeding with wild *O. rufipogon*.

TABLE 5

Sliding Window Ka/Ks Ratios for *O. rufipogon*, strain NSGC 5948, vs. *O. sativa* (strain "Teqing"). Note that all statistically significant comparisons are shown in bold.

|  | Ka | Ks | Ka/Ks | size bp | Position (bp) in CDS | t |
|---|---|---|---|---|---|---|
| Window #1 | 0.00985 | 0.000 | DIV/0 | 165 | 91–255 | 0.995 |
| Window #2 | 0.000 | 0.000 | DIV/0 | 150 | 256–405 | DIV/0 |
| Window #3 | 0.000 | 0.000 | DIV/0 | 150 | 355–504 | DIV/0 |
| Window #4 | 0.000 | 0.000 | DIV/0 | 150 | 454–603 | DIV/0 |
| Window #5 | 0.000 | 0.000 | DIV/0 | 150 | 556–705 | DIV/0 |
| Window #6 | 0.000 | 0.0343 | 0.000 | 150 | 655–804 | 0.987 |
| Window #7 | 0.00826 | 0.000 | DIV/0 | 150 | 754–903 | 0.999 |
| Window #8 | 0.00806 | 0.000 | DIV/0 | 150 | 856–1005 | 0.999 |
| Window #9 | 0.000 | 0.000 | DIV/0 | 150 | 955–1104 | DIV/0 |
| Window #10 | 0.000 | 0.000 | DIV/0 | 150 | 1054–1203 | DIV/0 |
| Window #11 | 0.000 | 0.0155 | 0.000 | 186 | 1156–1341 | 0.980 |
| 1st large Window | 0.000 | 0.0113 | 0.000 | 543 | 256–798 | 0.996 |
| 2nd large Window | 0.00218 | 0.00536 | 0.407 | 543 | 799–1341 | 0.547 |
| 80% CDS | 0.0011 | 0.00854 | 0.129 | 1086 | 256–1341 | 1.14 |
| Nearly full CDS | 0.00218 | 0.00767 | 0.284 | 1251 | 91–1341 | 0.909 |

Note that no comparisons between the EG307 sequences from *O. rufipogon* and *O. sativa* strain Teqing exhibit Ka/Ks ratios greater than one. However, as noted above, as a result of the stochastic nature of the nucleotide substitution process, not all comparisons to modern rice strains are expected to reveal evidence of positive selection. In addition, as noted above, cross breeding has occurred between *O. rufipogon* and some domesticated strains, further obscuring the signal of selection.

TABLE 6

Sliding Window Ka/Ks Ratios for *O. rufipogon*, strain NSGC 5948, vs. *O. sativa* (strain "Azucena"). Note that all statistically significant comparisons are shown in bold.

|  | Ka | Ks | Ka/Ks | size bp | Position (bp) in CDS | t |
|---|---|---|---|---|---|---|
| Window #1 | 0.000 | 0.0178 | 0.000 | 165 | 91–255 | 0.965 |
| Window #2 | 0.00790 | 0.000 | DIV/0 | 150 | 256–405 | 0.999 |
| Window #3 | 0.000 | 0.000 | DIV/0 | 150 | 355–504 | DIV/0 |

TABLE 6-continued

Sliding Window Ka/Ks Ratios for *O. rufipogon*, strain NSGC 5948, vs. *O. sativa* (strain "Azucena"). Note that all statistically significant comparisons are shown in bold.

|  | Ka | Ks | Ka/Ks | size bp | Position (bp) in CDS | t |
|---|---|---|---|---|---|---|
| Window #4 | 0.000 | 0.000 | DIV/0 | 150 | 454–603 | DIV/0 |
| Window #5 | 0.0203 | 0.000 | DIV/0 | 150 | 556–705 | 1.40 |
| Window #6 | 0.0106 | 0.000 | DIV/0 | 150 | 655–804 | 0.994 |
| Window #7 | 0.0083 | 0.000 | DIV/0 | 150 | 754–903 | 0.999 |
| Window #8 | 0.0183 | 0.000 | DIV/0 | 150 | 856–1005 | 1.40 |
| Window #9 | 0.000 | 0.000 | DIV/0 | 150 | 955–1104 | DIV/0 |
| Window #10 | 0.00990 | 0.02231 | 0.444 | 150 | 1054–1203 | 0.493 |
| Window #11 | 0.00847 | 0.03236 | 0.262 | 186 | 1156–1341 | 0.942 |
| 1st large Window | 0.00791 | 0.000 | DIV/0 | 543 | 256–798 | 1.72 |
| 2nd large Window | 0.00788 | 0.0108 | 0.728 | 543 | 799–1341 | 0.326 |
| 80% CDS | 0.00789 | 0.00540 | 1.46 | 1086 | 256–1341 | 0.495 |
| Nearly full CDS | 0.00684 | 0.00701 | 0.976 | 1251 | 91–1341 | 0.0343 |

It is important to note here that there is statistical support for positive selection displayed in the comparison between *O. rufipogon* and Azucena, when the first large window is used. This is again good evidence that positive selection has occurred (as a result of human domestication) between the ancestral *O. rufipogon*, and the domesticated *O. sativa* (strain Azucena) EG307 homologs. As noted above, as a result of the stochastic nature of the nucleotide substitution process, not all comparisons to modern rice strains are expected to reveal evidence of positive selection. In addition, as noted above, cross breeding has occurred between *O. rufipogon* and some domesticated strains, further obscuring the signal of selection. What this analysis once again makes clear, however, is that positive selection has occurred on the EG307 gene.

TABLE 7

Sliding Window Ka/Ks Ratios for *O. rufipogon*, strain NSGC 5948, vs. *O. sativa* (strain "Kasalath 4"). Note that all statistically significant comparisons are shown in bold.

|  | Ka | Ks | Ka/Ks | size bp | Position (bp) in CDS | t |
|---|---|---|---|---|---|---|
| Window #1 | 0.000 | 0.000 | DIV/0 | 150 | 1–150 | DIV/0 |
| Window #2 | 0.000 | 0.000 | DIV/0 | 150 | 100–249 | DIV/0 |
| Window #3 | 0.000 | 0.000 | DIV/0 | 150 | 199–348 | DIV/0 |
| Window #4 | 0.000 | 0.000 | DIV/0 | 150 | 301–450 | DIV/0 |
| Window #5 | 0.000 | 0.000 | DIV/0 | 150 | 400–549 | DIV/0 |
| Window #6 | 0.00826 | 0.000 | DIV/0 | 150 | 499–648 | 0.999 |
| Window #7 | 0.0163 | 0.000 | DIV/0 | 150 | 601–750 | 1.41 |
| Window #8 | 0.00790 | 0.000 | DIV/0 | 150 | 700–849 | 0.999 |
| Window #9 | 0.000 | 0.000 | DIV/0 | 150 | 799–948 | DIV/0 |
| Window #10 | 0.000 | 0.0155 | 0.000 | 186 | 901–1086 | 0.980 |
| 1st Half Window | 0.000 | 0.000 | DIV/0 | 543 | 1–543 | DIV/0 |
| 2nd Half Window | 0.00437 | 0.00534 | 0.818 | 543 | 544–1086 | 0.157 |
| Full CDS: Kasalath 1 | 0.000 | 0.00268 | 0.000 | 1086 | 1–1086 | 0.996 |
| Full CDS: Kasalath 2 | 0.00110 | 0.00268 | 0.410 | 1086 | 1–1086 | 0.544 |
| Full CDS: Kasalath 3 | 0.00110 | 0.00268 | 0.410 | 1086 | 1–1086 | 0.544 |
| Full CDS: Kasalath 4 | 0.00220 | 0.00268 | 0.821 | 1086 | 1–1086 | 0.154 |

Note that sliding windows are shown only for Kasalath 4. There are 4 allelic differences (designated as Kasalath 1, 2, 3, and 4) in this sequence, and as they differ only by single nucleotides, we have chosen to show only one, for purposes of clarity. The Ka/Ks ratios for each of the full CDS sequences, is shown, however. Note that no comparisons between the EG307 sequences from *O. rufipogon* and *O. sativa* strain Kasalath exhibit Ka/Ks ratios greater than one. However, as noted above, as a result of the stochastic nature of the nucleotide substitution process, not all comparisons to modern rice strains are expected to reveal evidence of positive selection. In addition, as noted above, cross breeding has occurred between *O. rufipogon* and some domesticated strains, further obscuring the signal of selection.

Upon completion of sequencing of EG307 in the NSGC 5953 strain of *O. rufipogon*, the completed sequence was used to design amplification primers. These primers were then used in the Polymerase Chain Reaction (PCR) to amplify the EG307 gene from several other *O. rufipogon* strains, including NSGC 5948, NSGC 5949, and IRGC105491. The amplified EG307 gene was then sequenced for each of these strains.

Example 12

Mapping EG307

EG307 was then physically mapped in rice. Clemson University has developed a Rice Nipponbare bacterial artificial chromosome (BAC) Library; See Budiman, M. A. 1999, "Construction and characterization of deep coverage BAC libraries for two model crops: Tomato and rice, and initiation of a chromosome walk to jointless-2 in tomato". Ph.D. thesis, Texas A & M University, College Station, Tex. Library clones are available from Clemson in the form of hybridization filters.

Two different rice BAC libraries used in screening were purchased from the Clemson University Genomics Institute (CUGI). The OSJNBa library was constructed at CUGI from genomic DNA of the japonica rice strain (Nipponbare variety), and has an average insert size of 130 kb, covering 11 genome equivalents. This is one of the most widely used libraries for the International Rice Genome Sequencing Project. It was constructed in the HindIII site of pBeloBAC11 and contains 36,864 clones. The OSJNBb library was also constructed at CUGI from genomic DNA of the japonica rice strain (Nipponbare variety), and has an average insert size of 120 kb, covering 15 genome equivalents. This is another of the most widely used libraries for the International Rice Genome Sequencing Project. It was constructed in the EcoR1 site of pIndigoBac536 and contains 55,296 clones.

The DIG protocol (BMB-Roche PCR DIG Probe Synthesis Kit cat #1636090) successfully labeled a unique EG307 494 bp PCR product (primers: 5'-GAGTTCACAGGACAG-CAGCA-3' (SEQ ID NO:87) and 5'-CAATTCTCTGAGAT-GCCTTGG-3') (SEQ ID NO:88) to screen against rice BAC filters. The blots were detected easily using chemiluminescence as per the DIG protocol (BMB-Roche DIG Luminescent Detection Kit: cat #1636090). Two different *O. sativa* libraries, OSJNBa, and OSJNBb were screened for a total of 5 different filters, three covering the OSJNBb library, and two covering the OSJNBa library. Table 8 shows the individual BACs identified by all three screens:

TABLE 8

Individual BACs identified in all screens of BAC library with EG307 494bp PCR product.

| BAC | Contig | *O. sativa* chromosome |
| --- | --- | --- |
| b0008J24 | contig 80 | chromosome 3 |
| b0022E21 | contig 80 | chromosome 3 |
| b0025P07 | not mapped | — |
| b0029I04 | not mapped | — |
| b0047E13 | contig 80 | chromosome 3 |
| b0023J20 | contig 80 | chromosome 3 |
| b0033B08 | contig 80 | chromosome 3 |
| b0050N19 | contig 80 | chromosome 3 |
| b0054B15 | contig 80 | chromosome 3 |

TABLE 8-continued

Individual BACs identified in all screens of BAC library with EG307 494bp PCR product.

| BAC | Contig | *O. sativa* chromosome |
| --- | --- | --- |
| b0071C04 | contig 80 | chromosome 3 |
| b0053G15 | contig 80 | chromosome 3 |
| a0078K13 | contig 80 | chromosome 3 |
| a0087K16 | contig 80 | chromosome 3 |
| a0076M22 | contig 80 | chromosome 3 |
| a0095O02 | contig 80 | chromosome 3 |

The reference data that allows physical mapping of a gene to a particular contig or chromosomes are known to those skilled in the art, and are available on a web page made known to purchasers of filter sets or libraries from CUGI. There were also several faint, not significant hybridizations to contig 113, which was also on chromosome 3.

Rice contig 80 was on chromosome 3 and contained 66 BACs and 7 markers. Judging by the overlap of all these BACs within contig 80, EG307 was approximately 200 kb upstream of marker CDO1387 on the short arm of chromosome 3.

RiceGenes is a publicly accessible genome database developed and curated by the USDA-ARS and available through a Cornell University website. It provides a collection of rice genetic maps from Cornell University, the Japanese Rice Genome Research Program (JRGP), and the Korea Rice Genome Research Program (KRGRP), as well as comparisons with maps from other grasses (maize, oat, and wheat). The CDO1387 marker was mapped to several different rice maps using the RiceGenes website.

There were also several QTLs mapped to this region, but many of them had rather wide ranges that covered almost the entire chromosome. One well-documented QTL for 1000 grain weight was mapped to this region of chromosome 3 and was associated with marker RZ672 (S. R. McCouch, et al. *Genetics* 150:899-909 October 1998). On one map (R3) CDO1387 mapped to 30.4 cM and RZ672 mapped to 39 cM, and both of these markers mapped to four other rice maps (Rice-CU-3, 3RC94, 3RC00, and 3RW99) in similar ranges (FIG. 5). Thus, EG307 was within ~10 cM of this QTL marker. The R3 map also had a BAC, OSJNBa0091P11, mapped to 21.45 cM-21.95 cM. EG307 was negative for this BAC and any others in the same contig upon screening the rice BAC libraries. The grain weight QTL region of rice had also been involved in some synteny studies between rice and maize that indicated synteny between rice chromosome 3S and maize chromosomes 1S and 9L (W. A. Wilson, et al. *Genetics* 153(1): 453-473 September 1999).

Example 13

Identification of EG307 in Maize and Teosinte

Searching the maize genome in GenBank by BLAST (using rice EG307 sequences) identified two maize ESTs, accession numbers BE511288 and BG320985, which appeared to be homologous. Primers were designed that allowed successful amplification of the maize (*Zea mays*) and teosinte (*Zea mays parviglumis*) EG307 homologs (SEQ ID NO:33 and SEQ ID NO:34), having a suggested open reading frame represented by SEQ ID NO:35, and SEQ ID NO:66, having a suggested open reading frame represented by SEQ ID NO:67). (Protein sequences for maize and teosinte were deduced; and are represented by SEQ ID NO:36 and SEQ ID NO:68.) Table 9 shows Ka/Ks estimates for a comparison between maize and teosinte.

TABLE 9

Ka/Ks Ratios for teosinte (Zea mays parviglumis) vs. modern maize (Zea mays).

| Maize (BS7) | Ka | Ks | Ka/Ks | size bp | Position (bp) in CDS | t |
|---|---|---|---|---|---|---|
| Teosinte (Benz 967) | 0.00970 | 0.0210 | 0.462 | 1347 | 1–1347 | 1.16 |

Although these Ka/Ks values do not show ratios that are greater than one, there is still evidence for positive selection. All amino acid replacements between ancestral rice and its modern domesticated descendant were characterized, and the same analysis was performed for teosinte and its descendant, modern maize. In both (independent) cases of domestication, a consistent pattern is observed: nearly all amino acid replacements in the modern crop (whether maize or rice), as compared to the ancestral plant (teosinte or ancestral rice) result in increased charge/polarity, increased solubility, and decreased hydrophobicity. This pattern is most unlikely to have occurred by chance in these two independent domestication events. This suggests that these replacements were a similar response to human imposed domestication. This is powerful evidence that EG307 has been selected as a result of human domestication of these two cereals.

Upon completion of sequencing of EG307 in one strain of teosinte, the completed sequence was used to design amplification primers. These primers were then used in the Polymerase Chain Reaction (PCR) to amplify the EG307 gene from several other teosinte strains, as well as several strains of modern maize. The amplified EG307 gene was then sequenced for each of these strains.

Although the foregoing invention has been described in some detail by way of illustration and example for purposes of clarity and understanding, it will be apparent to those of ordinary skill in the art that certain changes and modifications can be practiced. Therefore, the description and examples should not be construed as limiting the scope of the invention, which is delineated by the appended claims.

What is claimed is:

1. Plant cells, comprising heterologous DNA encoding an EG307 polypeptide, wherein said polypeptide is selected from the group consisting of:
   a) a polypeptide encoded by a polynucleotide selected from the group consisting of SEQ ID NO:4, SEQ ID NO:5, SEQ ID NO:91, SEQ ID NO:33, SEQ ID NO:34, and SEQ ID NO:35;
   b) a polypeptide encoded by a polynucleotide having at least 95% sequence identity to a polynucleotide in a), wherein the presence of said polynucleotide is a marker of increased yield in a plant of the genus *Oryza* or *Zea;*
   c) a polypeptide comprising SEQ ID NO:6 or SEQ ID NO:36; and
   d) a polypeptide having at least 95% sequence identity to a polypeptide of c), wherein the presence of a polynucleotide encoding a polypeptide of (d) is a marker of increased yield in a plant of the genus *Oryza* or *Zea*.

2. A propagation material of a transgenic plant comprising the transgenic plant cell according to claim 1.

3. A transgenic plant containing heterologous DNA which encodes an EG307 polypeptide that is expressed in plant tissue, and said polypeptide is selected from the group consisting of:
   a) a polypeptide encoded by a polynucleotide selected from the group consisting of SEQ ID NO:4, SEQ ID NO:5, SEQ ID NO:91, SEQ ID NO:33, SEQ ID NO:34, and SEQ ID NO:35;
   b) a polypeptide encoded by a polynucleotide having at least 95% sequence identity to a polynucleotide in a), wherein the presence of said polynucleotide is a marker of increased yield in a plant of the genus *Oryza* or *Zea;*
   c) a polypeptide comprising SEQ ID NO:6 or SEQ ID NO:36; and
   d) a polypeptide having at least 95% sequence identity to a polypeptide of c), wherein the presence of a polynucleotide encoding a polypeptide of (d) is a marker of increased yield in a plant of the genus *Oryza* or *Zea*.

4. An isolated polynucleotide which includes a promoter operably linked to a polynucleotide that encodes an EG307 gene in plant tissue, said polynucleotide selected from the group consisting of:
   a) a polynucleotide selected from the group consisting of SEQ ID NO:4, SEQ ID NO:5, SEQ ID NO:91, SEQ ID NO:33, SEQ ID NO:34, and SEQ ID NO:35;
   b) a polynucleotide having at least 95% sequence identity to a polynucleotide of a), wherein the presence of said polynucleotide is a marker of increased yield in a plant of the genus *Oryza* or *Zea;*
   c) a polynucleotide encoding a polypeptide comprising SEQ ID NO:6 or SEQ ID NO:36; and
   d) a polynucleotide encoding a polypeptide having at least 95% sequence identity to SEQ ID NO:6 or SEQ ID NO:36, wherein the presence of a polynucleotide encoding a polypeptide of (d) is a marker of increased yield in a plant of the genus *Oryza* or *Zea*.

5. The isolated polynucleotide of claim 4, wherein said polynucleotide is a recombinant polynucleotide.

6. The isolated polynucleotide of claim 4, wherein the promoter is the promoter native to an EG307 gene.

7. A transfected host cell comprising a host cell transfected with a construct comprising a promoter, enhancer or intron polynucleotide from an evolutionarily significant EG307 polynucleotide or any combination thereof, operably linked to a polynucleotide encoding a reporter protein, wherein said EG307 polynucleotide is capable of increasing the yield of a plant, wherein said EG307 polynucleotide is selected from the group consisting of:
   a) a polynucleotide selected from the group consisting of SEQ ID NO:4, SEQ ID NO:5, SEQ ID NO:91, SEQ ID NO:33, SEQ ID NO:34, and SEQ ID NO:35;
   b) a polynucleotide having at least 95% sequence identity to a polynucleotide of a), wherein the presence of said polynucleotide is a marker of increased yield in a plant of the genus *Oryza* or *Zea;* c) a polynucleotide encoding a polypeptide comprising SEQ ID NO:6 or SEQ ID NO:36; and
d) a polynucleotide encoding a polypeptide having at least 95% sequence identity to SEQ ID NO:6 or SEQ ID NO:36, wherein the presence of a polynucleotide encoding a polypeptide of (d) is a marker of increased yield in a plant of the genus *Oryza* or *Zea*.

8. A method of identifying an agent which may modulate yield, said method comprising contacting at least one candidate agent which may modulate function of an EG307 polynucleotide or polypeptide with a plant or cell comprising an EG307 gene, wherein the agent is identified by its ability to modulate yield, and wherein said EG307 gene comprises a polynucleotide selected from the group consisting of:
   a) a polynucleotide selected from the group consisting of SEQ ID NO:4, SEQ ID NO:5, SEQ ID NO:91, SEQ ID NO:33, SEQ ID NO:34, and SEQ ID NO:35;
   b) a polynucleotide having at least 95% sequence identity to a polynucleotide of a), wherein the presence of said polynucleotide is a marker of increased yield in a plant of the genus *Oryza* or *Zea;*
   c) a polynucleotide encoding a polypeptide comprising SEQ ID NO:6 or SEQ ID NO:36; and
   d) a polynucleotide encoding a polypeptide having at least 95% sequence identity to SEQ ID NO:6 or SEQ ID NO:36, wherein the presence of a polynucleotide encoding a polypeptide of (d) is a marker of increased yield in a plant of the genus *Oryza* or *Zea*.

9. The method of claim 8, wherein the plant or cell is transfected with a polynucleotide of a), b), c), or d).

10. The method of claim 8, wherein said identified agent modulates yield by modulating a function of the polynucleotide encoding the polypeptide.

11. The method of claim 8, wherein said identified agent modulates yield by modulating a function of the polypeptide.

12. A method of producing an EG307 polypeptide comprising:
   a) providing a cell transfected with a polynucleotide encoding an EG307 polypeptide positioned for expression in the cell;
   b) culturing the transfected cell under conditions for expressing the polynucleotide; and
   c) isolating the EG307 polypeptide, wherein said polypeptide is selected from the group consisting of:
      i) a polypeptide encoded by a polynucleotide selected from the group consisting of SEQ ID NO:4, SEQ ID NO:5, SEQ ID NO:91, SEQ ID NO:33, SEQ ID NO:34, and SEQ ID NO:35;
      ii) a polypeptide encoded by a polynucleotide having at least 95% sequence identity to a polynucleotide in i), wherein the presence of said polynucleotide is a marker of increased yield in a plant of the genus *Oryza* or *Zea;*
      iii) a polypeptide comprising SEQ ID NO:6 or SEQ ID NO:36; and
      iv) a polypeptide having at least 95% sequence identity to a polypeptide of iii), wherein the presence of a polynucleotide encoding a polypeptide of (d) is a marker of increased yield in a plant of the genus *Oryza* or *Zea*.

* * * * *

SEQUENCE LISTING

```
<160> NUMBER OF SEQ ID NOS: 91

<210> SEQ ID NO 1
<211> LENGTH: 2441
<212> TYPE: DNA
<213> ORGANISM: Oryza sativa cv. Azucena

<400> SEQUENCE: 1
ccatgtcgag gtgcttcccc tacccgccgc cggggtacgt gcgaaaccca gtggtggccg      60
tggccgcggc cgaagcgcag gcgaccacta aggtttgttg aaccatcgga tttacacacg     120
cacgtgccgg atcatttgct cttgcctgtt ggttttgatc ggatctgttg gttgtgcgtg     180
tgtgatttgg ggatcgcacg tgcggggaag ctaacctttg catggataac ttgagatttg     240
tgaggccgcg cttcgaccag atcggtcgcc aatcttttag tggctgaccg tggaaagagg     300
atattactga ccttcggttt gctaattttg gttgtgccgt tgaatctgaa ataaccagaa     360
tagtcatggg gaaaaaagtc tgatctggaa ggttcgaatt acatttctat atattgttgt     420
gctcccagac gatggttgca agaaatcact catgctggat aaaattgtgg atgtaagagt     480
ctgcagtcgt taaaatctgg aaacagcaca ttttgccgta gtaaatttga atccatgttg     540
ctgtctcgtt attggtgtgt tacgagtaac ctgtgtgttg ttatctccgc ttggactaga     600
ttccaagtaa tccagtgcct tcatgacctg caaattctat gcctatgaag taacatgaac     660
agtttgtatg tatgtattct gttgatgcat acttgcatta tttgtgagat gtacatgttg     720
tggtaaaatt ttgcattcac catatagaaa tagtaactga ctatccttgt ttagttcgaa     780
aactactgca ggtttagtta ttctctgttg ccaagagtgc ttgttatgat tgtaagggtt     840
acagttctgt gactaaccat gtaacaaata tattaaggat tatcaaatta ttctatgtga     900
agtgtccgtg ccctaattgt gttatcttct gtaactgata gcacaacatt tgtttcctgc     960
tgtgtgcttg tgtaaattgg tacttcatca ttactatata tttcaaagaa aattctgcat    1020
tgcattcccg tcgtccgttc taaatcagaa ctgacgattg ctctggtggc tgaagctcca    1080
```

-continued

```
gaaagaaagg gaaaaggctg aaaagaagaa agagaaaagg agtgacagga aagctcttcc    1140
acatggtgag atatccaagc attcaaagcg aacccaccac aagaagagaa acatgaaga     1200 catcaataat gctgatcaga agtcccggaa ggtttcctcc atggaacctg gtgagcaatt    1260
ggagaagagt ggactctcag aagagcatgg agctccttgc tttactcaga cagagcatgg    1320
ctctccagag agttcacagg acagcagcaa gagaagaaag gttgtgttac ccagtcctag    1380
ccaagctaag aatggtgagg ccctttcttg catttgtctt cttttagctg gtgatgttga    1440
attggtttga cttatcctga attatcatct tgcaggtaac atccttcgaa taaagataag    1500
aagagatcaa gattcttcag cttcccttc ggagaaatct aatgttgtac aaacaccagt    1560
tcatcaaatg ggatcagttt catctctgcc aagtaagaaa aactcaatgc aaccacacaa    1620
caccgaaatg atggtgagaa cagcatcaac ccagcagcaa agcatcaaag gtgattttca    1680
agcagtaccg aaacaaggta tgccaacccc agcaaaagtc atgccaagag tcgatgttcc    1740
tccatctatg agggcatcaa aggaaaggat tggccttcgt cctgcagaga tgttggccaa    1800
tgttggtcct tcaccctcca aggcaaaaca gattgtcaat cctgcagctg ctaaggttac    1860
acaaagagtt gatcctccac ctgccaaggc atctcagaga attgatcctc tgttgccatc    1920
caaggttcat atagatgcta ctcgatcttt tacgaaggtc tcccagacag agatcaagcc    1980
ggaagtacag cccccaattc tgaaggtgcc tgtggctatg cctaccatca atcgtcagca    2040
gattgacacc tcgcagccca agaagagcc ttgctcctct ggcaggaatg ctgaagctgc    2100
ttcagtatca gtagagaagc agtccaagtc agatcgcaaa aagagccgca aggctgagaa    2160
gaaagagaag aagttcaaag atttatttgt tacctgggat cctccgtcta tggaaatgga    2220
tgatatggat ctcggggacc aggattggct gcttgatagt acgaggaaac ctgatgctgg    2280
cattggcaac tgcagagaaa ttgttgatcc acttacttct caatcagcag agcagttctc    2340
attgcagcct agggcgattc atttaccaga ccttcatgtc tatcagttgc catatgtggt    2400
tccattctag gtttgtgtag tgagatggag taggtgagaa g                        2441
```

<210> SEQ ID NO 2
<211> LENGTH: 1344
<212> TYPE: DNA
<213> ORGANISM: Oryza sativa cv. Azucena
<220> FEATURE:
<221> NAME/KEY: CDS
<222> LOCATION: (1)..(1344)
<223> OTHER INFORMATION:

<400> SEQUENCE: 2

```
atg tcg agg tgc ttc ccc tac ccg ccg ccg ggg tac gtg cga aac cca         48
Met Ser Arg Cys Phe Pro Tyr Pro Pro Pro Gly Tyr Val Arg Asn Pro
1               5                   10                  15 gtg gtg gcc gtg gcc gcg gcc gaa gcg cag gcg acc act aag ctc cag         96
Val Val Ala Val Ala Ala Ala Glu Ala Gln Ala Thr Thr Lys Leu Gln
                20                  25                  30 aaa gaa agg gaa aag gct gaa aag aag aaa gag aaa agg agt gac agg        144
Lys Glu Arg Glu Lys Ala Glu Lys Lys Lys Glu Lys Arg Ser Asp Arg
            35                  40                  45 aaa gct ctt cca cat ggt gag ata tcc aag cat tca aag cga acc cac        192
Lys Ala Leu Pro His Gly Glu Ile Ser Lys His Ser Lys Arg Thr His
        50                  55                  60 cac aag aag aga aaa cat gaa gac atc aat aat gct gat cag aag tcc        240
His Lys Lys Arg Lys His Glu Asp Ile Asn Asn Ala Asp Gln Lys Ser
65                  70                  75                  80 cgg aag gtt tcc tcc atg gaa cct ggt gag caa ttg gag aag agt gga        288
```

|  |  |
|---|---|
| Arg Lys Val Ser Ser Met Glu Pro Gly Glu Gln Leu Glu Lys Ser Gly<br>                  85                   90                  95 |  |
| ctc tca gaa gag cat gga gct cct tgc ttt act cag aca gag cat ggc<br>Leu Ser Glu Glu His Gly Ala Pro Cys Phe Thr Gln Thr Glu His Gly<br>                100                  105                 110 | 336 |
| tct cca gag agt tca cag gac agc agc aag aga aga aag gtt gtg tta<br>Ser Pro Glu Ser Ser Gln Asp Ser Ser Lys Arg Arg Lys Val Val Leu<br>                115                  120                 125 | 384 |
| ccc agt cct agc caa gct aag aat ggt aac atc ctt cga ata aag ata<br>Pro Ser Pro Ser Gln Ala Lys Asn Gly Asn Ile Leu Arg Ile Lys Ile<br>      130                  135                  140 | 432 |
| aga aga gat caa gat tct tca gct tcc ctt tcg gag aaa tct aat gtt<br>Arg Arg Asp Gln Asp Ser Ser Ala Ser Leu Ser Glu Lys Ser Asn Val<br>145                  150                  155                 160 | 480 |
| gta caa aca cca gtt cat caa atg gga tca gtt tca tct ctg cca agt<br>Val Gln Thr Pro Val His Gln Met Gly Ser Val Ser Ser Leu Pro Ser<br>                    165                  170                 175 | 528 |
| aag aaa aac tca atg caa cca cac aac acc gaa atg atg gtg aga aca<br>Lys Lys Asn Ser Met Gln Pro His Asn Thr Glu Met Met Val Arg Thr<br>                180                  185                 190 | 576 |
| gca tca acc cag cag caa agc atc aaa ggt gat ttt caa gca gta ccg<br>Ala Ser Thr Gln Gln Gln Ser Ile Lys Gly Asp Phe Gln Ala Val Pro<br>            195                  200                 205 | 624 |
| aaa caa ggt atg cca acc cca gca aaa gtc atg cca aga gtc gat gtt<br>Lys Gln Gly Met Pro Thr Pro Ala Lys Val Met Pro Arg Val Asp Val<br>210                  215                  220 | 672 |
| cct cca tct atg agg gca tca aag gaa agg att ggc ctt cgt cct gca<br>Pro Pro Ser Met Arg Ala Ser Lys Glu Arg Ile Gly Leu Arg Pro Ala<br>225                  230                  235                240 | 720 |
| gag atg ttg gcc aat gtt ggt cct tca ccc tcc aag gca aaa cag att<br>Glu Met Leu Ala Asn Val Gly Pro Ser Pro Ser Lys Ala Lys Gln Ile<br>                    245                  250                 255 | 768 |
| gtc aat cct gca gct gct aag gtt aca caa aga gtt gat cct cca cct<br>Val Asn Pro Ala Ala Ala Lys Val Thr Gln Arg Val Asp Pro Pro Pro<br>                260                  265                 270 | 816 |
| gcc aag gca tct cag aga att gat cct ctg ttg cca tcc aag gtt cat<br>Ala Lys Ala Ser Gln Arg Ile Asp Pro Leu Leu Pro Ser Lys Val His<br>            275                  280                 285 | 864 |
| ata gat gct act cga tct ttt acg aag gtc tcc cag aca gag atc aag<br>Ile Asp Ala Thr Arg Ser Phe Thr Lys Val Ser Gln Thr Glu Ile Lys<br>          290                  295                 300 | 912 |
| ccg gaa gta cag ccc cca att ctg aag gtg cct gtg gct atg cct acc<br>Pro Glu Val Gln Pro Pro Ile Leu Lys Val Pro Val Ala Met Pro Thr<br>305                  310                  315                320 | 960 |
| atc aat cgt cag cag att gac acc tcg cag ccc aaa gaa gag cct tgc<br>Ile Asn Arg Gln Gln Ile Asp Thr Ser Gln Pro Lys Glu Glu Pro Cys<br>                    325                  330                 335 | 1008 |
| tcc tct ggc agg aat gct gaa gct gct tca gta tca gta gag aag cag<br>Ser Ser Gly Arg Asn Ala Glu Ala Ala Ser Val Ser Val Glu Lys Gln<br>                340                  345                 350 | 1056 |
| tcc aag tca gat cgc aaa aag agc cgc aag gct gag aag aaa gag aag<br>Ser Lys Ser Asp Arg Lys Lys Ser Arg Lys Ala Glu Lys Lys Glu Lys<br>            355                  360                 365 | 1104 |
| aag ttc aaa gat tta ttt gtt acc tgg gat cct ccg tct atg gaa atg<br>Lys Phe Lys Asp Leu Phe Val Thr Trp Asp Pro Pro Ser Met Glu Met<br>          370                  375                 380 | 1152 |
| gat gat atg gat ctc ggg gac cag gat tgg ctg ctt gat agt acg agg<br>Asp Asp Met Asp Leu Gly Asp Gln Asp Trp Leu Leu Asp Ser Thr Arg<br>385                  390                  395                400 | 1200 |

```
aaa cct gat gct ggc att ggc aac tgc aga gaa att gtt gat cca ctt    1248
Lys Pro Asp Ala Gly Ile Gly Asn Cys Arg Glu Ile Val Asp Pro Leu
                405                 410                 415 act tct caa tca gca gag cag ttc tca ttg cag cct agg gcg att cat    1296
Thr Ser Gln Ser Ala Glu Gln Phe Ser Leu Gln Pro Arg Ala Ile His
            420                 425                 430 tta cca gac ctt cat gtc tat cag ttg cca tat gtg gtt cca ttc tag    1344
Leu Pro Asp Leu His Val Tyr Gln Leu Pro Tyr Val Val Pro Phe
        435                 440                 445
```

<210> SEQ ID NO 3
<211> LENGTH: 447
<212> TYPE: PRT
<213> ORGANISM: Oryza sativa cv. Azucena

<400> SEQUENCE: 3

```
Met Ser Arg Cys Phe Pro Tyr Pro Pro Gly Tyr Val Arg Asn Pro
1               5                   10                  15

Val Val Ala Val Ala Ala Ala Glu Ala Gln Ala Thr Thr Lys Leu Gln
                20                  25                  30

Lys Glu Arg Glu Lys Ala Glu Lys Lys Glu Lys Arg Ser Asp Arg
            35                  40                  45

Lys Ala Leu Pro His Gly Glu Ile Ser Lys His Ser Lys Arg Thr His
        50                  55                  60

His Lys Lys Arg Lys His Glu Asp Ile Asn Asn Ala Asp Gln Lys Ser
65                  70                  75                  80

Arg Lys Val Ser Ser Met Glu Pro Gly Glu Gln Leu Glu Lys Ser Gly
                85                  90                  95

Leu Ser Glu Glu His Gly Ala Pro Cys Phe Thr Gln Thr Glu His Gly
            100                 105                 110

Ser Pro Glu Ser Ser Gln Asp Ser Ser Lys Arg Arg Lys Val Val Leu
        115                 120                 125

Pro Ser Pro Ser Gln Ala Lys Asn Gly Asn Ile Leu Arg Ile Lys Ile
130                 135                 140

Arg Arg Asp Gln Asp Ser Ser Ala Ser Leu Ser Glu Lys Ser Asn Val
145                 150                 155                 160

Val Gln Thr Pro Val His Gln Met Gly Ser Val Ser Ser Leu Pro Ser
                165                 170                 175

Lys Lys Asn Ser Met Gln Pro His Asn Thr Glu Met Met Val Arg Thr
            180                 185                 190

Ala Ser Thr Gln Gln Ser Ile Lys Gly Asp Phe Gln Ala Val Pro
        195                 200                 205

Lys Gln Gly Met Pro Thr Pro Ala Lys Val Met Pro Arg Val Asp Val
210                 215                 220

Pro Pro Ser Met Arg Ala Ser Lys Glu Arg Ile Gly Leu Arg Pro Ala
225                 230                 235                 240

Glu Met Leu Ala Asn Val Gly Pro Ser Pro Lys Ala Lys Gln Ile
                245                 250                 255

Val Asn Pro Ala Ala Lys Val Thr Gln Arg Val Asp Pro Pro
            260                 265                 270

Ala Lys Ala Ser Gln Arg Ile Asp Pro Leu Leu Pro Ser Lys Val His
        275                 280                 285

Ile Asp Ala Thr Arg Ser Phe Thr Lys Val Ser Gln Thr Glu Ile Lys
290                 295                 300

Pro Glu Val Gln Pro Pro Ile Leu Lys Val Pro Val Ala Met Pro Thr
305                 310                 315                 320
```

```
Ile Asn Arg Gln Gln Ile Asp Thr Ser Gln Pro Lys Glu Pro Cys
            325                 330                 335

Ser Ser Gly Arg Asn Ala Glu Ala Ser Val Ser Val Glu Lys Gln
            340                 345                 350

Ser Lys Ser Asp Arg Lys Lys Ser Arg Lys Ala Glu Lys Lys Glu Lys
            355                 360                 365

Lys Phe Lys Asp Leu Phe Val Thr Trp Asp Pro Ser Met Glu Met
370                 375                 380

Asp Asp Met Asp Leu Gly Asp Gln Asp Trp Leu Leu Asp Ser Thr Arg
385                 390                 395                 400

Lys Pro Asp Ala Gly Ile Gly Asn Cys Arg Glu Ile Val Asp Pro Leu
                    405                 410                 415

Thr Ser Gln Ser Ala Glu Gln Phe Ser Leu Gln Pro Arg Ala Ile His
                420                 425                 430

Leu Pro Asp Leu His Val Tyr Gln Leu Pro Tyr Val Val Pro Phe
                435                 440                 445

<210> SEQ ID NO 4
<211> LENGTH: 126
<212> TYPE: DNA
<213> ORGANISM: Oryza sativa cv. Nipponbare

<400> SEQUENCE: 4
gggggtgagc ttaggccgga cgccggggca tcagccatgt cgaggtgctt cccctacccg    60
ccgccggggt acgtgcgaaa cccagtggtg gccgtggccg cggccgaagc gcaggcgacc   120
actaag                                                              126

<210> SEQ ID NO 5
<211> LENGTH: 1344
<212> TYPE: DNA
<213> ORGANISM: Oryza sativa cv. Nipponbare
<220> FEATURE:
<221> NAME/KEY: CDS
<222> LOCATION: (1)..(1344)
<223> OTHER INFORMATION:

<400> SEQUENCE: 5 atg tcg agg tgc ttc ccc tac ccg ccg ccg ggg tac gtg cga aac cca     48
Met Ser Arg Cys Phe Pro Tyr Pro Pro Pro Gly Tyr Val Arg Asn Pro
1               5                   10                  15 gtg gtg gcc gtg gcc gcg gcc gaa gcg cag gcg acc act aag ctc cag    96
Val Val Ala Val Ala Ala Ala Glu Ala Gln Ala Thr Thr Lys Leu Gln
            20                  25                  30 aaa gaa agg gaa aag gct gaa aag aag aaa gag aaa agg agt gac agg   144
Lys Glu Arg Glu Lys Ala Glu Lys Lys Lys Glu Lys Arg Ser Asp Arg
        35                  40                  45 aaa gct ctt cca cat ggt gag ata tcc aag cat tca aag cga acc cac   192
Lys Ala Leu Pro His Gly Glu Ile Ser Lys His Ser Lys Arg Thr His
    50                  55                  60 cac aag aag aga aaa cat gaa gac atc aat aat gct gat cag aag tcc   240
His Lys Lys Arg Lys His Glu Asp Ile Asn Asn Ala Asp Gln Lys Ser
65                  70                  75                  80 cgg aag gtt tcc tcc atg gaa cct ggt gag caa ttg gag aag agt gga   288
Arg Lys Val Ser Ser Met Glu Pro Gly Glu Gln Leu Glu Lys Ser Gly
                85                  90                  95 ctc tca gaa gag cat gga gct cct tgc ttt act cag aca gag cat ggc   336
Leu Ser Glu Glu His Gly Ala Pro Cys Phe Thr Gln Thr Glu His Gly
            100                 105                 110
```

-continued

| | | |
|---|---|---|
| tct cca gag agt tca cag gac agc agc aag aga aga aag gtt gtg tta<br>Ser Pro Glu Ser Ser Gln Asp Ser Ser Lys Arg Arg Lys Val Val Leu<br>115                       120                  125 | 384 |
| ccc agt cct agc caa gct aag aat ggt aac atc ctt cga ata aag ata<br>Pro Ser Pro Ser Gln Ala Lys Asn Gly Asn Ile Leu Arg Ile Lys Ile<br>    130                   135                    140 | 432 |
| aga aga gat caa gat tct tca gct tcc ctt tcg gag aaa tct aat gtt<br>Arg Arg Asp Gln Asp Ser Ser Ala Ser Leu Ser Glu Lys Ser Asn Val<br>145                       150                 155             160 | 480 |
| gta caa aca cca gtt cat caa atg gga tca gtt tca tct ctg cca agt<br>Val Gln Thr Pro Val His Gln Met Gly Ser Val Ser Ser Leu Pro Ser<br>                 165                 170                175 | 528 |
| aag aaa aac tca atg caa cca cac aac acc gaa atg atg gtg aga aca<br>Lys Lys Asn Ser Met Gln Pro His Asn Thr Glu Met Met Val Arg Thr<br>180                       185                 190 | 576 |
| gca tca acc cag cag caa agc atc aaa ggt gat ttt caa gca gta ccg<br>Ala Ser Thr Gln Gln Gln Ser Ile Lys Gly Asp Phe Gln Ala Val Pro<br>               195                 200              205 | 624 |
| aaa caa ggt atg cca acc cca gca aaa gtc atg cca aga gtc gat gtt<br>Lys Gln Gly Met Pro Thr Pro Ala Lys Val Met Pro Arg Val Asp Val<br>210                       215                 220 | 672 |
| cct cca tct atg agg gca tca aag gaa agg att ggc ctt cgt cct gca<br>Pro Pro Ser Met Arg Ala Ser Lys Glu Arg Ile Gly Leu Arg Pro Ala<br>225                       230                 235             240 | 720 |
| gag atg ttg gcc aat gtt ggt cct tca ccc tcc aag gca aaa cag att<br>Glu Met Leu Ala Asn Val Gly Pro Ser Pro Ser Lys Ala Lys Gln Ile<br>               245                 250              255 | 768 |
| gtc aat cct gca gct gct aag gtt aca caa aga gtt gat cct cca cct<br>Val Asn Pro Ala Ala Ala Lys Val Thr Gln Arg Val Asp Pro Pro Pro<br>260                       265                 270 | 816 |
| gcc aag gca tct cag aga att gat cct ctg ttg cca tcc aag gtt cat<br>Ala Lys Ala Ser Gln Arg Ile Asp Pro Leu Leu Pro Ser Lys Val His<br>               275                 280              285 | 864 |
| ata gat gct act cga tct ttt acg aag gtc tcc cag aca gag atc aag<br>Ile Asp Ala Thr Arg Ser Phe Thr Lys Val Ser Gln Thr Glu Ile Lys<br>290                       295                 300 | 912 |
| ccg gaa gta cag ccc cca att ctg aag gtg cct gtg gct atg cct acc<br>Pro Glu Val Gln Pro Pro Ile Leu Lys Val Pro Val Ala Met Pro Thr<br>305                       310                 315             320 | 960 |
| atc aat cgt cag cag att gac acc tcg cag ccc aaa gaa gag cct tgc<br>Ile Asn Arg Gln Gln Ile Asp Thr Ser Gln Pro Lys Glu Glu Pro Cys<br>               325                 330              335 | 1008 |
| tcc tct ggc agg aat gct gaa gct gct tca gta tca gta gag aag cag<br>Ser Ser Gly Arg Asn Ala Glu Ala Ala Ser Val Ser Val Glu Lys Gln<br>340                       345                 350 | 1056 |
| tcc aag tca gat cgc aaa aag agc cgc aag gct gag aag aaa gag aag<br>Ser Lys Ser Asp Arg Lys Lys Ser Arg Lys Ala Glu Lys Lys Glu Lys<br>               355                 360              365 | 1104 |
| aag ttc aaa gat tta ttt gtt acc tgg gat cct ccg tct atg gaa atg<br>Lys Phe Lys Asp Leu Phe Val Thr Trp Asp Pro Pro Ser Met Glu Met<br>370                       375                 380 | 1152 |
| gat gat atg gat ctc ggg gac cag gat tgg ctg ctt gat agt acg agg<br>Asp Asp Met Asp Leu Gly Asp Gln Asp Trp Leu Leu Asp Ser Thr Arg<br>385                       390                 395             400 | 1200 |
| aaa cct gat gct ggc att ggc aac tgc aga gaa att gtt gat cca ctt<br>Lys Pro Asp Ala Gly Ile Gly Asn Cys Arg Glu Ile Val Asp Pro Leu<br>               405                 410              415 | 1248 |
| act tct caa tca gca gag cag ttc tca ttg cag cct agg gcg att cat<br>Thr Ser Gln Ser Ala Glu Gln Phe Ser Leu Gln Pro Arg Ala Ile His<br>420                       425                 430 | 1296 |

```
tta cca gac ctt cat gtc tat cag ttg cca tat gtg gtt cca ttc tag    1344
Leu Pro Asp Leu His Val Tyr Gln Leu Pro Tyr Val Val Pro Phe
        435                 440                 445
```

<210> SEQ ID NO 6
<211> LENGTH: 447
<212> TYPE: PRT
<213> ORGANISM: Oryza sativa cv. Nipponbare

<400> SEQUENCE: 6

```
Met Ser Arg Cys Phe Pro Tyr Pro Pro Gly Tyr Val Arg Asn Pro
1               5                   10                  15

Val Val Ala Val Ala Ala Glu Ala Gln Ala Thr Thr Lys Leu Gln
                20                  25                  30

Lys Glu Arg Glu Lys Ala Glu Lys Lys Glu Lys Arg Ser Asp Arg
            35                  40                  45

Lys Ala Leu Pro His Gly Glu Ile Ser Lys His Ser Lys Arg Thr His
 50                  55                  60

His Lys Lys Arg Lys His Glu Asp Ile Asn Asn Ala Asp Gln Lys Ser
 65                  70                  75                  80

Arg Lys Val Ser Ser Met Glu Pro Gly Glu Gln Leu Glu Lys Ser Gly
                85                  90                  95

Leu Ser Glu Glu His Gly Ala Pro Cys Phe Thr Gln Thr Glu His Gly
                100                 105                 110

Ser Pro Glu Ser Ser Gln Asp Ser Ser Lys Arg Arg Lys Val Val Leu
                115                 120                 125

Pro Ser Pro Ser Gln Ala Lys Asn Gly Asn Ile Leu Arg Ile Lys Ile
        130                 135                 140

Arg Arg Asp Gln Asp Ser Ser Ala Ser Leu Ser Glu Lys Ser Asn Val
145                 150                 155                 160

Val Gln Thr Pro Val His Gln Met Gly Ser Val Ser Ser Leu Pro Ser
                165                 170                 175

Lys Lys Asn Ser Met Gln Pro His Asn Thr Glu Met Met Val Arg Thr
                180                 185                 190

Ala Ser Thr Gln Gln Gln Ser Ile Lys Gly Asp Phe Gln Ala Val Pro
            195                 200                 205

Lys Gln Gly Met Pro Thr Pro Ala Lys Val Met Pro Arg Val Asp Val
        210                 215                 220

Pro Pro Ser Met Arg Ala Ser Lys Glu Arg Ile Gly Leu Arg Pro Ala
225                 230                 235                 240

Glu Met Leu Ala Asn Val Gly Pro Ser Pro Ser Lys Ala Lys Gln Ile
                245                 250                 255

Val Asn Pro Ala Ala Lys Val Thr Gln Arg Val Asp Pro Pro Pro
                260                 265                 270

Ala Lys Ala Ser Gln Arg Ile Asp Pro Leu Leu Pro Ser Lys Val His
            275                 280                 285

Ile Asp Ala Thr Arg Ser Phe Thr Lys Val Ser Gln Thr Glu Ile Lys
        290                 295                 300

Pro Glu Val Gln Pro Pro Ile Leu Lys Val Pro Val Ala Met Pro Thr
305                 310                 315                 320

Ile Asn Arg Gln Gln Ile Asp Thr Ser Gln Pro Lys Glu Glu Pro Cys
                325                 330                 335

Ser Ser Gly Arg Asn Ala Glu Ala Ala Ser Val Ser Val Glu Lys Gln
                340                 345                 350
```

-continued

```
        Ser Lys Ser Asp Arg Lys Lys Ser Arg Lys Ala Glu Lys Lys Glu Lys
                355                 360                 365

Lys Phe Lys Asp Leu Phe Val Thr Trp Asp Pro Pro Ser Met Glu Met
            370                 375                 380

Asp Asp Met Asp Leu Gly Asp Gln Asp Trp Leu Leu Asp Ser Thr Arg
        385                 390                 395                 400

Lys Pro Asp Ala Gly Ile Gly Asn Cys Arg Glu Ile Val Asp Pro Leu
                        405                 410                 415

Thr Ser Gln Ser Ala Glu Gln Phe Ser Leu Gln Pro Arg Ala Ile His
                    420                 425                 430

Leu Pro Asp Leu His Val Tyr Gln Leu Pro Tyr Val Val Pro Phe
                435                 440                 445

<210> SEQ ID NO 7
<211> LENGTH: 2461
<212> TYPE: DNA
<213> ORGANISM: Oryza sativa cv. Teqing

<400> SEQUENCE: 7
gcggacgcgg gacatcagcc atgtcgaggt gcttcccta  cccgccgccg gggtacgtgc       60
gaaacccagt ggtggccgtg gccgcggccg aagcgcaggc gaccactaag gtttgttgaa      120
ccatcggatt tacacacgca cgtgccggat catttgctct tgcctgttgg ttttgatcgg      180
atctgttggt tgtgcgtgtg tgatttgggg atcgcacgtg cggggaagct aacctttgca      240
tggataactt gagatttgtg aggccgcgct tcgaccagat cggtcgccaa tcttttagtg      300
gctgaccgtg gaaagaggat attactgacc ttcggtttgc taattttggt tgtgccgttg      360
aatctgaaat aaccagaata gtcatgggga aaaagtctg  atctggaagg ttcgaattac      420
atttctatat attgttgtgc tcccagacga tggttgcaag aaattactca tgctggataa      480
aattgtggat gtaagagtct gcagttgtta aatctggaa  acagcacatt tgccgtagt       540 aaatttgaat ccatgttgct gtctcgttat tggtgtgtta cgagtaacct gtgtgttgtt      600
atctccgctt ggactagatt ccaagtaatc cagtgcctt c atgacctgca aattctatgc      660
ctatgaagta acatgaacag tttgtatgta ttctgttgat gcatacttgc attatttgtg      720
agatgtacat gttgtggtaa aattttgcat tcaccatata gaaatagtaa ctgactatcc      780
ttgtttagtt cgaaaactac tgcaggttta gttattctct gttgccaaga gtgcttgtta      840
tgattgtaag ggttacagtt ctgtgactaa ccatgtaaca aatatattaa ggattatcaa      900
attattctat gtgaagtgtc cgtgccctaa ttgtgttatc ttctgtaact gatagcacaa      960
catttgtttc ctgctgtgtg cttgtgtaaa ttggtacttc atcattacta tatatttcaa     1020
agaaaattct gcattgcatt cccgtcgtcc gttctaaatc agaactgacg attgctctgg     1080
tggctgaagc tccagaaaga aagggaaaag gccgaaaaga agaaagagaa aaagagtgac     1140
aggaaagctc ttccacatgg tgagatatcc aagcattcaa agcgaaccca caagaagaga     1200
aaacatgaag acatcaataa tgctgatcag aagtcccgga aggtttcctc catggaacct     1260
ggtgagcaat tggagaagag tggactctca aagagcatg  gagctccttg ctttactcag     1320
acagtgcatg gctctccaga gagttcacag gacagcagca agagaagaaa ggttgtgtta     1380
cccagtccta gccaagctaa gaatggtgag gccctttctt gcatttgtct tcttttagct     1440
ggtgatgttg aattggtttg acttatcctg aattatcatc ttgcaggtaa catccttcga     1500
ataaagataa gaagagatca agattcttca gcttcccttt cggagaaatc taatgttgta     1560
caaacaccag ttcatcaaat gggatcagtt tcatctctgc caagtaagaa aaactcaatg     1620
```

```
caaccacaca acaccgaaat gatggtgaga acagcatcaa cccagcagca aagcatcaaa    1680
ggtgattttc aagcagtact gaaacaaggt atgccaaccc cagcaaaagt catgccaaga    1740
gtcgatgttc ctccatctat gagggcatca aggaaaggg ttggccttcg tcctgcagag    1800
atgttggcca atgttggtcc ttcaccatcc aaggcaaaac agattgtcaa tcctgcagct    1860
gctaaggtta cacaaagagt tgatcctcca cctgccaagg catctcagag aattgatcct    1920
ctgttgccat ccaaggttca tatagatgct actcgatctt ttacgaaggt ctcccagaca    1980
gagatcaagc cggaagtaca gcccccaatt ccgaaggtgc ctgtggctat gcctaccatc    2040
aatcgtcagc agattgacac ctcgcagccc aaagaagagc cttgctcctc tggcaggaat    2100
gctgaagctg cttcagtatc agtagagaag cagtccaagt cagatcgcaa aaagagccgc    2160
aaggctgaga agaaagagaa gaagttcaaa gatttatttg ttacctggga tcctccgtct    2220
atggaaatgg atgatatgga tcttggggac caggattggc tgcttggtag tacgaggaaa    2280
cctgatgctg gcattggcaa ctgcagagaa attgttgatc cacttacttc tcaatcagca    2340
gagcagttct cattgcagcc tagggcgatt catttaccag accttcatgt ctatcagttg    2400
ccatatgtgg ttccattcta ggtttgtgta gtgagatgga gtaggtgaga agtagagaga    2460
t                                                                    2461

<210> SEQ ID NO 8
<211> LENGTH: 1341
<212> TYPE: DNA
<213> ORGANISM: Oryza sativa cv. Teqing
<220> FEATURE:
<221> NAME/KEY: CDS
<222> LOCATION: (1)..(1341)
<223> OTHER INFORMATION:

<400> SEQUENCE: 8 atg tcg agg tgc ttc ccc tac ccg ccg ccg ggg tac gtg cga aac cca       48
Met Ser Arg Cys Phe Pro Tyr Pro Pro Pro Gly Tyr Val Arg Asn Pro
1               5                   10                  15 gtg gtg gcc gtg gcc gcg gcc gaa gcg cag gcg acc act aag ctc cag       96
Val Val Ala Val Ala Ala Ala Glu Ala Gln Ala Thr Thr Lys Leu Gln
            20                  25                  30 aaa gaa agg gaa aag gcc gaa aag aag aaa gag aaa aag agt gac agg      144
Lys Glu Arg Glu Lys Ala Glu Lys Lys Lys Glu Lys Lys Ser Asp Arg
        35                  40                  45 aaa gct ctt cca cat ggt gag ata tcc aag cat tca aag cga acc cac      192
Lys Ala Leu Pro His Gly Glu Ile Ser Lys His Ser Lys Arg Thr His
    50                  55                  60 aag aag aga aaa cat gaa gac atc aat aat gct gat cag aag tcc cgg      240
Lys Lys Arg Lys His Glu Asp Ile Asn Asn Ala Asp Gln Lys Ser Arg
65                  70                  75                  80 aag gtt tcc tcc atg gaa cct ggt gag caa ttg gag aag agt gga ctc      288
Lys Val Ser Ser Met Glu Pro Gly Glu Gln Leu Glu Lys Ser Gly Leu
                85                  90                  95 tca gaa gag cat gga gct cct tgc ttt act cag aca gtg cat ggc tct      336
Ser Glu Glu His Gly Ala Pro Cys Phe Thr Gln Thr Val His Gly Ser
            100                 105                 110 cca gag agt tca cag gac agc agc aag aga aga aag gtt gtg tta ccc      384
Pro Glu Ser Ser Gln Asp Ser Ser Lys Arg Arg Lys Val Val Leu Pro
        115                 120                 125 agt cct agc caa gct aag aat ggt aac atc ctt cga ata aag ata aga      432
Ser Pro Ser Gln Ala Lys Asn Gly Asn Ile Leu Arg Ile Lys Ile Arg
    130                 135                 140
```

-continued

| | |
|---|---|
| aga gat caa gat tct tca gct tcc ctt tcg gag aaa tct aat gtt gta<br>Arg Asp Gln Asp Ser Ser Ala Ser Leu Ser Glu Lys Ser Asn Val Val<br>145                   150                   155                 160 | 480 |
| caa aca cca gtt cat caa atg gga tca gtt tca tct ctg cca agt aag<br>Gln Thr Pro Val His Gln Met Gly Ser Val Ser Ser Leu Pro Ser Lys<br>                 165                   170                   175 | 528 |
| aaa aac tca atg caa cca cac aac acc gaa atg atg gtg aga aca gca<br>Lys Asn Ser Met Gln Pro His Asn Thr Glu Met Met Val Arg Thr Ala<br>            180                   185                   190 | 576 |
| tca acc cag cag caa agc atc aaa ggt gat ttt caa gca gta ctg aaa<br>Ser Thr Gln Gln Gln Ser Ile Lys Gly Asp Phe Gln Ala Val Leu Lys<br>     195                   200                   205 | 624 |
| caa ggt atg cca acc cca gca aaa gtc atg cca aga gtc gat gtt cct<br>Gln Gly Met Pro Thr Pro Ala Lys Val Met Pro Arg Val Asp Val Pro<br>210                   215                   220 | 672 |
| cca tct atg agg gca tca aag gaa agg gtt ggc ctt cgt cct gca gag<br>Pro Ser Met Arg Ala Ser Lys Glu Arg Val Gly Leu Arg Pro Ala Glu<br>225                   230                   235                 240 | 720 |
| atg ttg gcc aat gtt ggt cct tca cca tcc aag gca aaa cag att gtc<br>Met Leu Ala Asn Val Gly Pro Ser Pro Ser Lys Ala Lys Gln Ile Val<br>                   245                   250                   255 | 768 |
| aat cct gca gct gct aag gtt aca caa aga gtt gat cct cca cct gcc<br>Asn Pro Ala Ala Ala Lys Val Thr Gln Arg Val Asp Pro Pro Pro Ala<br>            260                   265                   270 | 816 |
| aag gca tct cag aga att gat cct ctg ttg cca tcc aag gtt cat ata<br>Lys Ala Ser Gln Arg Ile Asp Pro Leu Leu Pro Ser Lys Val His Ile<br>     275                   280                   285 | 864 |
| gat gct act cga tct ttt acg aag gtc tcc cag aca gag atc aag ccg<br>Asp Ala Thr Arg Ser Phe Thr Lys Val Ser Gln Thr Glu Ile Lys Pro<br>290                   295                   300 | 912 |
| gaa gta cag ccc cca att ccg aag gtg cct gtg gct atg cct acc atc<br>Glu Val Gln Pro Pro Ile Pro Lys Val Pro Val Ala Met Pro Thr Ile<br>305                   310                   315                 320 | 960 |
| aat cgt cag cag att gac acc tcg cag ccc aaa gaa gag cct tgc tcc<br>Asn Arg Gln Gln Ile Asp Thr Ser Gln Pro Lys Glu Glu Pro Cys Ser<br>                   325                   330                   335 | 1008 |
| tct ggc agg aat gct gaa gct gct tca gta tca gta gag aag cag tcc<br>Ser Gly Arg Asn Ala Glu Ala Ala Ser Val Ser Val Glu Lys Gln Ser<br>            340                   345                   350 | 1056 |
| aag tca gat cgc aaa aag agc cgc aag gct gag aag aaa gag aag aag<br>Lys Ser Asp Arg Lys Lys Ser Arg Lys Ala Glu Lys Lys Glu Lys Lys<br>                   355                   360                   365 | 1104 |
| ttc aaa gat tta ttt gtt acc tgg gat cct ccg tct atg gaa atg gat<br>Phe Lys Asp Leu Phe Val Thr Trp Asp Pro Pro Ser Met Glu Met Asp<br>370                   375                   380 | 1152 |
| gat atg gat ctt ggg gac cag gat tgg ctg ctt ggt agt acg agg aaa<br>Asp Met Asp Leu Gly Asp Gln Asp Trp Leu Leu Gly Ser Thr Arg Lys<br>385                   390                   395                 400 | 1200 |
| cct gat gct ggc att ggc aac tgc aga gaa att gtt gat cca ctt act<br>Pro Asp Ala Gly Ile Gly Asn Cys Arg Glu Ile Val Asp Pro Leu Thr<br>                   405                   410                   415 | 1248 |
| tct caa tca gca gag cag ttc tca ttg cag cct agg gcg att cat tta<br>Ser Gln Ser Ala Glu Gln Phe Ser Leu Gln Pro Arg Ala Ile His Leu<br>            420                   425                   430 | 1296 |
| cca gac ctt cat gtc tat cag ttg cca tat gtg gtt cca ttc tag<br>Pro Asp Leu His Val Tyr Gln Leu Pro Tyr Val Val Pro Phe<br>     435                   440                   445 | 1341 |

<210> SEQ ID NO 9
<211> LENGTH: 446

```
<212> TYPE: PRT
<213> ORGANISM: Oryza sativa cv. Teqing

<400> SEQUENCE: 9
```

| | | | | | | | | | | | | | | |
|---|---|---|---|---|---|---|---|---|---|---|---|---|---|---|
|Met|Ser|Arg|Cys|Phe|Pro|Tyr|Pro|Pro|Gly|Tyr|Val|Arg|Asn|Pro|
|1| | | |5| | | |10| | | | |15| |
|Val|Val|Ala|Val|Ala|Ala|Ala|Glu|Ala|Gln|Ala|Thr|Thr|Lys|Leu|Gln|
| | | |20| | | | |25| | | | |30| | |
|Lys|Glu|Arg|Glu|Lys|Ala|Glu|Lys|Lys|Glu|Lys|Lys|Ser|Asp|Arg|
| | |35| | | | |40| | | | |45| | |
|Lys|Ala|Leu|Pro|His|Gly|Glu|Ile|Ser|Lys|His|Ser|Lys|Arg|Thr|His|
| |50| | | | |55| | | | |60| | | | |
|Lys|Lys|Arg|Lys|His|Glu|Asp|Ile|Asn|Asn|Ala|Asp|Gln|Lys|Ser|Arg|
|65| | | | |70| | | | |75| | | | |80|
|Lys|Val|Ser|Ser|Met|Glu|Pro|Gly|Glu|Gln|Leu|Glu|Lys|Ser|Gly|Leu|
| | | | |85| | | | |90| | | | |95| |
|Ser|Glu|Glu|His|Gly|Ala|Pro|Cys|Phe|Thr|Gln|Thr|Val|His|Gly|Ser|
| | | |100| | | | |105| | | | |110| | |
|Pro|Glu|Ser|Ser|Gln|Asp|Ser|Ser|Lys|Arg|Arg|Lys|Val|Val|Leu|Pro|
| | |115| | | | |120| | | | |125| | | |
|Ser|Pro|Ser|Gln|Ala|Lys|Asn|Gly|Asn|Ile|Leu|Arg|Ile|Lys|Ile|Arg|
| |130| | | | |135| | | | |140| | | | |
|Arg|Asp|Gln|Asp|Ser|Ser|Ala|Ser|Leu|Ser|Glu|Lys|Ser|Asn|Val|Val|
|145| | | | |150| | | | |155| | | | |160|
|Gln|Thr|Pro|Val|His|Gln|Met|Gly|Ser|Val|Ser|Ser|Leu|Pro|Ser|Lys|
| | | | |165| | | | |170| | | | |175| |
|Lys|Asn|Ser|Met|Gln|Pro|His|Asn|Thr|Glu|Met|Met|Val|Arg|Thr|Ala|
| | | |180| | | | |185| | | | |190| | |
|Ser|Thr|Gln|Gln|Gln|Ser|Ile|Lys|Gly|Asp|Phe|Gln|Ala|Val|Leu|Lys|
| | | |195| | | | |200| | | | |205| | |
|Gln|Gly|Met|Pro|Thr|Pro|Ala|Lys|Val|Met|Pro|Arg|Val|Asp|Val|Pro|
| |210| | | | |215| | | | |220| | | | |
|Pro|Ser|Met|Arg|Ala|Ser|Lys|Glu|Arg|Val|Gly|Leu|Arg|Pro|Ala|Glu|
|225| | | | |230| | | | |235| | | | |240|
|Met|Leu|Ala|Asn|Val|Gly|Pro|Ser|Pro|Ser|Lys|Ala|Lys|Gln|Ile|Val|
| | | | |245| | | | |250| | | | |255| |
|Asn|Pro|Ala|Ala|Ala|Lys|Val|Thr|Gln|Arg|Val|Asp|Pro|Pro|Ala|
| | | |260| | | | |265| | | | |270| | |
|Lys|Ala|Ser|Gln|Arg|Ile|Asp|Pro|Leu|Leu|Pro|Ser|Lys|Val|His|Ile|
| | |275| | | | |280| | | | |285| | | |
|Asp|Ala|Thr|Arg|Ser|Phe|Thr|Lys|Val|Ser|Gln|Thr|Glu|Ile|Lys|Pro|
| |290| | | | |295| | | | |300| | | | |
|Glu|Val|Gln|Pro|Pro|Ile|Pro|Lys|Val|Pro|Val|Ala|Met|Pro|Thr|Ile|
|305| | | | |310| | | | |315| | | | |320|
|Asn|Arg|Gln|Gln|Ile|Asp|Thr|Ser|Gln|Pro|Lys|Glu|Glu|Pro|Cys|Ser|
| | | | |325| | | | |330| | | | |335| |
|Ser|Gly|Arg|Asn|Ala|Glu|Ala|Ala|Ser|Val|Ser|Val|Glu|Lys|Gln|Ser|
| | | |340| | | | |345| | | | |350| | |
|Lys|Ser|Asp|Arg|Lys|Ser|Arg|Lys|Ala|Glu|Lys|Lys|Glu|Lys|Lys|
| | |355| | | | |360| | | | |365| | | |
|Phe|Lys|Asp|Leu|Phe|Val|Thr|Trp|Asp|Pro|Pro|Ser|Met|Glu|Met|Asp|
| |370| | | | |375| | | | |380| | | | |
|Asp|Met|Asp|Leu|Gly|Asp|Gln|Asp|Trp|Leu|Leu|Gly|Ser|Thr|Arg|Lys|
|385| | | | |390| | | | |395| | | | |400|

```
Pro Asp Ala Gly Ile Gly Asn Cys Arg Glu Ile Val Asp Pro Leu Thr
            405                 410                 415

Ser Gln Ser Ala Glu Gln Phe Ser Leu Gln Pro Arg Ala Ile His Leu
        420                 425                 430

Pro Asp Leu His Val Tyr Gln Leu Pro Tyr Val Val Pro Phe
        435                 440                 445

<210> SEQ ID NO 10
<211> LENGTH: 451
<212> TYPE: DNA
<213> ORGANISM: Oryza sativa cv. Lemont

<400> SEQUENCE: 10
cgccacgcga aaccaaatcc cgccgcgcgg gatccttttc cgccggattc cacccgcgaa       60
tcggggttcc ccttacgatt cgcgggcgga ttagcgcgag gcgcgcctcc ccctacctct      120
gtgtgatccg ggggtgaggt taggccgggc gccggggcat cagccatgtc gaggtgcttc      180
ccctacccgc cgccggggta cgtgcgaaac ccagtggtgg ccgtggccgc ggccgaagcg      240
caggcgacca ctaaggtttg ttgaaccatc ggatttacac acgcacgtgc cggatcattt      300
gctcttgcct gttggttttg atcggatctg ttggttgtgc gtgtgtgatt tggggatcgc      360
acgtgcgggg aagctaaccct tgcatggat aacttgagat ttgtgaggcc gcgcttcgac      420
cagatcggtc gccaatcttt tagtggctga c                                     451

<210> SEQ ID NO 11
<211> LENGTH: 1616
<212> TYPE: DNA
<213> ORGANISM: Oryza sativa cv. Lemont

<400> SEQUENCE: 11
acaaatatat taaggattat caaattattc tatgtgaagt gtccgtgccc taattgtgtt       60
atcttctgta actgatagca acacatttgt ttcctgctgt gtgcttgtgt aaattggtac      120
ttcatcatta ctatatattt caaagaaaat tctgcattgc attcccgtcg tccgttctaa      180
atcagaactg acgattgctc tggtggctga agctccagaa agaaagggaa aaggctgaaa      240
agaagaaaga gaaaggagt gacaggaaag ctcttccaca tggtgagata tccaagcatt      300
caaagcgaac ccaccacaag aagagaaaac atgaagacat caataatgct gatcagaagt      360
cccggaaggt ttcctccatg gaacctggtg agcaattgga gaagagtgga ctctcagaag      420
agcatggagc tccttgcttt actcagacag agcatggctc tccagagagt tcacaggaca      480
gcagcaagag aagaaaggtt gtgttaccca gtcctagcca agctaagaat ggtgaggccc      540
tttcttgcat ttgtcttctt ttagctggtg atgttgaatt ggtttgactt atcctgaatt      600
atcatcttgc aggtaacatc cttcgaataa agataagaag agatcaagat tcttcagctt      660
cccttttcgga gaaatctaat gttgtacaaa caccagttca tcaaatggga tcagtttcat      720
ctctgccaag taagaaaaac tcaatgcaac cacacaacac cgaaatgatg gtgagaacag      780
catcaaccca gcagcaaagc atcaaaggtg attttcaagc agtaccgaaa caaggtatgc      840
caaccccagc aaaagtcatg ccaagagtcg atgttcctcc atctatgagg gcatcaaagg      900
aaaggattgg ccttcgtcct gcagagatgt tggccaatgt tggtccttca ccctccaagg      960
caaaacagat tgtcaatcct gcagctgcta aggttacaca aagagttgat cctccacctg     1020
ccaaggcatc tcagagaatt gatcctctgt tgccatccaa ggttcatata gatgctactc     1080
gatctttttac gaaggtctcc cagacagaga tcaagccgga agtacagccc ccaattctga     1140
```

-continued

| | |
|---|---|
| aggtgcctgt ggctatgcct accatcaatc gtcagcagat tgacacctcg cagcccaaag | 1200 |
| aagagccttg ctcctctggc aggaatgctg aagctgcttc agtatcagta gagaagcagt | 1260 |
| ccaagtcaga tcgcaaaaag agccgcaagg ctgagaagaa agagaagaag ttcaaagatt | 1320 |
| tatttgttac ctgggatcct ccgtctatgg aaatggatga tatggatctc ggggaccagg | 1380 |
| attggctgct tgatagtacg aggaaacctg atgctggcat tggcaactgc agagaaattg | 1440 |
| ttgatccact tacttctcaa tcagcagagc agttctcatt gcagcctagg gcgattcatt | 1500 |
| taccagacct tcatgtctat cagttgccat atgtggttcc attctaggtt tgtgtagtga | 1560 |
| gatggagtag gtgagaagta gagagatgtt gggagagagc tgtgtgggtc tgggag | 1616 |

<210> SEQ ID NO 12
<211> LENGTH: 1344
<212> TYPE: DNA
<213> ORGANISM: Oryza sativa cv. Lemont
<220> FEATURE:
<221> NAME/KEY: CDS
<222> LOCATION: (1)..(1344)
<223> OTHER INFORMATION:

<400> SEQUENCE: 12

| | |
|---|---|
| atg tcg agg tgc ttc ccc tac ccg ccg ccg ggg tac gtg cga aac cca<br>Met Ser Arg Cys Phe Pro Tyr Pro Pro Pro Gly Tyr Val Arg Asn Pro<br>1               5                  10              15 | 48 |
| gtg gtg gcc gtg gcc gcg gcc gaa gcg cag gcg acc act aag ctc cag<br>Val Val Ala Val Ala Ala Ala Glu Ala Gln Ala Thr Thr Lys Leu Gln<br>                 20                  25                  30 | 96 |
| aaa gaa agg gaa aag gct gaa aag aag aaa gag aaa agg agt gac agg<br>Lys Glu Arg Glu Lys Ala Glu Lys Lys Lys Glu Lys Arg Ser Asp Arg<br>               35                  40                  45 | 144 |
| aaa gct ctt cca cat ggt gag ata tcc aag cat tca aag cga acc cac<br>Lys Ala Leu Pro His Gly Glu Ile Ser Lys His Ser Lys Arg Thr His<br>50                55                  60 | 192 |
| cac aag aag aga aaa cat gaa gac atc aat aat gct gat cag aag tcc<br>His Lys Lys Arg Lys His Glu Asp Ile Asn Asn Ala Asp Gln Lys Ser<br>65                70                  75                  80 | 240 |
| cgg aag gtt tcc tcc atg gaa cct ggt gag caa ttg gag aag agt gga<br>Arg Lys Val Ser Ser Met Glu Pro Gly Glu Gln Leu Glu Lys Ser Gly<br>                 85                  90                  95 | 288 |
| ctc tca gaa gag cat gga gct cct tgc ttt act cag aca gag cat ggc<br>Leu Ser Glu Glu His Gly Ala Pro Cys Phe Thr Gln Thr Glu His Gly<br>                 100                105               110 | 336 |
| tct cca gag agt tca cag gac agc agc aag aga aga aag gtt gtg tta<br>Ser Pro Glu Ser Ser Gln Asp Ser Ser Lys Arg Arg Lys Val Val Leu<br>               115                120               125 | 384 |
| ccc agt cct agc caa gct aag aat ggt aac atc ctt cga ata aag ata<br>Pro Ser Pro Ser Gln Ala Lys Asn Gly Asn Ile Leu Arg Ile Lys Ile<br>               130                135               140 | 432 |
| aga aga gat caa gat tct tca gct tcc ctt tcg gag aaa tct aat gtt<br>Arg Arg Asp Gln Asp Ser Ser Ala Ser Leu Ser Glu Lys Ser Asn Val<br>145                150                155               160 | 480 |
| gta caa aca cca gtt cat caa atg gga tca gtt tca tct ctg cca agt<br>Val Gln Thr Pro Val His Gln Met Gly Ser Val Ser Ser Leu Pro Ser<br>                     165                170               175 | 528 |
| aag aaa aac tca atg caa cca cac aac acc gaa atg atg gtg aga aca<br>Lys Lys Asn Ser Met Gln Pro His Asn Thr Glu Met Met Val Arg Thr<br>               180                185               190 | 576 |
| gca tca acc cag cag caa agc atc aaa ggt gat ttt caa gca gta ccg<br>Ala Ser Thr Gln Gln Gln Ser Ile Lys Gly Asp Phe Gln Ala Val Pro | 624 |

```
                 195                 200                    205
aaa caa ggt atg cca acc cca gca aaa gtc atg cca aga gtc gat gtt        672
Lys Gln Gly Met Pro Thr Pro Ala Lys Val Met Pro Arg Val Asp Val
    210                 215                    220 cct cca tct atg agg gca tca aag gaa agg att ggc ctt cgt cct gca        720
Pro Pro Ser Met Arg Ala Ser Lys Glu Arg Ile Gly Leu Arg Pro Ala
225                 230                    235                 240 gag atg ttg gcc aat gtt ggt cct tca ccc tcc aag gca aaa cag att        768
Glu Met Leu Ala Asn Val Gly Pro Ser Pro Ser Lys Ala Lys Gln Ile
                245                    250                 255 gtc aat cct gca gct gct aag gtt aca caa aga gtt gat cct cca cct        816
Val Asn Pro Ala Ala Ala Lys Val Thr Gln Arg Val Asp Pro Pro Pro
            260                    265                 270 gcc aag gca tct cag aga att gat cct ctg ttg cca tcc aag gtt cat        864
Ala Lys Ala Ser Gln Arg Ile Asp Pro Leu Leu Pro Ser Lys Val His
        275                    280                 285 ata gat gct act cga tct ttt acg aag gtc tcc cag aca gag atc aag        912
Ile Asp Ala Thr Arg Ser Phe Thr Lys Val Ser Gln Thr Glu Ile Lys
    290                    295                 300 ccg gaa gta cag ccc cca att ctg aag gtg cct gtg gct atg cct acc        960
Pro Glu Val Gln Pro Pro Ile Leu Lys Val Pro Val Ala Met Pro Thr
305                    310                 315                 320 atc aat cgt cag cag att gac acc tcg cag ccc aaa gaa gag cct tgc       1008
Ile Asn Arg Gln Gln Ile Asp Thr Ser Gln Pro Lys Glu Glu Pro Cys
                   325                 330                 335 tcc tct ggc agg aat gct gaa gct gct tca gta tca gta gag aag cag       1056
Ser Ser Gly Arg Asn Ala Glu Ala Ala Ser Val Ser Val Glu Lys Gln
               340                 345                 350 tcc aag tca gat cgc aaa aag agc cgc aag gct gag aag aaa gag aag       1104
Ser Lys Ser Asp Arg Lys Lys Ser Arg Lys Ala Glu Lys Lys Glu Lys
           355                 360                 365 aag ttc aaa gat tta ttt gtt acc tgg gat cct ccg tct atg gaa atg       1152
Lys Phe Lys Asp Leu Phe Val Thr Trp Asp Pro Pro Ser Met Glu Met
370                 375                 380 gat gat atg gat ctc ggg gac cag gat tgg ctg ctt gat agt acg agg       1200
Asp Asp Met Asp Leu Gly Asp Gln Asp Trp Leu Leu Asp Ser Thr Arg
385                 390                 395                 400 aaa cct gat gct ggc att ggc aac tgc aga gaa att gtt gat cca ctt       1248
Lys Pro Asp Ala Gly Ile Gly Asn Cys Arg Glu Ile Val Asp Pro Leu
                405                 410                 415 act tct caa tca gca gag cag ttc tca ttg cag cct agg gcg att cat       1296
Thr Ser Gln Ser Ala Glu Gln Phe Ser Leu Gln Pro Arg Ala Ile His
            420                 425                 430 tta cca gac ctt cat gtc tat cag ttg cca tat gtg gtt cca ttc tag       1344
Leu Pro Asp Leu His Val Tyr Gln Leu Pro Tyr Val Val Pro Phe
        435                 440                 445

<210> SEQ ID NO 13
<211> LENGTH: 447
<212> TYPE: PRT
<213> ORGANISM: Oryza sativa cv. Lemont

<400> SEQUENCE: 13

Met Ser Arg Cys Phe Pro Tyr Pro Pro Gly Tyr Val Arg Asn Pro
1               5                  10                  15

Val Val Ala Val Ala Ala Glu Ala Gln Ala Thr Thr Lys Leu Gln
            20                  25                  30

Lys Glu Arg Glu Lys Ala Glu Lys Lys Glu Lys Arg Ser Asp Arg
        35                  40                  45
```

```
Lys Ala Leu Pro His Gly Glu Ile Ser Lys His Ser Lys Arg Thr His
 50                  55                  60

His Lys Lys Arg Lys His Glu Asp Ile Asn Asn Ala Asp Gln Lys Ser
 65                  70                  75                  80

Arg Lys Val Ser Ser Met Glu Pro Gly Glu Gln Leu Glu Lys Ser Gly
                 85                  90                  95

Leu Ser Glu Glu His Gly Ala Pro Cys Phe Thr Gln Thr Glu His Gly
            100                 105                 110

Ser Pro Glu Ser Ser Gln Asp Ser Ser Lys Arg Arg Lys Val Val Leu
            115                 120                 125

Pro Ser Pro Ser Gln Ala Lys Asn Gly Asn Ile Leu Arg Ile Lys Ile
130                 135                 140

Arg Arg Asp Gln Asp Ser Ser Ala Ser Leu Ser Glu Lys Ser Asn Val
145                 150                 155                 160

Val Gln Thr Pro Val His Gln Met Gly Ser Val Ser Ser Leu Pro Ser
                165                 170                 175

Lys Lys Asn Ser Met Gln Pro His Asn Thr Glu Met Met Val Arg Thr
            180                 185                 190

Ala Ser Thr Gln Gln Gln Ser Ile Lys Gly Asp Phe Gln Ala Val Pro
            195                 200                 205

Lys Gln Gly Met Pro Thr Pro Ala Lys Val Met Pro Arg Val Asp Val
210                 215                 220

Pro Pro Ser Met Arg Ala Ser Lys Glu Arg Ile Gly Leu Arg Pro Ala
225                 230                 235                 240

Glu Met Leu Ala Asn Val Gly Pro Ser Pro Ser Lys Ala Lys Gln Ile
                245                 250                 255

Val Asn Pro Ala Ala Lys Val Thr Gln Arg Val Asp Pro Pro
                260                 265                 270

Ala Lys Ala Ser Gln Arg Ile Asp Pro Leu Leu Pro Ser Lys Val His
            275                 280                 285

Ile Asp Ala Thr Arg Ser Phe Thr Lys Val Ser Gln Thr Glu Ile Lys
290                 295                 300

Pro Glu Val Gln Pro Pro Ile Leu Lys Val Pro Val Ala Met Pro Thr
305                 310                 315                 320

Ile Asn Arg Gln Gln Ile Asp Thr Ser Gln Pro Lys Glu Pro Cys
                325                 330                 335

Ser Ser Gly Arg Asn Ala Glu Ala Ser Val Ser Val Glu Lys Gln
                340                 345                 350

Ser Lys Ser Asp Arg Lys Lys Ser Arg Lys Ala Glu Lys Lys Glu Lys
            355                 360                 365

Lys Phe Lys Asp Leu Phe Val Thr Trp Asp Pro Ser Met Glu Met
            370                 375                 380

Asp Asp Met Asp Leu Gly Asp Gln Asp Trp Leu Leu Asp Ser Thr Arg
385                 390                 395                 400

Lys Pro Asp Ala Gly Ile Gly Asn Cys Arg Glu Ile Val Asp Pro Leu
                405                 410                 415

Thr Ser Gln Ser Ala Glu Gln Phe Ser Leu Gln Pro Arg Ala Ile His
            420                 425                 430

Leu Pro Asp Leu His Val Tyr Gln Leu Pro Tyr Val Val Pro Phe
            435                 440                 445

<210> SEQ ID NO 14
<211> LENGTH: 2459
<212> TYPE: DNA
```

<213> ORGANISM: Oryza sativa strain IR64

<400> SEQUENCE: 14

| | | | | | |
|---|---|---|---|---|---|
| atgtcgaggt | gcttccccta | cccgccgccg | gggtacgtgc | gaaacccagt | ggtggccgtg | 60 |
| gccgcggccg | aagcgcaggc | gaccactaag | gtttgttgaa | ccatcggatt | tacacacgca | 120 |
| cgtgccggat | catttgctct | tgcctgttgg | ttttgatcgg | atctgttggt | tgtgcgtgtg | 180 |
| tgatttgggg | atcgcacgtg | cggggaagct | aacctttgca | tggataactt | gagatttgtg | 240 |
| aggccgcgct | tcgaccagat | cggtcgccaa | tcttttagtg | gctgaccgtg | gaaagaggat | 300 |
| attactgacc | ttcggtttgc | taattttggt | tgtgccgttg | aatctgaaat | aaccagaata | 360 |
| gtcatgggga | aaaagtctga | tctggaaggt | tcgaattaca | tttctatata | ttgttgtgct | 420 |
| cccagacgat | ggttgcaaga | aattactcat | gctggataaa | attgtggatg | taagagtctg | 480 |
| cagttgttaa | aatctggaaa | cagcacattt | tgccgtagta | aatttgaatc | catgttgctg | 540 |
| tctcgttatt | ggtgtgttac | gagtaacctg | tgtgttgtta | tctccgcttg | gactagattc | 600 |
| caagtaatcc | agtgccttca | tgacctgcaa | attctatgcc | tatgaagtaa | catgaacagt | 660 |
| ttgtatgtat | tctgttgatg | catacttgca | ttatttgtga | gatgtacatg | ttgtggtaaa | 720 |
| attttgcatt | caccatatag | aaatagtaat | tgactatcct | tgtttagttc | gaaaactact | 780 |
| gcaggtttag | ttattctctg | ttgccaagag | tgcttgttat | gattgtaagg | gttacagttc | 840 |
| tgtgactaac | catgtaacaa | atatattaag | gattatcaaa | ttattctatg | tgaagtgtcc | 900 |
| gtgccctaat | tgtgttatct | tctgtaactg | atagcacaac | atttgtttcc | tgctgtgtgc | 960 |
| ttgtgtaaat | tggtacttca | tcattactat | atatttcaaa | gaaaattctg | cattgcattc | 1020 |
| ccgtcgtccg | ttctaaatca | gaactgacga | ttgctctggt | ggctgaagct | ccagaaagaa | 1080 |
| agggaaaagg | ccgaaaagaa | gaaagagaaa | aggagtgaca | ggaaagctct | tccacatggt | 1140 |
| gagatatcca | agcattcaaa | gcgaacccac | aagaagagaa | acatgaaga | catcaataat | 1200 |
| gctgatcaga | agtcccggaa | ggtttcctcc | atggaacctg | gtgagcaatt | ggagaagagt | 1260 |
| ggactctcag | aagagcatgg | agctccttgc | tttactcaga | cagtgcatgg | ctctccagag | 1320 |
| agttcacagg | acagcagcaa | gagaagaaag | gttgtgttac | ccagtcctag | ccaagctaag | 1380 |
| aatggtgagg | ccctttcttg | catttgtctt | cttttagctg | gtgatgttga | attggtttga | 1440 |
| cttatcctga | attatcatct | tgcaggtaac | atccttcgaa | taaagataag | aagagatcaa | 1500 |
| gattcttcag | cttcccttc | ggagaaatct | aatgttgtac | aaacaccagt | tcatcaaatg | 1560 |
| ggatcagttt | catctctgcc | aagtaagaaa | aactcaatgc | aaccacacaa | caccgaaatg | 1620 |
| atggtgagaa | cagcatcaac | ccagcagcaa | agcatcaaag | gtgattttca | agcagtactg | 1680 |
| aaacaaggta | tgccaacccc | agcaaaagtc | atgccaagag | tcgatgttcc | tccatctatg | 1740 |
| agggcatcaa | aggaaagggt | tggccttcgt | cctgcagaga | tgttggccaa | tgttggtcct | 1800 |
| tcaccctcca | aggcaaaaca | gattgtcaat | cctgcagctg | ctaaggttac | acaaagagtt | 1860 |
| gatcctccac | ctgccaaggc | atctcagaga | attgatcctc | tgttgccatc | caaggttcat | 1920 |
| atagatgcta | ctcgatcttt | tacgaagctc | tcccagacag | agatcaagcc | ggaagtacag | 1980 |
| cccccaattc | cgaaggtgcc | tgtggctatg | cctaccatca | atcgtcagca | gattgacacc | 2040 |
| tcgcagccca | agaagagcc | ttgctcctct | ggcaggaatg | ctgaagctgc | ttcagtatca | 2100 |
| gtagagaagc | agtccaagtc | agatcgcaaa | aagagccgca | aggctgagaa | gaaagagaag | 2160 |
| aagttcaaag | atttatttgt | tacctgggat | cctccgtcta | tggaaatgga | tgatatggat | 2220 |
| cttggggacc | aggattggct | gcttggtagt | acgaggaaac | ctgatgctgg | cattggcaac | 2280 |

```
tgcagagaaa ttgttgatcc acttacttct caatcagcgg agcagttctc attgcagcct    2340
agggcgattc atttaccaga ccttcatgtc tatcagttgc catatgtggt tccattctag    2400
gtttgtgtag tgagatggag taggtgagaa gtagagagat gttgggagag agctgtgtg    2459

<210> SEQ ID NO 15
<211> LENGTH: 1341
<212> TYPE: DNA
<213> ORGANISM: Oryza sativa strain IR64
<220> FEATURE:
<221> NAME/KEY: CDS
<222> LOCATION: (1)..(1341)
<223> OTHER INFORMATION:

<400> SEQUENCE: 15 atg tcg agg tgc ttc ccc tac ccg ccg ggg tac gtg cga aac cca         48
Met Ser Arg Cys Phe Pro Tyr Pro Pro Gly Tyr Val Arg Asn Pro
1               5                   10                  15 gtg gtg gcc gtg gcc gcg gcc gaa gcg cag gcg acc act aag ctc cag    96
Val Val Ala Val Ala Ala Ala Glu Ala Gln Ala Thr Thr Lys Leu Gln
                20                  25                  30 aaa gaa agg gaa aag gcc gaa aag aag aaa gag aaa agg agt gac agg   144
Lys Glu Arg Glu Lys Ala Glu Lys Lys Lys Glu Lys Arg Ser Asp Arg
            35                  40                  45 aaa gct ctt cca cat ggt gag ata tcc aag cat tca aag cga acc cac   192
Lys Ala Leu Pro His Gly Glu Ile Ser Lys His Ser Lys Arg Thr His
        50                  55                  60 aag aag aga aaa cat gaa gac atc aat aat gct gat cag aag tcc cgg   240
Lys Lys Arg Lys His Glu Asp Ile Asn Asn Ala Asp Gln Lys Ser Arg
65                  70                  75                  80 aag gtt tcc tcc atg gaa cct ggt gag caa ttg gag aag agt gga ctc   288
Lys Val Ser Ser Met Glu Pro Gly Glu Gln Leu Glu Lys Ser Gly Leu
                85                  90                  95 tca gaa gag cat gga gct cct tgc ttt act cag aca gtg cat ggc tct   336
Ser Glu Glu His Gly Ala Pro Cys Phe Thr Gln Thr Val His Gly Ser
            100                 105                 110 cca gag agt tca cag gac agc agc aag aga aga aag gtt gtg tta ccc   384
Pro Glu Ser Ser Gln Asp Ser Ser Lys Arg Arg Lys Val Val Leu Pro
        115                 120                 125 agt cct agc caa gct aag aat ggt aac atc ctt cga ata aag ata aga   432
Ser Pro Ser Gln Ala Lys Asn Gly Asn Ile Leu Arg Ile Lys Ile Arg
    130                 135                 140 aga gat caa gat tct tca gct tcc ctt tcg gag aaa tct aat gtt gta   480
Arg Asp Gln Asp Ser Ser Ala Ser Leu Ser Glu Lys Ser Asn Val Val
145                 150                 155                 160 caa aca cca gtt cat caa atg gga tca gtt tca tct ctg cca agt aag   528
Gln Thr Pro Val His Gln Met Gly Ser Val Ser Ser Leu Pro Ser Lys
                165                 170                 175 aaa aac tca atg caa cca cac aac acc gaa atg atg gtg aga aca gca   576
Lys Asn Ser Met Gln Pro His Asn Thr Glu Met Met Val Arg Thr Ala
            180                 185                 190 tca acc cag cag caa agc atc aaa ggt gat ttt caa gca gta ctg aaa   624
Ser Thr Gln Gln Gln Ser Ile Lys Gly Asp Phe Gln Ala Val Leu Lys
        195                 200                 205 caa ggt atg cca acc cca gca aaa gtc atg cca aga gtc gat gtt cct   672
Gln Gly Met Pro Thr Pro Ala Lys Val Met Pro Arg Val Asp Val Pro
    210                 215                 220 cca tct atg agg gca tca aag gaa agg gtt ggc ctt cgt cct gca gag   720
Pro Ser Met Arg Ala Ser Lys Glu Arg Val Gly Leu Arg Pro Ala Glu
225                 230                 235                 240
```

```
atg ttg gcc aat gtt ggt cct tca ccc tcc aag gca aaa cag att gtc        768
Met Leu Ala Asn Val Gly Pro Ser Pro Ser Lys Ala Lys Gln Ile Val
            245                 250                 255 aat cct gca gct gct aag gtt aca caa aga gtt gat cct cca cct gcc        816
Asn Pro Ala Ala Ala Lys Val Thr Gln Arg Val Asp Pro Pro Pro Ala
        260                 265                 270 aag gca tct cag aga att gat cct ctg ttg cca tcc aag gtt cat ata        864
Lys Ala Ser Gln Arg Ile Asp Pro Leu Leu Pro Ser Lys Val His Ile
    275                 280                 285 gat gct act cga tct ttt acg aag ctc tcc cag aca gag atc aag ccg        912
Asp Ala Thr Arg Ser Phe Thr Lys Leu Ser Gln Thr Glu Ile Lys Pro
290                 295                 300 gaa gta cag ccc cca att ccg aag gtg cct gtg gct atg cct acc atc        960
Glu Val Gln Pro Pro Ile Pro Lys Val Pro Val Ala Met Pro Thr Ile
305                 310                 315                 320 aat cgt cag cag att gac acc tcg cag ccc aaa gaa gag cct tgc tcc       1008
Asn Arg Gln Gln Ile Asp Thr Ser Gln Pro Lys Glu Glu Pro Cys Ser
            325                 330                 335 tct ggc agg aat gct gaa gct gct tca gta tca gta gag aag cag tcc       1056
Ser Gly Arg Asn Ala Glu Ala Ala Ser Val Ser Val Glu Lys Gln Ser
        340                 345                 350 aag tca gat cgc aaa aag agc cgc aag gct gag aag aaa gag aag aag       1104
Lys Ser Asp Arg Lys Lys Ser Arg Lys Ala Glu Lys Lys Glu Lys Lys
    355                 360                 365 ttc aaa gat tta ttt gtt acc tgg gat cct ccg tct atg gaa atg gat       1152
Phe Lys Asp Leu Phe Val Thr Trp Asp Pro Pro Ser Met Glu Met Asp
370                 375                 380 gat atg gat ctt ggg gac cag gat tgg ctg ctt ggt agt acg agg aaa       1200
Asp Met Asp Leu Gly Asp Gln Asp Trp Leu Leu Gly Ser Thr Arg Lys
385                 390                 395                 400 cct gat gct ggc att ggc aac tgc aga gaa att gtt gat cca ctt act       1248
Pro Asp Ala Gly Ile Gly Asn Cys Arg Glu Ile Val Asp Pro Leu Thr
            405                 410                 415 tct caa tca gcg gag cag ttc tca ttg cag cct agg gcg att cat tta       1296
Ser Gln Ser Ala Glu Gln Phe Ser Leu Gln Pro Arg Ala Ile His Leu
        420                 425                 430 cca gac ctt cat gtc tat cag ttg cca tat gtg gtt cca ttc tag           1341
Pro Asp Leu His Val Tyr Gln Leu Pro Tyr Val Val Pro Phe
    435                 440                 445
```

<210> SEQ ID NO 16
<211> LENGTH: 446
<212> TYPE: PRT
<213> ORGANISM: Oryza sativa strain IR64

<400> SEQUENCE: 16

```
Met Ser Arg Cys Phe Pro Tyr Pro Pro Gly Tyr Val Arg Asn Pro
1               5                   10                  15

Val Val Ala Val Ala Ala Ala Glu Ala Gln Ala Thr Thr Lys Leu Gln
            20                  25                  30

Lys Glu Arg Glu Lys Ala Glu Lys Lys Glu Lys Arg Ser Asp Arg
        35                  40                  45

Lys Ala Leu Pro His Gly Glu Ile Ser Lys His Ser Lys Arg Thr His
    50                  55                  60

Lys Lys Arg Lys His Glu Asp Ile Asn Asn Ala Asp Gln Lys Ser Arg
65                  70                  75                  80

Lys Val Ser Ser Met Glu Pro Gly Glu Gln Leu Glu Lys Ser Gly Leu
            85                  90                  95

Ser Glu Glu His Gly Ala Pro Cys Phe Thr Gln Thr Val His Gly Ser
```

```
                   100                 105                 110
Pro Glu Ser Ser Gln Asp Ser Ser Lys Arg Arg Lys Val Val Leu Pro
            115                 120                 125

Ser Pro Ser Gln Ala Lys Asn Gly Asn Ile Leu Arg Ile Lys Ile Arg
        130                 135                 140

Arg Asp Gln Asp Ser Ser Ala Ser Leu Ser Glu Lys Ser Asn Val Val
145                 150                 155                 160

Gln Thr Pro Val His Gln Met Gly Ser Val Ser Ser Leu Pro Ser Lys
                    165                 170                 175

Lys Asn Ser Met Gln Pro His Asn Thr Glu Met Met Val Arg Thr Ala
                180                 185                 190

Ser Thr Gln Gln Gln Ser Ile Lys Gly Asp Phe Gln Ala Val Leu Lys
            195                 200                 205

Gln Gly Met Pro Thr Pro Ala Lys Val Met Pro Arg Val Asp Val Pro
        210                 215                 220

Pro Ser Met Arg Ala Ser Lys Glu Arg Val Gly Leu Arg Pro Ala Glu
225                 230                 235                 240

Met Leu Ala Asn Val Gly Pro Ser Pro Ser Lys Ala Lys Gln Ile Val
                    245                 250                 255

Asn Pro Ala Ala Ala Lys Val Thr Gln Arg Val Asp Pro Pro Pro Ala
                260                 265                 270

Lys Ala Ser Gln Arg Ile Asp Pro Leu Leu Pro Ser Lys Val His Ile
            275                 280                 285

Asp Ala Thr Arg Ser Phe Thr Lys Leu Ser Gln Thr Glu Ile Lys Pro
        290                 295                 300

Glu Val Gln Pro Pro Ile Pro Lys Val Pro Val Ala Met Pro Thr Ile
305                 310                 315                 320

Asn Arg Gln Gln Ile Asp Thr Ser Gln Pro Lys Glu Glu Pro Cys Ser
                    325                 330                 335

Ser Gly Arg Asn Ala Glu Ala Ala Ser Val Ser Val Glu Lys Gln Ser
                340                 345                 350

Lys Ser Asp Arg Lys Lys Ser Arg Lys Ala Glu Lys Lys Glu Lys Lys
            355                 360                 365

Phe Lys Asp Leu Phe Val Thr Trp Asp Pro Pro Ser Met Glu Met Asp
        370                 375                 380

Asp Met Asp Leu Gly Asp Gln Asp Trp Leu Leu Gly Ser Thr Arg Lys
385                 390                 395                 400

Pro Asp Ala Gly Ile Gly Asn Cys Arg Glu Ile Val Asp Pro Leu Thr
                    405                 410                 415

Ser Gln Ser Ala Glu Gln Phe Ser Leu Gln Pro Arg Ala Ile His Leu
                420                 425                 430

Pro Asp Leu His Val Tyr Gln Leu Pro Tyr Val Val Pro Phe
            435                 440                 445

<210> SEQ ID NO 17
<211> LENGTH: 2432
<212> TYPE: DNA
<213> ORGANISM: Oryza sativa cv. Kasalath
<220> FEATURE:
<221> NAME/KEY: misc_feature
<222> LOCATION: (1950)..(1950)
<223> OTHER INFORMATION: N = G or C
<220> FEATURE:
<221> NAME/KEY: misc_feature
<222> LOCATION: (2032)..(2032)
<223> OTHER INFORMATION: N = G or C
```

```
<400> SEQUENCE: 17
catgtcgagg tgcttcccct acccgccgcc ggggtacgtg cgaaacccag tggtggccgt      60
ggccgcggcc gaagcgcagg cgaccactaa ggtttgttga accatcggat ttacacacgc     120
acgtgccgga tcatttgctc ttgcctgttg gttttgatcg gatctgttgg ttgtgcgtgt     180
gtgatttggg gatcgcacgt gcggggaagc taacctttgc atggataact tgagatttgt     240
gaggccgcgc ttcgaccaga tcggtcgcca atctttagt ggctgaccgt ggaaagagga      300
tattactgac cttcggtttg ctaattttgg ttgtgccgtt gaatctgaaa taaccagaat     360
agtcatgggg aaaaagtct gatctggaag gttcgaatta catttctata tattgttgtg      420
ctcccagacg atggttgcaa gaaattactc atgctggata aaattgtgga tgtaagagtc     480
tgcagttgtt aaaatctgga acagcacat tttgccgtag taaatttgaa tccatgttgc      540
tgtctcgtta ttggtgtgtt acgagtaacc tgtgtgttgt tatctccgct tggactagat     600
tccaagtaat ccagtgcctt catgacctgc aaattctatg cctatgaagt aacatgaaca     660
gtttgtatgt attctgttga tgcatacttg cattatttgt gagatgtaca tgttgtggta     720
aaattttgca ttcaccatat agaaatagta actgactatc cttgtttagt tcgaaaacta     780
ctgcaggttt agttattctc tgttgccaag agtgcttgtt atgattgtaa gggttacagt     840
tctgtgacta accatgtaac aaatatatta aggattatca aattattcta tgtgaagtgt     900
ccgtgcccta attgtgttat cttctgtaac tgatagcaca cattttgttt cctgctgtgt     960
gcttgtgtaa attggtactt catcattact atatatttca agaaaattc tgcattgcat     1020 tcccgtcgtc cgttctaaat cagaactgac gattgctctg gtggctgaag ctccagaaag    1080
aaagggaaaa ggccgaaaag aagaaagaga aaggagtga caggaaagct cttccacatg     1140
gtgagatatc caagcattca aagcgaaccc acaagaagag aaaacatgaa gacatcaata    1200
atgctgatca gaagtcccgg aaggtttcct ccatggaacc tggtgagcaa ttggagaaga    1260
gtggactctc agaagagcat ggagctcctt gctttactca gacagtgcat ggctctccag    1320
agagttcaca ggacagcagc aagagaagaa aggttgtgtt acccagtcct agccaagcta    1380
agaatggtga ggccctttct tgcatttgtc ttcttttagc tggtgatgtt gaattggttt    1440
gacttatcct gaattatcat cttgcaggta acatccttcg aataaagata gaagagatc    1500 aagattcttc agcttcccttt tcggagaaat ctaatgttgt acaaacacca gttcatcaaa    1560
tgggatcagt ttcatctctg ccaagtaaga aaaactcaat gcaaccacac aacaccgaaa    1620
tgatggtgag aacagcatca acccagcagc aaagcatcaa aggtgatttt caagcagtac    1680
tgaaacaagg tatgccaacc ccagcaaaag tcatgccaag agtcgatgtt cctccatcta    1740
tgagggcatc aaaggaaagg gttggccttc gtcctgcaga gatgttggcc aatgttggtc    1800
cttcaccctc caaggcaaaa cagattgtca atcctgcagc tgctaaggtt acacaaagag    1860
ttgatcctcc acctgccaag gcatctcaga gaattgatcc tctgttgcca tccaaggttc    1920
atatagatgc tactcgatct tttacgaagn tctcccagac agagatcaag ccggaagtac    1980
agcccccaat tccgaaggtg cctgtggcta tgcctaccat caatcgtcag cngattgaca    2040
cctcgcagcc caagaagag ccttgctcct ctggcaggaa tgctgaagct gcttcagtat     2100
cagtagagaa gcagtccaag tcagatcgca aaaagagccg caaggctgag aagaaagaga    2160
agaagttcaa agatttattt gttacctggg atcctccgtc tatggaaatg gatgatatgg    2220
atcttgggga ccaggattgg ctgcttggta gtacgaggaa acctgatgct ggcattggca    2280
actgcagaga aattgttgat ccacttactt ctcaatcagc agagcagttc tcattgcagc    2340
```

-continued

```
ctagggcgat tcatttacca gaccttcatg tctatcagtt gccatatgtg gttccattct    2400
aggtttgtgt agtgagatgg agtaggtgag aa                                  2432

<210> SEQ ID NO 18
<211> LENGTH: 1341
<212> TYPE: DNA
<213> ORGANISM: Oryza sativa cv. Kasalath
<220> FEATURE:
<221> NAME/KEY: CDS
<222> LOCATION: (1)..(1341)
<223> OTHER INFORMATION:
<220> FEATURE:
<221> NAME/KEY: misc_feature
<222> LOCATION: (889)..(889)
<223> OTHER INFORMATION: n = G, C
<220> FEATURE:
<221> NAME/KEY: misc_feature
<222> LOCATION: (971)..(971)
<223> OTHER INFORMATION: n = A, T

<400> SEQUENCE: 18 atg tcg agg tgc ttc ccc tac ccg ccg ccg ggg tac gtg cga aac cca      48
Met Ser Arg Cys Phe Pro Tyr Pro Pro Pro Gly Tyr Val Arg Asn Pro
 1               5                  10                  15 gtg gtg gcc gtg gcc gcg gcc gaa gcg cag gcg acc act aag ctc cag      96
Val Val Ala Val Ala Ala Ala Glu Ala Gln Ala Thr Thr Lys Leu Gln
                20                  25                  30 aaa gaa agg gaa aag gcc gaa aag aag aaa gag aaa agg agt gac agg     144
Lys Glu Arg Glu Lys Ala Glu Lys Lys Lys Glu Lys Arg Ser Asp Arg
            35                  40                  45 aaa gct ctt cca cat ggt gag ata tcc aag cat tca aag cga acc cac     192
Lys Ala Leu Pro His Gly Glu Ile Ser Lys His Ser Lys Arg Thr His
        50                  55                  60 aag aag aga aaa cat gaa gac atc aat aat gct gat cag aag tcc cgg     240
Lys Lys Arg Lys His Glu Asp Ile Asn Asn Ala Asp Gln Lys Ser Arg
 65                  70                  75                  80 aag gtt tcc tcc atg gaa cct ggt gag caa ttg gag aag agt gga ctc     288
Lys Val Ser Ser Met Glu Pro Gly Glu Gln Leu Glu Lys Ser Gly Leu
                 85                  90                  95 tca gaa gag cat gga gct cct tgc ttt act cag aca gtg cat ggc tct     336
Ser Glu Glu His Gly Ala Pro Cys Phe Thr Gln Thr Val His Gly Ser
                100                 105                 110 cca gag agt tca cag gac agc agc aag aga aga aag gtt gtg tta ccc     384
Pro Glu Ser Ser Gln Asp Ser Ser Lys Arg Arg Lys Val Val Leu Pro
            115                 120                 125 agt cct agc caa gct aag aat ggt aac atc ctt cga ata aag ata aga     432
Ser Pro Ser Gln Ala Lys Asn Gly Asn Ile Leu Arg Ile Lys Ile Arg
        130                 135                 140 aga gat caa gat tct tca gct tcc ctt tcg gag aaa tct aat gtt gta     480
Arg Asp Gln Asp Ser Ser Ala Ser Leu Ser Glu Lys Ser Asn Val Val
145                 150                 155                 160 caa aca cca gtt cat caa atg gga tca gtt tca tct ctg cca agt aag     528
Gln Thr Pro Val His Gln Met Gly Ser Val Ser Ser Leu Pro Ser Lys
                165                 170                 175 aaa aac tca atg caa cca cac aac acc gaa atg atg gtg aga aca gca     576
Lys Asn Ser Met Gln Pro His Asn Thr Glu Met Met Val Arg Thr Ala
            180                 185                 190 tca acc cag cag caa agc atc aaa ggt gat ttt caa gca gta ctg aaa     624
Ser Thr Gln Gln Gln Ser Ile Lys Gly Asp Phe Gln Ala Val Leu Lys
        195                 200                 205 caa ggt atg cca acc cca gca aaa gtc atg cca aga gtc gat gtt cct     672
Gln Gly Met Pro Thr Pro Ala Lys Val Met Pro Arg Val Asp Val Pro
```

|  |  |  |  |  |  |  |  |  |  |  |  |  |  |  |  |
|---|---|---|---|---|---|---|---|---|---|---|---|---|---|---|---|
| | 210 | | | | 215 | | | | 220 | | | | | | |
| cca | tct | atg | agg | gca | tca | aag | gaa | agg | gtt | ggc | ctt | cgt | cct | gca | gag | 720 |
| Pro | Ser | Met | Arg | Ala | Ser | Lys | Glu | Arg | Val | Gly | Leu | Arg | Pro | Ala | Glu | |
| 225 | | | | | 230 | | | | | 235 | | | | | 240 | |
| atg | ttg | gcc | aat | gtt | ggt | cct | tca | ccc | tcc | aag | gca | aaa | cag | att | gtc | 768 |
| Met | Leu | Ala | Asn | Val | Gly | Pro | Ser | Pro | Ser | Lys | Ala | Lys | Gln | Ile | Val | |
| | | | | 245 | | | | | 250 | | | | | 255 | | |
| aat | cct | gca | gct | gct | aag | gtt | aca | caa | aga | gtt | gat | cct | cca | cct | gcc | 816 |
| Asn | Pro | Ala | Ala | Ala | Lys | Val | Thr | Gln | Arg | Val | Asp | Pro | Pro | Pro | Ala | |
| | | | 260 | | | | | 265 | | | | | 270 | | | |
| aag | gca | tct | cag | aga | att | gat | cct | ctg | ttg | cca | tcc | aag | gtt | cat | ata | 864 |
| Lys | Ala | Ser | Gln | Arg | Ile | Asp | Pro | Leu | Leu | Pro | Ser | Lys | Val | His | Ile | |
| | | 275 | | | | | 280 | | | | | 285 | | | | |
| gat | gct | act | cga | tct | ttt | acg | aag | ntc | tcc | cag | aca | gag | atc | aag | ccg | 912 |
| Asp | Ala | Thr | Arg | Ser | Phe | Thr | Lys | Xaa | Ser | Gln | Thr | Glu | Ile | Lys | Pro | |
| | 290 | | | | | 295 | | | | | 300 | | | | | |
| gaa | gta | cag | ccc | cca | att | ccg | aag | gtg | cct | gtg | gct | atg | cct | acc | atc | 960 |
| Glu | Val | Gln | Pro | Pro | Ile | Pro | Lys | Val | Pro | Val | Ala | Met | Pro | Thr | Ile | |
| 305 | | | | | 310 | | | | | 315 | | | | | 320 | |
| aat | cgt | cag | cng | att | gac | acc | tcg | cag | ccc | aaa | gaa | gag | cct | tgc | tcc | 1008 |
| Asn | Arg | Gln | Xaa | Ile | Asp | Thr | Ser | Gln | Pro | Lys | Glu | Glu | Pro | Cys | Ser | |
| | | | 325 | | | | | 330 | | | | | 335 | | | |
| tct | ggc | agg | aat | gct | gaa | gct | gct | tca | gta | tca | gta | gag | aag | cag | tcc | 1056 |
| Ser | Gly | Arg | Asn | Ala | Glu | Ala | Ala | Ser | Val | Ser | Val | Glu | Lys | Gln | Ser | |
| | | 340 | | | | | 345 | | | | | 350 | | | | |
| aag | tca | gat | cgc | aaa | aag | agc | cgc | aag | gct | gag | aag | aaa | gag | aag | aag | 1104 |
| Lys | Ser | Asp | Arg | Lys | Lys | Ser | Arg | Lys | Ala | Glu | Lys | Lys | Glu | Lys | Lys | |
| | 355 | | | | | 360 | | | | | 365 | | | | | |
| ttc | aaa | gat | tta | ttt | gtt | acc | tgg | gat | cct | ccg | tct | atg | gaa | atg | gat | 1152 |
| Phe | Lys | Asp | Leu | Phe | Val | Thr | Trp | Asp | Pro | Pro | Ser | Met | Glu | Met | Asp | |
| 370 | | | | | 375 | | | | | 380 | | | | | | |
| gat | atg | gat | ctt | ggg | gac | cag | gat | tgg | ctg | ctt | ggt | agt | acg | agg | aaa | 1200 |
| Asp | Met | Asp | Leu | Gly | Asp | Gln | Asp | Trp | Leu | Leu | Gly | Ser | Thr | Arg | Lys | |
| 385 | | | | | 390 | | | | | 395 | | | | | 400 | |
| cct | gat | gct | ggc | att | ggc | aac | tgc | aga | gaa | att | gtt | gat | cca | ctt | act | 1248 |
| Pro | Asp | Ala | Gly | Ile | Gly | Asn | Cys | Arg | Glu | Ile | Val | Asp | Pro | Leu | Thr | |
| | | | | 405 | | | | | 410 | | | | | 415 | | |
| tct | caa | tca | gca | gag | cag | ttc | tca | ttg | cag | cct | agg | gcg | att | cat | tta | 1296 |
| Ser | Gln | Ser | Ala | Glu | Gln | Phe | Ser | Leu | Gln | Pro | Arg | Ala | Ile | His | Leu | |
| | | | 420 | | | | | 425 | | | | | 430 | | | |
| cca | gac | ctt | cat | gtc | tat | cag | ttg | cca | tat | gtg | gtt | cca | ttc | tag | | 1341 |
| Pro | Asp | Leu | His | Val | Tyr | Gln | Leu | Pro | Tyr | Val | Val | Pro | Phe | | | |
| | | | 435 | | | | | 440 | | | | | 445 | | | |

```
<210> SEQ ID NO 19
<211> LENGTH: 446
<212> TYPE: PRT
<213> ORGANISM: Oryza sativa cv. Kasalath
<220> FEATURE:
<221> NAME/KEY: misc_feature
<222> LOCATION: (297)..(297)
<223> OTHER INFORMATION: The 'Xaa' at location 297 stands for Ile, Val,
      Leu, or Phe.
<220> FEATURE:
<221> NAME/KEY: misc_feature
<222> LOCATION: (324)..(324)
<223> OTHER INFORMATION: The 'Xaa' at location 324 stands for Gln, Arg,
      Pro, or Leu.
<220> FEATURE:
<221> NAME/KEY: misc_feature
<222> LOCATION: (889)..(889)
<223> OTHER INFORMATION: n = G, C
<220> FEATURE:
<221> NAME/KEY: misc_feature
```

<222> LOCATION: (971)..(971)
<223> OTHER INFORMATION: n = A, T

<400> SEQUENCE: 19

```
Met Ser Arg Cys Phe Pro Tyr Pro Pro Gly Tyr Val Arg Asn Pro
1               5                   10                  15

Val Val Ala Val Ala Ala Ala Glu Ala Gln Ala Thr Thr Lys Leu Gln
                20                  25                  30

Lys Glu Arg Glu Lys Ala Glu Lys Lys Glu Lys Arg Ser Asp Arg
            35                  40                  45

Lys Ala Leu Pro His Gly Glu Ile Ser Lys His Ser Lys Arg Thr His
50                  55                  60

Lys Lys Arg Lys His Glu Asp Ile Asn Asn Ala Asp Gln Lys Ser Arg
65                  70                  75                  80

Lys Val Ser Ser Met Glu Pro Gly Glu Gln Leu Glu Lys Ser Gly Leu
                85                  90                  95

Ser Glu Glu His Gly Ala Pro Cys Phe Thr Gln Thr Val His Gly Ser
                100                 105                 110

Pro Glu Ser Ser Gln Asp Ser Ser Lys Arg Arg Lys Val Val Leu Pro
            115                 120                 125

Ser Pro Ser Gln Ala Lys Asn Gly Asn Ile Leu Arg Ile Lys Ile Arg
130                 135                 140

Arg Asp Gln Asp Ser Ser Ala Ser Leu Ser Glu Lys Ser Asn Val Val
145                 150                 155                 160

Gln Thr Pro Val His Gln Met Gly Ser Val Ser Ser Leu Pro Ser Lys
                165                 170                 175

Lys Asn Ser Met Gln Pro His Asn Thr Glu Met Met Val Arg Thr Ala
            180                 185                 190

Ser Thr Gln Gln Gln Ser Ile Lys Gly Asp Phe Gln Ala Val Leu Lys
            195                 200                 205

Gln Gly Met Pro Thr Pro Ala Lys Val Met Pro Arg Val Asp Val Pro
            210                 215                 220

Pro Ser Met Arg Ala Ser Lys Glu Arg Val Gly Leu Arg Pro Ala Glu
225                 230                 235                 240

Met Leu Ala Asn Val Gly Pro Ser Pro Ser Lys Ala Lys Gln Ile Val
                245                 250                 255

Asn Pro Ala Ala Ala Lys Val Thr Gln Arg Val Asp Pro Pro Pro Ala
            260                 265                 270

Lys Ala Ser Gln Arg Ile Asp Pro Leu Leu Pro Ser Lys Val His Ile
            275                 280                 285

Asp Ala Thr Arg Ser Phe Thr Lys Xaa Ser Gln Thr Glu Ile Lys Pro
            290                 295                 300

Glu Val Gln Pro Pro Ile Pro Lys Val Pro Val Ala Met Pro Thr Ile
305                 310                 315                 320

Asn Arg Gln Xaa Ile Asp Thr Ser Gln Pro Lys Glu Glu Pro Cys Ser
                325                 330                 335

Ser Gly Arg Asn Ala Glu Ala Ala Ser Val Ser Val Glu Lys Gln Ser
            340                 345                 350

Lys Ser Asp Arg Lys Lys Ser Arg Lys Ala Glu Lys Lys Glu Lys Lys
            355                 360                 365

Phe Lys Asp Leu Phe Val Thr Trp Asp Pro Pro Ser Met Glu Met Asp
            370                 375                 380

Asp Met Asp Leu Gly Asp Gln Asp Trp Leu Leu Gly Ser Thr Arg Lys
385                 390                 395                 400
```

```
Pro Asp Ala Gly Ile Gly Asn Cys Arg Glu Ile Val Asp Pro Leu Thr
            405                 410                 415
Ser Gln Ser Ala Glu Gln Phe Ser Leu Gln Pro Arg Ala Ile His Leu
        420                 425                 430
Pro Asp Leu His Val Tyr Gln Leu Pro Tyr Val Val Pro Phe
    435                 440                 445

<210> SEQ ID NO 20
<211> LENGTH: 2447
<212> TYPE: DNA
<213> ORGANISM: Oryza rufipogon strain 5948

<400> SEQUENCE: 20
```

| | | | | | |
|---|---|---|---|---|---|
| ccctacccgc | cgccggggta | cgtgcgaaac | ccagtggtgg | ccgtggccgc | ggccgaagcg | 60 |
| caggcgacca | ctaaggtttg | ttgaaccatc | ggatttacac | acgcacgtgc | cggatcattt | 120 |
| gctcttgcct | gttggttttg | atcggatctg | ttggttgtgc | gtgtgtgatt | tggggatcgc | 180 |
| acgtgcgggg | aagctaaccct | ttgcatggat | aacttgagat | ttgtgaggcc | gcgcttcgac | 240 |
| cagatcggtc | gccaatcttt | tagtggctga | ccgtggaaag | aggatattac | tgaccttcgg | 300 |
| tttgctaatt | ttggttgtgc | cgttgaatct | gaaataacca | gaatagtcat | ggggaaaaag | 360 |
| tctgatctgg | aaggttcgaa | ttacatttct | atatattgtt | gtgctcccag | acgatggttg | 420 |
| caagaaatta | ctcatgctgg | ataaaattgt | ggatgtaaga | gtctgcagtt | gttaaaatct | 480 |
| ggaaacagca | cattttgccg | tagtaaattt | gaatccatgt | tgctgtctcg | ttattggtgt | 540 |
| gttacgagta | acctgtgtgt | tgttatctcc | gcttggacta | gattccaagt | aatccagtgc | 600 |
| cttcatgacc | tgcaaattct | atgcctatga | agtaacatga | acagtttgta | tgtattctgt | 660 |
| tgatgcatac | ttgcattatt | tgtgagatgt | acatgttgtg | gtaaaatttt | gcattcacca | 720 |
| tatagaaata | gtaattgact | atccttgttt | agttcgaaaa | cttctgcagg | tttagttatt | 780 |
| ctctgttgcc | aagagtgctt | gttatgattg | taagggttac | agttctgtga | ctaaccatgt | 840 |
| aacaaatata | ttaaggatta | tcaaattatt | ctatgtgaag | tgtccgtgcc | ctaattgtgt | 900 |
| tatcttctgt | aactgatagc | acaacatttg | tttcctgctg | tgtgcttgtg | taaattggta | 960 |
| cttcatcatt | actatatatt | tcaaagaaaa | ttctgcattg | cattcccgtc | gtccgttcta | 1020 |
| aatcagaact | gacgattgct | ctggtggctg | aagctccaga | aagaaaggga | aaaggccgaa | 1080 |
| aagaagaaag | agaaaaggag | tgacaggaaa | gctcttccac | atggtgagat | atccaagcat | 1140 |
| tcaaagcgaa | cccacaagaa | gagaaaacat | gaagacatca | taatgctga | tcagaagtcc | 1200 |
| cggaaggttt | cctccatgga | acctggtgag | caattggaga | agagtggact | ctcagaagag | 1260 |
| catggagctc | cttgctttac | tcagacagtg | catggctctc | cagagagttc | acaggacagc | 1320 |
| agcaagagaa | gaaaggttgt | gttacccagt | cctagccaag | ctaagaatgg | tgaggccctt | 1380 |
| tcttgcattt | gtcttctttt | agctggtgat | gttgaattgg | tttgacttat | cctgaattat | 1440 |
| catcttgcag | gtaacatcct | tcgaataaag | ataagaagag | atcaagattc | ttcagcttcc | 1500 |
| ctttcggaga | aatctaatgt | tgtacaaaca | ccagttcatc | aaatgggatc | agtttcatct | 1560 |
| ctgccaagta | agaaaaactc | aatgcaacca | cacaacaccg | aaatgatggt | gagaacagca | 1620 |
| tcaacccagc | agcaaagcat | caaaggtgat | tttcaagcag | tactgaaaca | aggtatgcca | 1680 |
| accccagcaa | aagtcatgcc | aagagtcgat | gttcctccat | ctatgagggc | atcaaaggaa | 1740 |
| agggttggcc | ttcgtcctgc | agagatgttg | gccaatgttg | gtccttcacc | ctccaaggca | 1800 |
| aaacagattg | tcaatcctgc | agctgctaag | gttacacaaa | gagttgatcc | tccacctgcc | 1860 |

-continued

```
aaggcatctc agagaattga tcctctgttg ccatccaagg ttcatataga tgctactcga    1920
tcttttacga agctctccca gacagagatc aagccggaag tacagccccc aattccgaag    1980
gtgcctgtgg ctatgcctac catcaatcgt cagcagattg acacctcgca gcccaaagaa    2040
gagccttgct cctctggcag gaatgctgaa gctgcttcag tatcagtaga aagcagtcc     2100 aagtcagatc gcaaaaagag ccgcaaggct gagaagaaaa agaagaagtt caaagattta    2160
tttgttacct gggatcctcc gtctatggaa atggatgata tggatcttgg ggaccaggat    2220
tggctgcttg gtagtacgag gaaacctgat gctggcattg gcaactgcag agaaattgtt    2280
gatccactta cttctcaatc agcggagcag ttctcattgc agcctagggc gattcattta    2340
ccagaccttc atgtctatca gttgccatat gtggttccat tctaggtttg tgtagtgaga    2400
tggagtaggt gagaagtaga gagatgttgg gagagagctg tgtgggt                  2447
```

<210> SEQ ID NO 21
<211> LENGTH: 1341
<212> TYPE: DNA
<213> ORGANISM: Oryza rufipogon strain 5948
<220> FEATURE:
<221> NAME/KEY: CDS
<222> LOCATION: (1)..(1341)
<223> OTHER INFORMATION:
<220> FEATURE:
<221> NAME/KEY: misc_feature
<222> LOCATION: (1)..(15)
<223> OTHER INFORMATION: n = A, C, G, T

<400> SEQUENCE: 21

```
nnn nnn nnn nnn nnn ccc tac ccg ccg ccg ggg tac gtg cga aac cca      48
Xaa Xaa Xaa Xaa Xaa Pro Tyr Pro Pro Pro Gly Tyr Val Arg Asn Pro
 1               5                  10                  15 gtg gtg gcc gtg gcc gcg gcc gaa gcg cag gcg acc act aag ctc cag      96
Val Val Ala Val Ala Ala Ala Glu Ala Gln Ala Thr Thr Lys Leu Gln
             20                  25                  30 aaa gaa agg gaa aag gcc gaa aag aag aaa gag aaa agg agt gac agg     144
Lys Glu Arg Glu Lys Ala Glu Lys Lys Lys Glu Lys Arg Ser Asp Arg
         35                  40                  45 aaa gct ctt cca cat ggt gag ata tcc aag cat tca aag cga acc cac     192
Lys Ala Leu Pro His Gly Glu Ile Ser Lys His Ser Lys Arg Thr His
     50                  55                  60 aag aag aga aaa cat gaa gac atc aat aat gct gat cag aag tcc cgg     240
Lys Lys Arg Lys His Glu Asp Ile Asn Asn Ala Asp Gln Lys Ser Arg
 65                  70                  75                  80 aag gtt tcc tcc atg gaa cct ggt gag caa ttg gag aag agt gga ctc     288
Lys Val Ser Ser Met Glu Pro Gly Glu Gln Leu Glu Lys Ser Gly Leu
                 85                  90                  95 tca gaa gag cat gga gct cct tgc ttt act cag aca gtg cat ggc tct     336
Ser Glu Glu His Gly Ala Pro Cys Phe Thr Gln Thr Val His Gly Ser
            100                 105                 110 cca gag agt tca cag gac agc agc aag aga aga aag gtt gtg tta ccc     384
Pro Glu Ser Ser Gln Asp Ser Ser Lys Arg Arg Lys Val Val Leu Pro
        115                 120                 125 agt cct agc caa gct aag aat ggt aac atc ctt cga ata aag ata aga     432
Ser Pro Ser Gln Ala Lys Asn Gly Asn Ile Leu Arg Ile Lys Ile Arg
    130                 135                 140 aga gat caa gat tct tca gct tcc ctt tcg gag aaa tct aat gtt gta     480
Arg Asp Gln Asp Ser Ser Ala Ser Leu Ser Glu Lys Ser Asn Val Val
145                 150                 155                 160 caa aca cca gtt cat caa atg gga tca gtt tca tct ctg cca agt aag     528
Gln Thr Pro Val His Gln Met Gly Ser Val Ser Ser Leu Pro Ser Lys
```

|  |  |  |  |  |  |  |  |  |  |  |  |  |  |  |
|---|---|---|---|---|---|---|---|---|---|---|---|---|---|---|
|  |  |  |  | 165 |  |  |  | 170 |  |  |  | 175 |  |  |

```
aaa aac tca atg caa cca cac aac acc gaa atg atg gtg aga aca gca     576
Lys Asn Ser Met Gln Pro His Asn Thr Glu Met Met Val Arg Thr Ala
            180                 185                 190 tca acc cag cag caa agc atc aaa ggt gat ttt caa gca gta ctg aaa     624
Ser Thr Gln Gln Gln Ser Ile Lys Gly Asp Phe Gln Ala Val Leu Lys
            195                 200                 205 caa ggt atg cca acc cca gca aaa gtc atg cca aga gtc gat gtt cct     672
Gln Gly Met Pro Thr Pro Ala Lys Val Met Pro Arg Val Asp Val Pro
        210                 215                 220 cca tct atg agg gca tca aag gaa agg gtt ggc ctt cgt cct gca gag     720
Pro Ser Met Arg Ala Ser Lys Glu Arg Val Gly Leu Arg Pro Ala Glu
225                 230                 235                 240 atg ttg gcc aat gtt ggt cct tca ccc tcc aag gca aaa cag att gtc     768
Met Leu Ala Asn Val Gly Pro Ser Pro Ser Lys Ala Lys Gln Ile Val
                245                 250                 255 aat cct gca gct gct aag gtt aca caa aga gtt gat cct cca cct gcc     816
Asn Pro Ala Ala Ala Lys Val Thr Gln Arg Val Asp Pro Pro Pro Ala
            260                 265                 270 aag gca tct cag aga att gat cct ctg ttg cca tcc aag gtt cat ata     864
Lys Ala Ser Gln Arg Ile Asp Pro Leu Leu Pro Ser Lys Val His Ile
        275                 280                 285 gat gct act cga tct ttt acg aag ctc tcc cag aca gag atc aag ccg     912
Asp Ala Thr Arg Ser Phe Thr Lys Leu Ser Gln Thr Glu Ile Lys Pro
    290                 295                 300 gaa gta cag ccc cca att ccg aag gtg cct gtg gct atg cct acc atc     960
Glu Val Gln Pro Pro Ile Pro Lys Val Pro Val Ala Met Pro Thr Ile
305                 310                 315                 320 aat cgt cag cag att gac acc tcg cag ccc aaa gaa gag cct tgc tcc    1008
Asn Arg Gln Gln Ile Asp Thr Ser Gln Pro Lys Glu Glu Pro Cys Ser
                325                 330                 335 tct ggc agg aat gct gaa gct gct tca gta tca gta gag aag cag tcc    1056
Ser Gly Arg Asn Ala Glu Ala Ala Ser Val Ser Val Glu Lys Gln Ser
            340                 345                 350 aag tca gat cgc aaa aag agc cgc aag gct gag aag aaa gag aag aag    1104
Lys Ser Asp Arg Lys Lys Ser Arg Lys Ala Glu Lys Lys Glu Lys Lys
        355                 360                 365 ttc aaa gat tta ttt gtt acc tgg gat cct ccg tct atg gaa atg gat    1152
Phe Lys Asp Leu Phe Val Thr Trp Asp Pro Pro Ser Met Glu Met Asp
    370                 375                 380 gat atg gat ctt ggg gac cag gat tgg ctg ctt ggt agt acg agg aaa    1200
Asp Met Asp Leu Gly Asp Gln Asp Trp Leu Leu Gly Ser Thr Arg Lys
385                 390                 395                 400 cct gat gct ggc att ggc aac tgc aga gaa att gtt gat cca ctt act    1248
Pro Asp Ala Gly Ile Gly Asn Cys Arg Glu Ile Val Asp Pro Leu Thr
                405                 410                 415 tct caa tca gcg gag cag ttc tca ttg cag cct agg gcg att cat tta    1296
Ser Gln Ser Ala Glu Gln Phe Ser Leu Gln Pro Arg Ala Ile His Leu
            420                 425                 430 cca gac ctt cat gtc tat cag ttg cca tat gtg gtt cca ttc tag       1341
Pro Asp Leu His Val Tyr Gln Leu Pro Tyr Val Val Pro Phe
        435                 440                 445

<210> SEQ ID NO 22
<211> LENGTH: 446
<212> TYPE: PRT
<213> ORGANISM: Oryza rufipogon strain 5948
<220> FEATURE:
<221> NAME/KEY: misc_feature
<222> LOCATION: (1)..(1)
<223> OTHER INFORMATION: The 'Xaa' at location 1 stands for Lys, Asn,
```

```
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (2)..(2)
<223> OTHER INFORMATION: The 'Xaa' at location 2 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (3)..(3)
<223> OTHER INFORMATION: The 'Xaa' at location 3 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (4)..(4)
<223> OTHER INFORMATION: The 'Xaa' at location 4 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (5)..(5)
<223> OTHER INFORMATION: The 'Xaa' at location 5 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (1)..(15)
<223> OTHER INFORMATION: n = A, C, G, T

<400> SEQUENCE: 22

Xaa Xaa Xaa Xaa Xaa Pro Tyr Pro Pro Gly Tyr Val Arg Asn Pro
1               5                   10                  15

Val Val Ala Val Ala Ala Glu Ala Gln Ala Thr Thr Lys Leu Gln
                20                  25                  30

Lys Glu Arg Glu Lys Ala Glu Lys Lys Glu Lys Arg Ser Asp Arg
            35                  40                  45

Lys Ala Leu Pro His Gly Glu Ile Ser Lys His Ser Lys Arg Thr His
        50                  55                  60

Lys Lys Arg Lys His Glu Asp Ile Asn Asn Ala Asp Gln Lys Ser Arg
65                  70                  75                  80

Lys Val Ser Ser Met Glu Pro Gly Glu Gln Leu Glu Lys Ser Gly Leu
                85                  90                  95

Ser Glu Glu His Gly Ala Pro Cys Phe Thr Gln Thr Val His Gly Ser
            100                 105                 110

Pro Glu Ser Ser Gln Asp Ser Ser Lys Arg Arg Lys Val Val Leu Pro
        115                 120                 125

Ser Pro Ser Gln Ala Lys Asn Gly Asn Ile Leu Arg Ile Lys Ile Arg
    130                 135                 140

Arg Asp Gln Asp Ser Ser Ala Ser Leu Ser Glu Lys Ser Asn Val Val
145                 150                 155                 160

Gln Thr Pro Val His Gln Met Gly Ser Val Ser Ser Leu Pro Ser Lys
                165                 170                 175

Lys Asn Ser Met Gln Pro His Asn Thr Glu Met Met Val Arg Thr Ala
            180                 185                 190

Ser Thr Gln Gln Gln Ser Ile Lys Gly Asp Phe Gln Ala Val Leu Lys
        195                 200                 205

Gln Gly Met Pro Thr Pro Ala Lys Val Met Pro Arg Val Asp Val Pro
    210                 215                 220

Pro Ser Met Arg Ala Ser Lys Glu Arg Val Gly Leu Arg Pro Ala Glu
225                 230                 235                 240

Met Leu Ala Asn Val Gly Pro Ser Pro Ser Lys Ala Lys Gln Ile Val
```

```
                245                 250                 255
Asn Pro Ala Ala Ala Lys Val Thr Gln Arg Val Asp Pro Pro Ala
            260                 265                 270
Lys Ala Ser Gln Arg Ile Asp Pro Leu Leu Pro Ser Lys Val His Ile
        275                 280                 285
Asp Ala Thr Arg Ser Phe Thr Lys Leu Ser Gln Thr Glu Ile Lys Pro
        290                 295                 300
Glu Val Gln Pro Pro Ile Pro Lys Val Pro Val Ala Met Pro Thr Ile
305                 310                 315                 320
Asn Arg Gln Gln Ile Asp Thr Ser Gln Pro Lys Glu Glu Pro Cys Ser
                325                 330                 335
Ser Gly Arg Asn Ala Glu Ala Ala Ser Val Ser Val Glu Lys Gln Ser
                340                 345                 350
Lys Ser Asp Arg Lys Lys Ser Arg Lys Ala Glu Lys Lys Glu Lys Lys
        355                 360                 365
Phe Lys Asp Leu Phe Val Thr Trp Asp Pro Pro Ser Met Glu Met Asp
    370                 375                 380
Asp Met Asp Leu Gly Asp Gln Asp Trp Leu Leu Gly Ser Thr Arg Lys
385                 390                 395                 400
Pro Asp Ala Gly Ile Gly Asn Cys Arg Glu Ile Val Asp Pro Leu Thr
                405                 410                 415
Ser Gln Ser Ala Glu Gln Phe Ser Leu Gln Pro Arg Ala Ile His Leu
                420                 425                 430
Pro Asp Leu His Val Tyr Gln Leu Pro Tyr Val Val Pro Phe
            435                 440                 445

<210> SEQ ID NO 23
<211> LENGTH: 146
<212> TYPE: DNA
<213> ORGANISM: Oryza rufipogon strain 5949

<400> SEQUENCE: 23
cccctacctc tgtgtgatcc gggggtgagc ttaggccgga cgccggggca tcagccatgt      60
cgaggtgctt cccctacccg ccgccggggt acgtgcgaaa cccagtggtg gccgtggccg     120
cggccgaagc gcaggcgacc actaag                                          146

<210> SEQ ID NO 24
<211> LENGTH: 1615
<212> TYPE: DNA
<213> ORGANISM: Oryza rufipogon strain 5949

<400> SEQUENCE: 24
tctgtgacta accatgtaac aaatatatta aggattatca aattattcta tgtgaagtgt      60
ccgtgcccta attgtgttat cttctgtaac tgatagcaca acatttgttt cctgctgtgt     120
gcttgtgtaa attggtactt catcattact atatatttca aagaaaattc tgcattgcat     180
tcccgtcgtc cgttctaaat cagaactgac gattgctctg gtggctgaag ctccagaaag     240
aaagggaaaa ggccgaaaag aagaaagaga aaaagagtga caggaaagct cttccacatg     300
gtgagatatc caagcattca aagcgaaccc acaagaagag aaaacatgaa gacatcaata     360
atgctgatca gaagtcccgg aaggtttcct ccatggaacc tggtgagcaa ttggagaaga     420
gtggactctc agaagagcat ggagctcctt gctttactca gacagtgcat ggctctccag     480
agagttcaca ggacagcagc aagagaagaa aggttgtgtt acccagtcct agccaagcta     540
agaatggtga ggccctttct tgcatttgtc ttctcttagc tggtgatgtt gaattggttt     600
```

-continued

```
gacttatcct gaattatcat cttgcaggta acatccttcg aataaagata agaagagatc    660
aagattcttc agcttccctt tcggagaaat ctaatgttgt acaaacacca gttcatcaaa    720
tgggatcagt ttcatctctg ccaagtaaga aaaactcaat gcaaccacac aacaccgaaa    780
tgatggtgag aacagcatca acccagcagc aaagcatcaa aggtgatttt caagcagtac    840
tgaaacaagg tatgccaacc ccagcaaaag tcatgccaag agtcgatgtt cctccatcta    900
tgagggcatc aaaggaaagg gttggccttc gtcctgcaga gatgttggcc aatgttggtc    960
cttcaccatc caaggcaaaa cagattgtca atcctgcagc tgctaaggtt acacaaagag   1020
ttgatcctcc acctgccaag gcatctcaga gaattgatcc tctgttgcca tccaaggttc   1080
atatagatgc tactcgatct tttacgaagg tctcccagac agagatcaag ccggaagtac   1140
agcccccaat tccgaaggtg cctgtggcta tgcctaccat caatcgtcag cagattgaca   1200
cctcgcagcc caagaagag ccttgctcct ctggcaggaa tgctgaagct gcttcagtat   1260
cagtagagaa gcagtccaag tcagatcgca aaaagagccg caaggctgag aagaaagaga   1320
agaagttcaa agatttatttt gttacctggg atcctccgtc tatggaaatg gatgatatgg   1380
atcttgggga ccaggattgg ctgcttggta gtacgaggaa acctgatgct ggcattggca   1440
actgcagaga aattgttgat ccacttactt ctcaatcagc agagcagttc tcattgcagc   1500
ctagggcgat tcatttacca gaccttcatg tctatcagtt gccatatgtg gttccattct   1560
aggtttgtgt agtgagatgg agtaggtgag aagtagagag atgttgggag agagc        1615
```

<210> SEQ ID NO 25
<211> LENGTH: 1341
<212> TYPE: DNA
<213> ORGANISM: Oryza rufipogon strain 5949
<220> FEATURE:
<221> NAME/KEY: CDS
<222> LOCATION: (1)..(1341)
<223> OTHER INFORMATION:

<400> SEQUENCE: 25

```
atg tcg agg tgc ttc ccc tac ccg ccg ccg ggg tac gtg cga aac cca     48
Met Ser Arg Cys Phe Pro Tyr Pro Pro Pro Gly Tyr Val Arg Asn Pro
1               5                   10                  15 gtg gtg gcc gtg gcc gcg gcc gaa gcg cag gcg acc act aag ctc cag     96
Val Val Ala Val Ala Ala Ala Glu Ala Gln Ala Thr Thr Lys Leu Gln
            20                  25                  30 aaa gaa agg gaa aag gcc gaa aag aag aaa gag aaa aag agt gac agg    144
Lys Glu Arg Glu Lys Ala Glu Lys Lys Lys Glu Lys Lys Ser Asp Arg
        35                  40                  45 aaa gct ctt cca cat ggt gag ata tcc aag cat tca aag cga acc cac    192
Lys Ala Leu Pro His Gly Glu Ile Ser Lys His Ser Lys Arg Thr His
    50                  55                  60 aag aag aga aaa cat gaa gac atc aat aat gct gat cag aag tcc cgg    240
Lys Lys Arg Lys His Glu Asp Ile Asn Asn Ala Asp Gln Lys Ser Arg
65                  70                  75                  80 aag gtt tcc tcc atg gaa cct ggt gag caa ttg gag aag agt gga ctc    288
Lys Val Ser Ser Met Glu Pro Gly Glu Gln Leu Glu Lys Ser Gly Leu
                85                  90                  95 tca gaa gag cat gga gct cct tgc ttt act cag aca gtg cat ggc tct    336
Ser Glu Glu His Gly Ala Pro Cys Phe Thr Gln Thr Val His Gly Ser
            100                 105                 110 cca gag agt tca cag gac agc agc aag aga aga aag gtt gtg tta ccc    384
Pro Glu Ser Ser Gln Asp Ser Ser Lys Arg Arg Lys Val Val Leu Pro
        115                 120                 125
```

```
agt cct agc caa gct aag aat ggt aac atc ctt cga ata aag ata aga      432
Ser Pro Ser Gln Ala Lys Asn Gly Asn Ile Leu Arg Ile Lys Ile Arg
    130                 135                 140 aga gat caa gat tct tca gct tcc ctt tcg gag aaa tct aat gtt gta      480
Arg Asp Gln Asp Ser Ser Ala Ser Leu Ser Glu Lys Ser Asn Val Val
145                 150                 155                 160 caa aca cca gtt cat caa atg gga tca gtt tca tct ctg cca agt aag      528
Gln Thr Pro Val His Gln Met Gly Ser Val Ser Ser Leu Pro Ser Lys
                165                 170                 175 aaa aac tca atg caa cca cac aac acc gaa atg atg gtg aga aca gca      576
Lys Asn Ser Met Gln Pro His Asn Thr Glu Met Met Val Arg Thr Ala
        180                 185                 190 tca acc cag cag caa agc atc aaa ggt gat ttt caa gca gta ctg aaa      624
Ser Thr Gln Gln Gln Ser Ile Lys Gly Asp Phe Gln Ala Val Leu Lys
            195                 200                 205 caa ggt atg cca acc cca gca aaa gtc atg cca aga gtc gat gtt cct      672
Gln Gly Met Pro Thr Pro Ala Lys Val Met Pro Arg Val Asp Val Pro
        210                 215                 220 cca tct atg agg gca tca aag gaa agg gtt ggc ctt cgt cct gca gag      720
Pro Ser Met Arg Ala Ser Lys Glu Arg Val Gly Leu Arg Pro Ala Glu
225                 230                 235                 240 atg ttg gcc aat gtt ggt cct tca cca tcc aag gca aaa cag att gtc      768
Met Leu Ala Asn Val Gly Pro Ser Pro Ser Lys Ala Lys Gln Ile Val
                245                 250                 255 aat cct gca gct gct aag gtt aca caa aga gtt gat cct cca cct gcc      816
Asn Pro Ala Ala Ala Lys Val Thr Gln Arg Val Asp Pro Pro Pro Ala
            260                 265                 270 aag gca tct cag aga att gat cct ctg ttg cca tcc aag gtt cat ata      864
Lys Ala Ser Gln Arg Ile Asp Pro Leu Leu Pro Ser Lys Val His Ile
        275                 280                 285 gat gct act cga tct ttt acg aag gtc tcc cag aca gag atc aag ccg      912
Asp Ala Thr Arg Ser Phe Thr Lys Val Ser Gln Thr Glu Ile Lys Pro
        290                 295                 300 gaa gta cag ccc cca att ccg aag gtg cct gtg gct atg cct acc atc      960
Glu Val Gln Pro Pro Ile Pro Lys Val Pro Val Ala Met Pro Thr Ile
305                 310                 315                 320 aat cgt cag cag att gac acc tcg cag ccc aaa gaa gag cct tgc tcc     1008
Asn Arg Gln Gln Ile Asp Thr Ser Gln Pro Lys Glu Glu Pro Cys Ser
                325                 330                 335 tct ggc agg aat gct gaa gct gct tca gta tca gta gag aag cag tcc     1056
Ser Gly Arg Asn Ala Glu Ala Ala Ser Val Ser Val Glu Lys Gln Ser
            340                 345                 350 aag tca gat cgc aaa aag agc cgc aag gct gag aag aaa gag aag aag     1104
Lys Ser Asp Arg Lys Lys Ser Arg Lys Ala Glu Lys Lys Glu Lys Lys
        355                 360                 365 ttc aaa gat tta ttt gtt acc tgg gat cct ccg tct atg gaa atg gat     1152
Phe Lys Asp Leu Phe Val Thr Trp Asp Pro Pro Ser Met Glu Met Asp
370                 375                 380 gat atg gat ctt ggg gac cag gat tgg ctg ctt ggt agt acg agg aaa     1200
Asp Met Asp Leu Gly Asp Gln Asp Trp Leu Leu Gly Ser Thr Arg Lys
385                 390                 395                 400 cct gat gct ggc att ggc aac tgc aga gaa att gtt gat cca ctt act     1248
Pro Asp Ala Gly Ile Gly Asn Cys Arg Glu Ile Val Asp Pro Leu Thr
                405                 410                 415 tct caa tca gca gag cag ttc tca ttg cag cct agg gcg att cat tta     1296
Ser Gln Ser Ala Glu Gln Phe Ser Leu Gln Pro Arg Ala Ile His Leu
            420                 425                 430 cca gac ctt cat gtc tat cag ttg cca tat gtg gtt cca ttc tag         1341
Pro Asp Leu His Val Tyr Gln Leu Pro Tyr Val Val Pro Phe
        435                 440                 445
```

<210> SEQ ID NO 26
<211> LENGTH: 446
<212> TYPE: PRT
<213> ORGANISM: Oryza rufipogon strain 5949

<400> SEQUENCE: 26

```
Met Ser Arg Cys Phe Pro Tyr Pro Pro Gly Tyr Val Arg Asn Pro
1               5                   10                  15

Val Val Ala Val Ala Ala Ala Glu Ala Gln Ala Thr Thr Lys Leu Gln
                20                  25                  30

Lys Glu Arg Glu Lys Ala Glu Lys Lys Glu Lys Lys Ser Asp Arg
            35                  40                  45

Lys Ala Leu Pro His Gly Glu Ile Ser Lys His Ser Lys Arg Thr His
        50                  55                  60

Lys Lys Arg Lys His Glu Asp Ile Asn Asn Ala Asp Gln Lys Ser Arg
65                  70                  75                  80

Lys Val Ser Ser Met Glu Pro Gly Glu Gln Leu Glu Lys Ser Gly Leu
                85                  90                  95

Ser Glu Glu His Gly Ala Pro Cys Phe Thr Gln Thr Val His Gly Ser
            100                 105                 110

Pro Glu Ser Ser Gln Asp Ser Ser Lys Arg Arg Lys Val Val Leu Pro
        115                 120                 125

Ser Pro Ser Gln Ala Lys Asn Gly Asn Ile Leu Arg Ile Lys Ile Arg
    130                 135                 140

Arg Asp Gln Asp Ser Ser Ala Ser Leu Ser Glu Lys Ser Asn Val Val
145                 150                 155                 160

Gln Thr Pro Val His Gln Met Gly Ser Val Ser Ser Leu Pro Ser Lys
                165                 170                 175

Lys Asn Ser Met Gln Pro His Asn Thr Glu Met Met Val Arg Thr Ala
            180                 185                 190

Ser Thr Gln Gln Gln Ser Ile Lys Gly Asp Phe Gln Ala Val Leu Lys
        195                 200                 205

Gln Gly Met Pro Thr Pro Ala Lys Val Met Pro Arg Val Asp Val Pro
    210                 215                 220

Pro Ser Met Arg Ala Ser Lys Glu Arg Val Gly Leu Arg Pro Ala Glu
225                 230                 235                 240

Met Leu Ala Asn Val Gly Pro Ser Pro Ser Lys Ala Lys Gln Ile Val
                245                 250                 255

Asn Pro Ala Ala Ala Lys Val Thr Gln Arg Val Asp Pro Pro Ala
            260                 265                 270

Lys Ala Ser Gln Arg Ile Asp Pro Leu Leu Pro Ser Lys Val His Ile
        275                 280                 285

Asp Ala Thr Arg Ser Phe Thr Lys Val Ser Gln Thr Glu Ile Lys Pro
    290                 295                 300

Glu Val Gln Pro Pro Ile Pro Lys Val Pro Val Ala Met Pro Thr Ile
305                 310                 315                 320

Asn Arg Gln Gln Ile Asp Thr Ser Gln Pro Lys Glu Pro Cys Ser
                325                 330                 335

Ser Gly Arg Asn Ala Glu Ala Ala Ser Val Ser Val Glu Lys Gln Ser
            340                 345                 350

Lys Ser Asp Arg Lys Ser Arg Lys Ala Glu Lys Lys Glu Lys Lys
        355                 360                 365

Phe Lys Asp Leu Phe Val Thr Trp Asp Pro Pro Ser Met Glu Met Asp
```

|     |     |     |     |     |     | 370 |     |     |     |     |     | 375 |     |     |     |     |     | 380 |     |
| --- | --- | --- | --- | --- | --- | --- | --- | --- | --- | --- | --- | --- | --- | --- | --- | --- | --- | --- | --- |
| Asp | Met | Asp | Leu | Gly | Asp | Gln | Asp | Trp | Leu | Leu | Gly | Ser | Thr | Arg | Lys |
| 385 |     |     |     |     | 390 |     |     |     |     | 395 |     |     |     |     | 400 |

Pro Asp Ala Gly Ile Gly Asn Cys Arg Glu Ile Val Asp Pro Leu Thr
                 405                        410                        415

Ser Gln Ser Ala Glu Gln Phe Ser Leu Gln Pro Arg Ala Ile His Leu
             420                       425                        430

Pro Asp Leu His Val Tyr Gln Leu Pro Tyr Val Pro Phe
             435                       440                        445

<210> SEQ ID NO 27
<211> LENGTH: 107
<212> TYPE: DNA
<213> ORGANISM: Oryza rufipogon strain 5953

<400> SEQUENCE: 27

```
acgccgggc atcagccatg tcgaggtgct tccctaccc gccgccgggg tacgtgcgaa     60
acccagtggt ggccgtggcc gcggccgaag cgcaggcgac cactaag                107
```

<210> SEQ ID NO 28
<211> LENGTH: 1332
<212> TYPE: DNA
<213> ORGANISM: Oryza rufipogon strain 5953

<400> SEQUENCE: 28

```
ctccagaaag aaagggaaaa ggccgaaaag aagaaagaga aaagagtga caggaaagct     60
cttccacatg gtgagatatc caagcattca agcgaaccc acaagaagag aaaacatgaa    120
gacatcaata atgctgatca gaagtcccgg aaggtttcct ccatggaacc tggtgagcaa    180
ttggagaaga gtggactctc agaagagcat ggagctcctt gctttactca gacagtgcat    240
ggctctccag agagttcaca ggacagcagc aagagaagaa aggttgtgtt acccagtcct    300
agccaagcta agaatggtga ggcccttttct tgcattttc ttcttttagc tggtgatgtt    360
gaattggttt gacttatcct gaattatcat cttgcaggta acatccttcg aataaagata    420
agaagagatc aagattcttc agcttccctt tcggagaaat ctaatgttgt acaaacacca    480
gttcatcaaa tgggatcagt ttcatctctg ccaagtaaga aaactcaat gcaaccacac    540
aacaccgaaa tgatggtgag aacagcatca acccagcagc aaagcatcaa aggtgatttt    600
caagcagtac tgaaacaagg tatgccaacc ccagcaaaag tcatgccaag agtcgatgtt    660
cctccatcta tgagggcatc aaaggaaagg gttggccttc gtcctgcaga gatgttggcc    720
aatgttggtc cttcaccctc caaggcaaaa cagattgtca atcctgcagc tgctaaggtt    780
acacaaagag ttgatcctcc acctgccaag gcatctcaga gaattgatcc tctgttgcca    840
tccaaggttc atatagatgc tactcgatct tttacgaagc tctcccagac agagatcaag    900
ccggaagtac agccccaat tccgaaggtg cctgtggcta tgcctaccat caatcgtcag    960
cagattgaca cctcgcagcc caagaagag ccttgctcct ctggcaggaa tgctgaagct   1020
gcttcagtat cagtagagaa gcagtccaag tcagatcgca aaaagagccg caaggctgag   1080
aagaaagaga agaagttcaa agatttattt gttacctggg atcctccgtc tatggaaatg   1140
gatgatatgg atcttgggga ccaggattgg ctgcttggta gtacgaggaa acctgatgct   1200
ggcattggca actgcagaga aattgttgat ccacttactt ctcaatcagc ggagcagttc   1260
tcattgcagc ctagggcgat tcatttacca gaccttcatg tctatcagtt gccatatgtg   1320
gttccattct ag                                                      1332
```

```
<210> SEQ ID NO 29
<211> LENGTH: 1341
<212> TYPE: DNA
<213> ORGANISM: Oryza rufipogon strain 5953
<220> FEATURE:
<221> NAME/KEY: CDS
<222> LOCATION: (1)..(1341)
<223> OTHER INFORMATION:

<400> SEQUENCE: 29 atg tcg agg tgc ttc ccc tac ccg ccg ccg ggg tac gtg cga aac cca      48
Met Ser Arg Cys Phe Pro Tyr Pro Pro Pro Gly Tyr Val Arg Asn Pro
1               5                   10                  15 gtg gtg gcc gtg gcc gcg gcc gaa gcg cag gcg acc act aag ctc cag      96
Val Val Ala Val Ala Ala Ala Glu Ala Gln Ala Thr Thr Lys Leu Gln
                20                  25                  30 aaa gaa agg gaa aag gcc gaa aag aag aaa gag aaa aag agt gac agg     144
Lys Glu Arg Glu Lys Ala Glu Lys Lys Lys Glu Lys Lys Ser Asp Arg
            35                  40                  45 aaa gct ctt cca cat ggt gag ata tcc aag cat tca aag cga acc cac     192
Lys Ala Leu Pro His Gly Glu Ile Ser Lys His Ser Lys Arg Thr His
        50                  55                  60 aag aag aga aaa cat gaa gac atc aat aat gct gat cag aag tcc cgg     240
Lys Lys Arg Lys His Glu Asp Ile Asn Asn Ala Asp Gln Lys Ser Arg
65                  70                  75                  80 aag gtt tcc tcc atg gaa cct ggt gag caa ttg gag aag agt gga ctc     288
Lys Val Ser Ser Met Glu Pro Gly Glu Gln Leu Glu Lys Ser Gly Leu
                85                  90                  95 tca gaa gag cat gga gct cct tgc ttt act cag aca gtg cat ggc tct     336
Ser Glu Glu His Gly Ala Pro Cys Phe Thr Gln Thr Val His Gly Ser
            100                 105                 110 cca gag agt tca cag gac agc agc aag aga aga aag gtt gtg tta ccc     384
Pro Glu Ser Ser Gln Asp Ser Ser Lys Arg Arg Lys Val Val Leu Pro
        115                 120                 125 agt cct agc caa gct aag aat ggt aac atc ctt cga ata aag ata aga     432
Ser Pro Ser Gln Ala Lys Asn Gly Asn Ile Leu Arg Ile Lys Ile Arg
    130                 135                 140 aga gat caa gat tct tca gct tcc ctt tcg gag aaa tct aat gtt gta     480
Arg Asp Gln Asp Ser Ser Ala Ser Leu Ser Glu Lys Ser Asn Val Val
145                 150                 155                 160 caa aca cca gtt cat caa atg gga tca gtt tca tct ctg cca agt aag     528
Gln Thr Pro Val His Gln Met Gly Ser Val Ser Ser Leu Pro Ser Lys
                165                 170                 175 aaa aac tca atg caa cca cac aac acc gaa atg atg gtg aga aca gca     576
Lys Asn Ser Met Gln Pro His Asn Thr Glu Met Met Val Arg Thr Ala
            180                 185                 190 tca acc cag cag caa agc atc aaa ggt gat ttt caa gca gta ctg aaa     624
Ser Thr Gln Gln Gln Ser Ile Lys Gly Asp Phe Gln Ala Val Leu Lys
        195                 200                 205 caa ggt atg cca acc cca gca aaa gtc atg cca aga gtc gat gtt cct     672
Gln Gly Met Pro Thr Pro Ala Lys Val Met Pro Arg Val Asp Val Pro
    210                 215                 220 cca tct atg agg gca tca aag gaa agg gtt ggc ctt cgt cct gca gag     720
Pro Ser Met Arg Ala Ser Lys Glu Arg Val Gly Leu Arg Pro Ala Glu
225                 230                 235                 240 atg ttg gcc aat gtt ggt cct tca ccc tcc aag gca aaa cag att gtc     768
Met Leu Ala Asn Val Gly Pro Ser Pro Ser Lys Ala Lys Gln Ile Val
                245                 250                 255 aat cct gca gct gct aag gtt aca caa aga gtt gat cct cca cct gcc     816
Asn Pro Ala Ala Ala Lys Val Thr Gln Arg Val Asp Pro Pro Pro Ala
```

```
                260                 265                 270
aag gca tct cag aga att gat cct ctg ttg cca tcc aag gtt cat ata    864
Lys Ala Ser Gln Arg Ile Asp Pro Leu Leu Pro Ser Lys Val His Ile
        275                 280                 285 gat gct act cga tct ttt acg aag ctc tcc cag aca gag atc aag ccg    912
Asp Ala Thr Arg Ser Phe Thr Lys Leu Ser Gln Thr Glu Ile Lys Pro
290                 295                 300 gaa gta cag ccc cca att ccg aag gtg cct gtg gct atg cct acc atc    960
Glu Val Gln Pro Pro Ile Pro Lys Val Pro Val Ala Met Pro Thr Ile
305                 310                 315                 320 aat cgt cag cag att gac acc tcg cag ccc aaa gaa gag cct tgc tcc   1008
Asn Arg Gln Gln Ile Asp Thr Ser Gln Pro Lys Glu Glu Pro Cys Ser
                325                 330                 335 tct ggc agg aat gct gaa gct gct tca gta tca gta gag aag cag tcc   1056
Ser Gly Arg Asn Ala Glu Ala Ala Ser Val Ser Val Glu Lys Gln Ser
            340                 345                 350 aag tca gat cgc aaa aag agc cgc aag gct gag aag aaa gag aag aag   1104
Lys Ser Asp Arg Lys Lys Ser Arg Lys Ala Glu Lys Lys Glu Lys Lys
        355                 360                 365 ttc aaa gat tta ttt gtt acc tgg gat cct ccg tct atg gaa atg gat   1152
Phe Lys Asp Leu Phe Val Thr Trp Asp Pro Pro Ser Met Glu Met Asp
370                 375                 380 gat atg gat ctt ggg gac cag gat tgg ctg ctt ggt agt acg agg aaa   1200
Asp Met Asp Leu Gly Asp Gln Asp Trp Leu Leu Gly Ser Thr Arg Lys
385                 390                 395                 400 cct gat gct ggc att ggc aac tgc aga gaa att gtt gat cca ctt act   1248
Pro Asp Ala Gly Ile Gly Asn Cys Arg Glu Ile Val Asp Pro Leu Thr
                405                 410                 415 tct caa tca gcg gag cag ttc tca ttg cag cct agg gcg att cat tta   1296
Ser Gln Ser Ala Glu Gln Phe Ser Leu Gln Pro Arg Ala Ile His Leu
            420                 425                 430 cca gac ctt cat gtc tat cag ttg cca tat gtg gtt cca ttc tag       1341
Pro Asp Leu His Val Tyr Gln Leu Pro Tyr Val Val Pro Phe
        435                 440                 445

<210> SEQ ID NO 30
<211> LENGTH: 446
<212> TYPE: PRT
<213> ORGANISM: Oryza rufipogon strain 5953

<400> SEQUENCE: 30

Met Ser Arg Cys Phe Pro Tyr Pro Pro Gly Tyr Val Arg Asn Pro
1               5                   10                  15

Val Val Ala Val Ala Ala Ala Glu Ala Gln Ala Thr Thr Lys Leu Gln
                20                  25                  30

Lys Glu Arg Glu Lys Ala Glu Lys Lys Glu Lys Lys Ser Asp Arg
            35                  40                  45

Lys Ala Leu Pro His Gly Glu Ile Ser Lys His Ser Lys Arg Thr His
50                  55                  60

Lys Lys Arg Lys His Glu Asp Ile Asn Asn Ala Asp Gln Lys Ser Arg
65                  70                  75                  80

Lys Val Ser Ser Met Glu Pro Gly Glu Gln Leu Glu Lys Ser Gly Leu
                85                  90                  95

Ser Glu Glu His Gly Ala Pro Cys Phe Thr Gln Thr Val His Gly Ser
            100                 105                 110

Pro Glu Ser Ser Gln Asp Ser Ser Lys Arg Arg Lys Val Val Leu Pro
        115                 120                 125

Ser Pro Ser Gln Ala Lys Asn Gly Asn Ile Leu Arg Ile Lys Ile Arg
```

-continued

```
            130                 135                 140
Arg Asp Gln Asp Ser Ser Ala Ser Leu Ser Glu Lys Ser Asn Val Val
145                 150                 155                 160

Gln Thr Pro Val His Gln Met Gly Ser Val Ser Ser Leu Pro Ser Lys
                165                 170                 175

Lys Asn Ser Met Gln Pro His Asn Thr Glu Met Met Val Arg Thr Ala
                180                 185                 190

Ser Thr Gln Gln Gln Ser Ile Lys Gly Asp Phe Gln Ala Val Leu Lys
                195                 200                 205

Gln Gly Met Pro Thr Pro Ala Lys Val Met Pro Arg Val Asp Val Pro
210                 215                 220

Pro Ser Met Arg Ala Ser Lys Glu Arg Val Gly Leu Arg Pro Ala Glu
225                 230                 235                 240

Met Leu Ala Asn Val Gly Pro Ser Pro Ser Lys Ala Lys Gln Ile Val
                245                 250                 255

Asn Pro Ala Ala Ala Lys Val Thr Gln Arg Val Asp Pro Pro Ala
                260                 265                 270

Lys Ala Ser Gln Arg Ile Asp Pro Leu Leu Pro Ser Lys Val His Ile
                275                 280                 285

Asp Ala Thr Arg Ser Phe Thr Lys Leu Ser Gln Thr Glu Ile Lys Pro
                290                 295                 300

Glu Val Gln Pro Pro Ile Pro Lys Val Pro Val Ala Met Pro Thr Ile
305                 310                 315                 320

Asn Arg Gln Gln Ile Asp Thr Ser Gln Pro Lys Glu Glu Pro Cys Ser
                325                 330                 335

Ser Gly Arg Asn Ala Glu Ala Ala Ser Val Ser Val Gly Lys Gln Ser
                340                 345                 350

Lys Ser Asp Arg Lys Ser Arg Lys Ala Glu Lys Lys Glu Lys Lys
                355                 360                 365

Phe Lys Asp Leu Phe Val Thr Trp Asp Pro Pro Ser Met Glu Met Asp
                370                 375                 380

Asp Met Asp Leu Gly Asp Gln Asp Trp Leu Leu Gly Ser Thr Arg Lys
385                 390                 395                 400

Pro Asp Ala Gly Ile Gly Asn Cys Arg Glu Ile Val Asp Pro Leu Thr
                405                 410                 415

Ser Gln Ser Ala Glu Gln Phe Ser Leu Gln Pro Arg Ala Ile His Leu
                420                 425                 430

Pro Asp Leu His Val Tyr Gln Leu Pro Tyr Val Val Pro Phe
                435                 440                 445
```

<210> SEQ ID NO 31
<211> LENGTH: 1341
<212> TYPE: DNA
<213> ORGANISM: Oryza rufipogon strain IRCG105491
<220> FEATURE:
<221> NAME/KEY: CDS
<222> LOCATION: (1)..(1341)
<223> OTHER INFORMATION:

<400> SEQUENCE: 31

```
atg tcg agg tgc ttc ccc tac ccg ccg ccg ggg tac gtg cga aac cca      48
Met Ser Arg Cys Phe Pro Tyr Pro Pro Pro Gly Tyr Val Arg Asn Pro
1               5                   10                  15 gtg gtg gcc gtg gcc gcg gcc gaa gcg cag gcg acc act aag ctc cag      96
Val Val Ala Val Ala Ala Ala Glu Ala Gln Ala Thr Thr Lys Leu Gln
                20                  25                  30
```

```
aaa gaa agg gaa aag gcc gaa aag aag aaa gag aaa aag agt gac agg      144
Lys Glu Arg Glu Lys Ala Glu Lys Lys Lys Glu Lys Lys Ser Asp Arg
            35                  40                  45 aaa gct ctt cca cat ggt gag ata tcc aag cat tca aag cga acc cac      192
Lys Ala Leu Pro His Gly Glu Ile Ser Lys His Ser Lys Arg Thr His
 50                  55                  60 aag aag aga aaa cat gaa gac atc aat aat gct gat cag aag tcc cgg      240
Lys Lys Arg Lys His Glu Asp Ile Asn Asn Ala Asp Gln Lys Ser Arg
 65                  70                  75                  80 aag gtt tcc tcc atg gaa cct ggt gag caa ttg gag aag agt gga ctc      288
Lys Val Ser Ser Met Glu Pro Gly Glu Gln Leu Glu Lys Ser Gly Leu
                 85                  90                  95 tca gaa gag cat gga gct cct tgc ttt act cag aca gtg cat ggc tct      336
Ser Glu Glu His Gly Ala Pro Cys Phe Thr Gln Thr Val His Gly Ser
            100                 105                 110 cca gag agt tca cag gac agc agc aag aga aga aag gtt gtg tta ccc      384
Pro Glu Ser Ser Gln Asp Ser Ser Lys Arg Arg Lys Val Val Leu Pro
        115                 120                 125 agt cct agc caa gct aag aat ggt aac atc ctt cga ata aag ata aga      432
Ser Pro Ser Gln Ala Lys Asn Gly Asn Ile Leu Arg Ile Lys Ile Arg
130                 135                 140 aga gat caa gat tct tca gct tcc ctt tcg gag aaa tct aat gtt gta      480
Arg Asp Gln Asp Ser Ser Ala Ser Leu Ser Glu Lys Ser Asn Val Val
145                 150                 155                 160 caa aca cca gtt cat caa atg gga tca gtt tca tct ctg cca agt aag      528
Gln Thr Pro Val His Gln Met Gly Ser Val Ser Ser Leu Pro Ser Lys
                165                 170                 175 aaa aac tca atg caa cca cac aac acc gaa atg atg gtg aga aca gca      576
Lys Asn Ser Met Gln Pro His Asn Thr Glu Met Met Val Arg Thr Ala
            180                 185                 190 tca acc cag cag caa agc atc aaa ggt gat ttt caa gca gta ctg aaa      624
Ser Thr Gln Gln Gln Ser Ile Lys Gly Asp Phe Gln Ala Val Leu Lys
        195                 200                 205 caa ggt atg cca acc cca gca aaa gtc atg cca aga gtc gat gtt cct      672
Gln Gly Met Pro Thr Pro Ala Lys Val Met Pro Arg Val Asp Val Pro
210                 215                 220 cca tct atg agg gca tca aag gaa agg gtt ggc ctt cgt cct gca gag      720
Pro Ser Met Arg Ala Ser Lys Glu Arg Val Gly Leu Arg Pro Ala Glu
225                 230                 235                 240 atg ttg gcc aat gtt ggt cct tca cca tcc aag gca aaa cag att gtc      768
Met Leu Ala Asn Val Gly Pro Ser Pro Ser Lys Ala Lys Gln Ile Val
                245                 250                 255 aat cct gca gct gct aag gtt aca caa aga gtt gat cct cca cct gcc      816
Asn Pro Ala Ala Ala Lys Val Thr Gln Arg Val Asp Pro Pro Pro Ala
            260                 265                 270 aag gca tct cag aga att gat cct ctg ttg cca tcc aag gtt cat ata      864
Lys Ala Ser Gln Arg Ile Asp Pro Leu Leu Pro Ser Lys Val His Ile
        275                 280                 285 gat gct act cga tct ttt acg aag gtc tcc cag aca gag atc aag ccg      912
Asp Ala Thr Arg Ser Phe Thr Lys Val Ser Gln Thr Glu Ile Lys Pro
290                 295                 300 gaa gta cag ccc cca att ccg aag gtg cct gtg gct atg cct acc atc      960
Glu Val Gln Pro Pro Ile Pro Lys Val Pro Val Ala Met Pro Thr Ile
305                 310                 315                 320 aat cgt cag cag att gac acc tcg cag ccc aaa gaa gag cct tgc tcc     1008
Asn Arg Gln Gln Ile Asp Thr Ser Gln Pro Lys Glu Glu Pro Cys Ser
                325                 330                 335 tct ggc agg aat gct gaa gct gct tca gta tca gta gag aag cag tcc     1056
Ser Gly Arg Asn Ala Glu Ala Ala Ser Val Ser Val Glu Lys Gln Ser
            340                 345                 350
```

-continued

```
aag tca gat cgc aaa aag agc cgc aag gct gag aag aaa gag aag aag      1104
Lys Ser Asp Arg Lys Lys Ser Arg Lys Ala Glu Lys Lys Glu Lys Lys
    355                 360                 365 ttc aaa gat tta ttt gtt acc tgg gat cct ccg tct atg gaa atg gat      1152
Phe Lys Asp Leu Phe Val Thr Trp Asp Pro Pro Ser Met Glu Met Asp
370                 375                 380 gat atg gat ctt ggg gac cag gat tgg ctg ctt ggt agt acg agg aaa      1200
Asp Met Asp Leu Gly Asp Gln Asp Trp Leu Leu Gly Ser Thr Arg Lys
385                 390                 395                 400 cct gat gct ggc att ggc aac tgc aga gaa att gtt gat cca ctt act      1248
Pro Asp Ala Gly Ile Gly Asn Cys Arg Glu Ile Val Asp Pro Leu Thr
                405                 410                 415 tct caa tca gca gag cag ttc tca ttg cag cct agg gcg att cat tta      1296
Ser Gln Ser Ala Glu Gln Phe Ser Leu Gln Pro Arg Ala Ile His Leu
            420                 425                 430 cca gac ctt cat gtc tat cag ttg cca tat gtg gtt cca ttc tag          1341
Pro Asp Leu His Val Tyr Gln Leu Pro Tyr Val Val Pro Phe
        435                 440                 445
```

<210> SEQ ID NO 32
<211> LENGTH: 446
<212> TYPE: PRT
<213> ORGANISM: Oryza rufipogon strain IRCG105491

<400> SEQUENCE: 32

```
Met Ser Arg Cys Phe Pro Tyr Pro Pro Gly Tyr Val Arg Asn Pro
1               5                   10                  15

Val Val Ala Val Ala Ala Glu Ala Gln Ala Thr Thr Lys Leu Gln
                20                  25                  30

Lys Glu Arg Glu Lys Ala Glu Lys Lys Glu Lys Lys Ser Asp Arg
            35                  40                  45

Lys Ala Leu Pro His Gly Glu Ile Ser Lys His Ser Lys Arg Thr His
50                  55                  60

Lys Lys Arg Lys His Glu Asp Ile Asn Asn Ala Asp Gln Lys Ser Arg
65                  70                  75                  80

Lys Val Ser Ser Met Glu Pro Gly Glu Gln Leu Glu Lys Ser Gly Leu
                85                  90                  95

Ser Glu Glu His Gly Ala Pro Cys Phe Thr Gln Thr Val His Gly Ser
            100                 105                 110

Pro Glu Ser Ser Gln Asp Ser Ser Lys Arg Arg Lys Val Val Leu Pro
        115                 120                 125

Ser Pro Ser Gln Ala Lys Asn Gly Asn Ile Leu Arg Ile Lys Ile Arg
    130                 135                 140

Arg Asp Gln Asp Ser Ser Ala Ser Leu Ser Glu Lys Ser Asn Val Val
145                 150                 155                 160

Gln Thr Pro Val His Gln Met Gly Ser Val Ser Ser Leu Pro Ser Lys
                165                 170                 175

Lys Asn Ser Met Gln Pro His Asn Thr Glu Met Met Val Arg Thr Ala
            180                 185                 190

Ser Thr Gln Gln Ser Ile Lys Gly Asp Phe Gln Ala Val Leu Lys
        195                 200                 205

Gln Gly Met Pro Thr Pro Ala Lys Val Met Pro Arg Val Asp Val Pro
    210                 215                 220

Pro Ser Met Arg Ala Ser Lys Glu Arg Val Gly Leu Arg Pro Ala Glu
225                 230                 235                 240

Met Leu Ala Asn Val Gly Pro Ser Pro Ser Lys Ala Lys Gln Ile Val
```

```
                   245                 250                 255
Asn Pro Ala Ala Ala Lys Val Thr Gln Arg Val Asp Pro Pro Ala
            260                 265                 270

Lys Ala Ser Gln Arg Ile Asp Pro Leu Leu Pro Ser Lys Val His Ile
            275                 280                 285

Asp Ala Thr Arg Ser Phe Thr Lys Val Ser Gln Thr Glu Ile Lys Pro
    290                 295                 300

Glu Val Gln Pro Pro Ile Pro Lys Val Pro Val Ala Met Pro Thr Ile
305                 310                 315                 320

Asn Arg Gln Gln Ile Asp Thr Ser Gln Pro Lys Glu Glu Pro Cys Ser
                325                 330                 335

Ser Gly Arg Asn Ala Glu Ala Ala Ser Val Ser Val Glu Lys Gln Ser
            340                 345                 350

Lys Ser Asp Arg Lys Lys Ser Arg Lys Ala Glu Lys Lys Glu Lys Lys
        355                 360                 365

Phe Lys Asp Leu Phe Val Thr Trp Asp Pro Pro Ser Met Glu Met Asp
    370                 375                 380

Asp Met Asp Leu Gly Asp Gln Asp Trp Leu Leu Gly Ser Thr Arg Lys
385                 390                 395                 400

Pro Asp Ala Gly Ile Gly Asn Cys Arg Glu Ile Val Asp Pro Leu Thr
                405                 410                 415

Ser Gln Ser Ala Glu Gln Phe Ser Leu Gln Pro Arg Ala Ile His Leu
            420                 425                 430

Pro Asp Leu His Val Tyr Gln Leu Pro Tyr Val Val Pro Phe
        435                 440                 445

<210> SEQ ID NO 33
<211> LENGTH: 180
<212> TYPE: DNA
<213> ORGANISM: Zea mays mays strain BS7

<400> SEQUENCE: 33
gcatgtcgag gtgcttcccc tacccgccac cggggtacgt gcggaaccca gtggccgtgg      60
ccgagccgga gtcgaccgct aaggtttgtt gaaccttcgg atttacacac gcacgtgcca     120
gatcgtttgt tcaatctgta ggttttgcgc ggatctgtgt gtttgcgcgt gcgtgatgtg     180

<210> SEQ ID NO 34
<211> LENGTH: 1447
<212> TYPE: DNA
<213> ORGANISM: Zea mays mays strain BS7

<400> SEQUENCE: 34
tcagaactga cgattgctct ggtggctgaa gctcctgaaa gaaaaggaaa aggccgaaaa      60
gaagaaagag aaaaggagtg acaggaaagc tcccaagcag tgtgagacgt ccaaacattc     120
aaagcacagc cataagaaga gaaagcttga agatgtcatc aaagctgagc agggtcccaa     180
aagagtaccc aaagaatcag ttgagcagtt ggagaagagt ggactctcag aagagcatgg     240
agctccttct tttgtacata cgatacgtga ctctcctgag agctcacagg acagcggcaa     300
gagacgaaag gttgtcctgt ccagtcctag ccaacctaag aatggtgaga ctattctctt     360
gtttttgcta ttctgattga ttttttatta tagaagaaat caatcgcttg ttcaggattt     420
tattcatccc aacttgattt tacaggaaac attcttcgct tcaagattaa agtagtcaa      480 gayccccaat cagctgttct ggagaaacca agggttcttg agcaaccatt ggtccaacaa     540
atgggatcag gttcatcccy gtcgggcaag caaaattcaa tccatcataa gatgaatgtg     600
```

-continued

```
agatctacct ctggtcagcg gagggtcgat ggtgactccc aagcagtaca aaaatgtttg      660
attacagaat ccccggcaaa gaccatgcag agacttgtcc cccagcctgc agctaaggtc      720
acacatcctg ttgatcccca gtcagctgtt aaggtgccag ttggaagatc gggcctacct      780
ctgaagtctt cgggaagtgt ggaccttcg cctgctagag ttatgagaag atttgatcct       840
ccacctgtta agatgatgtc acagagagtt caccatccag cttccatggt gtcgcagaaa      900
gttgatcctc cgtttccgaa ggtattacat aaggaaaccg atctgttgt tcgcctacca       960 gaagctaccc ggcctactgt tcttcaaaaa cccaaggact tgcctgctat caagcagcag     1020
gatatcagga cctcttcctc aaaagaagag ccctgcttct ctggtaggaa tgcagaagca     1080
gttcaagtgc aagatactaa gctctcccgg tcagacatga agaaaatccg caaagctgag     1140
aaaaaagata agaagttcag agatctgttt gttacctgga atccggtatt gatagagaat     1200
gaaggttcag atcttggtga tgaagactgg ctgttcagca gtaaaaggaa ctccgatgct     1260
atcatggttc aaagcagagc tactgatagt tcagtgccga tccatccaat ggtgcagcag     1320
aagccttctt tacaacccag ggcaacattt ttgccggacc ttaatatgta ccagctgcca     1380
tatgtcgtac cattttaaac atctggcgag gtagatgaga attagatgag atgttgggag     1440
agagctg                                                              1447
```

```
<210> SEQ ID NO 35
<211> LENGTH: 1347
<212> TYPE: DNA
<213> ORGANISM: Zea mays mays strain BS7
<220> FEATURE:
<221> NAME/KEY: CDS
<222> LOCATION: (1)..(1347)
<223> OTHER INFORMATION:

<400> SEQUENCE: 35
```

```
atg tcg agg tgc ttc ccc tac ccg cca ccg ggg tac gtg cgg aac cca        48
Met Ser Arg Cys Phe Pro Tyr Pro Pro Pro Gly Tyr Val Arg Asn Pro
1               5                   10                  15 gtg gcc gtg gcc gag ccg gag tcg acc gct aag ctc ctg aaa gaa aag        96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gct ccc       144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga       192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc       240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat       288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca       336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa       384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gay       432
Pro Lys Asn Gly Asn Ile Leu Arg Phe Lys Ile Lys Ser Ser Gln Asp
    130                 135                 140
```

-continued

| | | |
|---|---|---|
| ccc caa tca gct gtt ctg gag aaa cca agg gtt ctt gag caa cca ttg<br>Pro Gln Ser Ala Val Leu Glu Lys Pro Arg Val Leu Glu Gln Pro Leu<br>145                         150                    155                 160 | 480 |
| gtc caa caa atg gga tca ggt tca tcc cyg tcg ggc aag caa aat tca<br>Val Gln Gln Met Gly Ser Gly Ser Ser Xaa Ser Gly Lys Gln Asn Ser<br>                  165                    170                    175 | 528 |
| atc cat cat aag atg aat gtg aga tct acc tct ggt cag cgg agg gtc<br>Ile His His Lys Met Asn Val Arg Ser Thr Ser Gly Gln Arg Arg Val<br>             180                    185                    190 | 576 |
| gat ggt gac tcc caa gca gta caa aaa tgt ttg att aca gaa tcc ccg<br>Asp Gly Asp Ser Gln Ala Val Gln Lys Cys Leu Ile Thr Glu Ser Pro<br>        195                    200                    205 | 624 |
| gca aag acc atg cag aga ctt gtc ccc cag cct gca gct aag gtc aca<br>Ala Lys Thr Met Gln Arg Leu Val Pro Gln Pro Ala Ala Lys Val Thr<br>210                         215                    220 | 672 |
| cat cct gtt gat ccc cag tca gct gtt aag gtg cca gtt gga aga tcg<br>His Pro Val Asp Pro Gln Ser Ala Val Lys Val Pro Val Gly Arg Ser<br>225                         230                    235                  240 | 720 |
| ggc cta cct ctg aag tct tcg gga agt gtg gac cct tcg cct gct aga<br>Gly Leu Pro Leu Lys Ser Ser Gly Ser Val Asp Pro Ser Pro Ala Arg<br>                     245                    250                    255 | 768 |
| gtt atg aga aga ttt gat cct cca cct gtt aag atg atg tca cag aga<br>Val Met Arg Arg Phe Asp Pro Pro Pro Val Lys Met Met Ser Gln Arg<br>             260                    265                    270 | 816 |
| gtt cac cat cca gct tcc atg gtg tcg cag aaa gtt gat cct ccg ttt<br>Val His His Pro Ala Ser Met Val Ser Gln Lys Val Asp Pro Pro Phe<br>        275                    280                    285 | 864 |
| ccg aag gta tta cat aag gaa acc gga tct gtt gtt cgc cta cca gaa<br>Pro Lys Val Leu His Lys Glu Thr Gly Ser Val Val Arg Leu Pro Glu<br>290                         295                    300 | 912 |
| gct acc cgg cct act gtt ctt caa aaa ccc aag gac ttg cct gct atc<br>Ala Thr Arg Pro Thr Val Leu Gln Lys Pro Lys Asp Leu Pro Ala Ile<br>305                         310                    315                  320 | 960 |
| aag cag cag gat atc agg acc tct tcc tca aaa gaa gag ccc tgc ttc<br>Lys Gln Gln Asp Ile Arg Thr Ser Ser Ser Lys Glu Glu Pro Cys Phe<br>                     325                    330                    335 | 1008 |
| tct ggt agg aat gca gaa gca gtt caa gtg caa gat act aag ctc tcc<br>Ser Gly Arg Asn Ala Glu Ala Val Gln Val Gln Asp Thr Lys Leu Ser<br>             340                    345                    350 | 1056 |
| cgg tca gac atg aag aaa atc cgc aaa gct gag aaa aaa gat aag aag<br>Arg Ser Asp Met Lys Lys Ile Arg Lys Ala Glu Lys Lys Asp Lys Lys<br>        355                    360                    365 | 1104 |
| ttc aga gat ctg ttt gtt acc tgg aat ccg gta ttg ata gag aat gaa<br>Phe Arg Asp Leu Phe Val Thr Trp Asn Pro Val Leu Ile Glu Asn Glu<br>370                         375                    380 | 1152 |
| ggt tca gat ctt ggt gat gaa gac tgg ctg ttc agc agt aaa agg aac<br>Gly Ser Asp Leu Gly Asp Glu Asp Trp Leu Phe Ser Ser Lys Arg Asn<br>385                         390                    395                  400 | 1200 |
| tcc gat gct atc atg gtt caa agc aga gct act gat agt tca gtg ccg<br>Ser Asp Ala Ile Met Val Gln Ser Arg Ala Thr Asp Ser Ser Val Pro<br>                     405                    410                    415 | 1248 |
| atc cat cca atg gtg cag cag aag cct tct tta caa ccc agg gca aca<br>Ile His Pro Met Val Gln Gln Lys Pro Ser Leu Gln Pro Arg Ala Thr<br>             420                    425                    430 | 1296 |
| ttt ttg ccg gac ctt aat atg tac cag ctg cca tat gtc gta cca ttt<br>Phe Leu Pro Asp Leu Asn Met Tyr Gln Leu Pro Tyr Val Val Pro Phe<br>        435                    440                    445 | 1344 |
| taa | 1347 |

```
<210> SEQ ID NO 36
<211> LENGTH: 448
<212> TYPE: PRT
<213> ORGANISM: Zea mays mays strain BS7
<220> FEATURE:
<221> NAME/KEY: misc_feature
<222> LOCATION: (170)..(170)
<223> OTHER INFORMATION: The 'Xaa' at location 170 stands for Pro,
      or Leu.

<400> SEQUENCE: 36
```

Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
            20                  25                  30

Glu Lys Ala Glu Lys Lys Glu Lys Arg Ser Asp Arg Lys Ala Pro
            35                  40                  45

Lys Gln Cys Glu Thr Ser Lys His Ser Lys His Ser His Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Xaa Ser Gly Lys Gln Asn Ser
                165                 170                 175

Ile His His Lys Met Asn Val Arg Ser Thr Ser Gly Gln Arg Arg Val
            180                 185                 190

Asp Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
    275                 280                 285

Pro Lys Val Leu His Lys Glu Thr Gly Ser Val Val Arg Leu Pro Glu
    290                 295                 300

Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
                325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys

-continued

```
                355                 360                 365
Phe Arg Asp Leu Phe Val Thr Trp Asn Pro Val Leu Ile Glu Asn Glu
        370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Gln Lys Pro Ser Leu Gln Pro Arg Ala Thr
                420                 425                 430

Phe Leu Pro Asp Leu Asn Met Tyr Gln Leu Pro Tyr Val Val Pro Phe
            435                 440                 445
```

<210> SEQ ID NO 37
<211> LENGTH: 2646
<212> TYPE: DNA
<213> ORGANISM: Zea mays mays strain HuoBai

<400> SEQUENCE: 37

| | | | | | |
|---|---|---|---|---|---|
| gcggggtaga | gcgcggtcga | cgtcggcatg | tcgaggtgct | tccctaccc | gccaccgggg | 60 |
| tacgtgcgga | acccagtggc | cgtggccgag | ccggagtcga | ccgctaaggt | ttgttgaacc | 120 |
| ttcggattta | cacacgcacg | tgccagatcg | tttgttcaat | ctgtaggttt | tgcgcggatc | 180 |
| tgtggtttgc | gcgtgcgtga | tgtgggtatt | gcccgtgcct | tgaaagctaa | ccgagctgag | 240 |
| gaagtgtatg | gatcttgtgt | agctgcacga | ggtcctccaa | atcgattgta | aaatttaagt | 300 |
| tgtatggccg | gtaggccaag | attgggttat | tccggttttc | gaaaactggt | agcatggtta | 360 |
| tcggggacat | tgaaagaatg | gtagaacatc | aaattcgatt | caaaactgtg | ctagatttgc | 420 |
| atatttagtc | gccctaaaat | tacgtggacg | tgggtgatcc | gaattggttg | ttgtatgatg | 480 |
| gttggaagtg | actggccaaa | ttttttttgtt | tctcaaagtt | ttcttgaaa | aactgttttgt | 540 |
| cgagcgtcaa | ttcgtattta | cctgaattta | ctaattctta | atacagtatg | tcgttatttt | 600 |
| gggctaagct | tgtgtaagaa | gggtcgtttg | acattttgta | ctgtattgat | gctgttttgt | 660 |
| gtttctttgt | tcggagcagc | attcaatgct | ccttttgttg | tttgagagaa | tctgatattt | 720 |
| gccatcgtac | cgaaagtccg | aaaccaacta | ttcaaattgg | gatttcattt | ctttttttt | 780 |
| ctactgtttt | tagagttctc | tttttcgctg | ctgtgctctt | gtgggtcagt | acgtgcattt | 840 |
| ctctttttt | cttttttttt | ctgatgttac | tcttctgttg | accaaaggag | ttcagaatta | 900 |
| ttttggccct | gtatatcaat | agcaaccaac | accatttatt | gagcccattt | ttagttttct | 960 |
| tgttctgtag | agtatgcatt | gttgcaggtc | ttaactgttg | tcagggaagt | aacgtgttca | 1020 |
| acatgattgt | aaacgaatac | aattctgttg | ctaactgtgt | aatgatgaga | aggataattg | 1080 |
| aataatcttt | gtgaagtatt | actgtctgaa | ctgtacgcaa | atgctacatt | tattctttgt | 1140 |
| gttcgtgtaa | atatcattat | acataaaaat | gctgcattgc | attcccgtcg | tccgttctaa | 1200 |
| atcagaactg | acgattgctc | tggtggctga | agctcctgaa | agaaaggaa | aaggccgaaa | 1260 |
| agaagaaaga | gaaaggagt | gacaggaaag | ctcccaagca | gtgtgagacg | tccaaacatt | 1320 |
| caaagcacag | ccataagaag | agaaagcttg | aagatgtcat | caaagctgag | cagggtccca | 1380 |
| aaagagtacc | caaagaatca | gttgagcagt | tggagaagag | tggactctca | gaagagcatg | 1440 |
| gagctccttc | ttttgtacat | acgatacgtg | actctcctga | gagctcacag | acagcggca | 1500 |
| agagacgaaa | ggttgtcctg | tccagtccta | gccaacctaa | gaatggtgag | actattctct | 1560 |
| tgtttttgct | attctgattg | attttttatt | atagaagaaa | tcaatatctt | gttcaggatt | 1620 |

-continued

| | |
|---|---|
| ttattcatcc caacttgatt ttacaggaaa cattcttcgc ttcaagatta aaagtagtca | 1680 |
| agatccccaa tcagctgttc tggagaaacc aagggttctt gagcaaccat tggtccaaca | 1740 |
| aatgggatca ggttcatccc tgtcgggcaa gcaaaattca atccatcata agatgaatgt | 1800 |
| gagatctacc tctggtcagc ggagggtcaa tggtgactcc caagcagtac aaaaatgttt | 1860 |
| gattacagaa tccccggcaa agaccatgca gagacttgtc ccccagcctg cagctaaggt | 1920 |
| cacacatcct gttgatcccc agtcagctgt taaggtgcca gttggaagat cgggcctacc | 1980 |
| tctgaagtct tcgggaagtg tggacccttc gcctgctaga gttatgagaa gatttgatcc | 2040 |
| tccacctgtt aagatgatgt cacagagagt tcaccatcca gcttccatgg tgtcgcagaa | 2100 |
| agttgatcct ccgtttccga aggtattaca taaggaaacc ggatctgttg ttcgcctacc | 2160 |
| agaagctacc cggcctactg ttcttcaaaa acccaaggac ttgcctgcta tcaagcagca | 2220 |
| ggatatcagg acctcttcct caaaagaaga gccctgcttc tctggtagga atgcagaagc | 2280 |
| agttcaagtg caagatacta agctctcccg gtcagacatg aagaaaatcc gcaaagctga | 2340 |
| gaaaaaagat aagaagttca gagatctgtt tgttacctgg aatccggtat tgatagagaa | 2400 |
| tgaaggttca gatcttggtg atgaagactg gctgttcagc agtaaaagga actccgatgc | 2460 |
| tatcatggtt caaagcagag ctactgatag ttcagtgccg atccatccaa tggtgcagca | 2520 |
| gaagccttct ttacaaccca gggcaacatt tttgccggac cttaatatgt accagctgcc | 2580 |
| atatgtcgta ccattttaaa catctggcga ggtagatgag aattagatga gatgttggga | 2640 |
| gagagc | 2646 |

<210> SEQ ID NO 38
<211> LENGTH: 1347
<212> TYPE: DNA
<213> ORGANISM: Zea mays mays strain HuoBai
<220> FEATURE:
<221> NAME/KEY: CDS
<222> LOCATION: (1)..(1347)
<223> OTHER INFORMATION:

<400> SEQUENCE: 38

| | |
|---|---|
| atg tcg agg tgc ttc ccc tac ccg cca ccg ggg tac gtg cgg aac cca<br>Met Ser Arg Cys Phe Pro Tyr Pro Pro Pro Gly Tyr Val Arg Asn Pro<br>1               5                   10               15 | 48 |
| gtg gcc gtg gcc gag ccg gag tcg acc gct aag ctc ctg aaa gaa aag<br>Val Ala Val Ala Glu Pro Glu Ser Thr Ala Lys Leu Leu Lys Glu Lys<br>               20                   25                   30 | 96 |
| gaa aag gcc gaa aag aag aaa gag aaa agg agt gac agg aaa gct ccc<br>Glu Lys Ala Glu Lys Lys Lys Glu Lys Arg Ser Asp Arg Lys Ala Pro<br>         35                   40                   45 | 144 |
| aag cag tgt gag acg tcc aaa cat tca aag cac agc cat aag aag aga<br>Lys Gln Cys Glu Thr Ser Lys His Ser Lys His Ser His Lys Lys Arg<br>50                   55                   60 | 192 |
| aag ctt gaa gat gtc atc aaa gct gag cag ggt ccc aaa aga gta ccc<br>Lys Leu Glu Asp Val Ile Lys Ala Glu Gln Gly Pro Lys Arg Val Pro<br>65                   70                   75                   80 | 240 |
| aaa gaa tca gtt gag cag ttg gag aag agt gga ctc tca gaa gag cat<br>Lys Glu Ser Val Glu Gln Leu Glu Lys Ser Gly Leu Ser Glu Glu His<br>                   85                   90                   95 | 288 |
| gga gct cct tct ttt gta cat acg ata cgt gac tct cct gag agc tca<br>Gly Ala Pro Ser Phe Val His Thr Ile Arg Asp Ser Pro Glu Ser Ser<br>               100                  105                110 | 336 |
| cag gac agc ggc aag aga cga aag gtt gtc ctg tcc agt cct agc caa<br>Gln Asp Ser Gly Lys Arg Arg Lys Val Val Leu Ser Ser Pro Ser Gln<br>         115                   120                  125 | 384 |

-continued

| | | |
|---|---|---|
| cct aag aat gga aac att ctt cgc ttc aag att aaa agt agt caa gat<br>Pro Lys Asn Gly Asn Ile Leu Arg Phe Lys Ile Lys Ser Ser Gln Asp<br>130                       135                    140 | | 432 |
| ccc caa tca gct gtt ctg gag aaa cca agg gtt ctt gag caa cca ttg<br>Pro Gln Ser Ala Val Leu Glu Lys Pro Arg Val Leu Glu Gln Pro Leu<br>145                 150                   155              160 | | 480 |
| gtc caa caa atg gga tca ggt tca tcc ctg tcg ggc aag caa aat tca<br>Val Gln Gln Met Gly Ser Gly Ser Ser Leu Ser Gly Lys Gln Asn Ser<br>                  165                   170               175 | | 528 |
| atc cat cat aag atg aat gtg aga tct acc tct ggt cag cgg agg gtc<br>Ile His His Lys Met Asn Val Arg Ser Thr Ser Gly Gln Arg Arg Val<br>       180                   185                   190 | | 576 |
| aat ggt gac tcc caa gca gta caa aaa tgt ttg att aca gaa tcc ccg<br>Asn Gly Asp Ser Gln Ala Val Gln Lys Cys Leu Ile Thr Glu Ser Pro<br>                  195                   200               205 | | 624 |
| gca aag acc atg cag aga ctt gtc ccc cag cct gca gct aag gtc aca<br>Ala Lys Thr Met Gln Arg Leu Val Pro Gln Pro Ala Ala Lys Val Thr<br>210                       215                    220 | | 672 |
| cat cct gtt gat ccc cag tca gct gtt aag gtg cca gtt gga aga tcg<br>His Pro Val Asp Pro Gln Ser Ala Val Lys Val Pro Val Gly Arg Ser<br>225                       230                    235               240 | | 720 |
| ggc cta cct ctg aag tct tcg gga agt gtg gac cct tcg cct gct aga<br>Gly Leu Pro Leu Lys Ser Ser Gly Ser Val Asp Pro Ser Pro Ala Arg<br>                  245                   250               255 | | 768 |
| gtt atg aga aga ttt gat cct cca cct gtt aag atg atg tca cag aga<br>Val Met Arg Arg Phe Asp Pro Pro Pro Val Lys Met Met Ser Gln Arg<br>            260                    265               270 | | 816 |
| gtt cac cat cca gct tcc atg gtg tcg cag aaa gtt gat cct ccg ttt<br>Val His His Pro Ala Ser Met Val Ser Gln Lys Val Asp Pro Pro Phe<br>              275                   280               285 | | 864 |
| ccg aag gta tta cat aag gaa acc gga tct gtt gtt cgc cta cca gaa<br>Pro Lys Val Leu His Lys Glu Thr Gly Ser Val Val Arg Leu Pro Glu<br>290                       295                   300 | | 912 |
| gct acc cgg cct act gtt ctt caa aaa ccc aag gac ttg cct gct atc<br>Ala Thr Arg Pro Thr Val Leu Gln Lys Pro Lys Asp Leu Pro Ala Ile<br>305                       310                    315               320 | | 960 |
| aag cag cag gat atc agg acc tct tcc tca aaa gaa gag ccc tgc ttc<br>Lys Gln Gln Asp Ile Arg Thr Ser Ser Ser Lys Glu Glu Pro Cys Phe<br>                  325                   330               335 | | 1008 |
| tct ggt agg aat gca gaa gca gtt caa gtg caa gat act aag ctc tcc<br>Ser Gly Arg Asn Ala Glu Ala Val Gln Val Gln Asp Thr Lys Leu Ser<br>            340                    345               350 | | 1056 |
| cgg tca gac atg aag aaa atc cgc aaa gct gag aaa aaa gat aag aag<br>Arg Ser Asp Met Lys Lys Ile Arg Lys Ala Glu Lys Lys Asp Lys Lys<br>       355                   360                   365 | | 1104 |
| ttc aga gat ctg ttt gtt acc tgg aat ccg gta ttg ata gag aat gaa<br>Phe Arg Asp Leu Phe Val Thr Trp Asn Pro Val Leu Ile Glu Asn Glu<br>370                       375                    380 | | 1152 |
| ggt tca gat ctt ggt gat gaa gac tgg ctg ttc agc agt aaa agg aac<br>Gly Ser Asp Leu Gly Asp Glu Asp Trp Leu Phe Ser Ser Lys Arg Asn<br>385                       390                    395               400 | | 1200 |
| tcc gat gct atc atg gtt caa agc aga gct act gat agt tca gtg ccg<br>Ser Asp Ala Ile Met Val Gln Ser Arg Ala Thr Asp Ser Ser Val Pro<br>                  405                   410               415 | | 1248 |
| atc cat cca atg gtg cag cag aag cct tct tta caa ccc agg gca aca<br>Ile His Pro Met Val Gln Gln Lys Pro Ser Leu Gln Pro Arg Ala Thr<br>            420                    425               430 | | 1296 |
| ttt ttg ccg gac ctt aat atg tac cag ctg cca tat gtc gta cca ttt<br>Phe Leu Pro Asp Leu Asn Met Tyr Gln Leu Pro Tyr Val Val Pro Phe | | 1344 |

```
                      435                 440                 445
taa                                                                     1347

<210> SEQ ID NO 39
<211> LENGTH: 448
<212> TYPE: PRT
<213> ORGANISM: Zea mays mays strain HuoBai

<400> SEQUENCE: 39

Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
                20                  25                  30

Glu Lys Ala Glu Lys Lys Glu Lys Arg Ser Asp Arg Lys Ala Pro
            35                  40                  45

Lys Gln Cys Glu Thr Ser Lys His Ser Lys His Ser His Lys Lys Arg
        50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
        275                 280                 285

Pro Lys Val Leu His Lys Glu Thr Gly Ser Val Val Arg Leu Pro Glu
    290                 295                 300

Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
                325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
```

|       |     |     |     |     |       | 355 |     |     |     |     |       | 360 |     |     |     |     |       | 365 |     |

Phe Arg Asp Leu Phe Val Thr Trp Asn Pro Val Leu Ile Glu Asn Glu
    370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Lys Pro Ser Leu Gln Pro Arg Ala Thr
                420                 425                 430

Phe Leu Pro Asp Leu Asn Met Tyr Gln Leu Pro Tyr Val Val Pro Phe
        435                 440                 445

<210> SEQ ID NO 40
<211> LENGTH: 262
<212> TYPE: DNA
<213> ORGANISM: Zea mays mays strain Makki

<400> SEQUENCE: 40

```
gaacgaattt gaatcctttg tgatctctac ggcggggtag agcgcggtcg accgtcggcc    60
atgtcgaggt gcttcccta cccgccaccg gggtacgtgc ggaacccagt ggccgtggcc   120
gagccggagt cgaccgctaa ggtttgttga accttcggat ttacacacgc acgtgccaga   180
tcgtttgttc aatctgtagg ttttgcgcgg atctgtggtt tgcgcgtgcg tgatgtgggt   240
attgcccgtg ccttgaaagc ta                                           262
```

<210> SEQ ID NO 41
<211> LENGTH: 2311
<212> TYPE: DNA
<213> ORGANISM: Zea mays mays strain Makki

<400> SEQUENCE: 41

```
tttcgaaaac tggtagcatg gttatcgggg acattgaaag aatggtagaa catcaaattc    60
gattcaaaac tgtgctagat ttgcatattt agtcgccta aaattacgtg gacgtgggtg   120
atccgaattg gttgttgtat gatggttgga agtgactggc caaattttttt tgtttctcaa  180
agttttcttt gacaaactgt tgtcgagcg tcaattcgta tttacctgaa tttactaatt   240
cttaatacag tatgtcgtta ttttgggcta agcttgtgta agaagggtcg tttgacattt   300
tgtactgtat tgatgctgtt ttgtgtttct ttgttcggag cagcattcaa tgctccttttt 360
gttgtttgag agaatctgat atttgccatc gtaccgaaag tccgaaacca actattcaaa   420
ttgggatttc atttctttttt ttttctactg tttttagagt tctcttttc gctgctgtgc   480
tcttgtgggt cagtacgtgc atttctcttt tttttctttttt ttttctgatg ttactcttct 540
gttgaccaaa ggagttcaga attatttttgg acctgtatat caatagcaac caacaccatt   600
tattgagccc attttttagtt ttcttgttct gtagagtatg cattgttgca ggtcttaact   660
gttgtcaggg aagtaacgtg tcaacatga ttgtaaacga atacaattct gttgctaact    720
gtgtaatgat gagaaggata attgaataat ctttgtgaag tattactgtc tgaactgtac   780
gcaaatgcta cattcattct ttgtgttcgt gtaaatatca ttatacataa aaatgctgca   840
ttgcattccc gtcgtccgtt ctaaatcaga actgacgatt gctctggtgg ctgaagctcc   900
tgaaagaaaa ggaaaggcc gaaagaagaa agagaaaag gagtgacagg aaagctccca   960
agcagtgtga gacgtccaaa cattcaaagc acagccataa gaagagaaag cttgaagatg  1020
tcatcaaagc tgagcagggt cccaaaagag tacccaaaga atcagttgag cagttggaga  1080
```

-continued

```
agagtggact ctcagaagag catggagctc cttcttttgt acatacgata cgtgactctc      1140
ctgagagctc acaggacagc ggcaagagac gaaaggttgt cctgtccagt cctagccaac      1200
ctaagaatgg tgagactatt ctcttgtttt tgctattctg attgatttt  tattatagaa      1260 gaaatcaatc gcttgttcag gatttattc  atcccaactt gattttacag gaaacattct     1320
tcgcttcaag attaaaagta gtcaagatcc ccaatcagct gttctggaga accaagggt       1380 tcttgagcaa ccattggtcc aacaaatggg atcaggttca tccctgtcgg gcaagcaaaa     1440
ttcaatccat cataagatga atgtgagatc tacctctggt cagcggaggg tcaatggtga     1500
ctcccaagca gtacaaaaat gtttgattac agaatccccg gcaaagacca tgcagagact     1560
tgtcccccag cctgcagcta aggtcacaca tcctgttgat ccccagtcag ctgttaaggt     1620
gccagttgga gatcgggcc  tacctctgaa gtcttcrgga agtgtggacc cttcgcctgc     1680
tagagttatg agaagatttg atcctccacc tgttaagatg atgtcacaga gagttcacca     1740
tccagcttcc atggtgtcgc agaaagttga tcctccgttt ccgaaggtat tacataagga     1800
aaccggatct gttgttcgcc taccagaagc tacccggcct actgttcttc aaaaacccaa     1860
ggacttgcct gctatcaagc agcaggatat caggacctct tcctcaaaag aagagccctg     1920
cttctctggt aggaatgcag aagcagttca agtgcaagat actaagctct cccggtcaga     1980
catgaagaaa atccgcaaag ctgagaaaaa agataagaag ttcagagatc tgtttgttac     2040
ctggaatccg gtattgatag agaatgaagg ttcagatctt ggtgatgaag actggctgtt     2100
cagcagtaaa aggaactccg atgctatcat ggttcaaagc agagctactg atagttcagt     2160
gccgatccat ccaatggtgc agcagaagcc ttctttacaa cccagggcaa cattttttgcc    2220 ggaccttaat atgtaccagc tgccatatgt cgtaccattt taaacatctg gcgaggtaga     2280
tgagaattag atgagatgtt gggagagagc t                                    2311

<210> SEQ ID NO 42
<211> LENGTH: 1347
<212> TYPE: DNA
<213> ORGANISM: Zea mays mays strain Makki
<220> FEATURE:
<221> NAME/KEY: CDS
<222> LOCATION: (1)..(1347)
<223> OTHER INFORMATION:

<400> SEQUENCE: 42 atg tcg agg tgc ttc ccc tac ccg cca ccg ggg tac gtg cgg aac cca        48
Met Ser Arg Cys Phe Pro Tyr Pro Pro Pro Gly Tyr Val Arg Asn Pro
1               5                   10                  15 gtg gcc gtg gcc gag ccg gag tcg acc gct aag ctc ctg aaa gaa aag        96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gct ccc       144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga       192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc       240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat       288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca       336
```

```
                  -continued

Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa        384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gat        432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg        480
Pro Gln Ser Ala Val Leu Glu Lys Pro Arg Val Leu Glu Gln Pro Leu
145                 150                 155                 160 gtc caa caa atg gga tca ggt tca tcc ctg tcg ggc aag caa aat tca        528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc        576
Ile His His Lys Met Asn Val Arg Ser Thr Ser Gly Gln Arg Arg Val
            180                 185                 190 aat ggt gac tcc caa gca gta caa aaa tgt ttg att aca gaa tcc ccg        624
Asn Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca        672
Ala Lys Thr Met Gln Arg Leu Val Pro Gln Pro Ala Ala Lys Val Thr
    210                 215                 220 cat cct gtt gat ccc cag tca gct gtt aag gtg cca gtt gga aga tcg        720
His Pro Val Asp Pro Gln Ser Ala Val Lys Val Pro Val Gly Arg Ser
225                 230                 235                 240 ggc cta cct ctg aag tct tcr gga agt gtg gac cct tcg cct gct aga        768
Gly Leu Pro Leu Lys Ser Xaa Gly Ser Val Asp Pro Ser Pro Ala Arg
                245                 250                 255 gtt atg aga aga ttt gat cct cca cct gtt aag atg atg tca cag aga        816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt        864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa        912
Pro Lys Val Leu His Lys Glu Thr Gly Ser Val Val Arg Leu Pro Glu
    290                 295                 300 gct acc cgg cct act gtt ctt caa aaa ccc aag gac ttg cct gct atc        960
Ala Thr Arg Pro Thr Val Leu Gln Lys Pro Lys Asp Leu Pro Ala Ile
305                 310                 315                 320 aag cag cag gat atc agg acc tct tcc tca aaa gaa gag ccc tgc ttc       1008
Lys Gln Gln Asp Ile Arg Thr Ser Ser Ser Lys Glu Glu Pro Cys Phe
                325                 330                 335 tct ggt agg aat gca gaa gca gtt caa gtg caa gat act aag ctc tcc       1056
Ser Gly Arg Asn Ala Glu Ala Val Gln Val Gln Asp Thr Lys Leu Ser
            340                 345                 350 cgg tca gac atg aag aaa atc cgc aaa gct gag aaa aaa gat aag aag       1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa       1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac       1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg       1248
Ser Asp Ala Ile Met Val Gln Ser Arg Ala Thr Asp Ser Ser Val Pro
                405                 410                 415
```

-continued

```
atc cat cca atg gtg cag cag aag cct tct tta caa ccc agg gca aca    1296
Ile His Pro Met Val Gln Gln Lys Pro Ser Leu Gln Pro Arg Ala Thr
            420                 425                 430 ttt ttg ccg gac ctt aat atg tac cag ctg cca tat gtc gta cca ttt    1344
Phe Leu Pro Asp Leu Asn Met Tyr Gln Leu Pro Tyr Val Val Pro Phe
        435                 440                 445 taa                                                                 1347
```

<210> SEQ ID NO 43
<211> LENGTH: 448
<212> TYPE: PRT
<213> ORGANISM: Zea mays mays strain Makki
<220> FEATURE:
<221> NAME/KEY: misc_feature
<222> LOCATION: (247)..(247)
<223> OTHER INFORMATION: The 'Xaa' at location 247 stands for Ser.

<400> SEQUENCE: 43

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
                20                  25                  30

Glu Lys Ala Glu Lys Lys Glu Lys Arg Ser Asp Arg Lys Ala Pro
            35                  40                  45

Lys Gln Cys Glu Thr Ser Lys His Ser Lys His Ser Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Xaa Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
        275                 280                 285

Pro Lys Val Leu His Lys Glu Thr Gly Ser Val Val Arg Leu Pro Glu
    290                 295                 300
```

```
Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
            325                 330                 335

Ser Gly Arg Asn Ala Glu Ala Val Gln Val Gln Asp Thr Lys Leu Ser
                340                 345                 350

Arg Ser Asp Met Lys Lys Ile Arg Lys Ala Glu Lys Lys Asp Lys Lys
            355                 360                 365

Phe Arg Asp Leu Phe Val Thr Trp Asn Pro Val Leu Ile Glu Asn Glu
    370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Gln Lys Pro Ser Leu Gln Pro Arg Ala Thr
            420                 425                 430

Phe Leu Pro Asp Leu Asn Met Tyr Gln Leu Pro Tyr Val Val Pro Phe
    435                 440                 445
```

<210> SEQ ID NO 44
<211> LENGTH: 125
<212> TYPE: DNA
<213> ORGANISM: Zea mays mays strain Min13

<400> SEQUENCE: 44
ctttgtgatc tctcggcggg gtagagcgcg gtcgaccgtc ggccatgtcg aggtgcttcc    60
cctacccgcc accggggtac gtgcggaacc cagtggccgt ggccgagccg gagtcgaccg   120
ctaag                                                              125

<210> SEQ ID NO 45
<211> LENGTH: 198
<212> TYPE: DNA
<213> ORGANISM: Zea mays mays strain Min13

<400> SEQUENCE: 45
cttaatacag tatgtcgtta ttttgggcta agcttgtgta agaagggtcg tttgacattt    60
tgtactgtat tgatgctgtt ttgtgtttct ttgttcggag cagcattcaa tgctcctttt   120
gttgtttgag agaatctgat atttgccatc gtaccgaaag tccgaaacca actattcaaa   180
ttgggatttc atttctttt                                               198

<210> SEQ ID NO 46
<211> LENGTH: 1787
<212> TYPE: DNA
<213> ORGANISM: Zea mays mays strain Min13

<400> SEQUENCE: 46
ttctgatgtt actcttctgt tgaccaaagg agttcagaat tattttggcc ctgtatatca    60
atagcaacca acaccattta ttgagcccat ttttagtttt cttgttctgt agagtatgca   120
ttgttgcagg tcttaactgt tgtcagggaa gtaacgtgtt caacatgatt gtaaacgaat   180
acaattctgt tgctaactgt gtaatgatga aaggataat tgaataatct ttgtgaagta    240
ttactgtctg aactgtacgc aaatgctaca ttcattcttt gtgttcgtgt aaatatcatt   300
atacataaaa atgctgcatt gcattcccgt cgtccgttct aaatcagaac tgacgattgc   360
tctggtggct gaagctcctg aaagaaaagg aaaggccga aaagaagaaa gagaaaagga    420

```
gtgacaggaa agctcccaag cagtgtgaga cgtccaaaca ttcaaagcac agccataaga      480
agagaaagct tgaagatgtc atcaaagctg agcagggtcc caaagagta  cccaaagaat      540 cagttgagca gttggagaag agtggactct cagaagagca tggagctcct tcttttgtac      600
atacgatacg tgactctcct gagagctcac aggacagcgg caagagacga aaggttgtcc      660
tgtccagtcc tagccaacct aagaatggtg agactattct cttgtttttg ctattctgat      720 tgattttta  ttatagaaga aatcaatcgc ttgttcagga tttattcat  cccaacttga      780 ttttacagga acattcttc  gcttcaagat taaaagtagt caagatcccc aatcagctgt      840
tctggagaaa ccaagggttc ttgagcaacc attggtccaa caaatgggat caggttcatc      900
cctgtcgggc aagcaaaatt caatccatca taagatgaat gtgagatcta cctctggtca      960
gcggagggtc aatggtgact cccaagcagt acaaaaatgt ttgattacag aatccccggc     1020
aaagaccatg cagagacttg tcccccagcc tgcagctaag gtcacacatc ctgttgatcc     1080
ccagtcagct gttaaggtgc cagttggaag atcgggccta cctctgaagt cttcgggaag     1140
tgtggaccct tcgcctgcta gagttatgag aagatttgat cctccacctg ttaagatgat     1200
gtcacagaga gttcaccatc cagcttccat ggtgtcgcag aaagttgatc ctccgtttcc     1260
gaaggtatta cataaggaaa ccggatctgt tgttcgccta ccagaagcta cccggcctac     1320
tgttcttcaa aaacccaagg acttgcctgc tatcaagcag caggatatca ggacctcttc     1380
ctcaaaagaa gagccctgct tctctggtag aatgcagaa  gcagttcaag tgcaggatac     1440
taagctctcc cggtcagaya tgaagaaaat ccgcaaagct gagaaaaaag ataagaagtt     1500
cagagatctg tttgttacct ggaatccggt attgatagag aatgaaggtt cagatcttgg     1560
tgatgaagac tggctgttca gcagtaaaag gaactccgat gctatcatgg ttcaaagcag     1620
agctactgat agttcagtgc cgatccatcc aatggtgcag cagaagcctt ctttacaacc     1680
cagggcaaca ttttttgccgg accttaatat gtaccagctg ccatatgtcg taccatttta     1740
aacatctggc gaggtagatg agaattagat gagatgttgg gagagag                   1787
```

<210> SEQ ID NO 47
<211> LENGTH: 1347
<212> TYPE: DNA
<213> ORGANISM: Zea mays mays strain Min13
<220> FEATURE:
<221> NAME/KEY: CDS
<222> LOCATION: (1)..(1347)
<223> OTHER INFORMATION:

<400> SEQUENCE: 47

```
atg tcg agg tgc ttc ccc tac ccg cca ccg ggg tac gtg cgg aac cca         48
Met Ser Arg Cys Phe Pro Tyr Pro Pro Pro Gly Tyr Val Arg Asn Pro
1               5                  10                  15 gtg gcc gtg gcc gag ccg gag tcg acc gct aag ctc ctg aaa gaa aag         96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gct ccc        144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga        192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc        240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat        288
```

```
Lys Glu Ser Val Glu Gln Leu Glu Lys Ser Gly Leu Ser Glu Glu His
                 85                  90                  95 gga gct cct tct ttt gta cat acg ata cgt gac tct cct gag agc tca      336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa      384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gat      432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg      480
Pro Gln Ser Ala Val Leu Glu Lys Pro Arg Val Leu Glu Gln Pro Leu
145                 150                 155                 160 gtc caa caa atg gga tca ggt tca tcc ctg tcg ggc aag caa aat tca      528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc      576
Ile His His Lys Met Asn Val Arg Ser Thr Ser Gly Gln Arg Arg Val
            180                 185                 190 aat ggt gac tcc caa gca gta caa aaa tgt ttg att aca gaa tcc ccg      624
Asn Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca      672
Ala Lys Thr Met Gln Arg Leu Val Pro Gln Pro Ala Ala Lys Val Thr
    210                 215                 220 cat cct gtt gat ccc cag tca gct gtt aag gtg cca gtt gga aga tcg      720
His Pro Val Asp Pro Gln Ser Ala Val Lys Val Pro Val Gly Arg Ser
225                 230                 235                 240 ggc cta cct ctg aag tct tcg gga agt gtg gac cct tcg cct gct aga      768
Gly Leu Pro Leu Lys Ser Ser Gly Ser Val Asp Pro Ser Pro Ala Arg
                245                 250                 255 gtt atg aga aga ttt gat cct cca cct gtt aag atg atg tca cag aga      816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt      864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa      912
Pro Lys Val Leu His Lys Glu Thr Gly Ser Val Val Arg Leu Pro Glu
    290                 295                 300 gct acc cgg cct act gtt ctt caa aaa ccc aag gac ttg cct gct atc      960
Ala Thr Arg Pro Thr Val Leu Gln Lys Pro Lys Asp Leu Pro Ala Ile
305                 310                 315                 320 aag cag cag gat atc agg acc tct tcc tca aaa gaa gag ccc tgc ttc     1008
Lys Gln Gln Asp Ile Arg Thr Ser Ser Ser Lys Glu Glu Pro Cys Phe
                325                 330                 335 tct ggt agg aat gca gaa gca gtt caa gtg cag gat act aag ctc tcc     1056
Ser Gly Arg Asn Ala Glu Ala Val Gln Val Gln Asp Thr Lys Leu Ser
            340                 345                 350 cgg tca gay atg aag aaa atc cgc aaa gct gag aaa aaa gat aag aag     1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa     1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac     1200
Gly Ser Asp Leu Gly Asp Glu Asp Trp Leu Phe Ser Ser Lys Arg Asn
385                 390                 395                 400
```

```
tcc gat gct atc atg gtt caa agc aga gct act gat agt tca gtg ccg   1248
Ser Asp Ala Ile Met Val Gln Ser Arg Ala Thr Asp Ser Ser Val Pro
            405                 410                 415 atc cat cca atg gtg cag cag aag cct tct tta caa ccc agg gca aca   1296
Ile His Pro Met Val Gln Gln Lys Pro Ser Leu Gln Pro Arg Ala Thr
        420                 425                 430 ttt ttg ccg gac ctt aat atg tac cag ctg cca tat gtc gta cca ttt   1344
Phe Leu Pro Asp Leu Asn Met Tyr Gln Leu Pro Tyr Val Val Pro Phe
        435                 440                 445 taa                                                               1347
```

<210> SEQ ID NO 48
<211> LENGTH: 448
<212> TYPE: PRT
<213> ORGANISM: Zea mays mays strain Min13

<400> SEQUENCE: 48

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
                20                  25                  30

Glu Lys Ala Glu Lys Lys Glu Lys Arg Ser Asp Arg Lys Ala Pro
            35                  40                  45

Lys Gln Cys Glu Thr Ser Lys His Ser Lys His Ser Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
                100                 105                 110

Gln Asp Ser Gly Lys Arg Arg Lys Val Val Leu Ser Ser Pro Ser Gln
            115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
    195                 200                 205

Ala Lys Thr Met Gln Arg Leu Val Pro Gln Pro Ala Ala Lys Val Thr
210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
    275                 280                 285

Pro Lys Val Leu His Lys Glu Thr Gly Ser Val Val Arg Leu Pro Glu
    290                 295                 300
```

```
Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
            325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
        355                 360                 365

Phe Arg Asp Leu Phe Val Thr Trp Asn Pro Val Leu Ile Glu Asn Glu
    370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Gln Lys Pro Ser Leu Gln Pro Arg Ala Thr
            420                 425                 430

Phe Leu Pro Asp Leu Asn Met Tyr Gln Leu Pro Tyr Val Val Pro Phe
    435                 440                 445
```

<210> SEQ ID NO 49
<211> LENGTH: 495
<212> TYPE: DNA
<213> ORGANISM: Zea mays mays strain Pira

<400> SEQUENCE: 49

```
ctcggcgggt agagcgcggt cgacgtcggc atgtcgaggt gcttccccta cccgccaccg      60
gggtacgtgc ggaacccagt ggccgtggcc gagccggagt cgaccgctaa ggttgttgaa     120
ccttcggatt tacacacgca cgtgccagat cgttgttcaa tctgtaggtt ttgcgcggat     180
ctgtggtttg cgcgtgcgtg atgtgggtat tgsccgtgcc ttgaaagcta accgagctga     240
ggaagtgtat ggatcttgtg tagctgcacg aggtcctcca aatcgattgt aaaatttaag     300
ttgtatggsc ggtaggscaa gattgggtta gtccggtttt cgaaaactgg tagcatggtt     360
atcggggaca ttgaaagaat ggtagaacat caaattcgat tcaaaactgt gctagatttg     420
catatttagt cgccctaaaa ttacgtggac gtgggtgatc cgaattggtt attgtatgat     480
ggttggaata tgagc                                                      495
```

<210> SEQ ID NO 50
<211> LENGTH: 1768
<212> TYPE: DNA
<213> ORGANISM: Zea mays mays strain Pira

<400> SEQUENCE: 50

```
ctgttgacca atggagttca gaattatttt ggccctgtat atcaatagca accaacacca      60
tttattgagc ccattttag ttttcttgtt ctgtagagta tgcattgttg caggtcttaa     120
ctgttgtcag ggaagtaacg tgttcaacat gattgtaaac gaatacattc tgttgctaac     180
tgtgtaatga tgagaaggat aattgaataa tctttgtgaa gtattactgt ctgaactgta     240
cgcaatgcta cattcattct ttgtgttcgt gtaaatatca ttatacataa aaatgctgct     300
tgcattcccg tcgtccgttc taaatcagaa ctgacgattg ctctggtggc tgaagctcct     360
gaaagaaaag gaaaaagccg aaaagaagaa agagaaaagg agtgacagga agctcccaa     420 gcagtgtgag acgtccaaac attcaaagca cagccataag aagagaaagc ttgaagatgt     480
catcaaagct gagcagggtc ccaaaagagt acccaaagaa tcagttgagc agttggagaa     540
```

-continued

| | |
|---|---|
| gagtggactc tcagaagagc atggagctcc ttcttttgta catacgatac gtgactctcc | 600 |
| tgagagctca caggacagcg gcaagagacg aaaggttgtc ctgtccagtc ctagccaacc | 660 |
| taagaatggt gagactattc tcttgttttt gctattctga ttgatttatt attatagaag | 720 |
| aaatcaatca cttgttcagg attttattca tcccaacttg attttacagg aaacattctt | 780 |
| cgcttcaaga ttaaaagtag tcaagatccc aatcagctg ttctggagaa accaagggtt | 840 |
| cttgagcaac cattggtcca acaaatggga tcaggttcat ccctgtctgg caagcaaaat | 900 |
| tcaatccatc ataagatgaa tgtgagatct acctctggtc agcggagggt caatggtgac | 960 |
| tcccaagcag tacaaaaatg tttgattaca aatccccgg caaagaccat gcagagactt | 1020 |
| gtcccccagc ctgcagctaa ggtcacacat cctgttgatc cccagtcagc tgttaaggtg | 1080 |
| ccagttggaa gatcgggcct acctctgaag tcttcgggaa gtgtggaccc ttcgcctgct | 1140 |
| agagttatga gaagatttga tcctccacct gttaagatga tgtcacagag agttcaccat | 1200 |
| ccagcttcca tggtgtcgca gaaagttgat cctccgtttc cgaaggtatt acataaggaa | 1260 |
| accggatctg ttgttcgcct accagaagct acccggccta ctgttcttca aaaacccaag | 1320 |
| gacttgcctg ctatcaagca gcaggagatc aggacctctt yctcaaaaga gagccctgc | 1380 |
| ttctctggta ggaatgcaga agcagttcaa gtgcaggata ctaagctctc ccggtcagac | 1440 |
| atgaagaaaa tccgcaaagc tgagaaaaaa gataagaagt tcagagatct gtttgttacc | 1500 |
| tggaatccgg tattgataga gaatgaaggt tcagatcttg gtgatgaaga ctggctgttc | 1560 |
| agcagtaaaa ggaactccga tgctatcatg gttcaaagca gagctactga tagttcagtg | 1620 |
| ccgatccatc caatggtgca gcagaagcct tctttacaac ccagggcaac atttttgccg | 1680 |
| gaccttaata tgtaccagct gccatatgtc gtaccatttt aaacatctgg cgaggtagat | 1740 |
| gagaattaga tgagatgttg ggagagag | 1768 |

<210> SEQ ID NO 51
<211> LENGTH: 1347
<212> TYPE: DNA
<213> ORGANISM: Zea mays mays strain Pira
<220> FEATURE:
<221> NAME/KEY: CDS
<222> LOCATION: (1)..(1347)
<223> OTHER INFORMATION:

<400> SEQUENCE: 51

| | |
|---|---|
| atg tcg agg tgc ttc ccc tac ccg cca ccg ggg tac gtg cgg aac cca<br>Met Ser Arg Cys Phe Pro Tyr Pro Pro Pro Gly Tyr Val Arg Asn Pro<br>1              5              10             15 | 48 |
| gtg gcc gtg gcc gag ccg gag tcg acc gct aag ctc ctg aaa gaa aag<br>Val Ala Val Ala Glu Pro Glu Ser Thr Ala Lys Leu Leu Lys Glu Lys<br>               20                  25               30 | 96 |
| gaa aaa gcc gaa aag aag aaa gag aaa agg agt gac agg aaa gct ccc<br>Glu Lys Ala Glu Lys Lys Lys Glu Lys Arg Ser Asp Arg Lys Ala Pro<br>                   35                  40               45 | 144 |
| aag cag tgt gag acg tcc aaa cat tca aag cac agc cat aag aag aga<br>Lys Gln Cys Glu Thr Ser Lys His Ser Lys His Ser His Lys Lys Arg<br>50                       55                       60 | 192 |
| aag ctt gaa gat gtc atc aaa gct gag cag ggt ccc aaa aga gta ccc<br>Lys Leu Glu Asp Val Ile Lys Ala Glu Gln Gly Pro Lys Arg Val Pro<br>65                       70                  75                 80 | 240 |
| aaa gaa tca gtt gag cag ttg gag aag agt gga ctc tca gaa gag cat<br>Lys Glu Ser Val Glu Gln Leu Glu Lys Ser Gly Leu Ser Glu Glu His<br>                       85                  90               95 | 288 |
| gga gct cct tct ttt gta cat acg ata cgt gac tct cct gag agc tca | 336 |

```
Gly Ala Pro Ser Phe Val His Thr Ile Arg Asp Ser Pro Glu Ser Ser
                100                 105                 110 cag gac agc ggc aag aga cga aag gtt gtc ctg tcc agt cct agc caa        384
Gln Asp Ser Gly Lys Arg Arg Lys Val Val Leu Ser Ser Pro Ser Gln
            115                 120                 125 cct aag aat gga aac att ctt cgc ttc aag att aaa agt agt caa gat        432
Pro Lys Asn Gly Asn Ile Leu Arg Phe Lys Ile Lys Ser Ser Gln Asp
        130                 135                 140 ccc caa tca gct gtt ctg gag aaa cca agg gtt ctt gag caa cca ttg        480
Pro Gln Ser Ala Val Leu Glu Lys Pro Arg Val Leu Glu Gln Pro Leu
145                 150                 155                 160 gtc caa caa atg gga tca ggt tca tcc ctg tct ggc aag caa aat tca        528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc        576
Ile His His Lys Met Asn Val Arg Ser Thr Ser Gly Gln Arg Arg Val
            180                 185                 190 aat ggt gac tcc caa gca gta caa aaa tgt ttg att aca gaa tcc ccg        624
Asn Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca        672
Ala Lys Thr Met Gln Arg Leu Val Pro Gln Pro Ala Ala Lys Val Thr
210                 215                 220 cat cct gtt gat ccc cag tca gct gtt aag gtg cca gtt gga aga tcg        720
His Pro Val Asp Pro Gln Ser Ala Val Lys Val Pro Val Gly Arg Ser
225                 230                 235                 240 ggc cta cct ctg aag tct tcg gga agt gtg gac cct tcg cct gct aga        768
Gly Leu Pro Leu Lys Ser Ser Gly Ser Val Asp Pro Ser Pro Ala Arg
                245                 250                 255 gtt atg aga aga ttt gat cct cca cct gtt aag atg atg tca cag aga        816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt        864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa        912
Pro Lys Val Leu His Lys Glu Thr Gly Ser Val Val Arg Leu Pro Glu
290                 295                 300 gct acc cgg cct act gtt ctt caa aaa ccc aag gac ttg cct gct atc        960
Ala Thr Arg Pro Thr Val Leu Gln Lys Pro Lys Asp Leu Pro Ala Ile
305                 310                 315                 320 aag cag cag gag atc agg acc tct tyc tca aaa gaa gag ccc tgc ttc       1008
Lys Gln Gln Glu Ile Arg Thr Ser Xaa Ser Lys Glu Glu Pro Cys Phe
                325                 330                 335 tct ggt agg aat gca gaa gca gtt caa gtg cag gat act aag ctc tcc       1056
Ser Gly Arg Asn Ala Glu Ala Val Gln Val Gln Asp Thr Lys Leu Ser
            340                 345                 350 cgg tca gac atg aag aaa atc cgc aaa gct gag aaa aaa gat aag aag       1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa       1152
Phe Arg Asp Leu Phe Val Thr Trp Asn Pro Val Leu Ile Glu Asn Glu
370                 375                 380 ggt tca gat ctt ggt gat gaa gac tgg ctg ttc agc agt aaa agg aac       1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg       1248
Ser Asp Ala Ile Met Val Gln Ser Arg Ala Thr Asp Ser Ser Val Pro
                405                 410                 415
```

-continued

```
atc cat cca atg gtg cag cag aag cct tct tta caa ccc agg gca aca      1296
Ile His Pro Met Val Gln Gln Lys Pro Ser Leu Gln Pro Arg Ala Thr
        420                 425                 430 ttt ttg ccg gac ctt aat atg tac cag ctg cca tat gtc gta cca ttt      1344
Phe Leu Pro Asp Leu Asn Met Tyr Gln Leu Pro Tyr Val Val Pro Phe
        435                 440                 445 taa                                                                  1347
```

<210> SEQ ID NO 52
<211> LENGTH: 448
<212> TYPE: PRT
<213> ORGANISM: Zea mays mays strain Pira
<220> FEATURE:
<221> NAME/KEY: misc_feature
<222> LOCATION: (329)..(329)
<223> OTHER INFORMATION: The 'Xaa' at location 329 stands for Ser, or Phe.

<400> SEQUENCE: 52

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
                20                  25                  30

Glu Lys Ala Glu Lys Lys Glu Lys Arg Ser Asp Arg Lys Ala Pro
            35                  40                  45

Lys Gln Cys Glu Thr Ser Lys His Ser Lys His Ser His Lys Lys Arg
        50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
        275                 280                 285

Pro Lys Val Leu His Lys Glu Thr Gly Ser Val Val Arg Leu Pro Glu
    290                 295                 300
```

```
Ala Thr Arg Pro Thr Val Leu Gln Lys Pro Lys Asp Leu Pro Ala Ile
305                 310                 315                 320

Lys Gln Gln Glu Ile Arg Thr Ser Xaa Ser Lys Glu Pro Cys Phe
            325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
            355                 360                 365

Phe Arg Asp Leu Phe Val Thr Trp Asn Pro Val Leu Ile Glu Asn Glu
370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Gln Lys Pro Ser Leu Gln Pro Arg Ala Thr
                420                 425                 430

Phe Leu Pro Asp Leu Asn Met Tyr Gln Leu Pro Tyr Val Val Pro Phe
            435                 440                 445

<210> SEQ ID NO 53
<211> LENGTH: 212
<212> TYPE: DNA
<213> ORGANISM: Zea mays mays strain Sari

<400> SEQUENCE: 53
gcgcggtcga ccgtcggcat gtcgaggtgc ttcccctacc cgccaccggg gtacgtgcgg    60
aacccagtgg ccgtggccga gccggagtcg accgctaagg tttgttgaac cttcggattt   120
acacacgcac gtgccagatc gtttgttcaa tctgtaggtt ttgcgcggat ctgtggtttg   180
cgcgtgcgtg atgtgggtat tgcccgtgcc tt                                  212

<210> SEQ ID NO 54
<211> LENGTH: 1803
<212> TYPE: DNA
<213> ORGANISM: Zea mays mays strain Sari

<400> SEQUENCE: 54
ttttttcctt ttttttttctg atgttactct tctgttgacc aaaggagttc agaattattt    60
tggccctgta tatcaatagc aaccaacacc atttattgag cccatttttta gttttcttgt   120 tctgtagagt atgcattgtt gcaggtctta actgttgtca gggaagtaac gtgttcaaca   180
tgattgtaaa cgaatacaat tctgttgcta actgtgtaat gatgagaagg ataattgaat   240
aatctttgtg aagtattact gtctgaactg tacgcaaatg ctacattcat tctttgtgtt   300 cgtgtaaaata tcattataca taaaaatgct gcattgcatt cccgtcgtcc gttctaaatc   360
agaactgacg attgctctgg tggctgaagc tcctgaaaga aaaggaaaag gccgaaaaga   420
agaaagagaa aaggagtgac aggaaagctc ccaagcagtg tgagacgtcc aaacattcaa   480
agcacagcca taagaagaga aagcttgaag atgtcatcaa agctgagcag ggtcccaaaa   540
gagtacccaa agaatcagtt gagcagttgg agaagagtgg actctcagaa gagcatggag   600
ctccttcttt tgtacatacg atacgtgact ctcctgagag ctcacaggac agcggcaaga   660
gacgaaaggt tgtcctgtcc agtcctagcc aacctaagaa tggtgagact attctcttgt   720
ttttgctatt ctgattgatt ttttattata gaagaaatca atcgcttgtt caggatttta   780
ttcatcccaa cttgatttta caggaaacat tcttcgcttc aagattaaaa gtagtcaaga   840
```

-continued

```
tccccaatca gctgttctgg agaaaccaag ggttcttgag caaccattgg tccaacaaat      900
gggatcaggt tcatccctgt cgggcaagca aaattcaatc catcataaga tgaatgtgag      960
atctacctct ggtcagcgga gggtcaatgg tgactcccaa gcagtacaaa atgtttgat      1020 tacagaatcc ccggcaaaga ccatgcagag acttgtcccc cagcctgcag ctaaggtcac     1080
acatcctgtt gatccccagt cagctgttaw ggtgccagtt ggaagatcgg gcctacctct     1140
gaagtcttcg ggaagtgtgg acccttcgcc tgctagagtt atgagaagat tgatcctcc      1200 acctgttaag atgatgtcac agagagttca ccatccagct tccatggtgt cgcagaaagt     1260
tgatcctccg tttccgaagg tattacataa ggaaaccgga tctgttgttc gcctaccaga     1320
agctacccgg cctactgttc ttcaaaaacc caaggacttg cctgctatca gcagcagga     1380 tatcaggacc tcttcctcaa agaagagcc ctgcttctct ggtaggaatg cagaagcagt     1440
tcaagtgcar gatactaagc tctcccggtc agaytatgaag aaaatccgca agctgagaa     1500 aaaagataag aagttcagag atctgtttgt tacctggaat ccgtattga tagagaatga    1560 aggttcagat cttggtgatg aagactggct gttcagcagt aaaaggaact ccgatgctat    1620
catggttcaa agcagagcta ctgatagttc agtgccgatc catccaatgg tgcagcagaa    1680
gccttcttta caacccaggg caacattttt gccggacctt aatatgtacc agctgccata    1740
tgtcgtacca ttttaaacat ctggcgaggt agatgagaat tagatgagat gttgggagag    1800
agc                                                                  1803
```

<210> SEQ ID NO 55
<211> LENGTH: 1347
<212> TYPE: DNA
<213> ORGANISM: Zea mays mays strain Sari
<220> FEATURE:
<221> NAME/KEY: CDS
<222> LOCATION: (1)..(1347)
<223> OTHER INFORMATION:

<400> SEQUENCE: 55

```
atg tcg agg tgc ttc ccc tac ccg cca ccg ggg tac gtg cga aac cca       48
Met Ser Arg Cys Phe Pro Tyr Pro Pro Pro Gly Tyr Val Arg Asn Pro
1               5                   10                  15 gtg gcc gtg gcc gag ccg gag tcg acc gct aag ctc ctg aaa gaa aag       96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gct ccc      144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga      192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc      240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat      288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca      336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa      384
Gln Asp Ser Gly Lys Arg Arg Lys Val Val Leu Ser Ser Pro Ser Gln
        115                 120                 125
```

```
cct aag aat gga aac att ctt cgc ttc aag att aaa agt agt caa gat       432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg       480
Pro Gln Ser Ala Val Leu Glu Lys Pro Arg Val Leu Glu Gln Pro Leu
145                 150                 155                 160 gtc caa caa atg gga tca ggt tca tcc ctg tcg ggc aag caa aat tca       528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc       576
Ile His His Lys Met Asn Val Arg Ser Thr Ser Gly Gln Arg Arg Val
            180                 185                 190 aat ggt gac tcc caa gca gta caa aaa tgt ttg att aca gaa tcc ccg       624
Asn Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca       672
Ala Lys Thr Met Gln Arg Leu Val Pro Gln Pro Ala Ala Lys Val Thr
    210                 215                 220 cat cct gtt gat ccc cag tca gct gtt awg gtg cca gtt gga aga tcg       720
His Pro Val Asp Pro Gln Ser Ala Val Xaa Val Pro Val Gly Arg Ser
225                 230                 235                 240 ggc cta cct ctg aag tct tcg gga agt gtg gac cct tcg cct gct aga       768
Gly Leu Pro Leu Lys Ser Ser Gly Ser Val Asp Pro Ser Pro Ala Arg
                245                 250                 255 gtt atg aga aga ttt gat cct cca cct gtt aag atg atg tca cag aga       816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt       864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa       912
Pro Lys Val Leu His Lys Glu Thr Gly Ser Val Val Arg Leu Pro Glu
    290                 295                 300 gct acc cgg cct act gtt ctt caa aaa ccc aag gac ttg cct gct atc       960
Ala Thr Arg Pro Thr Val Leu Gln Lys Pro Lys Asp Leu Pro Ala Ile
305                 310                 315                 320 aag cag cag gat atc agg acc tct tcc tca aaa gaa gag ccc tgc ttc      1008
Lys Gln Gln Asp Ile Arg Thr Ser Ser Ser Lys Glu Glu Pro Cys Phe
                325                 330                 335 tct ggt agg aat gca gaa gca gtt caa gtg car gat act aag ctc tcc      1056
Ser Gly Arg Asn Ala Glu Ala Val Gln Val Gln Asp Thr Lys Leu Ser
            340                 345                 350 cgg tca gay atg aag aaa atc cgc aaa gct gag aaa aaa gat aag aag      1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa      1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac      1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg      1248
Ser Asp Ala Ile Met Val Gln Ser Arg Ala Thr Asp Ser Ser Val Pro
                405                 410                 415 atc cat cca atg gtg cag cag aag cct tct tta caa ccc agg gca aca      1296
Ile His Pro Met Val Gln Gln Lys Pro Ser Leu Gln Pro Arg Ala Thr
            420                 425                 430 ttt ttg ccg gac ctt aat atg tac cag ctg cca tat gtc gta cca ttt      1344
Phe Leu Pro Asp Leu Asn Met Tyr Gln Leu Pro Tyr Val Val Pro Phe
        435                 440                 445
``` taa 1347

<210> SEQ ID NO 56
<211> LENGTH: 448
<212> TYPE: PRT
<213> ORGANISM: Zea mays mays strain Sari
<220> FEATURE:
<221> NAME/KEY: misc_feature
<222> LOCATION: (234)..(234)
<223> OTHER INFORMATION: The 'Xaa' at location 234 stands for Lys, or Met.

<400> SEQUENCE: 56

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
            20                  25                  30

Glu Lys Ala Glu Lys Lys Glu Lys Arg Ser Asp Arg Lys Ala Pro
        35                  40                  45

Lys Gln Cys Glu Thr Ser Lys His Ser Lys His Ser Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Xaa Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
    275                 280                 285

Pro Lys Val Leu His Lys Glu Thr Gly Ser Val Val Arg Leu Pro Glu
290                 295                 300

Ala Thr Arg Pro Thr Val Leu Gln Lys Pro Lys Asp Leu Pro Ala Ile
305                 310                 315                 320

Lys Gln Gln Asp Ile Arg Thr Ser Ser Ser Lys Glu Glu Pro Cys Phe
                325                 330                 335
```

| | | | | | | | | | | | |
|---|---|---|---|---|---|---|---|---|---|---|---|
|Ser|Gly|Arg|Asn|Ala|Glu|Ala|Val|Gln|Val|Gln|Asp|Thr|Lys|Leu|Ser|
| | | |340| | | |345| | | |350|
|Arg|Ser|Asp|Met|Lys|Lys|Ile|Arg|Lys|Ala|Glu|Lys|Lys|Asp|Lys|Lys|
| | |355| | | | |360| | | | |365|
|Phe|Arg|Asp|Leu|Phe|Val|Thr|Trp|Asn|Pro|Val|Leu|Ile|Glu|Asn|Glu|
| |370| | | | |375| | | | |380|
|Gly|Ser|Asp|Leu|Gly|Asp|Glu|Asp|Trp|Leu|Phe|Ser|Ser|Lys|Arg|Asn|
|385| | | |390| | | |395| | | |400|
|Ser|Asp|Ala|Ile|Met|Val|Gln|Ser|Arg|Ala|Thr|Asp|Ser|Ser|Val|Pro|
| | | |405| | | |410| | | |415|
|Ile|His|Pro|Met|Val|Gln|Lys|Pro|Ser|Leu|Gln|Pro|Arg|Ala|Thr|
| | | |420| | | |425| | | |430|
|Phe|Leu|Pro|Asp|Leu|Asn|Met|Tyr|Gln|Leu|Pro|Tyr|Val|Val|Pro|Phe|
| | |435| | | | |440| | | |445|

<210> SEQ ID NO 57
<211> LENGTH: 305
<212> TYPE: DNA
<213> ORGANISM: Zea mays mays strain Smena

<400> SEQUENCE: 57

```
gattgatttc gagcgattcg attccttgtg atctctcggc ggggtagagc gcggtcgacc      60
gtcggccatg tcgaggtgct tccctaccc gccaccgggg tacgtgcgga acccagtggc     120
cgtggccgag ccggagtcga ccgctaaggt ttgttgaacc ttcggattta cacacgcacg    180
tgccagatcg tttgttcaat atgtaggttt tgcgcggatc tgtggttgc gcgtgcgtga      240
tgtgggtatt gcccgtgcct aagctaaccg agctgaggaa gtgtatggat cttgtgtagc     300
tgcac                                                                 305
```

<210> SEQ ID NO 58
<211> LENGTH: 2208
<212> TYPE: DNA
<213> ORGANISM: Zea mays mays strain Smena

<400> SEQUENCE: 58

```
tttagtcgcc ctaaaaatac gtggacgtgg gtgatccgaa ttggttgttg tatgatggtt      60
ggaatatgag ccatctagtg cttccgtgac tggccaaatt tttttgtttc tcaaagtttt    120
cttgaaaaa ctgtttgtcg agcgtcaatt cgtatttacc tgaatttact aattcttaat     180
acagtatgtc gttattttgg gctaagcttg tgtaagaagg tcgtttgac attttgtact    240
gtattaatgc tgttttgtgt ttctttgttc ggagcagcat tcaatgctcc ttttgttgtt    300
tgagagaatc tgatatttgc catcgtaccg aaagtccgaa accaactatt caaattggga    360
tttcatttct tttttttct actgtttta gagttctctt tttcgctgct gtgctcttgt     420
gggtcagtac gtgcatttct ctcttttttt cttttttttt ctgatgttac tcttctgttg    480
accaaaggag ttcagaatta ttttggccct gtatatcaat ttgcaaccaa caccatttat    540
tgagcccatt tttagttttc ttgttctgta gagttatgca ttgtttcagg tcttaactgt    600
tgtcagggaa gtaacgtgtt caacatgatt gtaaacgaat acaattctgt tgctaactgt    660
gtaatgatga aaggataat tgaatagtct ttgtgaagta ttactgtctg aactgtacgc     720
aaatgctaca ttcattctgt gttcatgtaa atatcattat acataaaaat gctgcattgc    780
attcccgtcg tccgttctaa atcagaactg acgattgctc tggtggctga agctcctgaa     840
agaaaaggaa aaggccgaaa agaagaaaga gaaaaggagt gacaggaaag atcccaagca    900
```

-continued

```
gtgtgagacg tccaaacact caaagcacag ccataagaag agaaagcttg aagatgtcat      960
caaagctgag cagggtccca aaagagtacc caaagaatca gttgagcagt tggagaagag     1020
tggactctca gaagagcatg gagctccttc ttttgtacat acgatacggg actctcctga     1080
gagctcacag gacagcggca agagacgaaa ggttgtcctg tccagtccta gccaacctaa     1140
gaatggtgag actattctct tgttttgct attctgattg atttattatt atagaagaaa      1200
tcaatcactt gttcaggatt ttattcatcc caacttgatt ttacaggaaa cattcttcgc     1260
ttcaagatta aaagtagtca agatccccaa tcagctgttc tggagaaacc aagggttctt    1320
gagcaaccat tggtccaaca aatgggatca ggttcatccc tgtcgggcaa gcaaaattca     1380
atccatcata agatgaatgt gagatctacc tctggtcagc ggagggtcaa tggtgactcc    1440
caagcagtac aaaaatgttt gattacagaa tccccggcaa agaccatgca gagacttgtc     1500
ccccagcctg cagctaaggt cacacatcct gttgatcccc agtcagctgt taaggtgcca     1560 gttgaagat cgggcctacc tctgaagtct tcaggaagtg tggacccttc gcctgctaga     1620
gttatgagaa gatttgatcc tccacctgtt aagatgatgt cacagagagt tcaccatcca     1680
gcttccatgg tgtcgcagaa agttgatcct ccgtttccga aggtattaca taaggaaacc     1740
ggatctgttg ttcgcctacc agaagctacc cggcctactg ttcttcaaaa acccaaggac    1800
ttgccttcta tcaagcagca ggagatcagg acctcttcct caaaagaaga gccctgcttc    1860
tctggtagga atgcagaagc tgttcaagtg caggatacta agctctcccg gtcagatatg    1920
aagaaaatcc gcaaagctga gaaaaaagat aagaagttca gagatctgtt tgttacctgg    1980
aatccggtat tgatagagaa tgaaggttca gatcttggtg atgaagactg gctgttcagc    2040
agtaaaagga actccgatgc tatcatggtt caaagcagag ctactgatag ttcagtgccg     2100
atccatccaa tggtgcagca gaagccttct ttacaaccca gggcaacatt tttgccggac    2160
cttaatatgt accagctgcc atatgtcgta ccatttaaa catctggc                  2208
```

<210> SEQ ID NO 59
<211> LENGTH: 1640
<212> TYPE: DNA
<213> ORGANISM: Zea mays parviglumis strain Wilkes

<400> SEQUENCE: 59

```
tcagggaagt aacgtgttca acatgattgt aaacgaatac cattctgttg ctaactgtgt       60
aatgatgaga aggataattg aataatcttt gtgaagtatt actgtctgaa ctgtacgcct      120
aatgctacat tcattctttg tgttcgtgta aatatcatta tacataaatg ctgcattgca      180
ttcccgtcgt ccgttctaaa tcagaactga cgattgctct ggtggctgaa gctcctgaaa      240 gaaaggaaa aggccgaaaa gaagaaagag aaaaggagtg acaggaaagc tcccaagcag       300
tgtgagacgt ccaaacattc aaagcacagc cataagaaga gaaagcttga agatgtcatc      360
aaagctgagc agggtcccaa aagagtaccc aaagaatcag ttgagcagtt ggagaagagt      420
ggactctcag aagagcatgg agctccttct tttgtacata cgatacgtga ctctcctgag      480
agctcacagg acagcggcaa gagacgaaag gttgtcctgt ccagtcctag ccaacctaag      540
aatggtgaga ctattctctt gtttttgcta ttctgattga ttttttatta tagaagaaat      600
caatcgcttg ttcaggattt tattcatccc aacttgattt tacaggaaac attcttcgct      660
tcaagattaa aagtagtcaa gatccccaat cagctgttct ggagaaacca agggttcttg      720
agcaaccatt ggtccaacaa atgggatcag gttcatccct gtcgggcaag caaaattcaa      780
tccatcataa gatgaatgtg agatctacct ctggtcagcg gagggtcaat ggtgactccc      840
```

-continued

```
aagcagtaca aaaatgtttg attacagaat ccccggcaaa gaccatgcag agacttgtcc      900
cccagcctgc agctaaggtc acacatcctg ttgatcccca gtcagctgtt aaggtgccag      960
ttggaagatc gggcctacct ctgaagtctt cgggaagtgt ggaccttcg cctgctagag      1020 ttatgagaag atttgatcct ccacctgtta agatgatgtc acagagagtt caccatccag     1080
cttccatggt gtcgcagaaa gttgatcctc cgtttccgaa ggtattacat aaggaaaccg     1140
gatctgttgt tcgcctacca gaagctaccc ggcctactgt tcttcaaaaa cccaaggact     1200
tgcctgctat caagcagcag gatatcagga cctcttcctc aaaagaagag ccctgcttct     1260
ctggtaggaa tgcagaagca gttcaagtgc aagatactaa gctctcccgg tcagacatga     1320
agaaaatccg caaagctgag aaaaaagata agaagttcag agatctgttt gttacctgga     1380
atccggtatt gatagagaat gaaggttcag atcttggtga tgaagactgg ctgttcagca     1440
gtaaaaggaa ctccgatgct atcatggttc aaagcagagc tactgatagt tcagtgccga     1500
tccatccaat ggtgcagcag aagccttctt tacaacccag ggcaacattt ttgccggacc     1560
ttaatatgta ccagctgcca tatgtcgtac cattttaaac atctggcgag gtagatgaga     1620
attagatgag atgttgggag                                                 1640
```

<210> SEQ ID NO 60
<211> LENGTH: 1347
<212> TYPE: DNA
<213> ORGANISM: Zea mays mays strain Smena
<220> FEATURE:
<221> NAME/KEY: CDS
<222> LOCATION: (1)..(1347)
<223> OTHER INFORMATION:

<400> SEQUENCE: 60

```
atg tcg agg tgc ttc ccc tac ccg cca ccg ggg tac gtg cgg aac cca         48
Met Ser Arg Cys Phe Pro Tyr Pro Pro Pro Gly Tyr Val Arg Asn Pro
1               5                   10                  15 gtg gcc gtg gcc gag ccg gag tcg acc gct aag ctc ctg aaa gaa aag         96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gat ccc        144
Glu Lys Ala Glu Lys Lys Lys Glu Lys Arg Ser Asp Arg Lys Asp Pro
        35                  40                  45 aag cag tgt gag acg tcc aaa cac tca aag cac agc cat aag aag aga        192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc        240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat        288
Lys Glu Ser Val Glu Gln Leu Glu Lys Ser Gly Leu Ser Glu Glu His
                85                  90                  95 gga gct cct tct ttt gta cat acg ata cgg gac tct cct gag agc tca        336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa        384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gat        432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg        480
Pro Gln Ser Ala Val Leu Glu Lys Pro Arg Val Leu Glu Gln Pro Leu
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |     |

| gtc | caa | caa | atg | gga | tca | ggt | tca | tcc | ctg | tcg | ggc | aag | caa | aat | tca | 528 |
| --- | --- | --- | --- | --- | --- | --- | --- | --- | --- | --- | --- | --- | --- | --- | --- | --- |
| Val | Gln | Gln | Met | Gly | Ser | Gly | Ser | Ser | Leu | Ser | Gly | Lys | Gln | Asn | Ser |     |
|     |     |     |     | 165 |     |     |     |     | 170 |     |     |     |     | 175 |     |     |

| atc | cat | cat | aag | atg | aat | gtg | aga | tct | acc | tct | ggt | cag | cgg | agg | gtc | 576 |
| --- | --- | --- | --- | --- | --- | --- | --- | --- | --- | --- | --- | --- | --- | --- | --- | --- |
| Ile | His | His | Lys | Met | Asn | Val | Arg | Ser | Thr | Ser | Gly | Gln | Arg | Arg | Val |     |
|     |     |     | 180 |     |     |     |     | 185 |     |     |     |     | 190 |     |     |     |

| aat | ggt | gac | tcc | caa | gca | gta | caa | aaa | tgt | ttg | att | aca | gaa | tcc | ccg | 624 |
| --- | --- | --- | --- | --- | --- | --- | --- | --- | --- | --- | --- | --- | --- | --- | --- | --- |
| Asn | Gly | Asp | Ser | Gln | Ala | Val | Gln | Lys | Cys | Leu | Ile | Thr | Glu | Ser | Pro |     |
|     |     | 195 |     |     |     |     | 200 |     |     |     |     | 205 |     |     |     |     |

| gca | aag | acc | atg | cag | aga | ctt | gtc | ccc | cag | cct | gca | gct | aag | gtc | aca | 672 |
| --- | --- | --- | --- | --- | --- | --- | --- | --- | --- | --- | --- | --- | --- | --- | --- | --- |
| Ala | Lys | Thr | Met | Gln | Arg | Leu | Val | Pro | Gln | Pro | Ala | Ala | Lys | Val | Thr |     |
| 210 |     |     |     |     | 215 |     |     |     |     | 220 |     |     |     |     |     |     |

| cat | cct | gtt | gat | ccc | cag | tca | gct | gtt | aag | gtg | cca | gtt | gga | aga | tcg | 720 |
| --- | --- | --- | --- | --- | --- | --- | --- | --- | --- | --- | --- | --- | --- | --- | --- | --- |
| His | Pro | Val | Asp | Pro | Gln | Ser | Ala | Val | Lys | Val | Pro | Val | Gly | Arg | Ser |     |
| 225 |     |     |     |     | 230 |     |     |     |     | 235 |     |     |     |     | 240 |     |

| ggc | cta | cct | ctg | aag | tct | tca | gga | agt | gtg | gac | cct | tcg | cct | gct | aga | 768 |
| --- | --- | --- | --- | --- | --- | --- | --- | --- | --- | --- | --- | --- | --- | --- | --- | --- |
| Gly | Leu | Pro | Leu | Lys | Ser | Ser | Gly | Ser | Val | Asp | Pro | Ser | Pro | Ala | Arg |     |
|     |     |     |     | 245 |     |     |     |     | 250 |     |     |     |     | 255 |     |     |

| gtt | atg | aga | aga | ttt | gat | cct | cca | cct | gtt | aag | atg | atg | tca | cag | aga | 816 |
| --- | --- | --- | --- | --- | --- | --- | --- | --- | --- | --- | --- | --- | --- | --- | --- | --- |
| Val | Met | Arg | Arg | Phe | Asp | Pro | Pro | Pro | Val | Lys | Met | Met | Ser | Gln | Arg |     |
|     |     |     | 260 |     |     |     |     | 265 |     |     |     |     | 270 |     |     |     |

| gtt | cac | cat | cca | gct | tcc | atg | gtg | tcg | cag | aaa | gtt | gat | cct | ccg | ttt | 864 |
| --- | --- | --- | --- | --- | --- | --- | --- | --- | --- | --- | --- | --- | --- | --- | --- | --- |
| Val | His | His | Pro | Ala | Ser | Met | Val | Ser | Gln | Lys | Val | Asp | Pro | Pro | Phe |     |
|     |     | 275 |     |     |     |     | 280 |     |     |     |     | 285 |     |     |     |     |

| ccg | aag | gta | tta | cat | aag | gaa | acc | gga | tct | gtt | gtt | cgc | cta | cca | gaa | 912 |
| --- | --- | --- | --- | --- | --- | --- | --- | --- | --- | --- | --- | --- | --- | --- | --- | --- |
| Pro | Lys | Val | Leu | His | Lys | Glu | Thr | Gly | Ser | Val | Val | Arg | Leu | Pro | Glu |     |
|     | 290 |     |     |     |     | 295 |     |     |     |     | 300 |     |     |     |     |     |

| gct | acc | cgg | cct | act | gtt | ctt | caa | aaa | ccc | aag | gac | ttg | cct | tct | atc | 960 |
| --- | --- | --- | --- | --- | --- | --- | --- | --- | --- | --- | --- | --- | --- | --- | --- | --- |
| Ala | Thr | Arg | Pro | Thr | Val | Leu | Gln | Lys | Pro | Lys | Asp | Leu | Pro | Ser | Ile |     |
| 305 |     |     |     |     | 310 |     |     |     |     | 315 |     |     |     |     | 320 |     |

| aag | cag | cag | gag | atc | agg | acc | tct | tcc | tca | aaa | gaa | gag | ccc | tgc | ttc | 1008 |
| --- | --- | --- | --- | --- | --- | --- | --- | --- | --- | --- | --- | --- | --- | --- | --- | --- |
| Lys | Gln | Gln | Glu | Ile | Arg | Thr | Ser | Ser | Ser | Lys | Glu | Glu | Pro | Cys | Phe |     |
|     |     |     |     | 325 |     |     |     |     | 330 |     |     |     |     | 335 |     |     |

| tct | ggt | agg | aat | gca | gaa | gct | gtt | caa | gtg | cag | gat | act | aag | ctc | tcc | 1056 |
| --- | --- | --- | --- | --- | --- | --- | --- | --- | --- | --- | --- | --- | --- | --- | --- | --- |
| Ser | Gly | Arg | Asn | Ala | Glu | Ala | Val | Gln | Val | Gln | Asp | Thr | Lys | Leu | Ser |     |
|     |     |     | 340 |     |     |     |     | 345 |     |     |     |     | 350 |     |     |     |

| cgg | tca | gat | atg | aag | aaa | atc | cgc | aaa | gct | gag | aaa | aaa | gat | aag | aag | 1104 |
| --- | --- | --- | --- | --- | --- | --- | --- | --- | --- | --- | --- | --- | --- | --- | --- | --- |
| Arg | Ser | Asp | Met | Lys | Lys | Ile | Arg | Lys | Ala | Glu | Lys | Lys | Asp | Lys | Lys |     |
|     |     | 355 |     |     |     |     | 360 |     |     |     |     | 365 |     |     |     |     |

| ttc | aga | gat | ctg | ttt | gtt | acc | tgg | aat | ccg | gta | ttg | ata | gag | aat | gaa | 1152 |
| --- | --- | --- | --- | --- | --- | --- | --- | --- | --- | --- | --- | --- | --- | --- | --- | --- |
| Phe | Arg | Asp | Leu | Phe | Val | Thr | Trp | Asn | Pro | Val | Leu | Ile | Glu | Asn | Glu |     |
| 370 |     |     |     |     | 375 |     |     |     |     | 380 |     |     |     |     |     |     |

| ggt | tca | gat | ctt | ggt | gat | gaa | gac | tgg | ctg | ttc | agc | agt | aaa | agg | aac | 1200 |
| --- | --- | --- | --- | --- | --- | --- | --- | --- | --- | --- | --- | --- | --- | --- | --- | --- |
| Gly | Ser | Asp | Leu | Gly | Asp | Glu | Asp | Trp | Leu | Phe | Ser | Ser | Lys | Arg | Asn |     |
| 385 |     |     |     |     | 390 |     |     |     |     | 395 |     |     |     |     | 400 |     |

| tcc | gat | gct | atc | atg | gtt | caa | agc | aga | gct | act | gat | agt | tca | gtg | ccg | 1248 |
| --- | --- | --- | --- | --- | --- | --- | --- | --- | --- | --- | --- | --- | --- | --- | --- | --- |
| Ser | Asp | Ala | Ile | Met | Val | Gln | Ser | Arg | Ala | Thr | Asp | Ser | Ser | Val | Pro |     |
|     |     |     |     | 405 |     |     |     |     | 410 |     |     |     |     | 415 |     |     |

| atc | cat | cca | atg | gtg | cag | cag | aag | cct | tct | tta | caa | ccc | agg | gca | aca | 1296 |
| --- | --- | --- | --- | --- | --- | --- | --- | --- | --- | --- | --- | --- | --- | --- | --- | --- |
| Ile | His | Pro | Met | Val | Gln | Gln | Lys | Pro | Ser | Leu | Gln | Pro | Arg | Ala | Thr |     |
|     |     |     | 420 |     |     |     |     | 425 |     |     |     |     | 430 |     |     |     |

| ttt | ttg | ccg | gac | ctt | aat | atg | tac | cag | ctg | cca | tat | gtc | gta | cca | ttt | 1344 |
| --- | --- | --- | --- | --- | --- | --- | --- | --- | --- | --- | --- | --- | --- | --- | --- | --- |
| Phe | Leu | Pro | Asp | Leu | Asn | Met | Tyr | Gln | Leu | Pro | Tyr | Val | Val | Pro | Phe |     |
|     | 435 |     |     |     |     | 440 |     |     |     |     | 445 |     |     |     |     |     |

| taa | 1347 |
| --- | --- |

<210> SEQ ID NO 61
<211> LENGTH: 448

```
<212> TYPE: PRT
<213> ORGANISM: Zea mays mays strain Smena

<400> SEQUENCE: 61

Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
            20                  25                  30

Glu Lys Ala Glu Lys Lys Glu Lys Arg Ser Asp Arg Lys Asp Pro
            35                  40                  45

Lys Gln Cys Glu Thr Ser Lys His Ser Lys His Ser His Lys Lys Arg
50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
            115                 120                 125

Pro Lys Asn Gly Asn Ile Leu Arg Phe Lys Ile Lys Ser Ser Gln Asp
130                 135                 140

Pro Gln Ser Ala Val Leu Glu Lys Pro Arg Val Leu Glu Gln Pro Leu
145                 150                 155                 160

Val Gln Gln Met Gly Ser Gly Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
            195                 200                 205

Ala Lys Thr Met Gln Arg Leu Val Pro Gln Pro Ala Ala Lys Val Thr
            210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
            275                 280                 285

Pro Lys Val Leu His Lys Glu Thr Gly Ser Val Val Arg Leu Pro Glu
        290                 295                 300

Ala Thr Arg Pro Thr Val Leu Gln Lys Pro Lys Asp Leu Pro Ser Ile
305                 310                 315                 320

Lys Gln Gln Glu Ile Arg Thr Ser Ser Lys Glu Glu Pro Cys Phe
                325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
            355                 360                 365

Phe Arg Asp Leu Phe Val Thr Trp Asn Pro Val Leu Ile Glu Asn Glu
370                 375                 380

Gly Ser Asp Leu Gly Asp Glu Asp Trp Leu Phe Ser Ser Lys Arg Asn
385                 390                 395                 400
```

```
Ser Asp Ala Ile Met Val Gln Ser Arg Ala Thr Asp Ser Ser Val Pro
            405                 410                 415

Ile His Pro Met Val Gln Gln Lys Pro Ser Leu Gln Pro Arg Ala Thr
            420                 425                 430

Phe Leu Pro Asp Leu Asn Met Tyr Gln Leu Pro Tyr Val Val Pro Phe
            435                 440                 445

<210> SEQ ID NO 62
<211> LENGTH: 893
<212> TYPE: DNA
<213> ORGANISM: Zea mays mays strain W22

<400> SEQUENCE: 62
atgtcgaggt gcttcccta cccgccaccg gggtacgtgc ggaacccagt ggccgtggcc      60
gagccggagt cgaccgctaa ggtttgttga accttcggat ttacacacgc acgtgccaga    120
tcgtttgttc aatctgtagg ttttgcgcgg atctgtggtt tgcgcgtgcg tgatgtggcc    180
ctgtgccttg aaagctaacc gagctgagga agtgtatgga tcttgtgtag ctgcacgagg    240
tcctccaaat cgattgtaaa atttaagttg tatggccggt aggccaagat tgggttagtc    300
cggttttcga aaactggtag catggttatc ggggacattg aaagaatggt agaacatcaa    360
attcgattca aaactgtgct agatttgcat atttagtcgc cctaaaatta cgtggacgtg    420
ggtgatccga attggttgtt gtatgatggt tggaagtgac tggccaaatt ttttttgtttc    480 tcaaagtttt ctttgaaaaa ctgtttgtcg agcgtcaatt cgtatttacc tgaatttact    540
aattcttaat acagtatttc gttattttcg gctaagcttg tgtaagaagg gtcgtttgac    600
attttgtact gtattaatgc tgttttgtgt ttctttgttc ggagcagcat tcaatgctcc    660
ttttgttgtt tgagagaatc tgatatttgc catcgtaccg aaagtccgaa accaactatt    720
caaattggga tttcatttct ttttttctact gttttttagag ttctcttttt cgctgctgtg    780
ctcttgtggg tcagtacgtg catttctctt ttttttttctg atgttactct tctgttgacc    840
aaaggagttc agaattattt tggccctgta tatcaatagc aaccaacacc att           893

<210> SEQ ID NO 63
<211> LENGTH: 1411
<212> TYPE: DNA
<213> ORGANISM: Zea mays mays strain W22

<400> SEQUENCE: 63
ctcctgaaag aaaaggaaaa ggccgaaaag aagaaagaga aaaggagtga caggaaagct      60
cccaagcagt gtgagacgtc caaacattca agcacagcc ataagaagag aaagcttgaa    120
gatgtcatca aagctgagca gggtcccaaa agagtaccca agaatcagt tgagcagttg    180 gagaagagtg gactctcaga gagcatgga gctccttctt ttgtacatac gatacgtgac    240
tctcctgaga gctcacagga cagcggcaag agacgaaagg ttgtcctgtc cagtcctagc    300
caacctaaga atggtgagac tattctcttg ttttttgctat tctgattgat ttttttattat    360 agaagaaatc aatcgcttgt tcaggatttt attcatccca acttgatttt acaggaaaca    420
ttcttcgctt caagattaaa agtagtcaag accccccaatc agctgttctg gagaaaccaa    480
gggttcttga gcaaccattg gtccaacaaa tgggatcagg ttcatccccg tcgggcaagc    540
aaaattcaat ccatcataag atgaatgtga gatctacctc tggtcagcgg agggtcgatg    600
gtgactccca agcagtacaa aaatgtttga ttacagaatc cccggcaaag accatgcaga    660
gacttgtccc ccagcctgca gctaaggtca cacatcctgt tgatccccag tcagctgtta    720
```

-continued

| | |
|---|---|
| aggtgccagt tggaagatcg ggcctacctc tgaagtcttc gggaagtgtg gaccccttcgc | 780 |
| ctgctagagt tatgagaaga tttgatcctc cacctgttaa gatgatgtca cagagagttc | 840 |
| accatccagc ttccatggtg tcgcagaaag ttgatcctcc gtttccgaag gtattacata | 900 |
| aggaaaccgg atctgttgtt cgcctaccag aagctacccg gcctactgtt cttcaaaaac | 960 |
| ccaaggactt gcctgctatc aagcagcagg atatcaggac ctcttcctca aagaagagc | 1020 |
| cctgcttctc tggtaggaat gcagaagcag ttcaagtgca agatactaag ctctcccggt | 1080 |
| cagacatgaa gaaaatccgc aaagctgaga aaaagataa gaagttcaga gatctgtttg | 1140 |
| ttacctggaa tccggtattg atagagaatg aaggttcaga tcttggtgat gaagactggc | 1200 |
| tgttcagcag taaaaggaac tccgatgcta tcatggttca aagcagagct actgatagtt | 1260 |
| cagtgccgat ccatccaatg gtgcagcaga agccttcttt acaacccagg gcaacatttt | 1320 |
| tgccggacct aatatgtac cagctgccat atgtcgtacc atttttaaaca tctggcgagg | 1380 |
| tagatagaat tagatagatg ttgggagaga g | 1411 |

<210> SEQ ID NO 64
<211> LENGTH: 1347
<212> TYPE: DNA
<213> ORGANISM: Zea mays mays strain W22
<220> FEATURE:
<221> NAME/KEY: CDS
<222> LOCATION: (1)..(1347)
<223> OTHER INFORMATION:

<400> SEQUENCE: 64

| | |
|---|---|
| atg tcg agg tgc ttc ccc tac ccg cca ccg ggg tac gtg cgg aac cca<br>Met Ser Arg Cys Phe Pro Tyr Pro Pro Pro Gly Tyr Val Arg Asn Pro<br>1               5                  10                  15 | 48 |
| gtg gcc gtg gcc gag ccg gag tcg acc gct aag ctc ctg aaa gaa aag<br>Val Ala Val Ala Glu Pro Glu Ser Thr Ala Lys Leu Leu Lys Glu Lys<br>            20                  25                  30 | 96 |
| gaa aag gcc gaa aag aag aaa gag aaa agg agt gac agg aaa gct ccc<br>Glu Lys Ala Glu Lys Lys Lys Glu Lys Arg Ser Asp Arg Lys Ala Pro<br>        35                  40                  45 | 144 |
| aag cag tgt gag acg tcc aaa cat tca aag cac agc cat aag aag aga<br>Lys Gln Cys Glu Thr Ser Lys His Ser Lys His Ser His Lys Lys Arg<br>    50                  55                  60 | 192 |
| aag ctt gaa gat gtc atc aaa gct gag cag ggt ccc aaa aga gta ccc<br>Lys Leu Glu Asp Val Ile Lys Ala Glu Gln Gly Pro Lys Arg Val Pro<br>65                  70                  75                  80 | 240 |
| aaa gaa tca gtt gag cag ttg gag aag agt gga ctc tca gaa gag cat<br>Lys Glu Ser Val Glu Gln Leu Glu Lys Ser Gly Leu Ser Glu Glu His<br>                85                  90                  95 | 288 |
| gga gct cct tct ttt gta cat acg ata cgt gac tct cct gag agc tca<br>Gly Ala Pro Ser Phe Val His Thr Ile Arg Asp Ser Pro Glu Ser Ser<br>            100                 105                 110 | 336 |
| cag gac agc ggc aag aga cga aag gtt gtc ctg tcc agt cct agc caa<br>Gln Asp Ser Gly Lys Arg Arg Lys Val Val Leu Ser Ser Pro Ser Gln<br>        115                 120                 125 | 384 |
| cct aag aat gga aac att ctt cgc ttc aag att aaa agt agt caa gac<br>Pro Lys Asn Gly Asn Ile Leu Arg Phe Lys Ile Lys Ser Ser Gln Asp<br>    130                 135                 140 | 432 |
| ccc caa tca gct gtt ctg gag aaa cca agg gtt ctt gag caa cca ttg<br>Pro Gln Ser Ala Val Leu Glu Lys Pro Arg Val Leu Glu Gln Pro Leu<br>145                 150                 155                 160 | 480 |
| gtc caa caa atg gga tca ggt tca tcc ccg tcg ggc aag caa aat tca<br>Val Gln Gln Met Gly Ser Gly Ser Ser Pro Ser Gly Lys Gln Asn Ser | 528 |

```
                  165                 170                 175
atc cat cat aag atg aat gtg aga tct acc tct ggt cag cgg agg gtc     576
Ile His His Lys Met Asn Val Arg Ser Thr Ser Gly Gln Arg Arg Val
            180                 185                 190 gat ggt gac tcc caa gca gta caa aaa tgt ttg att aca gaa tcc ccg     624
Asp Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca     672
Ala Lys Thr Met Gln Arg Leu Val Pro Gln Pro Ala Ala Lys Val Thr
    210                 215                 220 cat cct gtt gat ccc cag tca gct gtt aag gtg cca gtt gga aga tcg     720
His Pro Val Asp Pro Gln Ser Ala Val Lys Val Pro Val Gly Arg Ser
225                 230                 235                 240 ggc cta cct ctg aag tct tcg gga agt gtg gac cct tcg cct gct aga     768
Gly Leu Pro Leu Lys Ser Ser Gly Ser Val Asp Pro Ser Pro Ala Arg
                245                 250                 255 gtt atg aga aga ttt gat cct cca cct gtt aag atg atg tca cag aga     816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt     864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa     912
Pro Lys Val Leu His Lys Glu Thr Gly Ser Val Val Arg Leu Pro Glu
    290                 295                 300 gct acc cgg cct act gtt ctt caa aaa ccc aag gac ttg cct gct atc     960
Ala Thr Arg Pro Thr Val Leu Gln Lys Pro Lys Asp Leu Pro Ala Ile
305                 310                 315                 320 aag cag cag gat atc agg acc tct tcc tca aaa gaa gag ccc tgc ttc    1008
Lys Gln Gln Asp Ile Arg Thr Ser Ser Ser Lys Glu Glu Pro Cys Phe
                325                 330                 335 tct ggt agg aat gca gaa gca gtt caa gtg caa gat act aag ctc tcc    1056
Ser Gly Arg Asn Ala Glu Ala Val Gln Val Gln Asp Thr Lys Leu Ser
            340                 345                 350 cgg tca gac atg aag aaa atc cgc aaa gct gag aaa aaa gat aag aag    1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa    1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac    1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg    1248
Ser Asp Ala Ile Met Val Gln Ser Arg Ala Thr Asp Ser Ser Val Pro
                405                 410                 415 atc cat cca atg gtg cag cag aag cct tct tta caa ccc agg gca aca    1296
Ile His Pro Met Val Gln Gln Lys Pro Ser Leu Gln Pro Arg Ala Thr
            420                 425                 430 ttt ttg ccg gac ctt aat atg tac cag ctg cca tat gtc gta cca ttt    1344
Phe Leu Pro Asp Leu Asn Met Tyr Gln Leu Pro Tyr Val Val Pro Phe
        435                 440                 445 taa                                                                1347
```

<210> SEQ ID NO 65
<211> LENGTH: 448
<212> TYPE: PRT
<213> ORGANISM: Zea mays mays strain W22

<400> SEQUENCE: 65

-continued

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
                20                  25                  30

Glu Lys Ala Glu Lys Lys Glu Lys Arg Ser Asp Arg Lys Ala Pro
            35                  40                  45

Lys Gln Cys Glu Thr Ser Lys His Ser Lys His Ser His Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
                100                 105                 110

Gln Asp Ser Gly Lys Arg Lys Val Val Leu Ser Ser Pro Ser Gln
    115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Pro Ser Gly Lys Gln Asn Ser
                165                 170                 175

Ile His His Lys Met Asn Val Arg Ser Thr Ser Gly Gln Arg Arg Val
            180                 185                 190

Asp Gly Asp Ser Gln Ala Val Gln Lys Cys Leu Ile Thr Glu Ser Pro
    195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
                260                 265                 270

Val His His Pro Ala Ser Met Val Ser Gln Lys Val Asp Pro Pro Phe
            275                 280                 285

Pro Lys Val Leu His Lys Glu Thr Gly Ser Val Val Arg Leu Pro Glu
    290                 295                 300

Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
            325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
        355                 360                 365

Phe Arg Asp Leu Phe Val Thr Trp Asn Pro Val Leu Ile Glu Asn Glu
    370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415
```

-continued

```
Ile His Pro Met Val Gln Gln Lys Pro Ser Leu Gln Pro Arg Ala Thr
            420                 425                 430

Phe Leu Pro Asp Leu Asn Met Tyr Gln Leu Pro Tyr Val Val Pro Phe
        435                 440                 445
```

<210> SEQ ID NO 66
<211> LENGTH: 2644
<212> TYPE: DNA
<213> ORGANISM: Zea mays parviglumis strain Benz

<400> SEQUENCE: 66

| | | | | | |
|---|---|---|---|---|---|
| atgtcgaggt | gcttccccta | cccgccaccg | gggtacgtgc | ggaacccagt | ggccgtggcc | 60 |
| gagccggagt | cgaccgctaa | ggtttgttga | accttcggat | ttacacacgc | acgtgccaga | 120 |
| tcgtttgttc | aatctgtagg | ttttgcgcgg | atctgtggtt | tgcgcgtgcg | tgatgtgggt | 180 |
| attgcccgtg | ccttgaaagc | taaccgagct | gaggaagtgt | atggatcttg | tgtagctgca | 240 |
| cgaggtcctc | caaatcgatt | gtaaaattta | agttgtatgg | ccggtaggcc | aagattgggt | 300 |
| tattccggtt | ttcgaaaact | ggtagcatgg | ttatcgggga | cattgaaaga | atggtagaac | 360 |
| atcaaattcg | attcaaaact | gtgctagatt | tgcatattta | gtcgccctaa | aattacgtgg | 420 |
| acgtgggtga | tccgaattgg | ttgttgtatg | atggttggaa | gtgactggcc | aaatttttt | 480 |
| gtttctcaaa | gttttctttg | acaaactgtt | tgtcgagcgt | caattcgtat | ttacctgaat | 540 |
| ttactaattc | ttaatacagt | atgtcgttat | tttgggctaa | gcttgtgtaa | gaagggtcgt | 600 |
| ttgacatttt | gtactgtatt | gatgctgttt | tgtgtttctt | tgttcggagc | agcattcaat | 660 |
| gctccttttg | ttgtttgaga | gaatctgata | tttgccatcg | taccgaaagt | ccgaaaccaa | 720 |
| ctattcaaat | tgggatttca | tttctttttt | ttctactgtt | tttagagttc | tcttttttcgc | 780 |
| tgctgtgctc | ttgtgggtca | gtacgtgcat | ttctcttttt | ttcttttttt | ttctgatgtt | 840 |
| actcttctgt | tgaccaaagg | agttcagaat | tattttggcc | ctgtatatca | atagcaacca | 900 |
| acaccattta | ttgagcccat | ttttagtttt | cttgttctgt | agagtatgca | ttgttgcagg | 960 |
| tcttaactgt | tgtcagggaa | gtaacgtgtt | caacatgatt | gtaaacgaat | acaattctgt | 1020 |
| tgctaactgt | gtaatgatga | gaaggataat | tgaataatct | ttgtgaagta | ttactgtctg | 1080 |
| aactgtacgc | aaatgctaca | ttcattcttt | gtgttcgtgt | aaatatcatt | atacataaaa | 1140 |
| atgctgcatt | gcattcccgt | cgtccgttct | aaatcagaac | tgacgattgc | tctggtggct | 1200 |
| gaagctcctg | aaagaaaagg | aaaaggccga | aagaagaaa | gagaaaagga | gtgacaggaa | 1260 |
| agctcccaag | cagtgtgaga | cgtccaaaca | ttcaaagcac | agccataaga | agagaaagct | 1320 |
| tgaagatgtc | atcaaagctg | agcagggtcc | caaaagagta | cccaaagaat | cagttgagca | 1380 |
| gttggagaag | agtggactct | cagaagagca | tggagctcct | tcttttgtac | atacgatacg | 1440 |
| tgactctcct | gagagctcac | aggacagcgg | caagagacga | aaggttgtcc | tgtccagtcc | 1500 |
| tagccaacct | aagaatggtg | agactattct | cttgttttg | ctattctgat | tgattttta | 1560 |
| ttatagaaga | aatcaatcgc | ttgttcagga | ttttattcat | cccaacttga | ttttacagga | 1620 |
| aacattcttc | gcttcaagat | taaaagtagt | caagatcccc | aatcagctgt | tctggagaaa | 1680 |
| ccaagggttc | ttgagcaacc | attggtccaa | caaatgggat | caggttcatc | cctgtcgggc | 1740 |
| aagcaaaatt | caatccatca | taagatgaat | gtgagatcta | cctctggtca | gcggagggtc | 1800 |
| aatggtgact | cccaagcagt | acaaaaatgt | ttgattacag | aatccccggc | aaagaccatg | 1860 |
| cagagacttg | tccccagcc | tgcagctaag | gtcacacatc | ctgttgatcc | ccagtcagct | 1920 |
| gttaaggtgc | cagttggaag | atcgggccta | cctctgaagt | cttcgggaag | tgtggaccct | 1980 |

-continued

```
tcgcctgcta gagttatgag aagatttgat cctccacctg ttaagatgat gtcacagaga   2040
gttcaccatc cagcttccat ggtgtcgcag aaagttgatc ctccgtttcc gaaggtatta   2100
cataaggaaa ccggatctgt tgttcgccta ccagaagcta cccggcctac tgttcttcaa   2160
aaacccaagg acttgcctgc tatcaagcag caggatatca ggacctcttc ctcaaaagaa   2220
gagccctgct tctctggtag gaatgcagaa gcagttcaag tgcaagatac taagctctcc   2280
cggtcagaca tgaagaaaat ccgcaaagct gagaaaaaag ataagaagtt cagagatctg   2340
tttgttacct ggaatccggt attgatagag aatgaaggtt cagatcttgg tgatgaagac   2400
tggctgttca gcagtaaaag gaactccgat gctatcatgg ttcaaagcag agctactgat   2460
agttcagtgc cgatccatcc aatggtgcag cagaagcctt ctttacaacc cagggcaaca   2520
tttttgccgg accttaatat gtaccagctg ccatatgtcg taccatttta aacatctggc   2580
gaggtagatg agaattagat gagatgttgg gagagagctg tgtgaacagt aggccgggta   2640
gctt                                                                2644
```

<210> SEQ ID NO 67
<211> LENGTH: 1347
<212> TYPE: DNA
<213> ORGANISM: Zea mays parviglumis strain Benz
<220> FEATURE:
<221> NAME/KEY: CDS
<222> LOCATION: (1)..(1347)
<223> OTHER INFORMATION:

<400> SEQUENCE: 67

```
atg tcg agg tgc ttc ccc tac ccg cca ccg ggg tac gtg cgg aac cca         48
Met Ser Arg Cys Phe Pro Tyr Pro Pro Pro Gly Tyr Val Arg Asn Pro
1               5                  10                  15 gtg gcc gtg gcc gag ccg gag tcg acc gct aag ctc ctg aaa gaa aag         96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gct ccc        144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga        192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc        240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat        288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca        336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa        384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gat        432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg        480
Pro Gln Ser Ala Val Leu Glu Lys Pro Arg Val Leu Glu Gln Pro Leu
145                 150                 155                 160 gtc caa caa atg gga tca ggt tca tcc ctg tcg ggc aag caa aat tca        528
Val Gln Gln Met Gly Ser Gly Ser Ser Leu Ser Gly Lys Gln Asn Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 165 |     |     |     |     | 170 |     |     |     |     | 175 |     |     |     |      |
| atc | cat | cat | aag | atg | aat | gtg | aga | tct | acc | tct | ggt | cag | cgg | agg | gtc | 576  |
| Ile | His | His | Lys | Met | Asn | Val | Arg | Ser | Thr | Ser | Gly | Gln | Arg | Arg | Val |      |
|     |     | 180 |     |     |     |     | 185 |     |     |     |     | 190 |     |     |     |      |
| aat | ggt | gac | tcc | caa | gca | gta | caa | aaa | tgt | ttg | att | aca | gaa | tcc | ccg | 624  |
| Asn | Gly | Asp | Ser | Gln | Ala | Val | Gln | Lys | Cys | Leu | Ile | Thr | Glu | Ser | Pro |      |
|     | 195 |     |     |     |     | 200 |     |     |     |     | 205 |     |     |     |     |      |
| gca | aag | acc | atg | cag | aga | ctt | gtc | ccc | cag | cct | gca | gct | aag | gtc | aca | 672  |
| Ala | Lys | Thr | Met | Gln | Arg | Leu | Val | Pro | Gln | Pro | Ala | Ala | Lys | Val | Thr |      |
| 210 |     |     |     |     | 215 |     |     |     |     | 220 |     |     |     |     |     |      |
| cat | cct | gtt | gat | ccc | cag | tca | gct | gtt | aag | gtg | cca | gtt | gga | aga | tcg | 720  |
| His | Pro | Val | Asp | Pro | Gln | Ser | Ala | Val | Lys | Val | Pro | Val | Gly | Arg | Ser |      |
| 225 |     |     |     |     | 230 |     |     |     |     | 235 |     |     |     |     | 240 |      |
| ggc | cta | cct | ctg | aag | tct | tcg | gga | agt | gtg | gac | cct | tcg | cct | gct | aga | 768  |
| Gly | Leu | Pro | Leu | Lys | Ser | Ser | Gly | Ser | Val | Asp | Pro | Ser | Pro | Ala | Arg |      |
|     |     |     |     | 245 |     |     |     |     | 250 |     |     |     |     | 255 |     |      |
| gtt | atg | aga | aga | ttt | gat | cct | cca | cct | gtt | aag | atg | atg | tca | cag | aga | 816  |
| Val | Met | Arg | Arg | Phe | Asp | Pro | Pro | Pro | Val | Lys | Met | Met | Ser | Gln | Arg |      |
|     |     | 260 |     |     |     |     | 265 |     |     |     |     | 270 |     |     |     |      |
| gtt | cac | cat | cca | gct | tcc | atg | gtg | tcg | cag | aaa | gtt | gat | cct | ccg | ttt | 864  |
| Val | His | His | Pro | Ala | Ser | Met | Val | Ser | Gln | Lys | Val | Asp | Pro | Pro | Phe |      |
|     |     | 275 |     |     |     |     | 280 |     |     |     |     | 285 |     |     |     |      |
| ccg | aag | gta | tta | cat | aag | gaa | acc | gga | tct | gtt | gtt | cgc | cta | cca | gaa | 912  |
| Pro | Lys | Val | Leu | His | Lys | Glu | Thr | Gly | Ser | Val | Val | Arg | Leu | Pro | Glu |      |
|     | 290 |     |     |     |     | 295 |     |     |     |     | 300 |     |     |     |     |      |
| gct | acc | cgg | cct | act | gtt | ctt | caa | aaa | ccc | aag | gac | ttg | cct | gct | atc | 960  |
| Ala | Thr | Arg | Pro | Thr | Val | Leu | Gln | Lys | Pro | Lys | Asp | Leu | Pro | Ala | Ile |      |
| 305 |     |     |     |     | 310 |     |     |     |     | 315 |     |     |     |     | 320 |      |
| aag | cag | cag | gat | atc | agg | acc | tct | tcc | tca | aaa | gaa | gag | ccc | tgc | ttc | 1008 |
| Lys | Gln | Gln | Asp | Ile | Arg | Thr | Ser | Ser | Ser | Lys | Glu | Glu | Pro | Cys | Phe |      |
|     |     |     | 325 |     |     |     |     | 330 |     |     |     |     | 335 |     |     |      |
| tct | ggt | agg | aat | gca | gaa | gca | gtt | caa | gtg | caa | gat | act | aag | ctc | tcc | 1056 |
| Ser | Gly | Arg | Asn | Ala | Glu | Ala | Val | Gln | Val | Gln | Asp | Thr | Lys | Leu | Ser |      |
|     |     |     | 340 |     |     |     |     | 345 |     |     |     |     | 350 |     |     |      |
| cgg | tca | gac | atg | aag | aaa | atc | cgc | aaa | gct | gag | aaa | aaa | gat | aag | aag | 1104 |
| Arg | Ser | Asp | Met | Lys | Lys | Ile | Arg | Lys | Ala | Glu | Lys | Lys | Asp | Lys | Lys |      |
|     | 355 |     |     |     |     | 360 |     |     |     |     | 365 |     |     |     |     |      |
| ttc | aga | gat | ctg | ttt | gtt | acc | tgg | aat | ccg | gta | ttg | ata | gag | aat | gaa | 1152 |
| Phe | Arg | Asp | Leu | Phe | Val | Thr | Trp | Asn | Pro | Val | Leu | Ile | Glu | Asn | Glu |      |
| 370 |     |     |     |     | 375 |     |     |     |     | 380 |     |     |     |     |     |      |
| ggt | tca | gat | ctt | ggt | gat | gaa | gac | tgg | ctg | ttc | agc | agt | aaa | agg | aac | 1200 |
| Gly | Ser | Asp | Leu | Gly | Asp | Glu | Asp | Trp | Leu | Phe | Ser | Ser | Lys | Arg | Asn |      |
| 385 |     |     |     |     | 390 |     |     |     |     | 395 |     |     |     |     | 400 |      |
| tcc | gat | gct | atc | atg | gtt | caa | agc | aga | gct | act | gat | agt | tca | gtg | ccg | 1248 |
| Ser | Asp | Ala | Ile | Met | Val | Gln | Ser | Arg | Ala | Thr | Asp | Ser | Ser | Val | Pro |      |
|     |     |     |     | 405 |     |     |     |     | 410 |     |     |     |     | 415 |     |      |
| atc | cat | cca | atg | gtg | cag | cag | aag | cct | tct | tta | caa | ccc | agg | gca | aca | 1296 |
| Ile | His | Pro | Met | Val | Gln | Gln | Lys | Pro | Ser | Leu | Gln | Pro | Arg | Ala | Thr |      |
|     |     |     | 420 |     |     |     |     | 425 |     |     |     |     | 430 |     |     |      |
| ttt | ttg | ccg | gac | ctt | aat | atg | tac | cag | ctg | cca | tat | gtc | gta | cca | ttt | 1344 |
| Phe | Leu | Pro | Asp | Leu | Asn | Met | Tyr | Gln | Leu | Pro | Tyr | Val | Val | Pro | Phe |      |
|     |     | 435 |     |     |     |     | 440 |     |     |     |     | 445 |     |     |     |      |
| taa |     |     |     |     |     |     |     |     |     |     |     |     |     |     |     | 1347 |

<210> SEQ ID NO 68
<211> LENGTH: 448
<212> TYPE: PRT
<213> ORGANISM: Zea mays parviglumis strain Benz

<400> SEQUENCE: 68

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
            20                  25                  30

Glu Lys Ala Glu Lys Lys Glu Lys Arg Ser Asp Arg Lys Ala Pro
        35                  40                  45

Lys Gln Cys Glu Thr Ser Lys His Ser Lys His Ser His Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
        275                 280                 285

Pro Lys Val Leu His Lys Glu Thr Gly Ser Val Val Arg Leu Pro Glu
    290                 295                 300

Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
                325                 330                 335

Ser Gly Arg Asn Ala Glu Ala Val Gln Val Gln Asp Thr Lys Leu Ser
        340                 345                 350

Arg Ser Asp Met Lys Lys Ile Arg Lys Ala Glu Lys Lys Asp Lys Lys
    355                 360                 365

Phe Arg Asp Leu Phe Val Thr Trp Asn Pro Val Leu Ile Glu Asn Glu
370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
            405                 410                 415
```

Ile His Pro Met Val Gln Gln Lys Pro Ser Leu Gln Pro Arg Ala Thr
            420                 425                 430

Phe Leu Pro Asp Leu Asn Met Tyr Gln Leu Pro Tyr Val Pro Phe
        435                 440                 445

<210> SEQ ID NO 69
<211> LENGTH: 586
<212> TYPE: DNA
<213> ORGANISM: Zea mays parviglumis strain BK4

<400> SEQUENCE: 69

```
acgtcggcca tgtcgaggtg cttcccctac ccgccaccgg ggtacgtgcg gaacccagtg    60
gccgtggccg agccggagtc gaccgctaag gtttgttgaa ccttcggatt tacacacgca   120
cgtgccagat cgtttgttca atctgtaggt tttgcgcgga tctgtggttt gcgcgtgcgt   180
gatgtggccc gtgccttgaa agctaaccga gctgaggaag tgtatggatc ttgtgtagct   240
gcacgaggtc ctccaaatcg attgtaaaat ttaagttgta tggccggtag gccaagattg   300
ggttagtccg gttttcgaaa actggtagca tggttatcgg ggacattgaa agaatggtag   360
aacatcaaat tcgattcaaa actgtgctag atttgcatat ttagtcgccc taaaattacg   420
tggacgtggg tgatccgaat tggttgttgt atgatggttg gaagtgactg gccaaatttt   480
ttgtttctca aagttttctt tgaaaaactg tttgtcgagc gtcaattcgt atttacctga   540
atttactaat tcttaataca gtatttcgtt attttcggct aagctt               586
```

<210> SEQ ID NO 70
<211> LENGTH: 1775
<212> TYPE: DNA
<213> ORGANISM: Zea mays parviglumis strain BK4

<400> SEQUENCE: 70

```
tcttctgttg accaaaggag ttcagaatta ttttggccct gtatatcaat agcaaccaac    60
accatttatt gatcccattt ttagtttct tgttctgtag agtatgcatt gttgcaggtc   120
ttaactgttg tcagggaagt aacgtgttca acatgattgt aaacgaatac aattctgttg   180
ctaactgtgt aatgatgaga aggataattg ataatctttt gtgaagtatt actgtctgaa   240
ctgtacgcaa atgctacatt cattctttgt gttcgtgtaa atatcattat acataaaaat   300
gctgcattgc attcccgtcg tccgttctaa tcagaactga cgattgctct ggtggctgaa   360
gctcctgaaa gaaaggaaa aggccgaaaa gaagaaagag aaaaggagtg acaggaaagc   420
tcccaagcag tgtgagacgt ccaaacattc aaagcacagc cataagaaga gaaagcttga   480
agatgtcatc aaagctgagc agggtcccaa aagagtaccc aaagaatcag ttgagcagtt   540
ggagaagagt ggactctcag aagagcatgg agctccttct tttgtacata cgatacgtga   600
ctctcctgag agctcacagg acagcggcaa gagacgaaag gttgtcctgt ccagtcctag   660
ccaacctaag aatggtgaga ctattctctt gttttttgcta ttctgattga ttttttatta   720
tagaagaaat caatcgcttg ttcaggattt tattcatccc aacttgattt tacaggaaac   780
attcttcgct tcaagattaa aagtagtcaa gaccccccaat cagctgttct ggagaaacca   840
agggttcttg agcaaccatt ggtccaacaa atgggatcag gttcatcccc gtcgggcaag   900
caaaattcaa tccatcataa gatgaatgtg agatctacct ctggtcagcg gagggtcgat   960
ggtgactccc aagcagtaca aaatgtttg attacagaat ccccggcaaa gaccatgcag  1020
agacttgtcc cccagcctgc agctaaggtc acacatcctg ttgatcccca gtcagctgtt  1080
aaggtgccag ttggaagatc gggcctacct ctgaagtctt cgggaagtgt ggacccttcg  1140
```

```
cctgctagag ttatgagaag atttgatcct ccacctgtta agatgatgtc acagagagtt    1200
caccatccag cttccatggt gtcgcagaaa gttgatcctc cgtttccgaa ggtattacat    1260
aaggaaaccg gatctgttgt tcgcctacca gaagctaccc ggcctactgt tcttcaaaaa    1320
cccaaggact tgcctgctat caagcagcag gatatcagga cctcttcctc aaaagaagag    1380
ccctgcttct ctggtaggaa tgcagaagca gttcaagtgc aagatactaa gctctcccgg    1440
tcagacatga agaaaatccg caaagctgag aaaaaagata agaagttcag agatctgttt    1500
gttacctgga atccggtatt gatagagaat gaaggttcag atcttggtga tgaagactgg    1560
ctgttcagca gtaaaaggaa ctccgatgct atcatggttc aaagcagagc tactgatagt    1620
tcagtgccga tccatccaat ggtgcagcag aagccttctt tacaacccag ggcaacattt    1680
ttgccggacc ttaatatgta ccagctgcca tatgtcgtac cattttaaac atctggcgag    1740
gtagatgaga attagatgag atgttgggag agagc                               1775
```

```
<210> SEQ ID NO 71
<211> LENGTH: 1347
<212> TYPE: DNA
<213> ORGANISM: Zea mays parviglumis strain BK4
<220> FEATURE:
<221> NAME/KEY: CDS
<222> LOCATION: (1)..(1347)
<223> OTHER INFORMATION:

<400> SEQUENCE: 71
```

```
atg tcg agg tgc ttc ccc tac ccg cca ccg ggg tac gtg cgg aac cca     48
Met Ser Arg Cys Phe Pro Tyr Pro Pro Pro Gly Tyr Val Arg Asn Pro
1               5                  10                  15 gtg gcc gtg gcc gag ccg gag tcg acc gct aag ctc ctg aaa gaa aag     96
Val Ala Val Ala Glu Pro Glu Ser Thr Ala Lys Leu Leu Lys Glu Lys
            20                  25                  30 gaa aag gcc gaa aag aag aaa gag aaa agg agt gac agg aaa gct ccc    144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga    192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc    240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat    288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca    336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa    384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gac    432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg    480
Pro Gln Ser Ala Val Leu Glu Lys Pro Arg Val Leu Glu Gln Pro Leu
145                 150                 155                 160 gtc caa caa atg gga tca ggt tca tcc ccg tcg ggc aag caa aat tca    528
Val Gln Gln Met Gly Ser Gly Ser Ser Pro Ser Gly Lys Gln Asn Ser
                165                 170                 175
```

-continued

```
atc cat cat aag atg aat gtg aga tct acc tct ggt cag cgg agg gtc     576
Ile His His Lys Met Asn Val Arg Ser Thr Ser Gly Gln Arg Arg Val
            180                 185                 190 gat ggt gac tcc caa gca gta caa aaa tgt ttg att aca gaa tcc ccg     624
Asp Gly Asp Ser Gln Ala Val Gln Lys Cys Leu Ile Thr Glu Ser Pro
                195                 200                 205 gca aag acc atg cag aga ctt gtc ccc cag cct gca gct aag gtc aca     672
Ala Lys Thr Met Gln Arg Leu Val Pro Gln Pro Ala Ala Lys Val Thr
    210                 215                 220 cat cct gtt gat ccc cag tca gct gtt aag gtg cca gtt gga aga tcg     720
His Pro Val Asp Pro Gln Ser Ala Val Lys Val Pro Val Gly Arg Ser
225                 230                 235                 240 ggc cta cct ctg aag tct tcg gga agt gtg gac cct tcg cct gct aga     768
Gly Leu Pro Leu Lys Ser Ser Gly Ser Val Asp Pro Ser Pro Ala Arg
                245                 250                 255 gtt atg aga aga ttt gat cct cca cct gtt aag atg atg tca cag aga     816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt     864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa     912
Pro Lys Val Leu His Lys Glu Thr Gly Ser Val Val Arg Leu Pro Glu
    290                 295                 300 gct acc cgg cct act gtt ctt caa aaa ccc aag gac ttg cct gct atc     960
Ala Thr Arg Pro Thr Val Leu Gln Lys Pro Lys Asp Leu Pro Ala Ile
305                 310                 315                 320 aag cag cag gat atc agg acc tct tcc tca aaa gaa gag ccc tgc ttc    1008
Lys Gln Gln Asp Ile Arg Thr Ser Ser Ser Lys Glu Glu Pro Cys Phe
                325                 330                 335 tct ggt agg aat gca gaa gca gtt caa gtg caa gat act aag ctc tcc    1056
Ser Gly Arg Asn Ala Glu Ala Val Gln Val Gln Asp Thr Lys Leu Ser
            340                 345                 350 cgg tca gac atg aag aaa atc cgc aaa gct gag aaa aaa gat aag aag    1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa    1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac    1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg    1248
Ser Asp Ala Ile Met Val Gln Ser Arg Ala Thr Asp Ser Ser Val Pro
                405                 410                 415 atc cat cca atg gtg cag cag aag cct tct tta caa ccc agg gca aca    1296
Ile His Pro Met Val Gln Gln Lys Pro Ser Leu Gln Pro Arg Ala Thr
            420                 425                 430 ttt ttg ccg gac ctt aat atg tac cag ctg cca tat gtc gta cca ttt    1344
Phe Leu Pro Asp Leu Asn Met Tyr Gln Leu Pro Tyr Val Val Pro Phe
        435                 440                 445 taa                                                                1347
```

<210> SEQ ID NO 72
<211> LENGTH: 448
<212> TYPE: PRT
<213> ORGANISM: Zea mays parviglumis strain BK4

<400> SEQUENCE: 72

Met Ser Arg Cys Phe Pro Tyr Pro Pro Pro Gly Tyr Val Arg Asn Pro

```
            1               5                  10                 15
        Val Ala Val Ala Glu Pro Glu Ser Thr Ala Lys Leu Leu Lys Glu Lys
                        20                  25                  30

Glu Lys Ala Glu Lys Lys Glu Lys Arg Ser Asp Arg Lys Ala Pro
                        35                  40                  45

Lys Gln Cys Glu Thr Ser Lys His Ser Lys His Ser His Lys Lys Arg
         50                  55                  60

Lys Leu Glu Asp Val Ile Lys Ala Glu Gln Gly Pro Lys Arg Val Pro
         65                  70                  75                  80

Lys Glu Ser Val Glu Gln Leu Glu Lys Ser Gly Leu Ser Glu His
                        85                  90                  95

Gly Ala Pro Ser Phe Val His Thr Ile Arg Asp Ser Pro Glu Ser Ser
                       100                 105                 110

Gln Asp Ser Gly Lys Arg Arg Lys Val Val Leu Ser Ser Pro Ser Gln
                       115                 120                 125

Pro Lys Asn Gly Asn Ile Leu Arg Phe Lys Ile Lys Ser Ser Gln Asp
                       130                 135                 140

Pro Gln Ser Ala Val Leu Glu Lys Pro Arg Val Leu Glu Gln Pro Leu
        145                 150                 155                 160

Val Gln Gln Met Gly Ser Gly Ser Ser Pro Ser Gly Lys Gln Asn Ser
                       165                 170                 175

Ile His His Lys Met Asn Val Arg Ser Thr Ser Gly Gln Arg Arg Val
                       180                 185                 190

Asp Gly Asp Ser Gln Ala Val Gln Lys Cys Leu Ile Thr Glu Ser Pro
                       195                 200                 205

Ala Lys Thr Met Gln Arg Leu Val Pro Gln Pro Ala Ala Lys Val Thr
                       210                 215                 220

His Pro Val Asp Pro Gln Ser Ala Val Lys Val Pro Val Gly Arg Ser
        225                 230                 235                 240

Gly Leu Pro Leu Lys Ser Ser Gly Ser Val Asp Pro Ser Pro Ala Arg
                       245                 250                 255

Val Met Arg Arg Phe Asp Pro Pro Val Lys Met Met Ser Gln Arg
                       260                 265                 270

Val His His Pro Ala Ser Met Val Ser Gln Lys Val Asp Pro Pro Phe
                       275                 280                 285

Pro Lys Val Leu His Lys Glu Thr Gly Ser Val Val Arg Leu Pro Glu
                       290                 295                 300

Ala Thr Arg Pro Thr Val Leu Gln Lys Pro Lys Asp Leu Pro Ala Ile
        305                 310                 315                 320

Lys Gln Gln Asp Ile Arg Thr Ser Ser Lys Glu Glu Pro Cys Phe
                       325                 330                 335

Ser Gly Arg Asn Ala Glu Ala Val Gln Val Gln Asp Thr Lys Leu Ser
                       340                 345                 350

Arg Ser Asp Met Lys Lys Ile Arg Lys Ala Glu Lys Lys Asp Lys Lys
                       355                 360                 365

Phe Arg Asp Leu Phe Val Thr Trp Asn Pro Val Leu Ile Glu Asn Glu
                       370                 375                 380

Gly Ser Asp Leu Gly Asp Glu Asp Trp Leu Phe Ser Ser Lys Arg Asn
        385                 390                 395                 400

Ser Asp Ala Ile Met Val Gln Ser Arg Ala Thr Asp Ser Ser Val Pro
                       405                 410                 415

Ile His Pro Met Val Gln Gln Lys Pro Ser Leu Gln Pro Arg Ala Thr
                       420                 425                 430
```

Phe Leu Pro Asp Leu Asn Met Tyr Gln Leu Pro Tyr Val Val Pro Phe
         435                 440                 445

<210> SEQ ID NO 73
<211> LENGTH: 305
<212> TYPE: DNA
<213> ORGANISM: Zea mays parviglumis strain IA19

<400> SEQUENCE: 73
gattgatttc gagcgattcg actccttgtg atctctacgg cggggtagag cgcggtcgac     60
cgtcggccat gtcgaggtgc ttcccctacc cgccaccggg gtacgtgcgg aacccagtgg    120
ccgtggccga gccggagtcg accgctaagg tttgttgaac cttcggattt acacacgcac    180
gtgccagatc gtttgttcaa tctgtaggtt ttgcgcggat ctgtggtttg cgcgtgcgtg    240
atgtgggtat tgcccgtgcc ttgaaagcta accgagctga ggaagtgtat ggatcttgtg    300
tagct                                                                305

<210> SEQ ID NO 74
<211> LENGTH: 1309
<212> TYPE: DNA
<213> ORGANISM: Zea mays parviglumis strain IA19

<400> SEQUENCE: 74
tcaaagcaca gccataagaa gagaaagctt gaagatgtca tcaaagctga gcaggttccc     60
aaaagagtac ccaaagaatc agttgagcag ttggagaaga gtggactctc agaagagcat    120
ggagctcctt cttttgtaca tacgatacgt gactctcctg agagctcaca ggacagcggc    180
aagagacgaa aggttgtcct gtccagtcct agccaaccta gaatggtgaa gactattctc    240 ttgttttttgc tattctgatt gatttttttat tatagaagaa atcaatcgct tgttcaggat    300
tttattcatc ccaacttgat tttacaggaa acattcttcg cttcaagatt aaaagtagtc    360
aagatcccca atcagctgtt ctggagaaac caagggttct tgagcaacca ttggtccaac    420
aaatgggatc aggttcatcc ctgtcgggca agcaaaattc aatccatcat aagatgaatg    480
tgagatctac ctctggtcag cggagggtca atggtgactc ccaagcagta caaaaatgtt    540
tgattacaga atccccggca aagaccatgc agagacttgt cccccagcct gcagctaagg    600
tcacacatcc tgttgatccc cagtcagctg ttaaggtgcc agttggaaga tcgggcctac    660
ctctgaagtc ttcgggaagt gtggacccct cgcctgctag agttatgaga agatttgatc    720
ctccacctgt taagatgatg tcacagagag ttcaccatcc agcttccatg gtgtcgcaga    780
aagttgatcc tccgtttccg aaggtattac ataaggaaac cggatctgtt gttcgcctac    840
cagaagctac ccggcctact gttcttcaaa aacccaagga cttgcctgct atcaagcagc    900
aggakatcag gacctcttcc tcaaaagaag agccctgctt ctctggtagg aatgcagaag    960
cagttcaagt gcaggatact aagctctccc ggtcagacat gaagaaaatc cgcaaagctg   1020
agaaaaaaga taagaagttc agagatctgt tgttacctg gaatccggta ttgatagaga   1080
atgaaggttc agatcttggt gatgaagact ggctgttcag cagtaaaagg aactccgatg   1140
ctatcatggt tcaaagcaga gctactgata gttcagtgcc gatccatcca atggtgcagc   1200
agaagccttc tttacaaccc agggcaacat ttttgccgga ccttaatatg taccagctgc   1260
catatgtcgt accatttaa acatctgtcg aggtagatga gaattagat              1309

<210> SEQ ID NO 75
<211> LENGTH: 1347

```
<212> TYPE: DNA
<213> ORGANISM: Zea mays parviglumis strain IA19
<220> FEATURE:
<221> NAME/KEY: CDS
<222> LOCATION: (1)..(1332)
<223> OTHER INFORMATION:
<220> FEATURE:
<221> NAME/KEY: misc_feature
<222> LOCATION: (82)..(168)
<223> OTHER INFORMATION: n = A, C, T, or G

<400> SEQUENCE: 75
```

| | | | | | | | | | | | | | | | | |
|---|---|---|---|---|---|---|---|---|---|---|---|---|---|---|---|---|
| atg | tcg | agg | tgc | ttc | ccc | tac | ccg | cca | ccg | ggg | tac | gtg | cgg | aac | cca | 48 |
| Met | Ser | Arg | Cys | Phe | Pro | Tyr | Pro | Pro | Pro | Gly | Tyr | Val | Arg | Asn | Pro | |
| 1 | | | | 5 | | | | | 10 | | | | | 15 | | |
| gtg | gcc | gtg | gcc | gag | ccg | gag | tcg | acc | gct | aag | nnn | nnn | nnn | nnn | nnn | 96 |
| Val | Ala | Val | Ala | Glu | Pro | Glu | Ser | Thr | Ala | Lys | Xaa | Xaa | Xaa | Xaa | Xaa | |
| | | | 20 | | | | | 25 | | | | | 30 | | | |
| nnn | nnn | nnn | nnn | nnn | nnn | nnn | nnn | nnn | nnn | nnn | nnn | nnn | nnn | nnn | nnn | 144 |
| Xaa | Xaa | Xaa | Xaa | Xaa | Xaa | Xaa | Xaa | Xaa | Xaa | Xaa | Xaa | Xaa | Xaa | Xaa | Xaa | |
| | | 35 | | | | | 40 | | | | | 45 | | | | |
| nnn | nnn | nnn | nnn | nnn | nnn | nnn | nnn | tca | aag | cac | agc | cat | aag | aag | aga | 192 |
| Xaa | Xaa | Xaa | Xaa | Xaa | Xaa | Xaa | Xaa | Ser | Lys | His | Ser | His | Lys | Lys | Arg | |
| 50 | | | | | 55 | | | | | 60 | | | | | | |
| aag | ctt | gaa | gat | gtc | atc | aaa | gct | gag | cag | gtt | ccc | aaa | aga | gta | ccc | 240 |
| Lys | Leu | Glu | Asp | Val | Ile | Lys | Ala | Glu | Gln | Val | Pro | Lys | Arg | Val | Pro | |
| 65 | | | | 70 | | | | | 75 | | | | | 80 | | |
| aaa | gaa | tca | gtt | gag | cag | ttg | gag | aag | agt | gga | ctc | tca | gaa | gag | cat | 288 |
| Lys | Glu | Ser | Val | Glu | Gln | Leu | Glu | Lys | Ser | Gly | Leu | Ser | Glu | Glu | His | |
| | | | | 85 | | | | | 90 | | | | | 95 | | |
| gga | gct | cct | tct | ttt | gta | cat | acg | ata | cgt | gac | tct | cct | gag | agc | tca | 336 |
| Gly | Ala | Pro | Ser | Phe | Val | His | Thr | Ile | Arg | Asp | Ser | Pro | Glu | Ser | Ser | |
| | | | 100 | | | | | 105 | | | | | 110 | | | |
| cag | gac | agc | ggc | aag | aga | cga | aag | gtt | gtc | ctg | tcc | agt | cct | agc | caa | 384 |
| Gln | Asp | Ser | Gly | Lys | Arg | Arg | Lys | Val | Val | Leu | Ser | Ser | Pro | Ser | Gln | |
| | | 115 | | | | | 120 | | | | | 125 | | | | |
| cct | aag | aat | gga | aac | att | ctt | cgc | ttc | aag | att | aaa | agt | agt | caa | gat | 432 |
| Pro | Lys | Asn | Gly | Asn | Ile | Leu | Arg | Phe | Lys | Ile | Lys | Ser | Ser | Gln | Asp | |
| | 130 | | | | | 135 | | | | | 140 | | | | | |
| ccc | caa | tca | gct | gtt | ctg | gag | aaa | cca | agg | gtt | ctt | gag | caa | cca | ttg | 480 |
| Pro | Gln | Ser | Ala | Val | Leu | Glu | Lys | Pro | Arg | Val | Leu | Glu | Gln | Pro | Leu | |
| 145 | | | | | 150 | | | | | 155 | | | | | 160 | |
| gtc | caa | caa | atg | gga | tca | ggt | tca | tcc | ctg | tcg | ggc | aag | caa | aat | tca | 528 |
| Val | Gln | Gln | Met | Gly | Ser | Gly | Ser | Ser | Leu | Ser | Gly | Lys | Gln | Asn | Ser | |
| | | | | 165 | | | | | 170 | | | | | 175 | | |
| atc | cat | cat | aag | atg | aat | gtg | aga | tct | acc | tct | ggt | cag | cgg | agg | gtc | 576 |
| Ile | His | His | Lys | Met | Asn | Val | Arg | Ser | Thr | Ser | Gly | Gln | Arg | Arg | Val | |
| | | | 180 | | | | | 185 | | | | | 190 | | | |
| aat | ggt | gac | tcc | caa | gca | gta | caa | aaa | tgt | ttg | att | aca | gaa | tcc | ccg | 624 |
| Asn | Gly | Asp | Ser | Gln | Ala | Val | Gln | Lys | Cys | Leu | Ile | Thr | Glu | Ser | Pro | |
| | | 195 | | | | | 200 | | | | | 205 | | | | |
| gca | aag | acc | atg | cag | aga | ctt | gtc | ccc | cag | cct | gca | gct | aag | gtc | aca | 672 |
| Ala | Lys | Thr | Met | Gln | Arg | Leu | Val | Pro | Gln | Pro | Ala | Ala | Lys | Val | Thr | |
| | 210 | | | | | 215 | | | | | 220 | | | | | |
| cat | cct | gtt | gat | ccc | cag | tca | gct | gtt | aag | gtg | cca | gtt | gga | aga | tcg | 720 |
| His | Pro | Val | Asp | Pro | Gln | Ser | Ala | Val | Lys | Val | Pro | Val | Gly | Arg | Ser | |
| 225 | | | | | 230 | | | | | 235 | | | | | 240 | |
| ggc | cta | cct | ctg | aag | tct | tcg | gga | agt | gtg | gac | cct | tcg | cct | gct | aga | 768 |
| Gly | Leu | Pro | Leu | Lys | Ser | Ser | Gly | Ser | Val | Asp | Pro | Ser | Pro | Ala | Arg | |
| | | | | 245 | | | | | 250 | | | | | 255 | | |
| gtt | atg | aga | aga | ttt | gat | cct | cca | cct | gtt | aag | atg | atg | tca | cag | aga | 816 |
| Val | Met | Arg | Arg | Phe | Asp | Pro | Pro | Pro | Val | Lys | Met | Met | Ser | Gln | Arg | |

-continued

```
                     260                 265                 270
gtt cac cat cca gct tcc atg gtg tcg cag aaa gtt gat cct ccg ttt      864
Val His His Pro Ala Ser Met Val Ser Gln Lys Val Asp Pro Pro Phe
            275                 280                 285 ccg aag gta tta cat aag gaa acc gga tct gtt gtt cgc cta cca gaa      912
Pro Lys Val Leu His Lys Glu Thr Gly Ser Val Val Arg Leu Pro Glu
        290                 295                 300 gct acc cgg cct act gtt ctt caa aaa ccc aag gac ttg cct gct atc      960
Ala Thr Arg Pro Thr Val Leu Gln Lys Pro Lys Asp Leu Pro Ala Ile
    305                 310                 315                 320 aag cag cag gak atc agg acc tct tcc tca aaa gaa gag ccc tgc ttc     1008
Lys Gln Gln Xaa Ile Arg Thr Ser Ser Ser Lys Glu Glu Pro Cys Phe
                    325                 330                 335 tct ggt agg aat gca gaa gca gtt caa gtg cag gat act aag ctc tcc     1056
Ser Gly Arg Asn Ala Glu Ala Val Gln Val Gln Asp Thr Lys Leu Ser
                340                 345                 350 cgg tca gac atg aag aaa atc cgc aaa gct gag aaa aaa gat aag aag     1104
Arg Ser Asp Met Lys Lys Ile Arg Lys Ala Glu Lys Lys Asp Lys Lys
            355                 360                 365 ttc aga gat ctg ttt gtt acc tgg aat ccg gta ttg ata gag aat gaa     1152
Phe Arg Asp Leu Phe Val Thr Trp Asn Pro Val Leu Ile Glu Asn Glu
        370                 375                 380 ggt tca gat ctt ggt gat gaa gac tgg ctg ttc agc agt aaa agg aac     1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg     1248
Ser Asp Ala Ile Met Val Gln Ser Arg Ala Thr Asp Ser Ser Val Pro
                    405                 410                 415 atc cat cca atg gtg cag cag aag cct tct tta caa ccc agg gca aca     1296
Ile His Pro Met Val Gln Gln Lys Pro Ser Leu Gln Pro Arg Ala Thr
                420                 425                 430 ttt ttg ccg gac ctt aat atg tac cag ctg cca tat gtcgtaccat tttaa    1347
Phe Leu Pro Asp Leu Asn Met Tyr Gln Leu Pro Tyr
            435                 440
```

<210> SEQ ID NO 76
<211> LENGTH: 444
<212> TYPE: PRT
<213> ORGANISM: Zea mays parviglumis strain IA19
<220> FEATURE:
<221> NAME/KEY: misc_feature
<222> LOCATION: (28)..(28)
<223> OTHER INFORMATION: The 'Xaa' at location 28 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (29)..(29)
<223> OTHER INFORMATION: The 'Xaa' at location 29 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (30)..(30)
<223> OTHER INFORMATION: The 'Xaa' at location 30 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (32)..(32)
<223> OTHER INFORMATION: The 'Xaa' at location 32 stands for Lys, Asn,

```
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (34)..(34)
<223> OTHER INFORMATION: The 'Xaa' at location 34 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (35)..(35)
<223> OTHER INFORMATION: The 'Xaa' at location 35 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (36)..(36)
<223> OTHER INFORMATION: The 'Xaa' at location 36 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (37)..(37)
<223> OTHER INFORMATION: The 'Xaa' at location 37 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (38)..(38)
<223> OTHER INFORMATION: The 'Xaa' at location 38 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (39)..(39)
<223> OTHER INFORMATION: The 'Xaa' at location 39 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (40)..(40)
<223> OTHER INFORMATION: The 'Xaa' at location 40 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (41)..(41)
<223> OTHER INFORMATION: The 'Xaa' at location 41 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (42)..(42)
<223> OTHER INFORMATION: The 'Xaa' at location 42 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (43)..(43)
<223> OTHER INFORMATION: The 'Xaa' at location 43 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (44)..(44)
<223> OTHER INFORMATION: The 'Xaa' at location 44 stands for Lys, Asn,
        Arg, Ser, Thr, Ile, Met, Glu, Asp, Gly, Ala, Val, Gln, His, Pro,
        Leu, a stop codon, Tyr, Trp, Cys, or Phe.
<220> FEATURE:
<221> NAME/KEY: misc_feature
<222> LOCATION: (45)..(45)
<223> OTHER INFORMATION: The 'Xaa' at location 45 stands for Lys, Asn,
        Arg, Ser, Thr, Ile, Met, Glu, Asp, Gly, Ala, Val, Gln, His, Pro,
```

```
      Leu, a stop codon, Tyr, Trp, Cys, or Phe.
<220> FEATURE:
<221> NAME/KEY: misc_feature
<222> LOCATION: (46)..(46)
<223> OTHER INFORMATION: The 'Xaa' at location 46 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (47)..(47)
<223> OTHER INFORMATION: The 'Xaa' at location 47 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (48)..(48)
<223> OTHER INFORMATION: The 'Xaa' at location 48 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (49)..(49)
<223> OTHER INFORMATION: The 'Xaa' at location 49 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (51)..(51)
<223> OTHER INFORMATION: The 'Xaa' at location 51 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (52)..(52)
<223> OTHER INFORMATION: The 'Xaa' at location 52 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (53)..(53)
<223> OTHER INFORMATION: The 'Xaa' at location 53 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (54)..(54)
<223> OTHER INFORMATION: The 'Xaa' at location 54 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (55)..(55)
<223> OTHER INFORMATION: The 'Xaa' at location 55 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (56)..(56)
<223> OTHER INFORMATION: The 'Xaa' at location 56 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (324)..(324)
<223> OTHER INFORMATION: The 'Xaa' at location 324 stands for Glu,
      or Asp.
<220> FEATURE:
<221> NAME/KEY: misc_feature
<222> LOCATION: (82)..(168)
<223> OTHER INFORMATION: n = A, C, T, or G

<400> SEQUENCE: 76
```

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Ser Lys His Ser His Lys Arg
50                  55                  60

Lys Leu Glu Asp Val Ile Lys Ala Glu Gln Val Pro Lys Arg Val Pro
65              70                  75                  80

Lys Glu Ser Val Glu Gln Leu Glu Lys Ser Gly Leu Ser Glu Glu His
                85                  90                  95

Gly Ala Pro Ser Phe Val His Thr Ile Arg Asp Ser Pro Glu Ser Ser
                100                 105                 110

Gln Asp Ser Gly Lys Arg Arg Lys Val Val Leu Ser Ser Pro Ser Gln
            115                 120                 125

Pro Lys Asn Gly Asn Ile Leu Arg Phe Lys Ile Lys Ser Ser Gln Asp
130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
                180                 185                 190

Asn Gly Asp Ser Gln Ala Val Gln Lys Cys Leu Ile Thr Glu Ser Pro
            195                 200                 205

Ala Lys Thr Met Gln Arg Leu Val Pro Gln Pro Ala Ala Lys Val Thr
            210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
            275                 280                 285

Pro Lys Val Leu His Lys Glu Thr Gly Ser Val Val Arg Leu Pro Glu
290                 295                 300

Ala Thr Arg Pro Thr Val Leu Gln Lys Pro Lys Asp Leu Pro Ala Ile
305                 310                 315                 320

Lys Gln Gln Xaa Ile Arg Thr Ser Ser Lys Glu Glu Pro Cys Phe
                325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
            355                 360                 365

Phe Arg Asp Leu Phe Val Thr Trp Asn Pro Val Leu Ile Glu Asn Glu
            370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Gln Lys Pro Ser Leu Gln Pro Arg Ala Thr
```

-continued

```
                    420             425             430
Phe Leu Pro Asp Leu Asn Met Tyr Gln Leu Pro Tyr
        435                 440

<210> SEQ ID NO 77
<211> LENGTH: 86
<212> TYPE: DNA
<213> ORGANISM: Zea mays parviglumis strain Wilkes

<400> SEQUENCE: 77
ctctcggcgg ggtagagcgc ggtcgaccgt cggccatgtc gaggtgcttc ccctacccgc      60
caccggggta cgtgcggaac ccagtg                                          86

<210> SEQ ID NO 78
<211> LENGTH: 1347
<212> TYPE: DNA
<213> ORGANISM: Zea mays parviglumis strain Wilkes
<220> FEATURE:
<221> NAME/KEY: misc_feature
<222> LOCATION: (52)..(81)
<223> OTHER INFORMATION: N = A, C, G, or T
<220> FEATURE:
<221> NAME/KEY: CDS
<222> LOCATION: (1)..(1347)
<223> OTHER INFORMATION:

<400> SEQUENCE: 78 atg tcg agg tgc ttc ccc tac ccg cca ccg ggg tac gtg cgg aac cca       48
Met Ser Arg Cys Phe Pro Tyr Pro Pro Pro Gly Tyr Val Arg Asn Pro
1               5                   10                  15 gtg nnn nnn nnn nnn nnn nnn nnn nnn nnn ctc ctg aaa gaa aag           96
Val Xaa Xaa Xaa Xaa Xaa Xaa Xaa Xaa Xaa Leu Leu Lys Glu Lys
            20                  25                  30 gaa aag gcc gaa aag aag aaa gag aaa agg agt gac agg aaa gct ccc      144
Glu Lys Ala Glu Lys Lys Lys Glu Lys Arg Ser Asp Arg Lys Ala Pro
        35                  40                  45 aag cag tgt gag acg tcc aaa cat tca aag cac agc cat aag aag aga      192
Lys Gln Cys Glu Thr Ser Lys His Ser Lys His Ser His Lys Lys Arg
    50                  55                  60 aag ctt gaa gat gtc atc aaa gct gag cag ggt ccc aaa aga gta ccc      240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat      288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca      336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa      384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gat      432
Pro Lys Asn Gly Asn Ile Leu Arg Phe Lys Ile Lys Ser Ser Gln Asp
    130                 135                 140 ccc caa tca gct gtt ctg gag aaa cca agg gtt ctt gag caa cca ttg      480
Pro Gln Ser Ala Val Leu Glu Lys Pro Arg Val Leu Glu Gln Pro Leu
145                 150                 155                 160 gtc caa caa atg gga tca ggt tca tcc ctg tcg ggc aag caa aat tca      528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc      576
Ile His His Lys Met Asn Val Arg Ser Thr Ser Gly Gln Arg Arg Val
```

```
                    180                 185                 190
aat ggt gac tcc caa gca gta caa aaa tgt ttg att aca gaa tcc ccg      624
Asn Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca      672
Ala Lys Thr Met Gln Arg Leu Val Pro Gln Pro Ala Ala Lys Val Thr
    210                 215                 220 cat cct gtt gat ccc cag tca gct gtt aag gtg cca gtt gga aga tcg      720
His Pro Val Asp Pro Gln Ser Ala Val Lys Val Pro Val Gly Arg Ser
225                 230                 235                 240 ggc cta cct ctg aag tct tcg gga agt gtg gac cct tcg cct gct aga      768
Gly Leu Pro Leu Lys Ser Ser Gly Ser Val Asp Pro Ser Pro Ala Arg
                245                 250                 255 gtt atg aga aga ttt gat cct cca cct gtt aag atg atg tca cag aga      816
Val Met Arg Arg Phe Asp Pro Pro Pro Val Lys Met Met Ser Gln Arg
            260                 265                 270 gtt cac cat cca gct tcc atg gtg tcg cag aaa gtt gat cct ccg ttt      864
Val His His Pro Ala Ser Met Val Ser Gln Lys Val Asp Pro Pro Phe
        275                 280                 285 ccg aag gta tta cat aag gaa acc gga tct gtt gtt cgc cta cca gaa      912
Pro Lys Val Leu His Lys Glu Thr Gly Ser Val Val Arg Leu Pro Glu
    290                 295                 300 gct acc cgg cct act gtt ctt caa aaa ccc aag gac ttg cct gct atc      960
Ala Thr Arg Pro Thr Val Leu Gln Lys Pro Lys Asp Leu Pro Ala Ile
305                 310                 315                 320 aag cag cag gat atc agg acc tct tcc tca aaa gaa gag ccc tgc ttc     1008
Lys Gln Gln Asp Ile Arg Thr Ser Ser Ser Lys Glu Glu Pro Cys Phe
                325                 330                 335 tct ggt agg aat gca gaa gca gtt caa gtg caa gat act aag ctc tcc     1056
Ser Gly Arg Asn Ala Glu Ala Val Gln Val Gln Asp Thr Lys Leu Ser
            340                 345                 350 cgg tca gac atg aag aaa atc cgc aaa gct gag aaa aaa gat aag aag     1104
Arg Ser Asp Met Lys Lys Ile Arg Lys Ala Glu Lys Lys Asp Lys Lys
        355                 360                 365 ttc aga gat ctg ttt gtt acc tgg aat ccg gta ttg ata gag aat gaa     1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac     1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg     1248
Ser Asp Ala Ile Met Val Gln Ser Arg Ala Thr Asp Ser Ser Val Pro
                405                 410                 415 atc cat cca atg gtg cag cag aag cct tct tta caa ccc agg gca aca     1296
Ile His Pro Met Val Gln Gln Lys Pro Ser Leu Gln Pro Arg Ala Thr
            420                 425                 430 ttt ttg ccg gac ctt aat atg tac cag ctg cca tat gtc gta cca ttt     1344
Phe Leu Pro Asp Leu Asn Met Tyr Gln Leu Pro Tyr Val Val Pro Phe
        435                 440                 445 taa                                                                 1347

<210> SEQ ID NO 79
<211> LENGTH: 448
<212> TYPE: PRT
<213> ORGANISM: Zea mays parviglumis strain Wilkes
<220> FEATURE:
<221> NAME/KEY: misc_feature
<222> LOCATION: (18)..(18)
<223> OTHER INFORMATION: The 'Xaa' at location 18 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
```

```
<220> FEATURE:
<221> NAME/KEY: misc_feature
<222> LOCATION: (19)..(19)
<223> OTHER INFORMATION: The 'Xaa' at location 19 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (20)..(20)
<223> OTHER INFORMATION: The 'Xaa' at location 20 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (21)..(21)
<223> OTHER INFORMATION: The 'Xaa' at location 21 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (22)..(22)
<223> OTHER INFORMATION: The 'Xaa' at location 22 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (23)..(23)
<223> OTHER INFORMATION: The 'Xaa' at location 23 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (24)..(24)
<223> OTHER INFORMATION: The 'Xaa' at location 24 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (25)..(25)
<223> OTHER INFORMATION: The 'Xaa' at location 25 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (26)..(26)
<223> OTHER INFORMATION: The 'Xaa' at location 26 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (27)..(27)
<223> OTHER INFORMATION: The 'Xaa' at location 27 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (52)..(81)
<223> OTHER INFORMATION: N = A, C, G, or T

<400> SEQUENCE: 79

Met Ser Arg Cys Phe Pro Tyr Pro Pro Gly Tyr Val Arg Asn Pro
1               5                   10                  15

Val Xaa Xaa Xaa Xaa Xaa Xaa Xaa Xaa Xaa Leu Leu Lys Glu Lys
            20                  25                  30

Glu Lys Ala Glu Lys Lys Glu Lys Arg Ser Asp Arg Lys Ala Pro
        35                  40                  45

Lys Gln Cys Glu Thr Ser Lys His Ser Lys His Ser His Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu Glu His
                85                  90                  95
```

```
Gly Ala Pro Ser Phe Val His Thr Ile Arg Asp Ser Pro Glu Ser Ser
                100                 105                 110

Gln Asp Ser Gly Lys Arg Lys Val Val Leu Ser Ser Pro Ser Gln
        115                 120                 125

Pro Lys Asn Gly Asn Ile Leu Arg Phe Lys Ile Lys Ser Ser Gln Asp
    130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Ser Ser Gly Ser Val Asp Pro Ser Pro Ala Arg
                245                 250                 255

Val Met Arg Arg Phe Asp Pro Pro Val Lys Met Met Ser Gln Arg
            260                 265                 270

Val His His Pro Ala Ser Met Val Ser Gln Lys Val Asp Pro Pro Phe
        275                 280                 285

Pro Lys Val Leu His Lys Glu Thr Gly Ser Val Val Arg Leu Pro Glu
    290                 295                 300

Ala Thr Arg Pro Thr Val Leu Gln Lys Pro Lys Asp Leu Pro Ala Ile
305                 310                 315                 320

Lys Gln Gln Asp Ile Arg Thr Ser Ser Lys Glu Glu Pro Cys Phe
                325                 330                 335

Ser Gly Arg Asn Ala Glu Ala Val Gln Val Gln Asp Thr Lys Leu Ser
            340                 345                 350

Arg Ser Asp Met Lys Lys Ile Arg Lys Ala Glu Lys Lys Asp Lys Lys
        355                 360                 365

Phe Arg Asp Leu Phe Val Thr Trp Asn Pro Val Leu Ile Glu Asn Glu
    370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Met Val Gln Gln Lys Pro Ser Leu Gln Pro Arg Ala Thr
            420                 425                 430

Phe Leu Pro Asp Leu Asn Met Tyr Gln Leu Pro Tyr Val Val Pro Phe
        435                 440                 445

<210> SEQ ID NO 80
<211> LENGTH: 225
<212> TYPE: DNA
<213> ORGANISM: Zea diploperennis

<400> SEQUENCE: 80
agcgcggtcg accgtcggcc atgtcgaggt gcttcccta  cccgccaccg gggtacgtgc      60
ggaacccagt ggccgtggcc gagccggagt cgaccgctaa ggtttgttga accttcggat    120
ttacacacgc acgtgccaga tcgtttgttc aatctgtagg ttttgcgcgg atctgtggtt    180
```

```
tgcgcgtgcg tgatgtgggt attgcccgtg ccttgaaagc taacc            225

<210> SEQ ID NO 81
<211> LENGTH: 1672
<212> TYPE: DNA
<213> ORGANISM: Zea diploperennis

<400> SEQUENCE: 81
agcccatttt tagttttatt gttctgtaga gtatgcattg ttgcaggtct taactgttgt    60
cagggaagta acgtgttcaa catgattgta aacgaataca attctgttgc taactgtgta   120
atgatgagaa ggataattga ataatctttg tgaagtatta ctgtctgaac tgtacgcaaa   180
tgctacattc attctttgtg ttcgtgtaaa tatcattata cataaaaatg ctgcattgca   240
ttcccgtcgt ccgttctaaa tcagaactga cgattgctct ggtggctgaa gctcctgaaa   300
gaaaaggaaa aggccgaaaa gaagaaagag aaaaggagtg acaggaaagc tcccaagcag   360
tgtgagacgt ccaaacactc aaagcacagc cataagaaga gaaagcttga agatgtcatc   420
aaagctgagc agggtcccaa agagtaccc aaagaatcag ttgagcagtt ggagaagagt   480
ggactctcag aagagcatgg agctccttct tttgtacata cgatacgtga ctctcctgag   540
agctcacagg acagcggcaa gagacgaaag gttgtcctgt ccagtcctag ccaacctaag   600
aatggtgaga ctattctctt gttttgcta ttctgattga ttttttatta tagaagaaat   660
caatcacttg ttcaggattt tattcatccc aacttgattt tacaggaaac attcttcgct   720
tcaagattaa aagtagtcaa gatccccaat cagctgttct ggagaaacca agggttcttg   780
agcaaccatt ggtccaacaa atgggatcag gttcatccct gtcgggcaag caaaattcaa   840
tccatcataa gatgaatgtg agatctacct ctggtcagcg gagggtcaat ggtgactcgc   900
aagcagtaca aaatgtttg attacagaat ccccggcaaa gaccatgcag agacttgtcc   960
cccagcctgc agctaaggtc acacatcctg ttgatcccca gtcagctgtt aaggtgccag  1020
ttggaaggtc gggcctacct ctcaagtttt cgggaagtat ggaccctccg cctgctagag  1080
ttatgggaag atttgatcct ccacctgtta agatgatgtc acagagagtt caccatccag  1140
cttccatggt gtcgcagaaa gttgatcctc cgttaccgaa ggtattacat aaggaaaccg  1200
gatctgttgt tcgcctacca gaagctaccc ggcctactgt tcttcaaaaa cccaaggact  1260
tgcctgctat caagcagcag cagatcagga cctcttcctc aaaagaagag ccctgcttct  1320
ctggtaggaa tgcagaagca gttcaagtgc atgatactaa gctctcccgg tcagatatga  1380
agaaaatccg caaagctgag aaaaaagata agaagttcag agatctgttt gttacctgga  1440
atccggtatt gatagagaat gaaggttcag atcttggtga tgaagactgg ctgttcagca  1500
gtaaaaggaa ctccgatgct atcatggttc aaagcagagc tactgatagt tcagtgccga  1560
tccatccaat kgtgcagcag aaaccttctt tacaacccag gcaacatttt ttgccggacc  1620
ttaatatgta ccagctgcca tatgtcgtac cattttaaac atctgtcgag gt           1672

<210> SEQ ID NO 82
<211> LENGTH: 1347
<212> TYPE: DNA
<213> ORGANISM: Zea diploperennis
<220> FEATURE:
<221> NAME/KEY: CDS
<222> LOCATION: (1)..(1347)
<223> OTHER INFORMATION:

<400> SEQUENCE: 82
```

```
atg tcg agg tgc ttc ccc tac ccg cca ccg ggg tac gtg cgg aac cca      48
Met Ser Arg Cys Phe Pro Tyr Pro Pro Pro Gly Tyr Val Arg Asn Pro
1               5                   10                  15 gtg gcc gtg gcc gag ccg gag tcg acc gct aag ctc ctg aaa gaa aag      96
Val Ala Val Ala Glu Pro Glu Ser Thr Ala Lys Leu Leu Lys Glu Lys
                20                  25                  30 gaa aag gcc gaa aag aag aaa gag aaa agg agt gac agg aaa gct ccc     144
Glu Lys Ala Glu Lys Lys Lys Glu Lys Arg Ser Asp Arg Lys Ala Pro
        35                  40                  45 aag cag tgt gag acg tcc aaa cac tca aag cac agc cat aag aag aga     192
Lys Gln Cys Glu Thr Ser Lys His Ser Lys His Ser His Lys Lys Arg
50                  55                  60 aag ctt gaa gat gtc atc aaa gct gag cag ggt ccc aaa aga gta ccc     240
Lys Leu Glu Asp Val Ile Lys Ala Glu Gln Gly Pro Lys Arg Val Pro
65                  70                  75                  80 aaa gaa tca gtt gag cag ttg gag aag agt gga ctc tca gaa gag cat     288
Lys Glu Ser Val Glu Gln Leu Glu Lys Ser Gly Leu Ser Glu Glu His
                85                  90                  95 gga gct cct tct ttt gta cat acg ata cgt gac tct cct gag agc tca     336
Gly Ala Pro Ser Phe Val His Thr Ile Arg Asp Ser Pro Glu Ser Ser
            100                 105                 110 cag gac agc ggc aag aga cga aag gtt gtc ctg tcc agt cct agc caa     384
Gln Asp Ser Gly Lys Arg Arg Lys Val Val Leu Ser Ser Pro Ser Gln
        115                 120                 125 cct aag aat gga aac att ctt cgc ttc aag att aaa agt agt caa gat     432
Pro Lys Asn Gly Asn Ile Leu Arg Phe Lys Ile Lys Ser Ser Gln Asp
130                 135                 140 ccc caa tca gct gtt ctg gag aaa cca agg gtt ctt gag caa cca ttg     480
Pro Gln Ser Ala Val Leu Glu Lys Pro Arg Val Leu Glu Gln Pro Leu
145                 150                 155                 160 gtc caa caa atg gga tca ggt tca tcc ctg tcg ggc aag caa aat tca     528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc     576
Ile His His Lys Met Asn Val Arg Ser Thr Ser Gly Gln Arg Arg Val
            180                 185                 190 aat ggt gac tcg caa gca gta caa aaa tgt ttg att aca gaa tcc ccg     624
Asn Gly Asp Ser Gln Ala Val Gln Lys Cys Leu Ile Thr Glu Ser Pro
        195                 200                 205 gca aag acc atg cag aga ctt gtc ccc cag cct gca gct aag gtc aca     672
Ala Lys Thr Met Gln Arg Leu Val Pro Gln Pro Ala Ala Lys Val Thr
210                 215                 220 cat cct gtt gat ccc cag tca gct gtt aag gtg cca gtt gga agg tcg     720
His Pro Val Asp Pro Gln Ser Ala Val Lys Val Pro Val Gly Arg Ser
225                 230                 235                 240 ggc cta cct ctc aag ttt tcg gga agt atg gac cct tcg cct gct aga     768
Gly Leu Pro Leu Lys Phe Ser Gly Ser Met Asp Pro Ser Pro Ala Arg
                245                 250                 255 gtt atg gga aga ttt gat cct cca cct gtt aag atg atg tca cag aga     816
Val Met Gly Arg Phe Asp Pro Pro Pro Val Lys Met Met Ser Gln Arg
            260                 265                 270 gtt cac cat cca gct tcc atg gtg tcg cag aaa gtt gat cct ccg tta     864
Val His His Pro Ala Ser Met Val Ser Gln Lys Val Asp Pro Pro Leu
        275                 280                 285 ccg aag gta tta cat aag gaa acc gga tct gtt gtt cgc cta cca gaa     912
Pro Lys Val Leu His Lys Glu Thr Gly Ser Val Val Arg Leu Pro Glu
290                 295                 300 gct acc cgg cct act gtt ctt caa aaa ccc aag gac ttg cct gct atc     960
Ala Thr Arg Pro Thr Val Leu Gln Lys Pro Lys Asp Leu Pro Ala Ile
305                 310                 315                 320
```

-continued

```
aag cag cag cag atc agg acc tct tcc tca aaa gaa gag ccc tgc ttc      1008
Lys Gln Gln Gln Ile Arg Thr Ser Ser Ser Lys Glu Glu Pro Cys Phe
            325                 330                 335 tct ggt agg aat gca gaa gca gtt caa gtg cat gat act aag ctc tcc      1056
Ser Gly Arg Asn Ala Glu Ala Val Gln Val His Asp Thr Lys Leu Ser
        340                 345                 350 cgg tca gat atg aag aaa atc cgc aaa gct gag aaa aaa gat aag aag      1104
Arg Ser Asp Met Lys Lys Ile Arg Lys Ala Glu Lys Lys Asp Lys Lys
    355                 360                 365 ttc aga gat ctg ttt gtt acc tgg aat ccg gta ttg ata gag aat gaa      1152
Phe Arg Asp Leu Phe Val Thr Trp Asn Pro Val Leu Ile Glu Asn Glu
370                 375                 380 ggt tca gat ctt ggt gat gaa gac tgg ctg ttc agc agt aaa agg aac      1200
Gly Ser Asp Leu Gly Asp Glu Asp Trp Leu Phe Ser Ser Lys Arg Asn
385                 390                 395                 400 tcc gat gct atc atg gtt caa agc aga gct act gat agt tca gtg ccg      1248
Ser Asp Ala Ile Met Val Gln Ser Arg Ala Thr Asp Ser Ser Val Pro
                405                 410                 415 atc cat cca atk gtg cag cag aaa cct tct tta caa ccc agg gca aca      1296
Ile His Pro Xaa Val Gln Gln Lys Pro Ser Leu Gln Pro Arg Ala Thr
            420                 425                 430 ttt ttg ccg gac ctt aat atg tac cag ctg cca tat gtc gta cca ttt      1344
Phe Leu Pro Asp Leu Asn Met Tyr Gln Leu Pro Tyr Val Val Pro Phe
        435                 440                 445 taa                                                                   1347
```

<210> SEQ ID NO 83
<211> LENGTH: 448
<212> TYPE: PRT
<213> ORGANISM: Zea diploperennis
<220> FEATURE:
<221> NAME/KEY: misc_feature
<222> LOCATION: (420)..(420)
<223> OTHER INFORMATION: The 'Xaa' at location 420 stands for Met, or Ile.

<400> SEQUENCE: 83

```
Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Leu Lys Glu Lys
            20                  25                  30

Glu Lys Ala Glu Lys Lys Glu Lys Arg Ser Asp Arg Lys Ala Pro
        35                  40                  45

Lys Gln Cys Glu Thr Ser Lys His Ser Lys His Ser His Lys Lys Arg
    50                  55                  60

Lys Leu Glu Asp Val Ile Lys Ala Glu Gln Gly Pro Lys Arg Val Pro
65                  70                  75                  80

Lys Glu Ser Val Glu Gln Leu Glu Lys Ser Gly Leu Ser Glu His
            85                  90                  95

Gly Ala Pro Ser Phe Val His Thr Ile Arg Asp Ser Pro Glu Ser Ser
        100                 105                 110

Gln Asp Ser Gly Lys Arg Arg Lys Val Val Leu Ser Ser Pro Ser Gln
    115                 120                 125

Pro Lys Asn Gly Asn Ile Leu Arg Phe Lys Ile Lys Ser Ser Gln Asp
130                 135                 140

Pro Gln Ser Ala Val Leu Glu Lys Pro Arg Val Leu Glu Gln Pro Leu
145                 150                 155                 160

Val Gln Gln Met Gly Ser Gly Ser Ser Leu Ser Gly Lys Gln Asn Ser
```

```
                165                 170                 175
Ile His His Lys Met Asn Val Arg Ser Thr Ser Gly Gln Arg Arg Val
            180                 185                 190

Asn Gly Asp Ser Gln Ala Val Gln Lys Cys Leu Ile Thr Glu Ser Pro
        195                 200                 205

Ala Lys Thr Met Gln Arg Leu Val Pro Gln Pro Ala Ala Lys Val Thr
    210                 215                 220

His Pro Val Asp Pro Gln Ser Ala Val Lys Val Pro Val Gly Arg Ser
225                 230                 235                 240

Gly Leu Pro Leu Lys Phe Ser Gly Ser Met Asp Pro Ser Pro Ala Arg
                245                 250                 255

Val Met Gly Arg Phe Asp Pro Pro Val Lys Met Met Ser Gln Arg
            260                 265                 270

Val His His Pro Ala Ser Met Val Ser Gln Lys Val Asp Pro Pro Leu
        275                 280                 285

Pro Lys Val Leu His Lys Glu Thr Gly Ser Val Val Arg Leu Pro Glu
    290                 295                 300

Ala Thr Arg Pro Thr Val Leu Gln Lys Pro Lys Asp Leu Pro Ala Ile
305                 310                 315                 320

Lys Gln Gln Gln Ile Arg Thr Ser Ser Lys Glu Glu Pro Cys Phe
                325                 330                 335

Ser Gly Arg Asn Ala Glu Ala Val Gln Val His Asp Thr Lys Leu Ser
            340                 345                 350

Arg Ser Asp Met Lys Lys Ile Arg Lys Ala Glu Lys Lys Asp Lys Lys
        355                 360                 365

Phe Arg Asp Leu Phe Val Thr Trp Asn Pro Val Leu Ile Glu Asn Glu
    370                 375                 380

Gly Ser Asp Leu Gly Asp Glu Asp Trp Leu Phe Ser Ser Lys Arg Asn
385                 390                 395                 400

Ser Asp Ala Ile Met Val Gln Ser Arg Ala Thr Asp Ser Ser Val Pro
                405                 410                 415

Ile His Pro Xaa Val Gln Gln Lys Pro Ser Leu Gln Pro Arg Ala Thr
            420                 425                 430

Phe Leu Pro Asp Leu Asn Met Tyr Gln Leu Pro Tyr Val Val Pro Phe
        435                 440                 445

<210> SEQ ID NO 84
<211> LENGTH: 2423
<212> TYPE: DNA
<213> ORGANISM: Zea luxurians

<400> SEQUENCE: 84
ggccatgtcg aggtgcttcc cctacccgcc accggggtac gtgcggaacc cagtggccgt      60
ggccgagccg gagtcgaccg ctaaggtttg ttgaaccttc ggatttacac acgcacgtgc     120
cagatcgttt ggtcaatctg ttggttttgc gcggatctgt ggtttgcgcg tgcgtgatgt     180
gggtattgcc cgtgccttga agctaaccg agatgaggaa gtgtatggat cttgtttagc     240
tgcacgaggt cctccaaatc gattgaaaaa tttaagttgg atggccggta ggccaagatt     300
gggttagtcc ggttttgat aactggtacc atggttatcg gggacattga acagaacggt     360
agaacatcaa attcgattca aaactgtgct agatttgcac atttagtcgc cctaagatta     420
cgtggacgtg ggtggtccga attggttgtt gttgtatgat ggttggaata tgagccattt     480
agtgcttccg tgactggcca aatattttg tttctcaaat ttttctttga aaactgttt     540
```

```
gtcgagcgtc aattcttaat acagtatgtc gttattttgg gctaagcttg tgaaacaagg      600
gtcgtttgac atttgtactg tattaacctg atgttactct tctggttgac caaaggagtt      660
ttagaattat tttggtcctg taaatcaata gcaactaaca ccatctattg tgcccatttt      720
tagttttgta tagttttgta tgcagtgttg caggtcttaa ctgttgtcag gaaagtaacg      780
tgttcacatg attgtaaacg aatacaattc tgttgctaac tgtgtaatga tgagaacgat      840
aattgaataa tctttgtgaa gtattactgt ctgaactgta cacaaatgct acattcattc      900
tttgtgttcg tgtaaatgtc attatacata aaaaatgctg cattgcattc ccgtcgtccg      960
ttctaaatca gaactgacga ttgctctggt ggctgaagct cccgaaagaa aggaaaaggc     1020
ccgaaaagaa gaaagagaaa cggagtgaca ggaaagctcc caagcagtgt gagacgtcca     1080
aacattcaaa gcacatccat aagaagagaa agcttgaaga tgtcatcaaa gctgggcagg     1140
gtcccaaaag agtacccaaa gaatcagttg agcagttgga gaagagtgga ctctcagaag     1200
agcatggagc tccttctttt gtacataaga tacgcgactc tcctgagagc tcacaggaca     1260
gcggcaagag acgaaaggtt gtcctgtcca gtcctagcca acctaagaat ggtgagacta     1320
ttctcttgtt tttgctattc tgattgattt tttattatag aagaaatcaa tcacttgttc     1380
cggatttttat tcatcccaac ttgacatttt acaggaaaca ttcttcgctt caagattaaa     1440
agtaatcaag atccccaatc agctgttctg gagaaaccaa gggttcttga ccaaccattg     1500
gtccaacaaa tgggatcagg ttcatccctg tcgggcaagc aaaattcaat ccatcataag     1560
atgaatgtga gatctacctc tggtcagcgg agggtcaatg gtgaatccca agcagtacaa     1620
aaatgtttga ttacagaatc cccggcaaag accatgcaga gacttgtccc ccagcctgca     1680
gctaaggtca cacatcctgt tgatccccag tcagctgtta aggtgccagt tggaagatcg     1740
ggcctacctc tgaagttttc gggaagtgtg gacccttcgc ctgctagagt tatgggaaga     1800
tttgatcctc cacctgttaa gatgatgtca cagagagttc accatccagc ttccatggtg     1860
tcgcagaaag ttgatcctcc gttaccgaag gtattacata aggaaaccgg atctgttgtt     1920
cgcctaccag aagctacccg gcctactgtt cttcaaaaac ccaaggactt gcctgctatc     1980
aagcagcagg agatcaggac ctcttcctca aaagaagagc cctgcttctc tggtaggaat     2040
gcagaagcag ttcaagtgca ggatactaag ctctcccggt cagatgtgaa gaaaatccgc     2100
aaagctgaga aaaagataa gaagttcaga gatctgtttg ttacctggaa tccggtgttg     2160
atagagaatg aaggttcaga tcttggtgat gaagactggc tgttcagcag taaaaggaac     2220
tccgatgcta tcatggctca aagcagagct actgatagtt cagtgccgat ccatccaatg     2280
gtgcagcaga agccttcttt gcaacccagg gcaacgtttt tgccggacct taatatctac     2340
cagctgccat atgtcgtacc attttaaaca tctgtcgagg tagatgagaa ttagatgaga     2400
tgttgggaga gagctgtgtg aac                                             2423
```

<210> SEQ ID NO 85
<211> LENGTH: 1347
<212> TYPE: DNA
<213> ORGANISM: Zea luxurians
<220> FEATURE:
<221> NAME/KEY: CDS
<222> LOCATION: (1)..(1347)
<223> OTHER INFORMATION:

<400> SEQUENCE: 85

```
atg tcg agg tgc ttc ccc tac ccg cca ccg ggg tac gtg cgg aac cca        48
Met Ser Arg Cys Phe Pro Tyr Pro Pro Pro Gly Tyr Val Arg Asn Pro
1               5                   10                  15
```

```
gtg gcc gtg gcc gag ccg gag tcg acc gct aag ctc ccg aaa gaa aag      96
Val Ala Val Ala Glu Pro Glu Ser Thr Ala Lys Leu Pro Lys Glu Lys
            20                  25                  30 gaa aag gcc gaa aag aag aaa gag aaa cgg agt gac agg aaa gct ccc     144
Glu Lys Ala Glu Lys Lys Lys Glu Lys Arg Ser Asp Arg Lys Ala Pro
        35                  40                  45 aag cag tgt gag acg tcc aaa cat tca aag cac atc cat aag aag aga     192
Lys Gln Cys Glu Thr Ser Lys His Ser Lys His Ile His Lys Lys Arg
50                  55                  60 aag ctt gaa gat gtc atc aaa gct ggg cag ggt ccc aaa aga gta ccc     240
Lys Leu Glu Asp Val Ile Lys Ala Gly Gln Gly Pro Lys Arg Val Pro
65                  70                  75                  80 aaa gaa tca gtt gag cag ttg gag aag agt gga ctc tca gaa gag cat     288
Lys Glu Ser Val Glu Gln Leu Glu Lys Ser Gly Leu Ser Glu Glu His
                85                  90                  95 gga gct cct tct ttt gta cat aag ata cgc gac tct cct gag agc tca     336
Gly Ala Pro Ser Phe Val His Lys Ile Arg Asp Ser Pro Glu Ser Ser
            100                 105                 110 cag gac agc ggc aag aga cga aag gtt gtc ctg tcc agt cct agc caa     384
Gln Asp Ser Gly Lys Arg Arg Lys Val Val Leu Ser Ser Pro Ser Gln
        115                 120                 125 cct aag aat gga aac att ctt cgc ttc aag att aaa agt aat caa gat     432
Pro Lys Asn Gly Asn Ile Leu Arg Phe Lys Ile Lys Ser Asn Gln Asp
130                 135                 140 ccc caa tca gct gtt ctg gag aaa cca agg gtt ctt gac caa cca ttg     480
Pro Gln Ser Ala Val Leu Glu Lys Pro Arg Val Leu Asp Gln Pro Leu
145                 150                 155                 160 gtc caa caa atg gga tca ggt tca tcc ctg tcg ggc aag caa aat tca     528
Val Gln Gln Met Gly Ser Gly Ser Ser Leu Ser Gly Lys Gln Asn Ser
                165                 170                 175 atc cat cat aag atg aat gtg aga tct acc tct ggt cag cgg agg gtc     576
Ile His His Lys Met Asn Val Arg Ser Thr Ser Gly Gln Arg Arg Val
            180                 185                 190 aat ggt gaa tcc caa gca gta caa aaa tgt ttg att aca gaa tcc ccg     624
Asn Gly Glu Ser Gln Ala Val Gln Lys Cys Leu Ile Thr Glu Ser Pro
        195                 200                 205 gca aag acc atg cag aga ctt gtc ccc cag cct gca gct aag gtc aca     672
Ala Lys Thr Met Gln Arg Leu Val Pro Gln Pro Ala Ala Lys Val Thr
210                 215                 220 cat cct gtt gat ccc cag tca gct gtt aag gtg cca gtt gga aga tcg     720
His Pro Val Asp Pro Gln Ser Ala Val Lys Val Pro Val Gly Arg Ser
225                 230                 235                 240 ggc cta cct ctg aag ttt tcg gga agt gtg gac cct tcg cct gct aga     768
Gly Leu Pro Leu Lys Phe Ser Gly Ser Val Asp Pro Ser Pro Ala Arg
                245                 250                 255 gtt atg gga aga ttt gat cct cca cct gtt aag atg atg tca cag aga     816
Val Met Gly Arg Phe Asp Pro Pro Pro Val Lys Met Met Ser Gln Arg
            260                 265                 270 gtt cac cat cca gct tcc atg gtg tcg cag aaa gtt gat cct ccg tta     864
Val His His Pro Ala Ser Met Val Ser Gln Lys Val Asp Pro Pro Leu
        275                 280                 285 ccg aag gta tta cat aag gaa acc gga tct gtt gtt cgc cta cca gaa     912
Pro Lys Val Leu His Lys Glu Thr Gly Ser Val Val Arg Leu Pro Glu
290                 295                 300 gct acc cgg cct act gtt ctt caa aaa ccc aag gac ttg cct gct atc     960
Ala Thr Arg Pro Thr Val Leu Gln Lys Pro Lys Asp Leu Pro Ala Ile
305                 310                 315                 320 aag cag cag gag atc agg acc tct tcc tca aaa gaa gag ccc tgc ttc    1008
Lys Gln Gln Glu Ile Arg Thr Ser Ser Ser Lys Glu Glu Pro Cys Phe
```

-continued

```
                        325                 330                 335
tct ggt agg aat gca gaa gca gtt caa gtg cag gat act aag ctc tcc        1056
Ser Gly Arg Asn Ala Glu Ala Val Gln Val Gln Asp Thr Lys Leu Ser
            340                 345                 350 cgg tca gat gtg aag aaa atc cgc aaa gct gag aaa aaa gat aag aag        1104
Arg Ser Asp Val Lys Lys Ile Arg Lys Ala Glu Lys Lys Asp Lys Lys
        355                 360                 365 ttc aga gat ctg ttt gtt acc tgg aat ccg gtg ttg ata gag aat gaa        1152
Phe Arg Asp Leu Phe Val Thr Trp Asn Pro Val Leu Ile Glu Asn Glu
    370                 375                 380 ggt tca gat ctt ggt gat gaa gac tgg ctg ttc agc agt aaa agg aac        1200
Gly Ser Asp Leu Gly Asp Glu Asp Trp Leu Phe Ser Ser Lys Arg Asn
385                 390                 395                 400 tcc gat gct atc atg gct caa agc aga gct act gat agt tca gtg ccg        1248
Ser Asp Ala Ile Met Ala Gln Ser Arg Ala Thr Asp Ser Ser Val Pro
                405                 410                 415 atc cat cca atg gtg cag cag aag cct tct ttg caa ccc agg gca acg        1296
Ile His Pro Met Val Gln Gln Lys Pro Ser Leu Gln Pro Arg Ala Thr
            420                 425                 430 ttt ttg ccg gac ctt aat atc tac cag ctg cca tat gtc gta cca ttt        1344
Phe Leu Pro Asp Leu Asn Ile Tyr Gln Leu Pro Tyr Val Val Pro Phe
        435                 440                 445 taa                                                                    1347

<210> SEQ ID NO 86
<211> LENGTH: 448
<212> TYPE: PRT
<213> ORGANISM: Zea luxurians

<400> SEQUENCE: 86

Met Ser Arg Cys Phe Pro Tyr Pro Pro Gly Tyr Val Arg Asn Pro
1               5                   10                  15

Val Ala Val Ala Glu Pro Glu Ser Thr Ala Lys Leu Pro Lys Glu Lys
            20                  25                  30

Glu Lys Ala Glu Lys Lys Glu Lys Arg Ser Asp Arg Lys Ala Pro
        35                  40                  45

Lys Gln Cys Glu Thr Ser Lys His Ser Lys His Ile His Lys Lys Arg
    50                  55                  60

Lys Leu Glu Asp Val Ile Lys Ala Gly Gln Gly Pro Lys Arg Val Pro
65                  70                  75                  80

Lys Glu Ser Val Glu Gln Leu Glu Lys Ser Gly Leu Ser Glu His
                85                  90                  95

Gly Ala Pro Ser Phe Val His Lys Ile Arg Asp Ser Pro Glu Ser Ser
            100                 105                 110

Gln Asp Ser Gly Lys Arg Arg Lys Val Val Leu Ser Ser Pro Ser Gln
        115                 120                 125

Pro Lys Asn Gly Asn Ile Leu Arg Phe Lys Ile Lys Ser Asn Gln Asp
    130                 135                 140

Pro Gln Ser Ala Val Leu Glu Lys Pro Arg Val Leu Asp Gln Pro Leu
145                 150                 155                 160

Val Gln Gln Met Gly Ser Gly Ser Ser Leu Ser Gly Lys Gln Asn Ser
                165                 170                 175

Ile His His Lys Met Asn Val Arg Ser Thr Ser Gly Gln Arg Arg Val
            180                 185                 190

Asn Gly Glu Ser Gln Ala Val Gln Lys Cys Leu Ile Thr Glu Ser Pro
        195                 200                 205
```

```
Ala Lys Thr Met Gln Arg Leu Val Pro Gln Pro Ala Ala Lys Val Thr
    210                 215                 220
His Pro Val Asp Pro Gln Ser Ala Val Lys Val Pro Val Gly Arg Ser
225                 230                 235                 240
Gly Leu Pro Leu Lys Phe Ser Gly Ser Val Asp Pro Ser Pro Ala Arg
                    245                 250                 255
Val Met Gly Arg Phe Asp Pro Pro Val Lys Met Met Ser Gln Arg
                260                 265                 270
Val His His Pro Ala Ser Met Val Ser Gln Lys Val Asp Pro Pro Leu
            275                 280                 285
Pro Lys Val Leu His Lys Glu Thr Gly Ser Val Val Arg Leu Pro Glu
    290                 295                 300
Ala Thr Arg Pro Thr Val Leu Gln Lys Pro Lys Asp Leu Pro Ala Ile
305                 310                 315                 320
Lys Gln Gln Glu Ile Arg Thr Ser Ser Lys Glu Glu Pro Cys Phe
                325                 330                 335
Ser Gly Arg Asn Ala Glu Ala Val Gln Val Gln Asp Thr Lys Leu Ser
                340                 345                 350
Arg Ser Asp Val Lys Lys Ile Arg Lys Ala Glu Lys Lys Asp Lys Lys
            355                 360                 365
Phe Arg Asp Leu Phe Val Thr Trp Asn Pro Val Leu Ile Glu Asn Glu
    370                 375                 380
Gly Ser Asp Leu Gly Asp Glu Asp Trp Leu Phe Ser Ser Lys Arg Asn
385                 390                 395                 400
Ser Asp Ala Ile Met Ala Gln Ser Arg Ala Thr Asp Ser Ser Val Pro
                405                 410                 415
Ile His Pro Met Val Gln Gln Lys Pro Ser Leu Gln Pro Arg Ala Thr
            420                 425                 430
Phe Leu Pro Asp Leu Asn Ile Tyr Gln Leu Pro Tyr Val Val Pro Phe
    435                 440                 445

<210> SEQ ID NO 87
<211> LENGTH: 21
<212> TYPE: DNA
<213> ORGANISM: Artificial Sequence primer
<220> FEATURE:
<221> NAME/KEY: misc_feature
<222> LOCATION: (1)..(21)
<223> OTHER INFORMATION: primer

<400> SEQUENCE: 87
caattctctg agatgccttg g                                          21

<210> SEQ ID NO 88
<211> LENGTH: 21
<212> TYPE: DNA
<213> ORGANISM: Artificial Sequence primer
<220> FEATURE:
<221> NAME/KEY: misc_feature
<222> LOCATION: (1)..(21)
<223> OTHER INFORMATION: primer

<400> SEQUENCE: 88
caattctctg agatgccttg g                                          21

<210> SEQ ID NO 89
<211> LENGTH: 1402
<212> TYPE: DNA
<213> ORGANISM: Oryza rufipogon
<220> FEATURE:
```

```
<221> NAME/KEY: misc_feature
<222> LOCATION: (1)..(1402)
<223> OTHER INFORMATION: n= a, c, t, or g

<400> SEQUENCE: 89
gatgagctca cgcggggcgg cgcggctcga gctcgagccg cctatgaggg catcaaagga      60
aagggttggc cttcgtcctg cagagatgtt ggccaatgtt ggtccttcac cctccaaggc     120
aaaacagatt gtcaatcctg cagctgctaa ggttacacaa agagttgatc ctccacctgc     180
caaggcatct cagagaattg atcctctgtt gccatccaag gttcatatag atgctactca     240
atcttttacg aaggtctccc agacagagat caagccggaa gtacagcccc caattccgaa     300
ggtgcctgtg gctatgccta ccatcaatcg tcagcagatt gacacctcgc agcccaaaga     360
agagccttgc tcctctggca ggaatgctga agctgcttca gtatcagtag agaagcagtc     420
caagtcagat cgcaaaaaga gccgcaaggc tgagaagaaa gagaagaagt caaagatttt     480
atttgttacc tgggatcctc cgtctatgga aatggatgat atggatcttg ggaccagga     540 ttggctgctt ggtagtacga ggaaacctga tgctggcatt ggcaactgca gagaaattgt     600
tgatccactt tacttctcaa tcagcagagc agttctcatt gcagcctang gcgattcatt     660
tacccagacc ttcatgtcta tcagttgcca tatgtggttc cattctaggt ttgtgtagtg     720
agatggagta gtgagaagta agagatgttg ggaagagagc tgtgtgggtc tgggagatta     780
tggttccctg gcacagtttc ccagctttgt tcccagcgtt cttgtttcac ggttgctact     840
gtccaacttc ctgtgtnggt tttttggcgc cgctattgng gcttggactc cccattgatn     900
cctcacacaa ggaaattcga gtagttcaag cgctatttga ttaccggcga accacccaaa     960
gggggggggc cggtaccccca cgacctttgg ttccccctca actagaaggg gtnatattgt    1020
cgcgccgggg gtaacaatgn gcacanaacc agtcacggtg nngaaaagntt ttatccggtc    1080 cccaaaatat ntcccnccca ncaaatntna atacccgggg gcactacagt tnttataaac    1140
cngtggggcn ctacaanngt ggacgatctc acaaattata atcatatttg tagtatntgc    1200
cgangttcgc aaccgtcana cacnatcagt tgtcgacgcn acgattatt ttcnacagcc    1260 gngctacaca ancgaccgcc gaaangnatg tataggatga ngtacatacn ataccgact    1320 caanacgtac canacatcag catcntgcgc gnntgatgan tactcaggaa gnagcgtccc    1380
tacntccgat tgaaatngtg ac                                              1402

<210> SEQ ID NO 90
<211> LENGTH: 1341
<212> TYPE: DNA
<213> ORGANISM: Oryza rufipogon strain IRCG105491

<400> SEQUENCE: 90
atgtcgaggt gcttcccta cccgccgccg gggtacgtgc gaaacccagt ggtggccgtg      60
gccgcggccg aagcgcaggc gaccactaag ctccagaaag aaagggaaaa ggccgaaaag     120 agaaagaga aaagagtga caggaaagct cttccacatg gtgagatatc caagcattca     180
aagcgaaccc acaagaagag aaaacatgaa gacatcaata atgctgatca gaagtcccgg     240
aaggtttcct ccatggaacc tggtgagcaa ttggagaaga gtggactctc agaagagcat     300
ggagctcctt gctttactca gacagtgcat ggctctccag agagttcaca ggacagcagc     360
aagagaagaa aggttgtgtt acccagtcct agccaagcta agaatggtaa catccttcga     420
ataaagataa gaagagatca agattcttca gcttcccttt cggagaaatc taatgttgta     480
caaacaccag ttcatcaaat gggatcagtt tcatctctgc caagtaagaa aaactcaatg     540
```

```
caaccacaca acaccgaaat gatggtgaga acagcatcaa cccagcagca aagcatcaaa      600
ggtgattttc aagcagtact gaaacaaggt atgccaaccc cagcaaaagt catgccaaga      660
gtcgatgttc ctccatctat gagggcatca aggaaaggg ttggccttcg tcctgcagag       720
atgttggcca atgttggtcc ttcaccatcc aaggcaaaac agattgtcaa tcctgcagct      780
gctaaggtta cacaaagagt tgatcctcca cctgccaagg catctcagag aattgatcct      840
ctgttgccat ccaaggttca tatagatgct actcgatctt ttacgaaggt ctcccagaca      900
gagatcaagc cggaagtaca gcccccaatt ccgaaggtgc ctgtggctat gcctaccatc      960
aatcgtcagc agattgacac ctcgcagccc aaagaagagc cttgctcctc tggcaggaat     1020
gctgaagctg cttcagtatc agtagagaag cagtccaagt cagatcgcaa aaagagccgc     1080
aaggctgaga agaaagagaa gaagttcaaa gatttatttg ttacctggga tcctccgtct     1140
atggaaatgg atgatatgga tcttggggac caggattggc tgcttggtag tacgaggaaa     1200
cctgatgctg gcattggcaa ctgcagagaa attgttgatc cacttacttc tcaatcagca     1260
gagcagttct cattgcagcc tagggcgatt catttaccag accttcatgt ctatcagttg     1320
ccatatgtgg ttccattcta g                                              1341

<210> SEQ ID NO 91
<211> LENGTH: 2157
<212> TYPE: DNA
<213> ORGANISM: Oryza sativa cv. Nipponbare

<400> SEQUENCE: 91
tcgaccagat cggtcgccaa tcttttagtg gctgaccgtg aaagaggat attactgact        60 tcggtttgct aattttggtt gtgccgttga atctgaaata accagaatag tcatggggaa      120
aaaagtctga tctggaaggt tcgaattaca tttctatata ttgttgtgct cccagacgat      180
ggttgcaaga aatcactcat gctggataaa attgtggatg taagagtctg cagtcgttaa      240
aatctggaaa cagcacattt tgccgtagta aatttgaatc catgttgctg tctcgttatt      300
ggtgtgttac gagtaacctg tgtgttgtta tctccgcttg gactagattc caagtaatcc      360
agtgccttca tgacctgcaa attctatgcc tatgaagtaa catgaacagt ttgtatgtat      420
gtattctgtt gatgcatact tgcattattt gtgagatgta catgttgtgg taaaattttg      480
cattcaccat atagaaatag taactgacta tccttgttta gttcgaaaac tactgcaggt      540
ttagttattc tctgttgcca agagtgcttg ttatgattgt aagggttaca gttcctgtgac     600 taaccatgta acaaatatat taaggattat caaattattc tatgtgaagt gtccgtgccc      660
taattgtgtt atcttctgta actgatagca caacatttgt ttcctgctgt gtgcttgtgt      720
aaattggtac ttcatcatta ctatatattt caaagaaaat tctgcattgc attcccgtcg      780
tccgttctaa atcagaactg acgattgctc tggtggctga agctccagaa agaaagggaa      840
aaggctgaaa agaagaaaga gaaaggagt gacaggaaag ctcttccaca tggtgagata      900
tccaagcatt caaagcgaac ccaccacaag aagagaaaac atgaagacat caataatgct      960
gatcagaagt cccggaaggt ttcctccatg gaacctggtg agcaattgga gaagagtgga     1020
ctctcagaag agcatggagc tccttgcttt actcagacag agcatggctc tccagagagt     1080
tcacaggaca gcagcaagag aagaaaggtt gtgttaccca gtcctagcca agctaagaat     1140
ggtgaggccc tttcttgcat ttgtcttctt ttagctggtg atgttgaatt ggtttgactt     1200
atcctgaatt atcatcttgc aggtaacatc cttcgaataa agataagaag agatcaagat     1260
```

-continued

```
tcttcagctt ccctttcgga gaaatctaat gttgtacaaa caccagttca tcaaatggga    1320
tcagtttcat ctctgccaag taagaaaaac tcaatgcaac cacacaacac cgaaatgatg    1380
gtgagaacag catcaaccca gcagcaaagc atcaaaggtg attttcaagc agtaccgaaa    1440
caaggtatgc caacccagc aaaagtcatg ccaagagtcg atgttcctcc atctatgagg     1500
gcatcaaagg aaaggattgg ccttcgtcct gcagagatgt tggccaatgt tggtccttca    1560
ccctccaagg caaaacagat tgtcaatcct gcagctgcta aggttacaca aagagttgat    1620
cctccacctg ccaaggcatc tcagagaatt gatcctctgt tgccatccaa ggttcatata    1680
gatgctactc gatcttttac gaaggtctcc cagacagaga tcaagccgga agtacagccc    1740
ccaattctga aggtgcctgt ggctatgcct accatcaatc gtcagcagat tgacacctcg    1800
cagcccaaag aagagccttg ctcctctggc aggaatgctg aagctgcttc agtatcagta    1860
gagaagcagt ccaagtcaga tcgcaaaaag agccgcaagg ctgagaagaa agagaagaag    1920
ttcaaagatt tatttgttac ctgggatcct ccgtctatgg aaatggatga tatggatctc    1980
ggggaccagg attggctgct tgatagtacg aggaaacctg atgctggcat tggcaactgc    2040
agagaaattg ttgatccact tacttctcaa tcagcagagc agttctcatt gcagcctagg    2100
gcgattcatt taccagacct tcatgtctat cagttgccat atgtggttcc attctag      2157
```